(12) United States Patent
Jiang et al.

(10) Patent No.: US 6,586,572 B2
(45) Date of Patent: Jul. 1, 2003

(54) COMPOSITIONS AND METHODS FOR THE THERAPY AND DIAGNOSIS OF BREAST CANCER

(75) Inventors: Yuqiu Jiang, Kent, WA (US); Davin C. Dillon, Issaquah, WA (US); Jennifer L. Mitcham, Redmond, WA (US); Jiangchun Xu, Bellevue, WA (US); Susan L. Harlocker, Seattle, WA (US); William T. Hepler, Seattle, WA (US)

(73) Assignee: Corixa Corporation, Seattle, WA (US)

(*) Notice: Subject to any disclaimer, the term of this patent is extended or adjusted under 35 U.S.C. 154(b) by 0 days.

(21) Appl. No.: 09/604,287

(22) Filed: Jun. 22, 2000

(65) Prior Publication Data

US 2002/0064872 A1 May 30, 2002

Related U.S. Application Data

(63) Continuation-in-part of application No. 09/590,751, filed on Jun. 8, 2000, which is a continuation-in-part of application No. 09/551,621, filed on Apr. 17, 2000, which is a continuation-in-part of application No. 09/433,826, filed on Nov. 3, 1999, which is a continuation-in-part of application No. 09/389,681, filed on Sep. 2, 1999, which is a continuation-in-part of application No. 09/339,338, filed on Jun. 23, 1999, which is a continuation-in-part of application No. 09/285, 480, filed on Apr. 2, 1999, which is a continuation-in-part of application No. 09/222,575, filed on Dec. 28, 1998.

(51) Int. Cl.[7] .......................... C07K 1/100; C12P 21/08
(52) U.S. Cl. ..................... 530/350; 530/387.3
(58) Field of Search ............... 536/23.1, 23.5; 530/350, 388.8; 424/277.1; 435/6; 436/813, 811

(56) References Cited

U.S. PATENT DOCUMENTS

| | | |
|---|---|---|
| 5,215,926 A | 6/1993 | Etchells, III et al. |
| 5,240,856 A | 8/1993 | Goffe et al. |
| 5,891,857 A | 4/1999 | Holt et al. |
| 5,986,170 A | 11/1999 | Subjeck |

FOREIGN PATENT DOCUMENTS

| | | | |
|---|---|---|---|
| WO | WO 89/06280 | | 7/1989 |
| WO | WO 91/16116 | | 10/1991 |
| WO | WO 92/07243 | | 4/1992 |
| WO | WO 96/29430 | | 9/1996 |
| WO | WO 98/21331 | | 5/1998 |
| WO | WO 98/33915 | | 8/1998 |
| WO | WO 98/54963 | | 12/1998 |
| WO | WO 99/09155 | | 2/1999 |
| WO | WO 00/43420 | * | 1/2000 |
| WO | WO 00/08210 | | 2/2000 |
| WO | WO 00/60076 | | 10/2000 |
| WO | WO 00/73801 | | 12/2000 |
| WO | WO 01/37779 | | 5/2001 |
| WO | WO 01/47959 | | 7/2001 |

OTHER PUBLICATIONS

GenBank Accession No. AC069200, May 24, 2000.
Sulston et al., "Toward a complete human genome sequence," *Genome Research* 8(11):1097–1108, 1998.
GenBank Accession No. AF269087, Mar. 28, 2001.
GenBank Accession No. AAK27325, Mar. 28, 2001.
Chang and Shu, "Current status of adoptive immunotherapy of cancer,"*Critical Reviews in Oncology/Hematology* 22(3):213–228, Apr. 1996.
Cheever and Chen, "Therapy with cultured T cells: principles revisited," *Immunological Reviews*, 157:177–194, 1997.
Cheever et al., "Potential uses of interleukin 2 in cancer therapy," *Immunobiol*, 172:365–382, 1986.
Chen et al., "T–cells for tumor therapy can be obtained from anitgen–loaded sponge implants," *Cancer Research* 54(4):1065–1070, Feb. 15, 1994.
Cole et al., "Characterization of the functional specificity of a cloned T–cell receptor heterodimer recognizing the MART–1 melanoma antigen," *Cancer Research*, 55:748–752, Feb. 15, 1995.
Durrant L., "Cancer vaccines," *Anti–Cancer Drugs*, 8:727–733, 1997.
Eshhar Z., "Tumor–specific T–bodies: toward clinical application," *Cancer Immunol Immnother*, 45:131–136, 1997.
Hwu et al., "In vivo antitumor activity of T cells redirected with chimeric antibody/T–cell receptor genes," *Cancer Research*, 55:3369–3373, Aug. 1, 1995.
Porter–Jordan and Lippman, "Overview of the biologic markers of breast cancer," *Breast Cancer* 8:(1):73–100, Feb. 1994.
Prilliman et al., "HLA–B15 peptide ligands are preferentially anchored at their c termini," *The Journal of Immunology* 162(12):7277–7284, Jun. 15, 1999.
Wei et al., "Protection against mammary tumor growth by vaccination with full–length, modified human ErbB–2 DNA," *Int. J. Cancer*, 81:748–754, 1999.
GenBank Accession No. AA864891, Feb. 20, 1998.
GenBank Accession No. AA398925, Apr. 25, 1997.
Genseq Accession No. V84525 (Dec. 10, 1998).
Stratagene 1991 product catalog, Prime–It™ Random Labeling Kit, catalog No. 300387, p. 66.

* cited by examiner

*Primary Examiner*—Sean McGarry
*Assistant Examiner*—Janet L. Epps-Ford
(74) *Attorney, Agent, or Firm*—Seed Intellectual Property Law Group PLLC

(57) ABSTRACT

Compositions and methods for the therapy and diagnosis of cancer, such as breast cancer, are disclosed. Compositions may comprise one or more breast tumor proteins, immunogenic portions thereof, or polynucleotides that encode such portions. Alternatively, a therapeutic composition may comprise an antigen presenting cell that expresses a breast tumor protein, or a T cell that is specific for cells expressing such a protein. Such compositions may be used, for example, for the prevention and treatment of diseases such as breast cancer. Diagnostic methods based on detecting a breast tumor protein, or mRNA encoding such a protein, in a sample are also provided.

6 Claims, 1 Drawing Sheet

SYN18C6 NORTHERN BLOT 2.37 kb ⟶

1.35 kb ⟶

0.24 kb ⟶

SEQUENCE LISTING

<160> NUMBER OF SEQ ID NOS: 489

<210> SEQ ID NO 1
<211> LENGTH: 281
<212> TYPE: DNA
<213> ORGANISM: Homo sapien

<400> SEQUENCE: 1

```
caatgacagt caatctctat cgacagcctg cttcatattt agctattgtt cgtattgcct      60
tctgtcctag gaacagtcat atctcaagtt caaatgccac aacctgagaa gcggtgggct     120
aagataggtc ctactgcaaa ccaccoctcc atatttccgt acgcaattac aattcagttt     180
ctgtgacatc tctttacacc actggaggaa aaatgagata ttctctgatt tattctacta     240
taacactcta catagagcta tggtgagtgc taaccacatc g                          281
```

<210> SEQ ID NO 2
<211> LENGTH: 300
<212> TYPE: DNA
<213> ORGANISM: Homo sapien

<400> SEQUENCE: 2

| | | | | | |
|---|---|---|---|---|---|
| gaggtcctgg | gctaacctaa | tggtttatta | ttggtggaga | gaaagatctg | gaaatacttg | 60
| aggttattac | atactagatt | agcttctaat | gtgaaccatt | tttcttttaa | cagtgataaa | 120
| ttattatttc | cgaagttaac | tgttcccttg | gtcgtgatac | acactcgatt | aacaaacata | 180
| ctgttgtatt | ttttccagtt | ttgtttggct | atgccaccac | agtcatcccc | agggtctata | 240
| catactatgt | ctcaactgta | ttatttgcca | tttttggcat | tagaatgctt | cgggaaggct | 300

<210> SEQ ID NO 3
<211> LENGTH: 302
<212> TYPE: DNA
<213> ORGANISM: Homo sapien

<400> SEQUENCE: 3

| | | | | | |
|---|---|---|---|---|---|
| ggccgaggta | attggttaag | tctaaagaga | ttattattcc | ttgatgtttg | ctttgtattg | 60
| gctacaaatg | tgcagaggta | atacatatgt | gatgtcgatg | tctctgtctt | tttttttgtc | 120
| tttaaaaaat | aattggcagc | aactgtattt | gaataaaatg | atttcttagt | atgattgtac | 180
| agtaatgaat | gaaagtggaa | catgtttctt | tttgaaaggg | agagaattga | ccatttattg | 240
| ttgtgatgtt | taagttataa | cttatcgagc | acttttagta | gtgataactg | ttttaaact | 300
| tg | | | | | | 302

<210> SEQ ID NO 4
<211> LENGTH: 293
<212> TYPE: DNA
<213> ORGANISM: Homo sapien

<400> SEQUENCE: 4

| | | | | | |
|---|---|---|---|---|---|
| tgtaccaatc | ctttggcaca | agaatatgta | agaactatag | ttgttttat | tggtttttgt | 60
| tcttgagatt | gttttcattc | tgttttgac | tgtatctctt | taggaggctg | aggatggcat | 120
| tattgcttat | gatgactgtg | gggtgaaact | gactattgct | tttcaagcca | aggatgtgga | 180
| aggatctact | tctcctcaaa | tacgagataa | ggcaagataa | ttctgctcat | tcgagagagg | 240
| gttaagagtt | gtcatcttaa | tcataaatcc | tgcaggatgg | gttcttcaaa | ttt | 293

<210> SEQ ID NO 5
<211> LENGTH: 275
<212> TYPE: DNA
<213> ORGANISM: Homo sapien

<400> SEQUENCE: 5

| | | | | | |
|---|---|---|---|---|---|
| cgaggtttgg | aatcagactt | ctgtgtccag | taaaaaactc | ctgcactgaa | gtcattgtga | 60
| cttgagtagt | tacagactga | ttccagtgaa | cttgatctaa | tttcttttga | tctaatgaat | 120
| gtgtctgctt | accttgtctc | cttttaattg | ataagctcca | agtagttgct | aattttttga | 180
| caactttaaa | tgagtttcat | tcacttcttt | tacttaatgt | tttaagtata | gtaccaataa | 240
| tttcattaac | ctgttctcaa | gtggtttagc | tacca | | | 275

<210> SEQ ID NO 6
<211> LENGTH: 301
<212> TYPE: DNA
<213> ORGANISM: Homo sapien

<400> SEQUENCE: 6

| | | | | | |
|---|---|---|---|---|---|
| gaggtctggt | ttcctgggta | tgcctggact | gttgcccagt | gtaagatctg | tgcaagccat | 60

```
attggatgga agtttacggc caccaaaaaa gacatgtcac ctcaaaaatt ttggggctta      120
acgcgatctg ctctgttgcc cacgatccca gacactgaag atgaaataag tccagacaaa      180
gtaatacttt gcttgtaaac agatgtgata gagataaagt tatctaacaa attggttata      240
ttctaagatc tgctttggaa attattgcct ctgatacata cctaagtaaa cataacatta      300
a                                                                      301

<210> SEQ ID NO 7
<211> LENGTH: 301
<212> TYPE: DNA
<213> ORGANISM: Homo sapien

<400> SEQUENCE: 7
gtccagtttg tacacagtga ttccttatgc acgccgaaag ggtttccgta aaaatgacat       60
tatatacaaa tctgtacacc catccaccag agcgattctc cagctcccag agggagttat      120
caacttaaag caggatacct gaggtttcat gtctttagtt gccttatcat aatcccaaat      180
atacatttca gggtttgttt ttgtttttaa agacactttc ctggaatatg tgcactatgg      240
ttaaaattaa aaacaaaagt aataaaataa atgatcgct ggaaggactg acctcccac        300 c                                                                      301

<210> SEQ ID NO 8
<211> LENGTH: 301
<212> TYPE: DNA
<213> ORGANISM: Homo sapien

<400> SEQUENCE: 8
ctgtcctcat ctctgcaaag ttcagcttcc ttccccaggt ctctgtgcac tctgtcttgg       60
atgctctggg gagctcatgg gtggaggagt ctccaccaga gggaggctca ggggactggt      120
tgggccaggg atgaatattt gagggataaa aattgtgtaa gagccaaaga attggtagta      180
gggggagaac agagaggagc tgggctatgg gaaatgattt gaataatgga gctgggaata      240
tggctggata tctggtacta aaaagggtc tttaagaacc tacttcctaa tctcttcccc       300
a                                                                      301

<210> SEQ ID NO 9
<211> LENGTH: 301
<212> TYPE: DNA
<213> ORGANISM: Homo sapien

<400> SEQUENCE: 9
gaggtctgcc taagtagagg acaaagactt cctcctttca aaggagaact gagcccagga       60
ttggtaagtt taaggcactt aaccttgacc agctctgtag gtctggagca ttctggtccc      120
tggccgcttt caccaccagg cccttctcac ttatccacct cacatactgc cccagcattc      180
ctttggcatt gcgagctgtg acttgacaca ttttaatgac aagattgaag tagctacctt      240
gcaggataga ttttctgggg tatagggac aaaccaacag tgccatcagg tgtcttaaca       300
c                                                                      301

<210> SEQ ID NO 10
<211> LENGTH: 301
<212> TYPE: DNA
<213> ORGANISM: Homo sapien

<400> SEQUENCE: 10
ggcaggtcca acagttcttc cagttctggt cgagctttga atcgtccctt gaagtcttct       60
```

-continued

```
tcagtgtgct ccttcactga cagtctgact ccttcaggaa gactgctttg gattatttcc      120
aagaaaattt ctgcaaacgt agcactcaaa ccgctgatct gaaccactcg ctcatgggtg      180
gtaagcactg agtccaggag cattttgctg ccttggtcct gcaactgcaa cacttctatg      240
gttttggttg gcattgcata actttcctcg actttaatgg agagagattg cagaggttgt      300
g                                                                     301
```

<210> SEQ ID NO 11
<211> LENGTH: 301
<212> TYPE: DNA
<213> ORGANISM: Homo sapien

<400> SEQUENCE: 11

```
aggtctgtga ctttcaccca ggacccagga cgcagccctc cgtgggcact gccggcgcct      60
tgtctgcaca ctggaggtcc tccattacag aggcccagcg cacatcgctg gccccacaaa     120
cgttcagggg tacagccatg gcagctcctt cctctgccgt gagaaaagtg cttggagtac     180
ggtttgccac acacgtgact ggacagtgtc caattcaaat ctttcagggc agagtccgag     240
cagcgcttgg tgacagcctg tcctctcctg ctctccaaag gccctgctcc ctgtcctctc     300
t                                                                     301
```

<210> SEQ ID NO 12
<211> LENGTH: 301
<212> TYPE: DNA
<213> ORGANISM: Homo sapien

<400> SEQUENCE: 12

```
gaggtctggg attacaggca cgtgccacca cacctagcta attttttgagc atgggctca     60 aaggaactgc tctctggggc atgtcagatt tcggatttgg ggctgcacac tgatactctc     120
taagtggtgg aggaacttca tcccactgaa attcctttgg catttggggt tttgtttttc     180 ttttttttcct tcttcatcct cctcctttttt taaaagtcaa cgagagcctt cgctgactcc     240
accgaagaag tgcaccactg ggagccaccc cagtgccagg cgcccgtcca gggacacaca     300
c                                                                     301
```

<210> SEQ ID NO 13
<211> LENGTH: 256
<212> TYPE: DNA
<213> ORGANISM: Homo sapien

<400> SEQUENCE: 13

```
ttttttggca taaaaaacac aatgatttaa tttctaaagc acttatatta ttatggcatg      60
gtttgggaaa caggttatta tattccacat aggtaattat gcagtgcttc tcatggaaaa     120
aatgcttagg tattggcctt ttctctggaa accatatttt tccttttta ataatcaact      180 aaaatgtata tgttaaaaag cctcatcttt tgattttcaa tatacaaaat gctttcttta     240
aaagaacaag attcaa                                                    256
```

<210> SEQ ID NO 14
<211> LENGTH: 301
<212> TYPE: DNA
<213> ORGANISM: Homo sapien

<400> SEQUENCE: 14

```
ggtccttgat agaggaagag gaatatccaa ggcaaagcca ccaccacgtc caacctcctc      60
```

-continued

| | |
|---|---|
| atcctctacc tttcctgtcc ccagaggtat gagatagacc ccctggcctg gttcctgcac | 120 |
| tgtgctaggc ccacagtgga cacttccacc ttaatggaga ataggcccca tggagtggag | 180 |
| gtccctcctc catggcctgc aacccaatga ctatgggggt gacacaagtg acctctgccc | 240 |
| tgtgatggct caacaccatc acacgcaact gtccagacaa gcccctcaa cgggctgctg | 300 |
| t | 301 |

<210> SEQ ID NO 15
<211> LENGTH: 259
<212> TYPE: DNA
<213> ORGANISM: Homo sapien

<400> SEQUENCE: 15

| | |
|---|---|
| gtcttgaaag tatttattgt ttaataattc tttctcccct cagccccatc cggccactct | 60 |
| ctctttctgc ttttctgatc atcctaaagg ctgaatacat cctcctcctg tgtgggggac | 120 |
| acgaagcaat actaaaatca atacactcga tcaggtcttc atcagatacc acgtcactgt | 180 |
| gggtagagtg ctaattttca acaaatgtgg tgttcttagg gccccacaag gtagtccttt | 240 |
| ctcaaggtcg ctgggccac | 259 |

<210> SEQ ID NO 16
<211> LENGTH: 301
<212> TYPE: DNA
<213> ORGANISM: Homo sapien

<400> SEQUENCE: 16

| | |
|---|---|
| cgaggttgtt cacattttca aataaataat actccccgta agtaataact gcaaccaatc | 60 |
| agtgttattc agtgctatgc ctccttgtaa tgggtagtta ttaattattt tcagagcttt | 120 |
| ctggaaatac tgtcctaact ggctatgttt aggatctttg ttatctctga agacaaagaa | 180 |
| agaactagga ctcttaattt tggggtgctt cttgactctt agttgggaaa ctgaaaatat | 240 |
| ttccaacctt ttacccacgt caatggcata ttctgggaat caccaccacc accaccacta | 300 |
| c | 301 |

<210> SEQ ID NO 17
<211> LENGTH: 301
<212> TYPE: DNA
<213> ORGANISM: Homo sapien

<400> SEQUENCE: 17

| | |
|---|---|
| gcccgggcag gtctggggcc tagggtggct cttttgcaaag ctgaggggca agctaaggaa | 60 |
| gccaggcagg tcaggggccc tttcggcctt ctcaagcctc cacctgagtt ctcgtcaatg | 120 |
| ccagtctccc tggtatgatt ggggacatta tcagagaaac atctaatagc gcacatctgg | 180 |
| gcacccacac tctgcttcag ttgcatccat cctcccaccc caaattcaac tcctgaccca | 240 |
| atacaaaaga cttttttaac caggatttct tcttgcagga aagctgactt ggaaacacgg | 300 |
| g | 301 |

<210> SEQ ID NO 18
<211> LENGTH: 301
<212> TYPE: DNA
<213> ORGANISM: Homo sapien

<400> SEQUENCE: 18

| | |
|---|---|
| attacaggca cgtgccacca cacctagcta attttttgagc atggggctca aaggaactgc | 60 |
| tctctggggc atgtcagatt tcggatttgg ggctgcacac tgatactctc taagtggtgg | 120 |

```
aggaacttca tcccactgaa attcctttgg catttggggt tttgttttc ttttttcct      180
tcttcatcct cctcctttt taaaagtcaa cgagagcctt cgctgactcc accgaagaag      240
tgcaccactg gggaccaccc agtgccaggc gcccgtccag ggacacacac agtcttcact    300
g                                                                    301
```

<210> SEQ ID NO 19
<211> LENGTH: 301
<212> TYPE: DNA
<213> ORGANISM: Homo sapien

<400> SEQUENCE: 19

```
agaatctctg cactgtcatc aggtacaaca aaagatcaaa cccctgtccc gatgttaact     60
ttttaactta aaagaatgcc agaaaccca gatcaacact ttccagctac gagccgtcca    120
caaaggccac ccaaaggcca gtcagactcg tgcagatctt atttttaat agtagtaacc    180
acaatacaca gctctttaaa gctgttcata ttcttccccc attaaacacc tgccccgggc   240
ggccaagggc gaattctgca gatatccatc acactggcgg ccgctcgagc atgcatctag   300
a                                                                   301
```

<210> SEQ ID NO 20
<211> LENGTH: 290
<212> TYPE: DNA
<213> ORGANISM: Homo sapien

<400> SEQUENCE: 20

```
aggttttttt tttttttttt tttttttttt ttttccctt tcaattcatt taatttcaac    60
aatctgtcaa aaacagcca ataaacaaat actgaattac attctgctgg gttttttaaa   120
ggctctaaac tataaaaaca tcttgtgtct cccaccctga ccaccctgct acttttccat   180
ataccacagg ccacccataa acacaaagcc aggggggtgaa gctgacatgg tctatttgga  240
gccagtaaac aggagggcga taagtcctga taagcactta tggacaatat                290
```

<210> SEQ ID NO 21
<211> LENGTH: 301
<212> TYPE: DNA
<213> ORGANISM: Homo sapien

<400> SEQUENCE: 21

```
agaaaggtaa ctgccagcca ggcttgcatt gtttagccag aaattgctgc ttggttctag    60
actctttaaa aaaaaaaaat acccagggtt tgtcatcatt ttcagaggca gagtgccaaa   120
tatcacccaa agctcttgtg tcttttttttt accccttat tttattttta tttattaatt  180
ttttgtgcaa acatcaaatg tcactggtgt tcacagaagg cttttttgac tagccttaaa   240
ttcctgagtc aaaagattaa tcagatttc aggcagtgtt taatcaggtg ctttgtcctg   300
t                                                                   301
```

<210> SEQ ID NO 22
<211> LENGTH: 301
<212> TYPE: DNA
<213> ORGANISM: Homo sapien

<400> SEQUENCE: 22

```
gacgccatgc accctccggt aaccagcagc cgcctgtcca tccccaaga ccggaaaggc     60
agcagcagcc cccgggagcc cagggctgtc ctcggtgcat ctggctgcag agggaaattg   120
```

| | |
|---|---|
| atgacctac acagcaacta gcggccatgc agtccttcac tgacaagttc caggacctt | 180 |
| gaagttggag ccagcgtccg gagctgcagc caagcgagtt tcctccttat cctccttagc | 240 |
| cagggctttt tctcttccgc tgcatttgcc cccttcccaa cgcaattcaa agcagttgtg | 300 |
| a | 301 |

<210> SEQ ID NO 23
<211> LENGTH: 381
<212> TYPE: DNA
<213> ORGANISM: Homo sapien

<400> SEQUENCE: 23

| | |
|---|---|
| cgaggtccag acagtggacc aagagatacg ctacataaat tggggtttca caattcttac | 60 |
| attatttgtc tgtcacagaa gagagctgct tatgattttg aaggggtcag ggagggtggg | 120 |
| agttggtaaa gagtagggta tttctataac agatattatt cagtcttatt tcctaagatt | 180 |
| ttgttgtaac ttaaggtatc ttgctacagt agacagaatt ggtaatagca acttttaaaa | 240 |
| ttgtcattag ttctgcaata ttagctgaaa tgtagtacag aaaagaatgt acatttagac | 300 |
| atttgggttc agttgcttgt agtctgtaaa tttaaaacag cttaatttgg tacaggttac | 360 |
| acatatggac ctcccgggcg g | 381 |

<210> SEQ ID NO 24
<211> LENGTH: 214
<212> TYPE: DNA
<213> ORGANISM: Homo sapien

<400> SEQUENCE: 24

| | |
|---|---|
| aatgatgtaa aaattaatca acagggctgc cacttgcgaa tcccctccaa ggatgctgtg | 60 |
| caaagggtct cattggtcct gatgaataat cttgtgactg tacatattcc tgggtgcatg | 120 |
| tccacaaata ctgaggtata gcctgcatgc cactaaaaat aacaaggtt tcaggggtgg | 180 |
| aaacattgtc caccacactg tcatgaccat cttt | 214 |

<210> SEQ ID NO 25
<211> LENGTH: 302
<212> TYPE: DNA
<213> ORGANISM: Homo sapien

<400> SEQUENCE: 25

| | |
|---|---|
| gggggcactg agaactccct ctggaattct tgggggtgt tggggagaga ctgtgggcct | 60 |
| ggagataaaa cttgtctcct ctaccaccac cctgtaccct agcctgcacc tgtcctcatc | 120 |
| tctgcaaagt tcagcttcct tccccaggtc tctgtgcact ctgtcttgga tgctctgggg | 180 |
| agctcatggg tggaggagtc tccaccagag ggaggctcag gggactggtt gggccaggga | 240 |
| tgaatatttg agggataaaa attgtgtaag aagccaaaga aattggtagt agggggagaa | 300 |
| ac | 302 |

<210> SEQ ID NO 26
<211> LENGTH: 301
<212> TYPE: DNA
<213> ORGANISM: Homo sapien

<400> SEQUENCE: 26

| | |
|---|---|
| ttggagaacg cgctgacata ctgctcggcc acagtcagtg aagctgctgc atctccatta | 60 |
| tgttgtgtca gagctgcagc caggattcga atagcttcag ctttagcctt ggccttcgcc | 120 |
| agaactgcac tggcctctcc tgctgcctga tttatctgtg cagccttttc tgcttcggag | 180 |

```
gccaggatct gggcctgttt cttcccttct gccacattga tggccgactc tcgggtcccc    240
tcagactcta gaactgtggc ccgtttccgc cgctctgcct ccacctgcat ctgcatagac    300
t                                                                   301
```

<210> SEQ ID NO 27
<211> LENGTH: 301
<212> TYPE: DNA
<213> ORGANISM: Homo sapien

<400> SEQUENCE: 27

```
aaatcagtca tcacatctgt gaaaagagtg ctagttataa caaatgagat cacaaatttg     60
accattttat tagacaccct ctattagtgt taacagacaa agatgaaggt taagttgaaa    120
tcaaattgaa atcatcttcc ctctgtacag attgcaatat ctgataatac cctcaacttt    180
cttggtgcaa attaattgcc tggtactcac agtccagtgt taacaggcaa taatggtgtg    240
attccagagg agaggactag gtggcaggaa ataaatgag attagcagta tttgacttgg     300
a                                                                   301
```

<210> SEQ ID NO 28
<211> LENGTH: 286
<212> TYPE: DNA
<213> ORGANISM: Homo sapien

<400> SEQUENCE: 28

```
ttttttttg cacaggatgc acttattcta ttcattctcc cccacccttc ccatatttac      60
atccttagag gaagagaggg gtaaggtgat aaagtaactg aaggaccgca agacgggtat    120
gtcccttgtt caccaaatgg tcaaagggtc aaagatcgga ggaggtcagg gggtaacgca    180
ggaacaggtg agggcgtttc gccctctctc cctctcccct tttcaacctc ttaatcactg    240
gctaactcgc gacctcatgg gttaattcgt aagcttacac gcgttg                  286
```

<210> SEQ ID NO 29
<211> LENGTH: 301
<212> TYPE: DNA
<213> ORGANISM: Homo sapien

<400> SEQUENCE: 29

```
gtcatgttct tgctcttcct tctttacaca tttgagttgt gccttctgtt cttaaagaga     60
ttttcctttg ttcaaaggat ttattcctac catttcacaa atccgaaaat aattgaggaa    120
acaggttaca tcattccaat tttgccttgg gtttgaagag tctctcatgg tggcacagtc    180
ctccagggta gctatgttgt tgggctcccc tacatcccag aagctcagag actttgtcaa    240
aggtgtgccg tccacccatt gccactgacc ctcgacaacc tggtctgaca gtccaataaa    300
a                                                                   301
```

<210> SEQ ID NO 30
<211> LENGTH: 332
<212> TYPE: DNA
<213> ORGANISM: Homo sapien

<400> SEQUENCE: 30

```
gagcagaatt gatgcctatg gctccaagtc aaatactgct aatctcattt attttcctgc     60
cacctagtcc tctcctctgg aatcacacca ttattgcctg ttaacactgg actgtgagta    120
ccaggcaatt aatttgcacc aagaaagttg agggtattat cagatattgc aatctgtaca    180
```

-continued

| | |
|---|---|
| gagggaagat gatttcaatt tgatttcaac ttaaccttca tctttgtctg ttaacactaa | 240 |
| tagagggtgt ctaataaaat ggtcaaattt gtgatctcat ttgttataac tagcactctt | 300 |
| ttcacagatg tgatgactga tttccagcag ac | 332 |

<210> SEQ ID NO 31
<211> LENGTH: 141
<212> TYPE: DNA
<213> ORGANISM: Homo sapien

<400> SEQUENCE: 31

| | |
|---|---|
| aaaggctatc aagtactttg aaggacagga aggaatgaac acacccaggt ggacgtttgg | 60 |
| tttcatttgc aggggttcag ggagggttgc aggggttcag ggagggctct tgtcccacaa | 120 |
| ccggggggaag ggagagggca c | 141 |

<210> SEQ ID NO 32
<211> LENGTH: 201
<212> TYPE: DNA
<213> ORGANISM: Homo sapien

<400> SEQUENCE: 32

| | |
|---|---|
| gagctgatct cacagcacat acagaatgat gctactatgt agaccctcac tcccttggga | 60 |
| aatctgtcat ctaccttaaa gagagaaaaa agatggaaca taggcccacc tagtttcatc | 120 |
| catccaccta cataaccaac atagatgtga ggtccactgc actgatagcc agactgcctg | 180 |
| gggtaaacct tttcagggag g | 201 |

<210> SEQ ID NO 33
<211> LENGTH: 181
<212> TYPE: DNA
<213> ORGANISM: Homo sapien

<400> SEQUENCE: 33

| | |
|---|---|
| tttcaaaaca ctcatatgtt gcaaaaaaca catagaaaaa taaagtttgg tgggggtgct | 60 |
| gactaaactt caagtcacag acttttatgt gacagattgg agcagggttt gttatgcatg | 120 |
| tagagaaccc aaactaattt attaaacagg atagaaacag gctgtctggg tgaaatggtt | 180 |
| c | 181 |

<210> SEQ ID NO 34
<211> LENGTH: 151
<212> TYPE: DNA
<213> ORGANISM: Homo sapien

<400> SEQUENCE: 34

| | |
|---|---|
| atgtcctgca cagtatagct tggacctctg ggcctgaacc agggtgagca tcaaggcccc | 60 |
| catttctcct caccacgggg tcgcttgtca gctccaagaa ccagtctggc cccactgaga | 120 |
| acttttcagt cgagggcctg atgaatcttg g | 151 |

<210> SEQ ID NO 35
<211> LENGTH: 291
<212> TYPE: DNA
<213> ORGANISM: Homo sapien

<400> SEQUENCE: 35

| | |
|---|---|
| tctttagggc aaaatcatgt ttctgtgtac ctagcaatgt gttcccattt tattaagaaa | 60 |
| agctttaaca cgtgtaatct gcagtcctta acagtggcgt aattgtacgt acctgttgtg | 120 |
| tttcagtttg ttttcacct ataatgaatt gtaaaaacaa acatacttgt ggggtctgat | 180 |

| | |
|---|---|
| agcaaacata gaaatgatgt atattgtttt ttgttatcta tttattttca tcaatacagt | 240 |
| attttgatgt attgcaaaaa tagataataa tttatataac aggttttctg t | 291 |

<210> SEQ ID NO 36
<211> LENGTH: 201
<212> TYPE: DNA
<213> ORGANISM: Homo sapien

<400> SEQUENCE: 36

| | |
|---|---|
| ctgatacaat tataataacg gttccctgaa ccttttagag tgcaattaag aacaaaaact | 60 |
| aaatttgtt tacatgaata tggaataaat acaataatca aatatgact ctccctaaaa | 120 |
| gtgaaacaca caagccaatc cggaactgct gtgcgaaaga taaatcgag aaaggcaagg | 180 |
| tttcggtagg aggacgcgat g | 201 |

<210> SEQ ID NO 37
<211> LENGTH: 121
<212> TYPE: DNA
<213> ORGANISM: Homo sapien

<400> SEQUENCE: 37

| | |
|---|---|
| catcacactg gcggccgctc gagcatgcat ctagagggcc caattcgccc tataatgagt | 60 |
| cgtattacaa ttcactggcc gtcgttttac aacgtcgtga ctgggaaaac cctggcgtta | 120 |
| c | 121 |

<210> SEQ ID NO 38
<211> LENGTH: 200
<212> TYPE: DNA
<213> ORGANISM: Homo sapien

<400> SEQUENCE: 38

| | |
|---|---|
| aaacatgtat tactctatat ccccaagtcc tagagcatga cctgcatgtt ggagatgttg | 60 |
| tacagcaatg tatttatcca gacatacata tgatatt agagacacag tgattctttt | 120 |
| gataacacca cacatagaac attataatta cacacaaatt tatggtaaaa gaattaatat | 180 |
| gctgtctggt gctgctgtta | 200 |

<210> SEQ ID NO 39
<211> LENGTH: 760
<212> TYPE: DNA
<213> ORGANISM: Homo sapien

<400> SEQUENCE: 39

| | |
|---|---|
| gcgtggtcgt cggccgaggt cctgggctag acctaatggt ttattattgg tggagagaaa | 60 |
| gatctggaaa tacttgaggt tattacatac tagattagct tctaatgtga accattttc | 120 |
| ttttaacagt gatcaaatta ttatttcgaa gttaatcgtt cccttggtgg ctgcatacac | 180 |
| atcgcattaa caaacatact gttgtatttt ttcccagttt tgtttggcta tgccaccaca | 240 |
| gtcatcccca gggtctatac atactatgtt tcaactgtat tatttgccat ttttggcatt | 300 |
| agaatgcttc gggaaggctt aaagatgagc cctgatgagg tcaagagga actggaagaa | 360 |
| gttcaagctg aattaaagaa gaaagatgaa gaagtaagcc atggcactgt tgatctggac | 420 |
| caaaaggca ctcaactagg aataaacact ctacagaggt ttctcagtgg ccccatctgt | 480 |
| gtgatatgcg gggctacaca aaaatagctt cttttgcttt gttctgttct tatacctgtc | 540 |
| tgtgatctga cttggggttg gtgtgaatgt agtagagaaa ggaagctgac agatgaatac | 600 |

-continued

| | |
|---|---|
| tgaacacagg taatcagttt ccttaattag gttgattata agctcctgaa aagcaggaac | 660 |
| tgtattttat aattttacct gtttctcccg tggtgtctag gatagtaagt gagcagagca | 720 |
| gtaaatactg tttggtttgt tcagacctgc ccgggcggcc | 760 |

<210> SEQ ID NO 40
<211> LENGTH: 452
<212> TYPE: DNA
<213> ORGANISM: Homo sapien

<400> SEQUENCE: 40

| | |
|---|---|
| aatcactaaa gatattgact agagaatgct gtgtgctatt tcaattacat ttgttttct | 60 |
| tttattaaca ggaattttga ttcttcaagg aagtggctca atttcaattt caggtgacca | 120 |
| ggtttatcgt gacttttcct tcttgtttac ttttcgctag aaggggagt tgtagggca | 180 |
| gattcaggta ttggaatagg aaaattacgt ctaaaccatg gaaatcttgg aaatggaatt | 240 |
| ggtggaagtg ggcgaaatgg atatgggtaa gggaacacaa aaaccctga agctaattca | 300 |
| tcgctgtcac tgatacttct tttttctcgt tcctggtctt gagagactgg gaaaccaaca | 360 |
| gccactgcca agatggctgt gatcaggagg agaacttct tcatctcaaa cgtttcagtc | 420 |
| agttcttct ctcacctcgg ccgcgaccac gc | 452 |

<210> SEQ ID NO 41
<211> LENGTH: 676
<212> TYPE: DNA
<213> ORGANISM: Homo sapien

<400> SEQUENCE: 41

| | |
|---|---|
| aatctttgaa tgccaagtct cttctgtact ttcttttatt aacatcatag tctttgcatc | 60 |
| aagatacata gcaatgatag caggtttctt tttaagctt agtattaata ttaaatattt | 120 |
| ttccccattt aaattttaca ttacttgcca agaaaaaaaa aaaattaaaa ctcaagttac | 180 |
| ttgaagcctg gacacacttc catgattagc cgggctaggt aaaagttggt ggctttattc | 240 |
| ttcctgctct ataagcagat ccaggcccta gaaagatggg accagggtat ataattgttt | 300 |
| ttgaaaagtg tgctacaaaa atggatggcc tgttataagc caggatacaa agttaaggat | 360 |
| gggggtaagg gagggacatt tcttccaga agaaaagaca gaatttctga agagtcccag | 420 |
| tccataattt tcccaaaatg gttggaggag agggtaaaat ctcaacatga gtttcaaagt | 480 |
| actgtctctg tgaggggccg gtagatgcct tgctgaggag ggatggctaa tttgaccat | 540 |
| gccccatccc cagctaggag aatggaaatg gaaactttaa ttgcccagtg ggtgtgaaag | 600 |
| tgggctgaag cttggttggt actgaattct ctaagaggtt tcttctagaa acagacaact | 660 |
| cagacctgcc cgggcg | 676 |

<210> SEQ ID NO 42
<211> LENGTH: 468
<212> TYPE: DNA
<213> ORGANISM: Homo sapien

<400> SEQUENCE: 42

| | |
|---|---|
| agcgtggtcg cggccgaggt ttggccggga gcctgatcac ctgccctgct gagtcccagg | 60 |
| ctgagcctca gtctccctcc cttggggcct atgcagaggt ccacaacaca cagatttgag | 120 |
| ctcagccctg gtgggcagag aggtagggat ggggctgtgg ggatagtgag gcatcgcaat | 180 |
| gtaagactcg ggattagtac acacttgttg attaatggaa atgtttacag atccccaagc | 240 |
| ctggcaaggg aatttcttca actccctgcc ccccagccct ccttatcaaa ggacaccatt | 300 |

```
ttggcaagct ctatgaccaa ggagccaaac atcctacaag acacagtgac catactaatt    360
aaaaccccct gcaaagccca gcttgaaacc ttcacttagg aacgtaatcg tgtcccctat    420
cctacttccc cttcctaatt ccacagacct gcccgggcgg ccgctcga                 468

<210> SEQ ID NO 43
<211> LENGTH: 408
<212> TYPE: DNA
<213> ORGANISM: Homo sapien

<400> SEQUENCE: 43
atcatatcaa aacactatct tcccatctgt ttctcaatgc ctgctacttc ttgtagatat     60
ttcatttcag gagagcagca gttaaacccg tggattttgt agttaggaac ctgggttcaa    120
acctctttcc actaattggc tatgtctctg acagttttt tttttttttt tttttttaa    180 acccttctg aactttcact ttctatggct acctcaaaga attgttgtga ggcttgagat    240
aatgcatttg taaagggtct gccagatagg aagatgctag ttatggattt acaaggttgt    300
taaggctgta agagtctaaa acctacagtg aatcacaatg catttacccc cactgacttg    360
gacataagtg aaaactagcc cgaagtctct ttttcaaatt acttacag                 408

<210> SEQ ID NO 44
<211> LENGTH: 160
<212> TYPE: DNA
<213> ORGANISM: Homo sapien

<400> SEQUENCE: 44
tggtcgcggc cgaggtcttg tgtgccctgt ggtccagggg accaagaaca acaagatcca     60
ctctctgtgc tacaatgatt gcaccttctc acgcaacact ccaaccagga ctttcaacta    120
caacttctcc gctttggcaa acaccgtcac tcttgctgga                          160

<210> SEQ ID NO 45
<211> LENGTH: 231
<212> TYPE: DNA
<213> ORGANISM: Homo sapien

<400> SEQUENCE: 45
cgagcggccg cccgggcagg tctggggagg tgattccatc cagagtcata tctgttgtca     60
ccccaataag tcgatcagca aggctgacag gctgtgagga aaccccggcc ttgtagcctg    120
tcacctctgg ggggatgatg actgcctggc agacgtaggc tgtgatagat ttgggagaaa    180
acctgactca ccctcaggaa tccggaggtc ggtgacattg tcggtgcaca c             231

<210> SEQ ID NO 46
<211> LENGTH: 371
<212> TYPE: DNA
<213> ORGANISM: Homo sapien

<400> SEQUENCE: 46
cccgggcagg tctgtgtaac atgccaaggc tttgcacttt ctgcagagca gttttttatt     60
ttccttatca ggtacaggtt ttggtttttc ttgactatct ctgatgaatt tttcatgagt    120
ctgtatatgc agaatctttt ccctaaatac tgcttcgtcc catgtctgaa ggcgtaaaat    180
aaagtcattc atcatttttt ctttgtacat gtttatttgt tcttttcaa ttacaccaag     240 cattactagt cagaaggaag cacttgctac ctcttgctct tcctctgcct ctggtttgga    300
tcattttgat gacattgccc acattactca tgaaggatga caagattgca ctgtgcaatg    360
```

```
tcaattgcct t                                                    371
```

<210> SEQ ID NO 47
<211> LENGTH: 261
<212> TYPE: DNA
<213> ORGANISM: Homo sapien

<400> SEQUENCE: 47

```
gccctgtttt tatacacttc acatttgcag aaatataatg atgccctcat tatcagtgag    60
catgcacgaa tgaaagatgc tctggattac ttgaaagact tcttcagcaa tgtccgagca   120
gcaggattcg atgagattga gcaagatctt actcagagat ttgaagaaaa gctgcaggaa   180
ctagaaagtg tttccaggga tcccagcaat gagaatccta aacttgaaga cctctgcttc   240
atcttacaag aagagtacca c                                            261
```

<210> SEQ ID NO 48
<211> LENGTH: 701
<212> TYPE: DNA
<213> ORGANISM: Homo sapien

<400> SEQUENCE: 48

```
cgagcggccc ccgggcaggt ccaattagta caagtctcat gatataatca ctgcctgcat    60
acatatgcac agatccagtt agtgagtttg tcaagcttaa tctaattggt taagtctcaa   120
agagattatt attcttgatg tttgctttgt attggctaac aaatgtgcag aggtaataca   180
tatgtgatgt ccgatgtctc tgtctttttt tttgtcttta aaaataatt ggcagcaact    240
gtatttgaat aaaatgattt cttagtatga ttgtaccgta atgaatgaaa gtggaacatg   300
tttcttttg aaagggagag aattgaccat ttattattgt gatgtttaag ttataactta   360
ttgagcactt ttagtagtga taactgtttt taaacttgcc taatacccttt cttgggtatt   420
gtttgtaatg tgacttattt aacccccttt tttgtttgtt taagttgctg ctttaggtta   480
acagcgtgtt ttagaagatt taaattttt tcctgtctgc acaattagtt attcagagca   540
agagggcctg atttttataga agccccttga aaagaggtcc agatgagagc agagatacag   600
tgagaaatta tgtgatctgt gtgttgtggg aagagaattt tcaatatgta actacggagc   660
tgtagtgcca ttagaaactg tgaatttcca aataaatttg a                      701
```

<210> SEQ ID NO 49
<211> LENGTH: 270
<212> TYPE: DNA
<213> ORGANISM: Homo sapien

<400> SEQUENCE: 49

```
agcggccgcc cgggcaggtc tgatattagt agctttgcaa ccctgataga gtaaataaat    60
tttatgggcg ggtgccaaat actgctgtga atctatttgt atagtatcca tgaatgaatt   120
tatggaaata gatatttgtg cagctcaatt tatgcagaga ttaaatgaca tcataatact   180
ggatgaaaac ttgcatagaa ttctgattaa atagtgggtc tgtttcacat gtgcagtttg   240
aagtatttaa attaaccact cctttcacag                                   270
```

<210> SEQ ID NO 50
<211> LENGTH: 271
<212> TYPE: DNA
<213> ORGANISM: Homo sapien

<400> SEQUENCE: 50

-continued

| | |
|---|---|
| atgcatttat ccatatgaac ttgattattc tgaattactg actataaaaa ggctattgtg | 60 |
| aaagatatca cactttgaaa cagcaaatga attttcaatt ttacatttaa ttataagacc | 120 |
| acaataaaaa gttgaacatg cgcatatcta tgcatttcac agaagattag taaaactgat | 180 |
| ggcaacttca gaattatttc atgaagggta caaacagtct ttaccacaat tttcccatgg | 240 |
| tcttatcctt caaaataaaa ttccacacac t | 271 |

<210> SEQ ID NO 51
<211> LENGTH: 241
<212> TYPE: DNA
<213> ORGANISM: Homo sapien

<400> SEQUENCE: 51

| | |
|---|---|
| tggtcgcggc cgaggtgtga ggagatgaac tttgtgttaa tgggggggcac tttaaatcga | 60 |
| aatggcttat ccccaccgcc atgtaagtta ccatgcctgt ctcctccctc ctacacattt | 120 |
| ccagctcctg ctgcagttat tcctacagaa gctgccattt accagccctc tgtgattttg | 180 |
| aatccacgag cactgcaggc cctccacagc gttactaccc agcaggcact cagctcttca | 240 |
| t | 241 |

<210> SEQ ID NO 52
<211> LENGTH: 271
<212> TYPE: DNA
<213> ORGANISM: Homo sapien

<400> SEQUENCE: 52

| | |
|---|---|
| tccaagactt aaaacttagg aaacacctat gatgccactt taactggaag taatggagac | 60 |
| atctgattcc aaattcacat tttaaatgcc tatttgcaat cagcaaagag ccaggtatgc | 120 |
| tgcatgctgc ttgctgtaag ttacgatttg gcttcactag ctcaaatttt ttcactccac | 180 |
| caaagataa ggcacaggcc cgtttgtcca atcaagtttg ctgaaaatac tgcagcctga | 240 |
| gtgtagacaa acttcccctg aatttgctag a | 271 |

<210> SEQ ID NO 53
<211> LENGTH: 493
<212> TYPE: DNA
<213> ORGANISM: Homo sapien

<400> SEQUENCE: 53

| | |
|---|---|
| ttagcgtggt cgcggtccga ggtctggcct gactagctca ctctgaagag tgtctttcac | 60 |
| atggattaac caaaaaatgc attactgcct ttggcacact gtcttgaata ttctttctga | 120 |
| caatgagaaa atatgatttta atggagtcgt tcaataacct cacaatctcg ctgttccgag | 180 |
| cagatagttt tcgtgccaac aggaactggc acatctagca ggttcacggc atgaccttt | 240 |
| tgtggactgg ctggcataat tggaatgggt ttttgatttttt cttctgctaa taactcttca | 300 |
| agcttttgaa gttttcaagc attcctctcc agttgcctgt ggttggttct tgaacaccat | 360 |
| ctccaacccc accacctcca gatgcaacct tgtctcgtga tacagacctg cccgggcggc | 420 |
| cctcaagggc gaattctgca gatatccatc acactggcgg ccgctcgagc atgcatctag | 480 |
| agggcccaat tcg | 493 |

<210> SEQ ID NO 54
<211> LENGTH: 321
<212> TYPE: DNA
<213> ORGANISM: Homo sapien

<400> SEQUENCE: 54

```
cgtggtcgcg gccgaggtct gtttgcttgt tggtgtgagt ttttcttctg gagactttgt      60
actgaatgtc aataaactct gtgattttgt taggaagtaa aactgggatc tatttagcca     120
ctggtaagct tctgaggtga aggattcagg gacatctcgt ggaacaaaca ctccccactg     180
gactttctct ctggagatac ccttttgaat atacaatggc cttggctcac taggtttaaa     240
tacaaacaag tctgaaaccc actgaagact gagagattgc agcaatattc tctgaattag     300
gatcgggttc cataactcta a                                               321

<210> SEQ ID NO 55
<211> LENGTH: 281
<212> TYPE: DNA
<213> ORGANISM: Homo sapien

<400> SEQUENCE: 55
ttgcaaatga aactgtggat gtataataag aaaacacaag ggtttattct taacactaaa      60
attaacatgc cacacgaaga ctgcattaca gctctctgtt tctgtaatgc agaaaaatct     120
gaacagccca ccttggttac agctagcaaa gatggttact tcaaagtatg gatattaaca     180
gatgactctg acatatacaa aaaagctgtt ggctggacct gtgactttgt tggtagttat     240
cacaagtatc aagcaactaa ctgttgtttc tccgaagatg g                         281

<210> SEQ ID NO 56
<211> LENGTH: 612
<212> TYPE: DNA
<213> ORGANISM: Homo sapien

<400> SEQUENCE: 56
gcgtggtcgc ggccgaggtc ctgtccgggg gcactgagaa ctccctctgg aattcttggg      60
gggtgttggg gagagactgt gggcctggag ataaaacttg tctcctctac caccaccctg     120
taccctagcc tgcacctgtc ctcatctctg caaagttcag cttccttccc caggtctctg     180
tgccactctg tcttggatgc tctggggagc tcatgggtgg aggagtctcc accagaggga     240
ggctcagggg actggttggg ccagggatga atatttgagg gataaaaatt gtgtaagagc     300
caaagaattg gtagtagggg gagaacagag aggagctggg ctatgggaaa tgatttgaat     360
aatggagctg ggaatatggc tggatatctg gtactaaaaa agggtcttta agaacctact     420
tcctaatctc ttccccaatc caaaccatag ctgtctgtcc agtgctctct tcctgcctcc     480
agctctgccc caggctcctc ctagactctg tccctgggct agggcagggg aggagggaga     540
gcagggttgg gggagaggct gaggagagtg tgacatgtgg ggagaggacc agacctgccc     600
gggcggccgt cg                                                         612

<210> SEQ ID NO 57
<211> LENGTH: 363
<212> TYPE: DNA
<213> ORGANISM: Homo sapien

<400> SEQUENCE: 57
gtcgcggccg aggtcctgag cgtcacccta gttctgcccc ttttagctg tgtagacttg       60 gacaagacat ttgacttccc tttctccttg tctataaaat gtggacagtg gacgtctgtc     120
acccaagaga gttgtgggag acaagatcac agctatgagc acctcgcacg gtgtccagga     180
tgcacagcac aatccatgat gcgttttctc cccttacgca ctttgaaacc catgctagaa     240
aagtgaatac atctgactgt gctccactcc aacctccagc gtggatgtcc ctgtctgggc     300
```

```
ccttttctg tttttattc tatgttcagc accactggca ccaaatacat tttaattcac    360
cga                                                                363
```

```
<210> SEQ ID NO 58
<211> LENGTH: 750
<212> TYPE: DNA
<213> ORGANISM: Homo sapien

<400> SEQUENCE: 58
cgtggtcgcg gccgaggtct aattccacct gactggcaga acctgcgccc ctcgcctaac    60
ctgcgccctt ctcccaactc gcgtgcctca cagaacccag gtgctgcaca gccccgagat   120
gtggcccttc ttcaggaaag agcaaataag ttggtccaag tacttgatgc ttaaggaata   180
cacaaaggtg cccatcaagc gctcagaaat gctgagagat atcatccgtg aatacactga   240
tgtttatcca gaaatcattg aacgtgcatg ctttgtccta gagaagaaat ttggggattca  300
actgaaagaa attgacaaag aagaacacct gtatattctc atcagtaccc ccgagtccct   360
ggctggcata ctgggaacga ccaaagcac acccaagctc ggtctcttct tggtgattct   420
gggtgtcatc ttcatgaatg caaccgtgc cagtgaggct gtcttttggg aggcactacg   480
caagatggga ctgcgtcctg gggtgagaca tccctccct tggagatcta aggaaacttc    540
tcacctatga gtttgtaaag cagaaatacc tggactacac acgagtgccc aacagcaacc   600
ccccggagta tgagttcctc tggggcctcc gtccctacca tgagactagc aagatgaaaa   660
tgctgagatt cattgcagag gttcagaaaa gagaccctcg tgactggact gcacagttca   720
tggaggctgc agatgaggac ctgcccgggc                                    750
```

```
<210> SEQ ID NO 59
<211> LENGTH: 505
<212> TYPE: DNA
<213> ORGANISM: Homo sapien

<400> SEQUENCE: 59
tggccgcccg ggcaggtcca gtctacaagc agagcactct catggggagc accagatgag    60
ttccagccgc agttctttta agcttaa gtgcctcatg aagacgcgag gatctcttcc      120
aagtgcaacc tggtcacatc agggcacatt cagcagcaga agtctgtttc cagtatagtc   180
cttggtatgg ctaaattcca ctgtccctt ctcagcagtc aataatccat gataaattct    240
gtacaacact gtagtcaata acagcagcac cagacagcat attaattctt ttaccataaa   300
tttgtgtgta attataatgt tctatgtgtg gtgttatcaa agaatcact gtgtctctaa    360
atatcatata tgtatgtctg gataaataca ttgctgtaca acatctccaa catgcaggtc   420
atgctctaag acttggggat atagagtaat acatgtttcg tggacctcgg ccgcgaccac   480
gctaagggcg aattctgcag atatc                                         505
```

```
<210> SEQ ID NO 60
<211> LENGTH: 520
<212> TYPE: DNA
<213> ORGANISM: Homo sapien

<400> SEQUENCE: 60
cgtggtcgcg gccgaggtcc tcaggacaag gaaacaggta tcagcatgat ggtagcagaa    60
accttatcac caaggtgcag gagctgactt cttccaaaga gttgtggttc cgggcagcgg   120
tcattgcctg cccttgctgg agggctgatt ttagtgttgc ttattatgtt ggccctgagg   180
atgcttcgaa gtgaaaataa gaggctgcag gatcagcggc aacagatgct ctcccgtttg   240
```

-continued

| | |
|---|---|
| cactacagct ttcacggaca ccattccaaa aagggcagg ttgcaaagtt agacttggaa | 300 |
| tgcatggtgc cggtcagtgg gcacgagaac tgctgtctga cctgtgataa aatgagacaa | 360 |
| gcagacctca gcaacgataa gatcctctcg cttgttcact ggggcatgta cagtgggcac | 420 |
| gggaagctgg aattcgtatg acggagtctt atctgaacta cacttactga acagcttgaa | 480 |
| ggacctgccc gggcggccgc tcgaaagggg cgaattctgc | 520 |

<210> SEQ ID NO 61
<211> LENGTH: 447
<212> TYPE: DNA
<213> ORGANISM: Homo sapien

<400> SEQUENCE: 61

| | |
|---|---|
| agagaggtgt ttttattctt tggggacaaa gccgggttct gtgggtgtag gattctccag | 60 |
| gttctccagg ctgtagggcc cagaggctta atcagaattt tcagacaaaa ctggaacctt | 120 |
| tctttttttcc cgttggttta tttgtagtcc ttgggcaaac caatgtcttt gttcgaaaga | 180 |
| gggaaaataa tccaaacgtt tttcttttaa cttttttttt aggttcaggg gcacatgtgt | 240 |
| aggcttgcta tataggtaaa ttgcatgtca ccagggtttg ttgtacagat tatttcatca | 300 |
| tccagataaa aagcatagta ccagataggt agttttttga tcctcaccct ccttccatgc | 360 |
| tccgacctca ggtaggcccc agtgtctgac ctgcccggcg gcccgctcga aagggccaat | 420 |
| tctgcagata tccatcacac tggccgg | 447 |

<210> SEQ ID NO 62
<211> LENGTH: 83
<212> TYPE: PRT
<213> ORGANISM: Homo sapien

<400> SEQUENCE: 62

Lys Lys Val Leu Leu Ile Thr Ala Ile Leu Ala Val Ala Val Gly
1               5                  10                  15

Phe Pro Val Ser Gln Asp Gln Glu Arg Glu Lys Arg Ser Ile Ser Asp
            20                  25                  30

Ser Asp Glu Leu Ala Ser Gly Phe Phe Val Phe Pro Tyr Pro Tyr Pro
        35                  40                  45

Phe Arg Pro Leu Pro Pro Ile Pro Phe Pro Arg Phe Pro Trp Phe Arg
    50                  55                  60

Arg Asn Phe Pro Ile Pro Ile Pro Ser Ala Pro Thr Thr Pro Leu Pro
65                  70                  75                  80

Ser Glu Lys

<210> SEQ ID NO 63
<211> LENGTH: 683
<212> TYPE: DNA
<213> ORGANISM: Homo sapien

<400> SEQUENCE: 63

| | |
|---|---|
| acaaagattg gtagctttta tatttttttta aaaatgctat actaagagaa aaacaaaag | 60 |
| accacaacaa tattccaaat tataggttga gagaatgtga ctatgaagaa agtattctaa | 120 |
| ccaactaaaa aaaatattga aaccactttt gattgaagca aaatgaataa tgctagattt | 180 |
| aaaaacagtg tgaaatcaca ctttggtctg taaacatatt tagctttgct tttcattcag | 240 |
| atgtatacat aaacttattt aaaatgtcat ttaagtgaac cattccaagg cataataaaa | 300 |
| aaagwggtag caaatgaaaa ttaaagcatt tattttggta gttcttcaat aatgatrcga | 360 |

```
gaaactgaat tccatccagt agaagcatct ccttttgggt aatctgaaca agtrccaacc    420
cagatagcaa catccactaa tccagcacca attccttcac aaagtccttc cacagaagaa    480
gtgcgatgaa tattaattgt tgaattcatt tcagggcttc cttggtccaa ataaattata    540
gcttcaatgg gaagaggtcc tgaacattca gctccattga atgtgaaata ccaacgctga    600
cagcatgcat ttctgcattt tagccgaagt gagccactga acaaaactct tagagcacta    660
tttgaacgca tctttgtaaa tgt                                            683
```

<210> SEQ ID NO 64
<211> LENGTH: 749
<212> TYPE: DNA
<213> ORGANISM: Homo sapien
<220> FEATURE:
<221> NAME/KEY: misc_feature
<222> LOCATION: (1)...(749)
<223> OTHER INFORMATION: n = A,T,C or G

<400> SEQUENCE: 64

```
ctgttcattt gtccgccagc tcctggactg gatgtgtgaa aggcatcaca tttccatttt     60
cctccgtgta aatgttttat gtgttcgcct actgatccca ttcgttgctt ctattgtaaa    120
tatttgtcat ttgtatttat tatctctgtg ttttcccct aaggcataaa atggtttact     180
gtgttcattt gaacccattt actgatctct gttgtatatt tttcatgcca ctgctttgtt    240
ttctcctcag aagtcgggta gatagcattt ctatcccatc cctcacgtta ttggaagcat    300
gcaacagtat ttattgctca gggtcttctg cttaaaactg aggaaggtcc acattcctgc    360
aagcattgat tgagacattt gcacaatcta aatgtaagc aaagtaagtc attaaaaata     420
caccctctac ttgggcttta tactgcatac aaatttactc atgagccttc ctttgaggaa    480
ggatgtggat ctccaaataa agatttagtg tttattttga gctctgcatc ttancaagat    540
gatctgaaca cctctccttt gtatcaataa atagccctgt tattctgaag tgagaggacc    600
aagtatagta aaatgctgac atctaaaact aaataaatag aaaacaccag gccagaacta    660
tagtcatact cacacaaagg gagaaattta aactcgaacc aagcaaaagg cttcacggaa    720
atagcatgga aaaacaatgc ttccagtgg                                      749
```

<210> SEQ ID NO 65
<211> LENGTH: 612
<212> TYPE: DNA
<213> ORGANISM: Homo sapien

<400> SEQUENCE: 65

```
acagcagcag tagatggctg caacaacctt cctcctaccc cagcccagaa aatatttctg     60
ccccacccca ggatccggga ccaaaataaa gagcaagcag ccccccttca ctgaggtgct    120
gggtagggct cagtgccaca ttactgtgct ttgagaaaga ggaagggat ttgtttggca     180 ctttaaaaat agaggagtaa gcaggactgg agaggccaga aagatacca aaattggcag     240 ggagagacca tttggcgcca gtcccctagg agatgggagg agggagatag gtatgagggt    300
aggcgctaag aagagtagga ggggtccact ccaagtggca gggtgctgaa atgggctagg    360
accaacagga cactgactct aggtttatga cctgtccata cccgttccac agcagctggg    420
tgggagaaat caccattttg tgacttctaa taaataatg ggtctaggca acagttttca     480
atggatgcta aaacgattag gtgaaaagtt gatggaagat tttaattcag gggaattagg    540
ctgataccat ctgaaaccat ttggcatcat taaaaatgtg acaacctggt ggctgccagg    600
```

-continued

```
gaggaagggg ag                                                         612

<210> SEQ ID NO 66
<211> LENGTH: 703
<212> TYPE: DNA
<213> ORGANISM: Homo sapien

<400> SEQUENCE: 66
tagcgtggtc gcggccgagg tacattgatg ggctggagag cagggttggc agcctgttct      60
gcacagaacc aagaattaca gaaaaaagtc caggagctgg agaggcacaa catctccttg     120
gtagctcagc tccgccagct gcagacgcta attgctcaaa cttccaacaa agctgcccag     180
accagcactt gtgttttgat tcttcttttt tccctggctc tcatcatcct gcccagcttc     240
agtccattcc agagtcgacc agaagctggg tctgaggatt accagcctca cggagtgact     300
tccagaaata tcctgaccca caaggacgta acagaaaatc tggagaccca agtggtagag     360
tccagactga gggagccacc tggagccaag gatgcaaatg gctcaacaag gacactgctt     420
gagaagatgg gagggaagcc aagacccagt gggcgcatcc ggtccgtgct gcatgcagat     480
gagatgtgag ctggaacaga ccttcctggc ccacttcctg atcacaagga atcctgggct     540
tccttatggc tttgcttccc actgggattc ctacttaggt gtctgccctc agggtccaa      600 atcacttcag gacacccccaa gagatgtcct ttagtctctg cctgaggcct agtctgcatt    660
tgtttgcata tatgagaggg tacctgcccg ggcggccgct cga                       703

<210> SEQ ID NO 67
<211> LENGTH: 1022
<212> TYPE: DNA
<213> ORGANISM: Homo sapien

<400> SEQUENCE: 67
cttgagaaag caggattgtt ttaagttcca agatttaaca aacttactgt tcagcatcat      60
attcaagcct aaaaggaaga taggattttc aagatatatt tccaacttct ttaacatggc     120
accatggatg aactgtttct cagcactgtg ctgcttcact tggaattaag gatgaattgg     180
gaggagacag tatgacatag gtgggtaggt tgggtggtga ggggaaccag ttctaatagt     240
cctcaactcc actccagctg ttcctgttcc acacggtcca ctgagctggc ccagtccctt     300
tcactcagtg tgtcaccaaa ggcagcttca aggctcaatg gcaagagacc acctataacc     360
tcttcacctt ctgctgcctc tttctgctgc cactgactgc catggccatc tgctatagcc     420
gcattgtcct cagtgtgtcc aggccccaga caaggaaggg gagccatggt gagactccaa     480
ttcccaggcc ttaatcctta accctagacc tgttgcctct agcatcattt atttatctac     540
ctacctaata gctatctacc agtcattaaa ccatggtgag attctaacca tgtctagcac     600
ctgatgctag agataatttt gttgaatccc ttcaattata aacagctgag ttagctggac     660
aaggactagg gaggcaatca gtattattta ttcttgaaca ccatcaagtc tagacttggt     720
ggcttcatat ttctatcata atccctgggg gtaagaaatc atatagcccc aggttgggaa     780
ggggaaaacg gtttgcaaca ttctcctcct tgtaggaggc gagctctgtc tcactagcta     840
tgcccctcca tcaattcacc ctatactcag atcagaagct gagtgtctga attacagtat     900
attttctaaa ttcctagccc ctgctggtga atttgccctc cccgctcct ttgacaattg      960 tccccgtgtt cgtctccggg ccctgagact ggccctgctt atcttgctga ccttcatcct    1020
ct                                                                   1022
```

<210> SEQ ID NO 68
<211> LENGTH: 449
<212> TYPE: DNA
<213> ORGANISM: Homo sapien

<400> SEQUENCE: 68

| | | | | | |
|---|---|---|---|---|---|
| ccagatccat | tttcagtggt | ctggatttct | ttttattttc | ttttcaactt | gaaagaaact | 60 |
| ggacattagg | ccactatgtg | ttgttactgc | cactagtgtt | caagtgcctc | ttgttttccc | 120 |
| agagatttcc | tgggtctgcc | agaggcccag | acaggctcac | tcaagctctt | taactgaaaa | 180 |
| gcaacaagcc | actccaggac | aaggttcaaa | atggttacaa | cagcctctac | ctgtcgcccc | 240 |
| agggagaaag | gggtagtgat | acaagtctca | tagccagaga | tggttttcca | ctccttctag | 300 |
| atattcccaa | aaagaggctg | agacaggagg | ttattttcaa | ttttattttg | gaattaaata | 360 |
| cttttttccc | tttattactg | ttgtagtccc | tcacttggat | atacctctgt | tttcacgata | 420 |
| gaaataaggg | aggtctagag | cttctattc | | | | 449 |

<210> SEQ ID NO 69
<211> LENGTH: 387
<212> TYPE: DNA
<213> ORGANISM: Homo sapien
<220> FEATURE:
<221> NAME/KEY: misc_feature
<222> LOCATION: (1)...(387)
<223> OTHER INFORMATION: n = A,T,C or G

<400> SEQUENCE: 69

| | | | | | |
|---|---|---|---|---|---|
| gcccttagcg | tgggtcgcgg | cncgangtct | ggagcntatg | tgatncctat | ggtncncagg | 60 |
| cnnatactgc | tantctcatt | tattctcctg | cnacctantc | ctctnctctg | gaatcacacc | 120 |
| attattgcct | gttaacactg | gactgtgagt | accangcaat | taatttgcac | caanaaagtt | 180 |
| gagggtatta | tcanatattg | caatctgtac | agagggaaga | tgatttcaat | ttgatttcaa | 240 |
| cttaaccttc | atctttgtct | gttaacacta | atagagggtg | tctaataaaa | tggcaaattt | 300 |
| gngatctcat | tnggtataac | tacactcttt | ttcacagatg | tgatgactga | atttccanca | 360 |
| acctgcccgg | gcggncgntc | naagggc | | | | 387 |

<210> SEQ ID NO 70
<211> LENGTH: 836
<212> TYPE: DNA
<213> ORGANISM: Homo sapien

<400> SEQUENCE: 70

| | | | | | |
|---|---|---|---|---|---|
| tattccattt | acaaaataaa | ttcagccctg | cactttcttt | agatgccttg | atttccagaa | 60 |
| tggagcttag | tgctactgaa | taccctggcc | acagagccac | ctcaggatat | tcttttctcc | 120 |
| accctagttt | atttatttat | agatatctgt | ttacaaagtc | tgtagtaaat | cctgatgctg | 180 |
| accatctgaa | atgtactttt | tttctgaatg | ctgttttcaat | ctaaaatagc | agcttttgag | 240 |
| aaaacaatga | tgtaaattcc | ttatgataaa | aggatgattc | tatatattct | ttaatgatat | 300 |
| taaatatgcc | gaagccaagc | acacagtctt | tctaaagtgt | gtgtatgttt | gtgtgaatgt | 360 |
| gaatgatact | gatcttatat | ctgttaaaag | ttgttttaaa | aagctgtggc | atcccattgt | 420 |
| tcatatttgc | caagtcttct | gtaaagatgt | ctaggacgaa | atattttatg | tgctaatgca | 480 |
| tgtatttgta | aaccagattt | gtttaccact | caaaattaac | ttgttttctt | catccaaaaa | 540 |
| agtttatttc | ttccacgtac | ttaaattttc | tgtgtgggta | taatatagct | ttctaatttt | 600 |
| tttctttcac | aaaggcaggt | tcaaaattct | gttgaaagaa | aaatgctttc | tgaaactgag | 660 |

```
gtataacacc agagcttgct gtttaaagga ttatatgatg tacatcagtt ctataaatgt      720
gctcagcagt ttaacatgtg aatcctgttt taaagtgctc agatttcaac tgtgtaagcc      780
attgatataa cgctgtaatt aaaaatgttt atatgaaaaa aaaaaaaaaa aaaaaa          836
```

<210> SEQ ID NO 71
<211> LENGTH: 618
<212> TYPE: DNA
<213> ORGANISM: Homo sapien

<400> SEQUENCE: 71

```
gttgcagtga gctcaagtgt tgggtgtatc agctcaaaac accatgtgat gccaatcatc       60
tccacaggag caatttgttt acctttttttt tctgatgctt tactaacttc atcttttaga     120
tttaaatcat tagtagatcc tagaggagcc agtttcagaa aatatagatt ctagttcagc     180
accacccgta gttgtgcatt gaaataatta tcattatgat tatgtatcag agcttctggt     240
tttctcattc tttattcatt tattcaacaa ccacgtgaca aacactggaa ttacaggatg     300
aagatgagat aatccgctcc ttggcagtgt tatactatta taacctga aaaacaaac       360 aggtaatttt cacacaaagt aatagatatc atgacacatt taaaataggg cactactgga     420
acacacagat aggacatcca ggttttgggt caatattgta gacttttttgg tggatgagat    480 atgcaggttg atrccagaag gacaacaaaa acatatgtca gatagaaggg aggagcaaat     540
gccaagagct ggagctgagg aagatcactg tgaaattcta tgtagtctag ttggctggat     600
gctagagcaa agaggtgg                                                   618
```

<210> SEQ ID NO 72
<211> LENGTH: 806
<212> TYPE: DNA
<213> ORGANISM: Homo sapien

<400> SEQUENCE: 72

```
tctacgatgg ccatttgctc attgtctttc ctctgtgtgt agtgagtgac cctggcagtg       60
tttgcctgct cagagtggcc cctcagaaca acagggctgg ccttggaaaa accccaaaac     120
aggactgtgg tgacaactct ggtcaggtgt gatttgacat gagggccgga ggcggttgct     180
gacggcagga ctggagaggc tgcgtgcccg gcactggcag cgaggctcgt gtgtccccca     240
ggcagatctg ggcactttcc caacccaggt ttatgccgtc tccagggaag cctcggtgcc     300
agagtggtgg gcagatctga ccatccccac agaccagaaa caaggaattt ctgggattac     360
ccagtccccc ttcaacccag ttgatgtaac cacctcattt tttacaaata cagaatctat     420
tctactcagg ctatgggcct cgtcctcact cagttattgc gagtgttgct gtccgcatgc     480
tccgggcccc acgtggctcc tgtgctctag atcatggtga ctccccgcc ctgtggttgg      540 aatcgatgcc acggattgca ggccaaattt cagatcgtgt ttccaaacac ccttgctgtg     600 cccttttaatg ggattgaaag cacttttacc acatggagaa atatatttt aatttgtgat     660 gcttttctac aaggtccact atttctgagt ttaatgtgtt tccaacactt aaggagactc     720
taatgaaagc tgatgaattt tctttttctgt ccaaacaagt aaaataaaaa taaagtcta     780 tttagatgtt gaaaaaaaaa aaaaaa                                          806
```

<210> SEQ ID NO 73
<211> LENGTH: 301
<212> TYPE: DNA
<213> ORGANISM: Homo sapien
<220> FEATURE:
<221> NAME/KEY: misc_feature

```
<222> LOCATION: (1)...(301)
<223> OTHER INFORMATION: n = A,T,C or G

<400> SEQUENCE: 73
actctggtaa gcttgttgtt gtccaagtga agctccctca gatgaggcgt gttggccana      60
gagccattgt caacagcaga gatgctgttg aaactcaatc ccaacttagc caaattattc     120
agtcctttca ggctagctgc atcaactctg ctgattttgt tgccatcaag atgtaattcc     180
gtaagggaag gaggaagacc ttgaggaatg ctggygatat tggyatcagc aatgcggatg     240
tasgaagagc ttcttcmttc cctggaaagc cccattttca atyccttgag ctcttcakcg     300
g                                                                    301

<210> SEQ ID NO 74
<211> LENGTH: 401
<212> TYPE: DNA
<213> ORGANISM: Homo sapien

<400> SEQUENCE: 74
agtttacatg atccctgtaa cagccatggt ctcaaactca gatgcttcct ccatctgcca      60
agtgtgttct ggatacagag cacatcgtgg cttctggggt cacactcagc ttaggctgtg     120
ggtccacaga gcactcatct ggctgggcta tggtggtggg ggctctactc aagaagcaaa     180
gcagttacca gcacattcaa acagtgtatt gaacatcttt taaatatcaa agtgagaaac     240
aagaaggcaa cataataatg ttatcagaaa gatgttagga agtaaggaca gctgtgtaaa     300
gcttgaggct gaaaagtagc ttgccagctt catttctttg gtttcttggg tagtgggccg     360
ccggaacagc aagatgtgag gttctggttc atggatcata t                        401

<210> SEQ ID NO 75
<211> LENGTH: 612
<212> TYPE: DNA
<213> ORGANISM: Homo sapien

<400> SEQUENCE: 75 ttattttttca attttttattt tggttttctt acaaaggttg acattttcca taacaggtgt     60
aagagtgttg aaaaaaaaat tcaaattttt ggggagcgag ggaaggagtt aatgaaactg     120
tattgcacaa tgctctgatc aatccttctt tttctctttt gcccacaatt taagcaagta     180
gatgtgcaga agaaatggaa ggattcagct ttcagttaaa aaagaagaag aagaaatggc     240
aaagagaaag ttttttcaaa tttctttctt ttttaattta gattgagttc atttatttga     300
aacagactgg gccaatgtcc acaaagaatt cctggtcagc accaccgatg tccaaaggtg     360
caatatcaag gaagggcagg cgtgatggct tatttgtttt gtattcaatg attgtctttc     420
cccattcatt tgtctttta gagcagccat ctacaagaac agtgtaagtg aacctgctgt     480
tgccctcagc aacaagttca acatcattag agccctgtag aatgacagcc ttttttcaggt     40 tgccagtctc ctcatccatg tatgcaatgc tgttcttgca gtggtaggtg atgttctgag     600
aggcatagtt gg                                                       612

<210> SEQ ID NO 76
<211> LENGTH: 844
<212> TYPE: DNA
<213> ORGANISM: Homo sapien

<400> SEQUENCE: 76
ggctttcgag cggccgcccg ggcaggtctg atggttctcg taaaaacccc gctagaaact      60
```

-continued

```
gcagagacct gaaattctgc catcctgaac tcaagagtgg agaatactgg gttgaccta      120
accaaggatg caaattggat gctatcaagg tattctgtaa tatggaaact ggggaaacat    180
gcataagtgc caatcctttg aatgttccac ggaaacactg gtggacagat tctagtgctg    240
agaagaaaca cgtttggttt ggagagtcca tggatggtgg ttttcagttt agctacggca    300
atcctgaact tcctgaagat gtccttgatg tgcagcykgc attccttcga cttctctcca    360
gccgagcttc ccagaacatc acatatcact gcaaaatag cattgcatac atggatcagg     420
ccagtggaaa tgtaaagaag ccctgaagc tgatggggtc aaatgaaggt gaattcaagg     480
ctgaaggaaa tagcaaattc acctacacag ttctggagga tggttgcacg aaacacactg    540
gggaatggag caaacagtc tttgaatatc aacacgcaa tgctgttcct tgacattgca      600
ccaccaatgt ccagaggtgc aatgtcaagg aacggcaggc gagatggctt atttgttttg   660
tattcaatga ttgtcttgcc ccattcattt gtcttttgg agcagccatc gactaggaca    720
gagtaggtga acctgctgtt gccctcagca acaagttcca catcgttgga accctgcaga   780
agcacagcct tgttcaarct gcccgtctcc tcatccagat acctcggccg cgaccacgct   840
aatc                                                                 844

<210> SEQ ID NO 77
<211> LENGTH: 314
<212> TYPE: DNA
<213> ORGANISM: Homo sapien

<400> SEQUENCE: 77
ccagtcctcc acttggcctg atgagagtgg ggagtggcaa gggacgtttc tcctgcaata   60
gacacttaga tttctctctt gtgggaagaa accacctgtc catccactga ctcttctaca   120
ttgatgtgga aattgctgct gctaccacca cctcctgaag aggcttccct gatgccaatg   180
ccagccatcc tggcatcctg gccctcgagc aggctgcgt aagtagcgat ctcctgctcc    240
agccgtgtct ttatgtcaag cagcatcttg tactcctggt tctgagcctc catctcgcat   300
cggagctcac tcag                                                      314

<210> SEQ ID NO 78
<211> LENGTH: 548
<212> TYPE: DNA
<213> ORGANISM: Homo sapien

<400> SEQUENCE: 78
accaagagcc aagtgttaca caggatattt taaaaataaa atgttttttgg aatcctcacc   60
tcccatgcta tcttctaaga taactacaaa tattcttcaa agatttaact gagttctgcc   120
aaggacctcc caggactcta tccagaatga ttattgtaaa gctttacaaa tcccaccttg   180
gccctagcga taattaggaa atcacaggca aacctcctct ctcggagacc aatgaccagg   240
ccaatcagtc tgcacattgg ttttgttaga tactttgtgg agaaaaacaa aggctcgtga   300
tagtgcagct ctgtgcctac agagagcctc ccttttggtt ctgaaattgc tgatgtgaca   360
gagacaaagc tgctatgggt ctaaaacctt caataaagta actaatgaca ctcaaggtcc   420
tgggactctg agacagacgg tggtaaaacc cacagctgcg attcacattt ccaatttatt   480
ttgagctctt tctgaagctg ttgcttccta cctgagaatt cccatttaga gagctgcaca   540
gcacagtc                                                             548

<210> SEQ ID NO 79
<211> LENGTH: 646
```

<212> TYPE: DNA
<213> ORGANISM: Homo sapien

<400> SEQUENCE: 79

| | | | | | |
|---|---|---|---|---|---|
| accccgtcac | tatgtgaata | aaggcagcta | gaaaatggac | tcaattctgc | aagccttcat | 60 |
| ggcaacagcc | catattaaga | cttctagaac | aagttaaaaa | aaatcttcca | tttccatcca | 120 |
| tgcatgggaa | aagggcttta | gtatagttta | ggatggatgt | gtgtataata | ataaaatgat | 180 |
| aagatatgca | tagtggggga | ataaagcctc | agagtccttc | cagtatgggg | aatccattgt | 240 |
| atcttagaac | cgagggattt | gtttagattg | ttgatctact | aattttttc | ttcacttata | 300 |
| tttgaatttt | caatgatagg | acttattgga | aattggggat | aattctgttg | tggtattaaa | 360 |
| taatattcat | tttttaaaaa | ctcatcttgg | tattgagtta | gtgcattgac | ttccaatgaa | 420 |
| ttgacataag | cccatatttc | attttaacca | gaaacaaaaa | ctagaaaatg | ttactcccta | 480 |
| aataggcaac | aatgtatttt | ataagcactg | cagagattta | gtaaaaaaca | tgtatagtta | 540 |
| ctttagaaac | aacttctgac | acttgagggt | tacccaatgg | tctccttccc | attctttata | 600 |
| tgaggtaaat | gcaaaccagg | gagccaccga | ataaacagcc | ctgagt | | 646 |

<210> SEQ ID NO 80
<211> LENGTH: 276
<212> TYPE: DNA
<213> ORGANISM: Homo sapien
<220> FEATURE:
<221> NAME/KEY: misc_feature
<222> LOCATION: (1)...(276)
<223> OTHER INFORMATION: n = A,T,C or G

<400> SEQUENCE: 80

| | | | | | |
|---|---|---|---|---|---|
| gtctgaatga | gcttcnctgc | gagatgganc | ancataaccc | agaantccaa | aancntanng | 60 |
| aacgnnaaaa | cccgntngaa | caagnaaaacn | gcaactnacg | gccgcctgnt | gnagggcgag | 120 |
| gacgcccacc | tctcctcctc | ccagttctcc | tctggatcgc | agncatccan | agatgtgacc | 180 |
| tcttccagcc | gccaaatccg | caccaaggtc | atggatgtgc | acgatggcaa | ggtgggtgtc | 240 |
| cacccacgaa | caggtccttc | gcaccaagaa | ctgagg | | | 276 |

<210> SEQ ID NO 81
<211> LENGTH: 647
<212> TYPE: DNA
<213> ORGANISM: Homo sapien

<400> SEQUENCE: 81

| | | | | | |
|---|---|---|---|---|---|
| gtcctgcctt | tcatcttttc | tttaaaaaaa | ataaatgttt | acaaaacatt | tccctcagat | 60 |
| tttaaaattc | atggaagtaa | taaacagtaa | taaaatatgg | atactatgaa | aactgacaca | 120 |
| cagaaaaaca | taaccataaa | atattgttcc | aggatacaga | tattaattaa | gagtgacttc | 180 |
| gttagcaaca | cgtagacatt | catacatatc | cggtggaaga | ctggtttctg | agatgcgatt | 240 |
| gccatccaaa | cgcaaatgct | tgatcttgga | gtaggrtaat | ggccccagga | tcttgcagaa | 300 |
| gctctttatg | tcaaacttct | caagttgatt | gacctccagg | taatagtttt | caaggttttc | 360 |
| attgacagtt | ggtatgtttt | taagcttgtt | ataggacaga | tccagctcaa | ccagggatga | 420 |
| cacattgaaa | gaatttccag | gtattccact | atcagccagt | tcgttgtgag | ataaacgcag | 480 |
| atactgcaat | gcattaaaac | gcttgaaata | ctcatcaggg | atgttgctga | tcttattgtt | 540 |
| gtctaagtag | agagttagaa | gagagacagg | gagaccagaa | ggcagtctgg | ctatctgatt | 600 |
| gaagctcaag | tcaaggtatt | cgagtgattt | aagacctttaa | aaagcag | | 647 |

<210> SEQ ID NO 82
<211> LENGTH: 878
<212> TYPE: DNA
<213> ORGANISM: Homo sapien

<400> SEQUENCE: 82

| ccttctttcc ccactcaatt cttcctgccc tgttattaat taagatatct tcagcttgta | 60 |
| gtcagacaca atcagaatya cagaaaaatc ctgcctaagg caaagaaata taagacaaga | 120 |
| ctatgatatc aatgaatgtg ggttaagtaa tagatttcca gctaaattgg tctaaaaaag | 180 |
| aatattaagt gtggacagac ctatttcaaa ggagcttaat tgatctcact tgttttagtt | 240 |
| ctgatccagg gagatcaccc ctctaattat ttctgaactt ggttaataaa agtttataag | 300 |
| attttatga agcagccact gtatgatatt ttaagcaaat atgttattta aaatattgat | 360 |
| ccttcccttg gaccaccttc atgttagttg ggtattataa ataagagata caaccatgaa | 420 |
| tatattatgt ttatacaaaa tcaatctgaa cacaattcat aaagatttct cttttatacc | 480 |
| ttcctcactg gccccctcca cctgcccata gtcaccaaat tctgttttaa atcaatgacc | 540 |
| taagatcaac aatgaagtat tttataaatg tatttatgct gctagactgt gggtcaaatg | 600 |
| tttccatttt caaattattt agaattctta tgagtttaaa atttgtaaat ttctaaatcc | 660 |
| aatcatgtaa aatgaaactg ttgctccatt ggagtagtct cccacctaaa tatcaagatg | 720 |
| gctatatgct aaaagagaa atatggtca agtctaaaat ggctaattgt cctatgatgc | 780 |
| tattatcata gactaatgac atttatcttc aaaacaccaa attgtcttta gaaaaattaa | 840 |
| tgtgattaca ggtagagaac ctcggccgcg accacgct | 878 |

<210> SEQ ID NO 83
<211> LENGTH: 645
<212> TYPE: DNA
<213> ORGANISM: Homo sapien

<400> SEQUENCE: 83

| acaaacattt tacaaaaaag aacattacca atatcagtgg cagtaagggc aagctgaaga | 60 |
| ataaatagac tgagtttccg ggcaatgtct gtcctcaaag acatccaaac tgcgttcagg | 120 |
| cagctgaaac aggcttcttt cccagtgaca agcatatgtg gtcagtaata caaacgatgg | 180 |
| taaatgaggc tactacatag gcccagttaa caaactcctc ttctcctcgg gtaggccatg | 240 |
| atacaagtgg aactcatcaa ataatttaaa cccaaggcga taacaacgct atttcccatc | 300 |
| taaactcatt taagccttca caatgtcgca atggattcag ttacttgcaa cgatcccgg | 360 |
| gttgtcatac agatacttgt ttttacacat aacgctgtgc catcccttcc ttcactgccc | 420 |
| cagtcaggtt tcctgttgtt ggaccgaaag gggatacatt ttagaaatgc ttccctcaag | 480 |
| acagaagtga gaaagaaagg agaccctgag gccaggatca ttaaacctg gtgtgtgcgc | 540 |
| aaaagggagg gggaaggcag gaatttgaaa ggataaacgt ctcctttgcg ccgaggaatc | 600 |
| aggaagcgtg actcacttgg gtctgggacg ataccgaaat ccggt | 645 |

<210> SEQ ID NO 84
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 84

```
tctgatgtca atcacaactt gaaggatgcc aatgatgtac caatccaatg tgaaatctct      60
cctcttatct cctatgctgg agaaggatta gaaggttatg tggcagataa agaattccat     120
gcacctctaa tcatcgatga gaatggagtt catgggctgg tgaaaaatgg tatttgaacc     180
agataccaag ttttgtttgc cacgatagga atagctttta ttttgatag accaactgtg      240 aacctacaag acgtcttgga caactgaagn ttaaatatcc acangggttt attttgcttg     300
g                                                                     301
```

<210> SEQ ID NO 85
<211> LENGTH: 296
<212> TYPE: DNA
<213> ORGANISM: Homo sapien
<220> FEATURE:
<221> NAME/KEY: misc_feature
<222> LOCATION: (1)...(296)
<223> OTHER INFORMATION: n = A,T,C or G

<400> SEQUENCE: 85

```
agcgtgggtc gcggcncgan gtagagaacc gactgaaacg tttgagatga agaaagttct      60
cctcctgatc acagccatct tggcagtggc tgttggtttc ccagtctctc aagaccagga     120
acgagaaaaa agaagtatca gtgacagcga tgaattagct tcagggtttt ttgtgttccc     180
ttacccatat ccatttcgcc cacttccacc aattccattt ccaagatttc catggtttan     240
acgtaatttt cctattccaa tacctgaatc tgcccctaca actccccttc ctagcg         296
```

<210> SEQ ID NO 86
<211> LENGTH: 806
<212> TYPE: DNA
<213> ORGANISM: Homo sapien

<400> SEQUENCE: 86

```
tctacgatgg ccatttgctc attgtctttc ctctgtgtgt agtgagtgac cctggcagtg      60
tttgcctgct cagagtggcc cctcagaaca cagggctgg ccttggaaaa accccaaaac      120
aggactgtgg tgacaactct ggtcaggtgt gatttgacat gagggccgga ggcggttgct     180
gacggcagga ctggagaggc tgcgtgcccg gcactggcag cgaggctcgt gtgtccccca     240
ggcagatctg ggcactttcc caacccaggt ttatgccgtc tccagggaag cctcggtgcc     300
agagtggtgg gcagatctga ccatccccac agaccagaaa caaggaattt ctgggattac     360
ccagtccccc ttcaacccag ttgatgtaac cacctcattt tttacaaata cagaatctat     420
tctactcagg ctatgggcct cgtcctcact cagttattgc gagtgttgct gtccgcatgc     480
tccgggcccc acgtggctcc tgtgctctag atcatggtga ctcccccgcc ctgtggttgg     540
aatcgatgcc acggattgca ggccaaattt cagatcgtgt ttccaaacac ccttgctgtg     600
ccctttaatg ggattgaaag cacttttacc acatggagaa atatatttt aatttgtgat      660 gcttttctac aaggtccact atttctgagt ttaatgtgtt ccaacactt aaggagactc      720 taatgaaagc tgatgaattt ctttttctgt ccaaacaagt aaaataaaaa taaagtcta      780 tttagatgtt gaaaaaaaaa aaaaaa                                          806
```

<210> SEQ ID NO 87
<211> LENGTH: 620
<212> TYPE: DNA
<213> ORGANISM: Homo sapien

<400> SEQUENCE: 87

-continued

| | |
|---|---|
| tttttgcatc agatctgaaa tgtctgagag taatagtttc tgttgaattt ttttttgttc | 60 |
| attttctgc acagtccatt ctgtttttat tactatctag gcttgaaata tatagtttga | 120 |
| aattatgaca tccttcctct ttgttatttt cctcatgatt gctttggcta ttcaaagttt | 180 |
| attttagttt catgtaaatt tttgaattgt attttccatt attgtgaaaa tagtaccact | 240 |
| gcaattttaa taggaagttt attgaatcta tagattactt tggataatat ggcacttcaa | 300 |
| taatattcat gttttcaatt catagacaaa atattttaaa atttatttgt atcttttcta | 360 |
| attttccttt tttttattgt aaagatttac ctccttggtt aatattttcc tcagaaattt | 420 |
| attatttaag gtatagtcaa taaaattttc ttcctctatt ttgtcagata gtttaagtgt | 480 |
| atgaaaccat agatatactt gtatgttaat tttatatttt gctaatttac tgagtgtatt | 540 |
| tattagttta gagaggtttt aatgtactgt ttatggtttt taaatataa gattacttat | 600 |
| tttttaaaaa aaaaaaaaaa | 620 |

<210> SEQ ID NO 88
<211> LENGTH: 308
<212> TYPE: DNA
<213> ORGANISM: Homo sapien
<220> FEATURE:
<221> NAME/KEY: misc_feature
<222> LOCATION: (1)...(308)
<223> OTHER INFORMATION: n = A,T,C or G

<400> SEQUENCE: 88

| | |
|---|---|
| tagctgtgnt cagcaggccg aggttttttt tttttttgag atggagtctc gccctgtcac | 60 |
| ccaggctgga gtgcagtggc ctgatctcag ctcactgcaa gctccacctc ctggattcac | 120 |
| gctattctcc tgcctcagcc tcccaagtag ctgggactaa aggcgcccgc caccacgccc | 180 |
| agctaattnt ttgnattttt agtacnagat gcggtttcat cgtgttagcc agcatggnct | 240 |
| cgatctcctg acctcgtgaa ctgcccgcct cggcctccca agacctgcc cgggcnggcc | 300 |
| gctcgaaa | 308 |

<210> SEQ ID NO 89
<211> LENGTH: 492
<212> TYPE: DNA
<213> ORGANISM: Homo sapien
<220> FEATURE:
<221> NAME/KEY: misc_feature
<222> LOCATION: (1)...(492)
<223> OTHER INFORMATION: n = A,T,C or G

<400> SEQUENCE: 89

| | |
|---|---|
| agcggccgcc cgggcaggtc tgttaagtaa catacatatc accttaataa aaatcaagat | 60 |
| gaaatgtttt agaaactatt ttatcaaaag tggctctgat acaaagactt gtacatgatt | 120 |
| gttcacagca gcactattaa tgccaaaaag tagacaaaac ctaaatgtcc attaactgat | 180 |
| aagcaaaatg tggtatatcc atacaatgga atattatgta gcccacaaca tggcatggag | 240 |
| tactacaaca tggatgagcc tcaaaaacgt tatgctaaat gaaaaagtc agatatagga | 300 |
| aaccacatgt catatgatcc catttatatg aaatagccag aaaaggcaag tcatagaaac | 360 |
| aagatagatc ggaaaatggg ttggaggact acaaatggca ccaggatct ttgaagttga | 420 |
| tggaaatggt ctaaaatcag actgtggntg tggttgaaca agtctgtaaa tttaccaaaa | 480 |
| tgcgttaata ca | 492 |

<210> SEQ ID NO 90
<211> LENGTH: 390

```
<212> TYPE: DNA
<213> ORGANISM: Homo sapien
<220> FEATURE:
<221> NAME/KEY: misc_feature
<222> LOCATION: (1)...(390)
<223> OTHER INFORMATION: n = A,T,C or G

<400> SEQUENCE: 90
tcgagcggcc gcccgggcag gtacaagctt tttttttttt tttttttttt ttttctaaca    60
gttctctgtt ttattgcaat acagcaaagt ctggttaata ttaagngata tcaacataaa   120
gtattggtga ggagtctttt gtgacatttt ttaccatccc accttaaata tttctgtgca   180
aaanaatcca catcattgtt tggtancana ggatctctta aaaagttccc taanacactg   240
agggcataaa accaaacaaa ataaaataag gagtgatagg ctaaagcagt atcttcccct   300
ccatccacat ttgncaagca ttatattcta accaaaaaat gatcacacca ggccatgcaa   360
aactgtccaa tattaccgag aaaaaaccct                                    390

<210> SEQ ID NO 91
<211> LENGTH: 192
<212> TYPE: DNA
<213> ORGANISM: Homo sapien

<400> SEQUENCE: 91
agcgtggtcg cggccgaggt ctgtcaatta atgctagtcc tcaggattta aaaaataatc    60
ttaactcaaa gtccaatgca aaaacattaa gttggtaatt actcttgatc ttgaattact   120
tccgttacga aagtccttca catttttcaa actaagctac tatatttaag gcctgcccgg   180
gcggccgctc ga                                                       192

<210> SEQ ID NO 92
<211> LENGTH: 570
<212> TYPE: DNA
<213> ORGANISM: Homo sapien
<220> FEATURE:
<221> NAME/KEY: misc_feature
<222> LOCATION: (1)...(570)
<223> OTHER INFORMATION: n = A,T,C or G

<400> SEQUENCE: 92
agcgtggtcg cggccgaggt ctgacaacta acaagaagc aaaaactggc atcttggaca    60
tcctagtatt acacttgcaa gcaattagaa cacaaggagg gccaaggaaa agtttagct   120 ttgaatcact tccaaatcta ctgattttga ggttccgcag tagttctaac aaaacttttc   180
agacaatgtt aactttcgat taagaaagaa aaaaacccca aacatcttca ggaattccat   240
gccaggttca gtctcttcca gtgagcccgc ttgctaaaag tccacgtgca ccattaatta   300
gctgggctgg cagcaccatg taaaaagaag cctattcacc accaaccaca cagactagac   360
atgtaaagta ggatcaagta atggatgaca accatggtcg tggaatatgg tcaatgagag   420
tcagaaaagt acaggcacca gtacaagcag cagataacag aattgacggg ccaaaggata   480 aaataggct tatttaaata ggatgctaca gaacacatnc acttctaatt ggaagctgct   540
ttacactggg tggcattgna ccatatgcat                                    570

<210> SEQ ID NO 93
<211> LENGTH: 446
<212> TYPE: DNA
<213> ORGANISM: Homo sapien
<220> FEATURE:
<221> NAME/KEY: misc_feature
<222> LOCATION: (1)...(446)
```

<223> OTHER INFORMATION: n = A,T,C or G

<400> SEQUENCE: 93

| | | | | | |
|---|---|---|---|---|---|
| tcgagcggcc | gcccgggcag | gtccaggttt | ttatttagtt | gtgtaatctt | ggacaagtta | 60 |
| cctaactttt | ttgagtctga | atatatttaa | tctgcaaaat | gagaatcatg | ataatacgtc | 120 |
| ataggcttaa | ttaggaggat | taaatgaaat | aatttatagg | tggtgccatg | gttacataca | 180 |
| agtattagta | gttaattctt | ttcctttgtt | tactttata | gtataggttg | gatgaaggtt | 240 |
| ccagtatagg | caaaaatact | acttgggggt | aagtagagt | gtgatacttt | atttgaaatg | 300 |
| ttccctgaat | ctgatcttta | cttttgnta | ctgctgcact | acccaaatcc | aaattttcat | 360 |
| cccaacattc | ttggatttgt | gggacagcng | tagcagcttt | tccaatataa | tctatactac | 420 |
| atctttctt | actttggtgc | ttttg | | | | 446 |

<210> SEQ ID NO 94
<211> LENGTH: 409
<212> TYPE: DNA
<213> ORGANISM: Homo sapien

<400> SEQUENCE: 94

| | | | | | |
|---|---|---|---|---|---|
| cgagcggccg | cccgggcagg | tccatcagct | cttctgctta | gaatacgagg | cagacagtgg | 60 |
| agaggtcaca | tcagttatcg | tctatcaggg | tgatgaccca | agaaaggtga | gtgagaaggt | 120 |
| gtcggcacac | acgcctctgg | atccacccat | gcgagaagcc | ctcaagttgc | gtatccagga | 180 |
| ggagattgca | aagcgccaga | gccaacactg | accatgttga | aggcgttctc | tccaggctgg | 240 |
| attcactgca | ctcggaagaa | ttctgcccag | ggaatttagt | gtgggggtac | caggaccagt | 300 |
| tgtcttgat | cttgagaccc | ccagagctgc | tgcatccata | gggtgttgca | ggactacacc | 360 |
| tggcctgcct | tgcagtcatt | ctttcttata | tgttgaccca | tttgcccaa | | 409 |

<210> SEQ ID NO 95
<211> LENGTH: 490
<212> TYPE: DNA
<213> ORGANISM: Homo sapien
<220> FEATURE:
<221> NAME/KEY: misc_feature
<222> LOCATION: (1)...(490)
<223> OTHER INFORMATION: n = A,T,C or G

<400> SEQUENCE: 95

| | | | | | |
|---|---|---|---|---|---|
| tcgagcggcc | gcccgggcag | gtcctacttg | tttgcagctt | ccacacactg | cacctaccta | 60 |
| ctacctctct | tccatgctta | actgggttta | gaaaggtgag | ctatgcgtag | aagaactact | 120 |
| tgggatattc | aagtgctgta | tttgaacgat | aagcctatag | ataacagtct | gaagctgcaa | 180 |
| gggagacttt | gttagtacac | tactataaac | aggtaaacta | cctgtttgta | cttgatatag | 240 |
| tgcatatgaa | atgactgatt | taatacaaaa | ctacagaaca | tgcaaaattt | tttctgagat | 300 |
| gttaagtatt | acttcagtgg | agaacaaaac | ttacttaacc | tttcgctaat | gcatgtagta | 360 |
| ccagaaagca | aacatggttt | tagcttcctt | tactcaaaat | atgaacatta | agtggttgtg | 420 |
| aattttgtct | gccaagtggt | tcagaaaata | cattataaat | aacctaagtt | aaaaaaaaga | 480 |
| aactgngaac | | | | | | 490 |

<210> SEQ ID NO 96
<211> LENGTH: 223
<212> TYPE: DNA
<213> ORGANISM: Homo sapien

<400> SEQUENCE: 96
agcgtggtcg cggccgaggt ctggaagccc accctaggac ttgaatggca ccttgtcctt    60
tctctgccag taatgcaatc aacacaata tgctacaggg aaaacagaat ttccacggtg    120
ccgccctctg gtacaaggga acagcacgc aaagcaaaag ccacagagg gctccctgag     180 aatccagtac aactaagcga ggacctgccc gggcggccgc tcg                      223

<210> SEQ ID NO 97
<211> LENGTH: 527
<212> TYPE: DNA
<213> ORGANISM: Homo sapien
<220> FEATURE:
<221> NAME/KEY: misc_feature
<222> LOCATION: (1)...(527)
<223> OTHER INFORMATION: n = A,T,C or G

<400> SEQUENCE: 97
tcgagcggcc gcccgggcag gtctgtgcag gagacactga agtgggtagt gtccataatc    60
tttttagcct gttgctgaaa ttccagttgt actccttcaa accaaaatgc ttacaggatc    120
atgggaaagc ctcggttgca gaaatcaaga caggcaagtg ggaagataac tcggctttga   180
ggttaaacag atctgggttc aaagcatagt ttcactctct gtcttgtgaa gtgtcctggg    240
tgaagtcatt tcctctcttg aatttcagag aggatgaaaa tataaaaagt ataataacta    300
tcttcataat ctttgtgagg attaaagaag acgaagtgtg tgaaaagcta agcacagagc    360
aggcattcta caataagtag ttattatttt tggaaccatc ccgncccctag ccccagccca   420 attaccttct cttagnctct tcatatcgaa ngccgtaatc ttgaccttct cttgcnactg    480
gattggtgct ggttgatgcc caaacttccc gagatgctgt ctgggaa                  527

<210> SEQ ID NO 98
<211> LENGTH: 514
<212> TYPE: DNA
<213> ORGANISM: Homo sapien
<220> FEATURE:
<221> NAME/KEY: misc_feature
<222> LOCATION: (1)...(514)
<223> OTHER INFORMATION: n = A,T,C or G

<400> SEQUENCE: 98
tcgagcggcc gcccgggcag gtctggctcc catggccctt ggggtggcct gactctgtca    60
ctattcctaa aaccttctag gacatctgct ccaggaagaa ctttcaacac caaaattcat    120 ctcaattta cagatgggaa aagtgattct gagaccagac cagggtcagg ccaaggtcat    180
ccagcatcag tggctgggct gagactgggc ccagggaacc ctgtctgctc ctcttttcc    240 cagagctgtg agttctctag ccaaggctgc actcttgagg gagagccagg aagcatagct    300
gaggccatga caacctcact cttcacctga aaatttaacc cgtggcagag gatccaggca    360
catataggct tcggagccaa acaggacctc ggccgcgacc acgctaagcc gaattccagc    420
acactggcgg ccgttactag tggatcccga gcttnggtac caagcttggc gtaatcatgg    480
gcatagctgg ttcctggggt gaaaatggta tccg                                514

<210> SEQ ID NO 99
<211> LENGTH: 530
<212> TYPE: DNA
<213> ORGANISM: Homo sapien
<220> FEATURE:
<221> NAME/KEY: misc_feature
<222> LOCATION: (1)...(530)
<223> OTHER INFORMATION: n = A,T,C or G

```
<400> SEQUENCE: 99
tcgagcggcc gcccgggcag gtctgaagaa acaggtataa atttggcagc cagtaatttt      60
gacagggaag ttacagcttg catgacttta aatatgtaaa tttgaaaata ctgaatttcg     120
agtaatcatt gtgctttgtg ttgatctgaa aaatataaca ctggctgtcg aagaagcatg     180
ttcaaaaata tttaattcac ttcaaaatgt catacaaatt atggtggttt ctatgcaccc     240
ctaaagcttc aagtcattta gctcaggtac atactaaagt aatatattaa ttcttccagt     300
acagtggtgt ttcataccat tgacatttgc atacctaga ataatttaag aaagacatgt      360
gtaatattca caatgttcag aaaagcaagc aaaggtcaa ggaacctgct ttggttcttc      420
tggagatggn ctcatatcag cttcataaac attcattcta caaaatagta agctaaccat     480
ttgaacccca atttccagat taagcatatt ttctcataaa tnatgaagcc                530

<210> SEQ ID NO 100
<211> LENGTH: 529
<212> TYPE: DNA
<213> ORGANISM: Homo sapien

<400> SEQUENCE: 100
agcgtggtcg cggccgaggt ccaggcacgg tggcttatgt gtgtaatccc agcacttggg      60
gaggctgagg gaggtggatc acttgagtcc aggagtttga ccagtctg ggcaacatgg      120 cgaaacttca tcactaccaa agaagaaaaa aattagccag gtgtggtggt gtatgcctgt     180
agtcccagat actctggtgg ctgaggtgag aggatagctt gagcccagga aattgaggct     240
gcagtgaact atgattgcac tactgtgctc cagcttgggc aacagagtga gatcttgtct     300
ccaaaagtcc ttgaaggatt ttaggaagtt gttaaaagtc ttgaaacgat gtttgggggc     360
atgttagggt tcttgaatgt ttaattcctc taataactgc ttattcaaga gaagcatttc     420
tgactgggtg cggggcagtg gcttcatgcc ccataatccc agtactttgg gaggctgaag     480
caggaacatt gcttgagccc aggacttcaa gaacagcctg ggtaacata                529

<210> SEQ ID NO 101
<211> LENGTH: 277
<212> TYPE: DNA
<213> ORGANISM: Homo sapien

<400> SEQUENCE: 101
tcgagcggcc gcccgggcag gtcgcaggaa gaggatggaa actgaggagt ccaggaagaa      60
gagggaacga gatcttgagc tggaaatggg agatgattat atttttggatc ttcagaagta    120 ctgggatttta atgaatttgt ctgaaaaaca tgataagata ccagaaatct gggaaggcca    180
taatatagct gattatattg atccagccat catgaagaaa ttggaagaat tagaaaaaga    240
agaagagctg agaacagacc tcggccgcga ccacgct                             277

<210> SEQ ID NO 102
<211> LENGTH: 490
<212> TYPE: DNA
<213> ORGANISM: Homo sapien

<400> SEQUENCE: 102
gcgtggtcgc ggccgaggtc tgacggcttt gctgtcccag agccgcctaa acgcaagaaa      60
agtcgatggg acagttagag gggatgtgct aaagcgtgaa atcagttgtc cttaattttt     120
agaaagattt tggtaactag gtgtctcagg gctgggttgg ggtccaaagt gtaaggaccc     180
cctgccctta gtggagagct ggagcttgga gacattaccc cttcatcaga aggaattttc     240
```

```
ggatgttttc ttgggaagct gttttggtcc ttggaagcag tgagagctgg gaagcttctt    300
ttggctctag gtgagttgtc atgtgggtaa gttgaggtta tcttgggata agggtcttc    360 tagggcacaa aactcactct aggtttatat tgtatgtagc ttatatttt  tactaaggtg    420 tcaccttata agcatctata aattgacttc tttttcttag ttgtatgacc tgccccgggc    480
ggccgctcga                                                             490
```

<210> SEQ ID NO 103
<211> LENGTH: 490
<212> TYPE: DNA
<213> ORGANISM: Homo sapien

<400> SEQUENCE: 103

```
gagcggccgc ccgggcaggt ccaaaccagc ttgctcataa gtcattaacc aaatccatta     60
taggtaattt gttcagttca atgtttacaa ttcttatgga aaaaattagc aacacacaca    120
tttaaaacgt gtgcatttac ctttgcgtga gtgcttaaaa tacatatttc tatttcaaga    180
tgacatttaa aaattattct aatatatcag cagcaaaaat ataatttgca attacaaaaa    240
actaaactag aatccttaag ttattctcat gtttacagtt gtgattcttt aataaatact    300
attatgcagc tctattgttt aagctttctg gatttggttt aaacatgc  atatatattg    360 tcaattgtgg gaagctttac aagttatatt ccatgcactt tttggacaga gttctaacag    420
agccagccag tccacaaaac aggcaagaca aagttgaat  taactggggc aaaataggac    480
tcttatgcaa                                                             490
```

<210> SEQ ID NO 104
<211> LENGTH: 489
<212> TYPE: DNA
<213> ORGANISM: Homo sapien

<400> SEQUENCE: 104

```
cgtggtcgcg gccgaggtcc aggctggtct cgaactcctg accttgtgat ctgcccgcct     60
cggcctccca aagtgttggg attacaggca tgagccactg cgcccgaccg agttgaacat    120
ttaatgtcag actaggccag agtttctcaa tcttttatt  ctcacttccc aaaggagccg    180
ttggagattt tcccctcaat ctctctcctt catgaaattt cataccacaa atatagtatg    240
ttttatttat gtactgtgac cctttgaagg atcacaaacc aatataatag ttttctttt    300 taacccgtca aggaccaagt ttttgcccct gttggaaatg cataaactgg actgatgaat    360
tggtatagat ggcttttatc atgaggatca gaaaaacttg aaattccttg gctacgacac    420
tccatattta tcaccgtata gggaggacct tggtatgggg aagtagaaac acttctacac    480
tttacagca                                                              489
```

<210> SEQ ID NO 105
<211> LENGTH: 479
<212> TYPE: DNA
<213> ORGANISM: Homo sapien
<220> FEATURE:
<221> NAME/KEY: misc_feature
<222> LOCATION: (1)...(479)
<223> OTHER INFORMATION: n = A,T,C or G

<400> SEQUENCE: 105

```
gcgtggtcgc ggccgaggtc tgactggctt cagccccaga agttgagctg gcctttagac     60
aaaataattg cacctccctc tgctgcttat tcccttccgt ttttcatttg agtgtgaaca    120
gttagataaa atctgtggct gnctcttcca ccttgctcta gtttccattg ctgtgagcag    180
```

```
gccctcctat gccccgcatt tagctacaat gctgtggact cacttgattc tttttctccg    240
agctttgtct agaaatatgt gaaggtgagg ttaagtgctt ctctgtgtag atccacttag    300
ccctgtctgc tgtctcgatg ggcgttgctt cgtctctcct ctcttccatc ctttccattt    360
gcttctcacc accttctggc ttcttttctt aatgcaataa aggcagtttc taacaaagaa    420
agaatgtggg ctttggagtt agacagacct ggntttaaat tctgcttctg gctctccaa    479

<210> SEQ ID NO 106
<211> LENGTH: 511
<212> TYPE: DNA
<213> ORGANISM: Homo sapien

<400> SEQUENCE: 106
tcgcggccga ggtccaaaac gtggattcca atgacctgcc ttgagcccgc ggttgccagg     60
agttggacct gcagtagtat gggaagctca cggcctaaat accgactgcc ctctgacccc    120
accgtccagc gattctagaa catttctagt aggaaagaca tagcaaggga ttttcatgat    180
tgggaaatac tgggagacaa gctgaagatt tgttaagggc tatgcttctg tcatctttta    240
ggtatttaag gctactcctt tagctagcta ctttgagctg tttaaagtga ctatctccct    300
acacagagtt acacaatgag catctctgaa agagaatatt accctggatt ccaaagatg     360 tactctaaca ggatgaccag gcaaaaggtg acccggggga ggagtctgtt ataacactcg    420
gacccacatg ttctcaaggc acttcagaac tttgggaaat cattttgtac cggatcctca    480
gaaagcattt atggaaatac acatccttta g                                   511

<210> SEQ ID NO 107
<211> LENGTH: 451
<212> TYPE: DNA
<213> ORGANISM: Homo sapien

<400> SEQUENCE: 107
ggccgcccgg gcaggtccag aatatcaaat caaaaggtca caaatgttca cttcctcctc     60
caccctctta catattggat cttcaattgc aatagggagt gtaagatggg cattttagag    120
acgtagttgc atcagcagaa gcaaacccat cttatacaaa tgggttttgg ggataggaaa    180
aggctgctaa aaattcacaa gtcaccattc cccagaagca atgaatagcc gtagaagacc    240
aaggaagatc aacaagtttc caaagtgcta aagccagaga tttggccctt ccaaaatacc    300
accaggacgc ctggacccgt gggctctccg catgtcacca ctgactgcca ggatgctgct    360
gcacctccct tccttgagac acaacagaga gacagtgaag tcacccaaga ctgggatcat    420
cagaggctcc tcatgcttgc tacagagaag c                                   451

<210> SEQ ID NO 108
<211> LENGTH: 461
<212> TYPE: DNA
<213> ORGANISM: Homo sapien

<400> SEQUENCE: 108
ccgcccgggc aggtcctgaa acattcagac taatcaaaat ggtactact gtaacttctt      60 ataatacata atataaaagt ttttgaaaga tatagacaca attaacccct aaacaacaca    120
ctatctgatt ctcaaaagca atggctattt aacaagatgt aaaaggacaa taacatatca    180
aagaactttc acacacctaa agatagcatt tagcagcaag ttagtcagac aaaacaaaca    240
caaatatttt cacatttcct atgtttgttt ttaactttac ttcataaagc cactgataat    300
```

-continued

| | |
|---|---|
| tgaggtttct tcaagtata agatttctaa aattaaaaac tgttttgac atatttttat | 360 |
| aaagaaataa aaagcaaaac gcaatccaac tatttatatg agtccctctt ctccaacagc | 420 |
| tttagatggt tttctgagta cttttttaca cagaatattt t | 461 |

<210> SEQ ID NO 109
<211> LENGTH: 441
<212> TYPE: DNA
<213> ORGANISM: Homo sapien

<400> SEQUENCE: 109

| | |
|---|---|
| ggccgcccgg gcaggtctga ttataagaga aagaaatcca gtgacacgag ggcaggcagg | 60 |
| ccccgctctg ctctgatcga gaaaagcttc ctgatgtcag ggagatggaa ctgccaccat | 120 |
| cagaaccatg gcactttggg tgaaggtgtg tcagcgacca agggggcagg aaatgggcag | 180 |
| tgactaaggg ggcaggaaac aggcaggcac atggcaaggt tctcccagcc catcagccca | 240 |
| gtgatggcct cgattttgaa gctgcactac tgtctgaaaa gcacaattac tggtgactct | 300 |
| taacaaactt cagcatactg gggaaggaga ctgtcaagta actgaattgg aaagatgaaa | 360 |
| aagaaccatc tctaaaagtt gatgcttgtc agaagaataa cctcctttgt gcaagtcttg | 420 |
| caacatcttc attcaaccac a | 441 |

<210> SEQ ID NO 110
<211> LENGTH: 451
<212> TYPE: DNA
<213> ORGANISM: Homo sapien
<220> FEATURE:
<221> NAME/KEY: misc_feature
<222> LOCATION: (1)...(451)
<223> OTHER INFORMATION: n = A,T,C or G

<400> SEQUENCE: 110

| | |
|---|---|
| ggtcgcggcc gaggtctggg gaagggggtga gaatccctgg gccttgccca gtcctgagct | 60 |
| ctgggtgtct gcagggaagc acagtggtga gttagtgtta aagaaagcat ccagagaggt | 120 |
| aagagggget tgggtagcac cctttgcctc tgtcacttcc gcaaaaactt cttgttgagg | 180 |
| aggaagatga gaaggttgac attgactttg gccttgttga agagtttcat gacagccaca | 240 |
| ccctcatact ggagctgcan gagatcctga tagtgaagct tgaaatcgct ccatgtccac | 300 |
| acccaggaac ttggcattta cttcaaactt tcctgcctca tctcccggcg tgatgtcaaa | 360 |
| natgacgttt cttgaagtga gaggcgggaa agatcttcaa tttccaccaa agacacccctt | 420 |
| tttccaggaa gcttgagcaa caagtgtaat g | 451 |

<210> SEQ ID NO 111
<211> LENGTH: 407
<212> TYPE: DNA
<213> ORGANISM: Homo sapien
<220> FEATURE:
<221> NAME/KEY: misc_feature
<222> LOCATION: (1)...(407)
<223> OTHER INFORMATION: n = A,T,C or G

<400> SEQUENCE: 111

| | |
|---|---|
| ggccgacgtt cgacctgact tctttngagc agntgncact accgtcttg aggaatgccg | 60 |
| actgcagaca gtggcccang gcaaagagtg tgcgtcatcg atganattgg naagatggag | 120 |
| ctcttcagtc agntttcat tcaagctgnt cgtcagacgc tgtctacccc agggactata | 180 |
| atcctnggca caatcccagt tcctanagga aagccactgn ctcttgtaga agaaatcana | 240 |
| cacanaaagg atgtgaacng tgtttaatgt caccaaggga aaacatgaaa ccaccttctg | 300 |

```
ccagatatcg ggacgttgcg tgcagatcaa gcacgnaagt gaagacgcgt gcattccttg    360
ccttccgtga acgantgccc agntcaagaa gancctgatg gaaccct                  407
```

<210> SEQ ID NO 112
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 112

```
tcgcggccga ggtcggccga ggtctgacat ctgttgtctg tgataaccac ttctgtattg     60
cgtcttaacc acttctgtat tgtgtggttt taactgccta aggcggcaat gggcagtggg    120
cccctttccc ttaggatggg tatcaattca acaatattta taaggcattt actgtgtgct    180
aagcatttgg aagacccagg ctacaaaata agacatagtt cctgccctcc aggccagcag    240
agggaggcac aaatacccag gaatctctga tgggtgtgaa gtgcggtcgt gggccacaga    300
aaatgaccgt catggagacc ctgctaaagg tcggaccctg agcccaaagg ggtattcaga    360
agnggagatg attttggccc cactcataga tgggtggcaa a                        401
```

<210> SEQ ID NO 113
<211> LENGTH: 451
<212> TYPE: DNA
<213> ORGANISM: Homo sapien

<400> SEQUENCE: 113

```
gtcgcggccg aggtccatat taaaaagtcc atcataaaca aagactcctc ctcatggtat     60
gaatatgctc catatgccca taatggtgca taacggactt agaaattcca atgagtctta    120
gggttgaaat ttccaatgac ctgagcaagg cagctcccta tagcttctgg ataacatttt    180
acacccagag ttcaggctta aacagaccta tcaacacaat tattttcgga ttgtctgtct    240
agaaaacggc aatgctcaaa ggaatataaa taagggtggg gggacatatg cttccagcct    300
ggcctttctc catgtggtaa aaaacaatgg aatggctgtg ttaattttt tttaatcttt     360 tctgaccttt actatgtttg gtaatggaaa taagtcaggg aaaacaaaat gaacaggtct    420
catcacttaa ttaatactgg gttttcttct t                                   451
```

<210> SEQ ID NO 114
<211> LENGTH: 441
<212> TYPE: DNA
<213> ORGANISM: Homo sapien

<400> SEQUENCE: 114

```
ggccgcccgg gcaggtccat cctgtcagag atgggagaag tcacagacgg aatgatggat     60
acaaagatgg ttcactttct tacacactat gctgacaaga ttgaatctgt tcattttca    120 gaccagttct ctggtccaaa aattatgcaa gaggaaggtc agcctttaaa gctacctgac    180
actaagagga cactgttgtt tacatttaat gtgcctggct caggtaacac ttacccaaag    240
gatatggagg cactgctacc cctgatgaac atggtgattt attctattga taaagccaaa    300
aagttccgac tcaacagaga aggcaaacaa aaagcagata agaaccgtgc ccgagtagaa    360
gagaacttct tgaaacttga cacatgtgca agacaggaa gcagcacagt ctcggcggga    420
ggaagaaaaa aagaacagag a                                              441
```

<210> SEQ ID NO 115
<211> LENGTH: 431
<212> TYPE: DNA
<213> ORGANISM: Homo sapien
<220> FEATURE:
<221> NAME/KEY: misc_feature
<222> LOCATION: (1)...(431)
<223> OTHER INFORMATION: n = A,T,C or G

<400> SEQUENCE: 115

```
gccgcccggg caggtccatt ggcggtgaca aaaggaaaag aagcaaagag actcagtcca      60
taatgctgat tagttagaag aaagggctag gattgagaaa gtaccaggaa cttttaatta     120
tttaaaagag aatgctgact gttaatgttt taaatcttac tgttcaaatg tactaatatg     180
aattttttacc ctttgtgcat gaatattcta acaactaga agacctccac aatttagcag     240
ttatgaaagt taaactttt attataaaaa ttctaaacct tactgctcct ttaccaggaa     300
catgacacac tatttancat cagttgcata cctcgccaat agtataattc aactgtcttg     360
cccgaacaat catctccatc tggaagacgt aagcctttag aaacacattt ttctattaat     420
ttctctagaa c                                                          431
```

<210> SEQ ID NO 116
<211> LENGTH: 421
<212> TYPE: DNA
<213> ORGANISM: Homo sapien

<400> SEQUENCE: 116

```
gtcgcggccg aggtccagaa atgaagaaga agtttgcaga tgtatttgca aagaagacga      60
aggcagagtg gtgtcaaatc tttgacggca cagatgcctg tgtgactccg gttctgactt     120
ttgaggaggt tgttcatcat gatcacaaca aggaaccggg gctcgtttat caccagtgag     180
gagcaggacg tgagccccg ccctgcacct ctgctgttaa acaccccagc catcccttct     240
ttcaaaaggg atccttttcat aggagaacac actgaggaga tacttgaaga atttggattc     300
agcccgcgaa gagatttatc aagcttaact cagataaaat cattgaaagt aataaggtaa     360
aagctaagtc tctaacttcc aggcccacgg ctcaagtgaa tttcgaatac tgcatttaca     420
g                                                                     421
```

<210> SEQ ID NO 117
<211> LENGTH: 489
<212> TYPE: DNA
<213> ORGANISM: Homo sapien

<400> SEQUENCE: 117

```
agcgtggtcg cggccgaggt aaggctgcga ggttgtggtg tctgggaaac tccgaggaca      60
gagggctaaa tccatgaagt ttgtggatgg cctgatgatc cacagcggag accctgttaa     120
ctactacgtt gacactgctg tgcgccacgt gttgctcaga cagggtgtgc tgggcatcaa     180
ggtgaagatc atgctgccct gggacccaac tggtaagatt ggccctaaga agcccctgcc     240
tgaccacgtg agcattgtgg aacccaaaga tgagatactg cccaccaccc ccatctcaga     300
acagaagggt gggaagccag agccgcctgc catgccccag ccagtccca cagcataaca     360
gggtctcctt ggcagacctg cccgggcggc cgctcgaaag cccgaattcc agcacactgg     420
cggccgttac tagtggatcc cagctcggta ccaagcttgg cgtaatcatg gtcatagctg     480
gtttcctgt                                                             489
```

<210> SEQ ID NO 118
<211> LENGTH: 489
<212> TYPE: DNA
<213> ORGANISM: Homo sapien

<400> SEQUENCE: 118

| | | | | | |
|---|---|---|---|---|---|
| tcgagcggcc | gcccgggcag | gtattgaata | cagcaaaatt | ctatatacaa | agtgacctgg | 60 |
| acctgctgct | tcaaaacatg | atcctttctt | actaatatct | tgatagtcgg | tccatagagc | 120 |
| attagaaagc | aattgactct | taaataaaca | gaaaagtgcc | taatgcacat | taaatgaatg | 180 |
| gcctaactac | tggaactta | gtagttctat | aaggtgatta | acataggtag | gatccagttc | 240 |
| ctatgacagg | ctgctgaaga | acagatatga | gcatcaagag | gccatttgt | gcactgccac | 300 |
| cgtgatgcca | tcgtgtttct | ggatcataat | gttcccatta | tctgattcta | gacacaccac | 360 |
| aggaatatca | gtggggtcag | aggttagctt | agctgcttgc | tgggctagaa | cagatatcac | 420 |
| tccagcatgc | tcatctgaca | gggtcccgcg | gcaacccaga | ttaagtcctt | gtgaatctgt | 480 |
| gcacaggga | | | | | | 489 |

<210> SEQ ID NO 119
<211> LENGTH: 181
<212> TYPE: DNA
<213> ORGANISM: Homo sapien

<400> SEQUENCE: 119

| | | | | | |
|---|---|---|---|---|---|
| taggttccag | agacttttgg | cccaggagga | atatttactt | ttagctctgg | acatcattac | 60 |
| aaaaaggaat | atttcccaaa | cctcttcaga | ccgagaatac | atgggtaaaa | ttattaaata | 120 |
| gttgtataat | aaaaataatt | ttttccttaa | aaaaaaaaa | aacctcggcc | gcgaccacgc | 180 |
| t | | | | | | 181 |

<210> SEQ ID NO 120
<211> LENGTH: 489
<212> TYPE: DNA
<213> ORGANISM: Homo sapien
<220> FEATURE:
<221> NAME/KEY: misc_feature
<222> LOCATION: (1)...(489)
<223> OTHER INFORMATION: n = A,T,C or G

<400> SEQUENCE: 120

| | | | | | |
|---|---|---|---|---|---|
| gcgtggtcgc | ggccgaggtc | catttaaaac | aaagaaaaat | actaaagcca | ctagtaaaca | 60 |
| tctgatgtgc | aaaatacaac | atcctctagt | tggctttatg | ccattattac | ataagctcca | 120 |
| aatagctcat | cttaaattaa | aaagaaaaag | tggctgtccc | atctctgctg | cataaatcag | 180 |
| atttttttt | aaaggtttag | agtactttaa | ggaagggaag | ttcaaaactg | ccagtgaaat | 240 |
| tcacagagaa | tacaaattta | gcaatttaat | ttcccaaagc | tctttgaaga | agcaagagag | 300 |
| tctctcttct | taatgcagtg | ttctcccaag | aggaactgta | attttgcttg | gtacttatgc | 360 |
| tgggagatat | gcaaaatgtg | tttttcaatg | tttgctagaa | tataatggtt | cctcttcagt | 420 |
| gnctggttca | tcctggaact | catgggttaa | gaaggacttc | ttggagccga | actgcccggg | 480 |
| cgggccntt | | | | | | 489 |

<210> SEQ ID NO 121
<211> LENGTH: 531
<212> TYPE: DNA
<213> ORGANISM: Homo sapien

<400> SEQUENCE: 121

-continued

```
cgagcggccg cccgggcagg tggccagcgc tggtcccgca gacgccgaga tggaggaaat      60
atttgatgat gcgtcacctg gaaagcaaaa ggaaatccaa gaaccagatc ctacctatga     120
agaaaaaatg caaactgacc gggcaaatag attcgagtat ttattaaagc agacagaact     180
ttttgcacat tcattcaac ctgctgctca gaagactcca acttcacctt tgaagatgaa      240
accagggcgc ccacgaataa aaaagatgaa gaagcagaac ttactatccg ttggcgatta    300
ccgacaccgt agaacagagc aagaggagga tgaagagcta ttaacagaaa gctccaaagc    360
aaccaatgtt tgcactcgat ttgaagactc tccatcgtat gtaaaatggg gtaaactgag    420
agattatcag gtcccgagga ttaaactggc tcatttcttt gtatgagaat ggcatcaatg    480
gtatccttgc agatgaaatg ggcctaggaa agactcttca acaatttctc t             531
```

<210> SEQ ID NO 122
<211> LENGTH: 174
<212> TYPE: DNA
<213> ORGANISM: Homo sapien

<400> SEQUENCE: 122

```
tcgagcggcc gcccgggcag gtctgccaac agcagaggcg gggcctccgg catcttcaaa      60
gcacctctga gcaggctcca gccctctggc tgcgggaggg gtctgggtc tcctctgagc     120 tcggcagcaa agcagatgtt atttctctcc cgcgacctcg ccgcgacca cgct            174
```

<210> SEQ ID NO 123
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 123

```
agcgtggtcg cggccgaggt cctcaaccaa gagggttgat ggcctccagt caagaaactg      60
tggctcatgc cagcagagct ctctcctcgt ccagcaggcg ccatgcaagg gcaggctaaa    120
agacctccag tgcatcaaca tccatctagc anagagaaaa ggggcactga agcagctatg    180
tctgccaggg gctaggggct cccttgcaga cagcaatgct acaataaagg acacagaaat    240
gggggaggtg ggggaagccc tatttttata acaaagtcaa acagatctgt gccgttcatt    300
cccccagaca cacaagtaga aaaaaaccaa tgcttgtggt ttctgccaag atggaatatt    360
cctccttcct aanttccaca catggccgtt tgcaatgctc gacagcattg cactgggctg    420
cttgtctctg tggtctgggc accagtagct tgggccccat atacacttct cagttcccac    480
anggcttatg gccnanggc angctccaat tttcaagcac cacgaaggaa g              531
```

<210> SEQ ID NO 124
<211> LENGTH: 416
<212> TYPE: DNA
<213> ORGANISM: Homo sapien

<400> SEQUENCE: 124

```
tcgagcggcc gcccgggcag gtccatctat actttctaga gcagtaaatc tcataaattc      60
acttaccaag cccaggaata atgacttta aagccttgaa tatcaactaa gacaaattat     120
gccaattctg atttctcaca tatacttaga ttacacaaag ataaagcttt agatgtgatc    180
attgtttaat gtagacttat ctttaaagtt tttaattaaa aactacagaa gggagtaaac    240
agcaagccaa atgatttaac caaatgattt aagagtaaaa ctcactcaga aagcattata    300
```

```
cgtaactaaa tatacatgag catgattata tacatacatg aaactgcaat tttatggcat      360
tctaagtaac tcatttaagt acattttggg catttaaaca aagatcaaat caagct          416

<210> SEQ ID NO 125
<211> LENGTH: 199
<212> TYPE: DNA
<213> ORGANISM: Homo sapien
<220> FEATURE:
<221> NAME/KEY: misc_feature
<222> LOCATION: (1)...(199)
<223> OTHER INFORMATION: n = A,T,C or G

<400> SEQUENCE: 125
agcgtggtcg cggccgaggt gctttttttt tttttttttt tttttttttt gctattctaa       60
aggggaaggc ccctttttat taaacttgta cattttactt tccttctttc anaatgctaa     120
taaaaaactt ttgtttatac ttaaaaaaac cataaatcan acaaacaaaa gaaacgattc     180
caacatcact tctgngatg                                                  199

<210> SEQ ID NO 126
<211> LENGTH: 490
<212> TYPE: DNA
<213> ORGANISM: Homo sapien

<400> SEQUENCE: 126
cgtggtcgcg gccgaggtcc agttgctcta agtggattgg atatggttgg agtggcacag       60
actggatctg ggaaaacatt gtcttatttg cttcctgcca ttgtccacat caatcatcag     120
ccattcctag agagaggcga tgggcctatt tgtttggtgc tggcaccaac tcgggaactg     180
gcccaacagg tgcagcaagt agctgctgaa tattgtagag catgtcgctt gaagtctact     240
tgtatctacg gtggtgctcc taagggacca caaatacgtg atttggagag aggtgtggaa     300
atctgtattg caacacctgg aagactgatt gacttttag agtgtggaaa aaccaatctg      360
agaagaacaa cctaccttgt ccttgatgaa gcagatagaa tgcttgatat gggctttgaa     420
ccccaaataa ggaagattgt ggatcaaata agacctgata ggcaaactct aatgtggagt     480
gcgacttggc                                                             490

<210> SEQ ID NO 127
<211> LENGTH: 490
<212> TYPE: DNA
<213> ORGANISM: Homo sapien

<400> SEQUENCE: 127
cgtggtcgcg gccgaggtcg gccgaggtct ggagatctga gaacgggcag actgcctcct      60
caagtgggtc cctgacccct gaccccgag cagcctaact gggaggcacc ccccagcagg     120
ggcacactga cacctcacac ggcagggtat tccaacagac ctgaagctga gggtcctgtc     180
tgttagaagg aaaactaaca agcagaaagg acagccacat caaaaaccca tctgtacatc     240
accatcatca aagaccaaaa gtaaatcaaaa ccacaaagat gggaaaaaaa cagaacagaa     300
aaactggaaa ctctaaaaag cagagcacct ctcctcttcc aaaggaacgc agttcctcac     360
cagcaatgga acaaagctgg atggagaatg actttgacga gctgagaaaa gaacgcttca     420
gacgatcaaa ttactctgag ctacgggagg acattcaaac caaaggcaaa gaagttgaaa     480
actttgaaaa                                                             490

<210> SEQ ID NO 128
```

<211> LENGTH: 469
<212> TYPE: DNA
<213> ORGANISM: Homo sapien
<220> FEATURE:
<221> NAME/KEY: misc_feature
<222> LOCATION: (1)...(469)
<223> OTHER INFORMATION: n = A,T,C or G

<400> SEQUENCE: 128

| | | | | |
|---|---|---|---|---|
| cgtggtcgcg gccgaggtgc tttttttttt tttttttttt tttttttttt tgctgattta | 60 |
| ttttttctnt ttattgttac atacaatgta taaacacata aaacanaaaa cagtagggat | 120 |
| cctctaggat ctctagggan acagtaaagt anaagaggt ctcanaaaca ttttttttaaa | 180 |
| gtacaagaca ttcagngctc ggcccaaagg cgtaaaaggt ttanagccag canatagctg | 240 |
| nactaaaggc tccgtctntn tccccanagc caggacaacc ccagggagct ntccattagc | 300 |
| agccagtcca cgcaggcagg atgctgcgga aaaagctcta tgctganaac attccccttg | 360 |
| atggaaagaa gggcaacaca aaaggggtaa ctaanagctc cttcctctcg tgagggcgac | 420 |
| aactgaggaa cagaaaagga gtgtcccatg tcacttttga ccccctccc | 469 |

<210> SEQ ID NO 129
<211> LENGTH: 419
<212> TYPE: DNA
<213> ORGANISM: Homo sapien

<400> SEQUENCE: 129

| | | | | |
|---|---|---|---|---|
| gcgtggtcgc ggccgaggtc tgattttcat ttaaatattt cagagctata gcatttgcct | 60 |
| ccatgctcaa atccacacca ttggggctta agccgctcat gccaacatta gcaaatgaca | 120 |
| tgcagtttaa tccagagatc actgcttctg ggctgatgca tgccaacaca ctggcgtgat | 180 |
| ccacgttatg tgcattttc ttcactttag tgggagaatc aatttttact ccaaggcttc | 240 |
| ttagttgctt aagagttgca ttaaggacac aatctttgtc caccagtctt gaatgatgtg | 300 |
| tttttttctt tgtatggtaa acgttttggg ttctggtgca ttcatgactg ataattactg | 360 |
| ctttggtaga cggctgctca agtttccttg gaggaactat ttaataggtg ggttacttg | 419 |

<210> SEQ ID NO 130
<211> LENGTH: 354
<212> TYPE: DNA
<213> ORGANISM: Homo sapien

<400> SEQUENCE: 130

| | | | | |
|---|---|---|---|---|
| agcgtggtcg cggccgaggt ccatctgagg agataaccac atcactaaca aagtgggagt | 60 |
| gaccccgcag agcacgctgt ggaattccat agttggtctc atccctggtc agtttccaca | 120 |
| tgatgatggt cttatctcga gaggcggaga ggatcatgtc cgggaactgc ggggtagtag | 180 |
| cgatctgggt tacccagccg ttgtggccct tgagggtgcc acgaagggtc atctgctcag | 240 |
| tcatggcggc ggcgagagcg tgtgtcgctg cagcgacgag gatggcactg gatggcttag | 300 |
| agaaactagc accacaacct ctcctgccgc acctgcccgg gcggcccgct cgaa | 354 |

<210> SEQ ID NO 131
<211> LENGTH: 474
<212> TYPE: DNA
<213> ORGANISM: Homo sapien
<220> FEATURE:
<221> NAME/KEY: misc_feature
<222> LOCATION: (1)...(474)
<223> OTHER INFORMATION: n = A,T,C or G

<400> SEQUENCE: 131

```
cgagcggccg cccgggcagg tctggcagca gcttcctctg gaataattga cagctttgtg      60
ctgcctgact aaaatttgaa atgacaaccg ctgaatgtaa aatgatgtac ctacaatgag     120
agagatttag gaatactatc tgtcaatcca tagatgtaga aacaaaacaa actacagaat     180
gaaaacaaac ttatttttaaa ccaaagaaac aaatgtatcc aaaatatagt ccatgatata     240
tttgattact agtataacca cagttgaaaa cttaaaaaaa aaaattgaca ttttttgtaa     300
tgggtactaa tggatttata aaggtttct gtttccaaag atgttattgg ggtccacata      360
ttccttgaag acttcagcat cccaaagccc gacatcagag atactttcct ttagccattg     420
nttcccgtaa cttgcccact ccatggtgat gtgacaggct tcccttcatt agca           474
```

<210> SEQ ID NO 132
<211> LENGTH: 474
<212> TYPE: DNA
<213> ORGANISM: Homo sapien
<220> FEATURE:
<221> NAME/KEY: misc_feature
<222> LOCATION: (1)...(474)
<223> OTHER INFORMATION: n = A,T,C or G

<400> SEQUENCE: 132

```
ggccgaggtg gggaattcat gtggaggtca gagtggaagc aggtgtgaga gggtccagca      60
gaaggaaaca tggctgccaa agtgtttgag tccattggca agtttggcct ggccttagct     120
gttgcaggag gcgtggtgaa ctctgcctta tataatgtgg atgctgggca cagagctgtc     180
atctttgacc gattccgtgg agtgcaggac attgtggtag gggaagggac tcatttctc      240 atcccgtggg tacagaaacc aattatcttt gactgccgtt ctcgaccacg taatgtgcca     300
gtcatcactg gtagcaaaga tttacagaat gtcaacatca cactgcgcat cctcttccgg     360
cctgtcgcca gccagcttcc tcgcatcttc accagcatcg ganaggacta tgatgaaccg     420
tgtgctgccg tccatcacaa ctgagatcct caagtcagtg gtggctcgct ttga           474
```

<210> SEQ ID NO 133
<211> LENGTH: 387
<212> TYPE: DNA
<213> ORGANISM: Homo sapien

<400> SEQUENCE: 133

```
tgctcgagcg gccgccagtg tgatggatat ctgcagaatt cggcttagcg tggtcgcggc      60
cgaggtctgc gggcccctta gcctgccctg cttccaagcg acggccatcc cagtagggga     120 cttcccaca ctgtgccttt acgatcagcg tgacagagta gaagctggag tgcctcacca      180
cacggcccgg aaacagcggg aagtaactgg aaagagcttt aggacagctt agatgccgag     240
tgggcgaatg ccagaccaat gatacccaga gctacctgcc gccaacttgt tgagatgtgt     300
gtttgactgt gagagagtgt gtgtttgtgt gtgtgttttg ccatgaactg tggccccagt     360
gtatagtgtt tcagtggggg agaactg                                         387
```

<210> SEQ ID NO 134
<211> LENGTH: 401
<212> TYPE: DNA
<213> ORGANISM: Homo sapien

<400> SEQUENCE: 134

```
ggccgccccgg gcaggtctga tgaagaacac gggtgtgatc cttgccaatg acgccaatgc      60
tgagcggctc aagagtgttg tgggcaactt gcatcggctg ggagtcacca acaccattat     120
```

-continued

| | |
|---|---|
| cagccactat gatgggcgcc agttccccaa ggtggtgggg ggctttgacc gagtactgct | 180 |
| ggatgctccc tgcagtggca ctggggtcat ctccaaggat ccagccgtga agactaacaa | 240 |
| ggatgagaag gacatcctgc gcttgtgctc acctccagaa ggaagttgct cctgagtgct | 300 |
| attgactctt gtcaatgcga ccttcaagac aggaggctac ctggtttact gcacctgttc | 360 |
| tatcacagtg agacctctgc catggcagaa cagggggaagc t | 401 |

<210> SEQ ID NO 135
<211> LENGTH: 451
<212> TYPE: DNA
<213> ORGANISM: Homo sapien

<400> SEQUENCE: 135

| | |
|---|---|
| ggtcgcggcc gaggtctgtt cctgagaaca gcctgcattg gaatctacag agaggacaac | 60 |
| taatgtgagt gaggaagtga ctgtatgtgg actgtggaga aagtaagtca cgtgggccct | 120 |
| tgaggacctg gactgggtta ggaacagttg tactttcaga ggtgaggtgt cgagaaggga | 180 |
| aagtgaatgt ggtctggagt gtgtccttgg ccttggctcc acagggtgtg ctttcctctg | 240 |
| gggccgtcag ggagctcatc ccttgtgttc tgccagggtg gggtaccggg gtttgacact | 300 |
| gaggagggta acctgctggc tggagcggca gaacagtggc cttgatttgt cttttggaag | 360 |
| atttttaaaaa ccaaaaagca taaacattct ggtccttcac aatgctttct ctgaagaaat | 420 |
| acttaacgga aggacttctc cattcaccat t | 451 |

<210> SEQ ID NO 136
<211> LENGTH: 411
<212> TYPE: DNA
<213> ORGANISM: Homo sapien

<400> SEQUENCE: 136

| | |
|---|---|
| ggccgcccgg gcaggtctga atcacgtaga atttgaagat caagatgatg aagccagagt | 60 |
| tcagtatgag ggttttcgac ctgggatgta tgtccgcgtt gagattgaaa atgttccctg | 120 |
| tgaatttgtg cagaactttg acccccttta ccccattatc ctgggtggct gggcaacag | 180 |
| tgagggaaat gttggacatg tgcaggtggg tccctttgct gcgtatttgg tgcctgaggc | 240 |
| tctgtggatt tcccctccat caatcatctt accctctcat ccccctcaga tgcgtctgaa | 300 |
| gaaacatctc tggtataaga aaatcctcaa gtcccaagat ccaatcatat tttctgtagg | 360 |
| gtggaggaag tttcagacca tcctgctcta ttatatccga agaccacaat g | 411 |

<210> SEQ ID NO 137
<211> LENGTH: 211
<212> TYPE: DNA
<213> ORGANISM: Homo sapien
<220> FEATURE:
<221> NAME/KEY: misc_feature
<222> LOCATION: (1)...(211)
<223> OTHER INFORMATION: n = A,T,C or G

<400> SEQUENCE: 137

| | |
|---|---|
| cggccgcccg ggcaggtcgg ttggtgcggc ctccattgtt cgtgttttaa ggcgccatga | 60 |
| ggggtgacag aggccgtggt cgtggtgggc gctttggttc cagaggaggc ccaggaggag | 120 |
| ggttcaggcc ctttgcacca catatcccat ttgacttcta tttgtgtgaa atggcctttc | 180 |
| cccggntcaa gccagcacct cgatgaaact t | 211 |

<210> SEQ ID NO 138
<211> LENGTH: 471

```
<212> TYPE: DNA
<213> ORGANISM: Homo sapien

<400> SEQUENCE: 138
gccgcccggg caggtctggg ctggcgactg gcatccaggc cgtaactgca aatctatgct      60 aggcgggtc tcccttctgt gtgttcaagt gttctcgact tggattctta actattttaa     120
aaaatgcact gagtttgggt taaaaaccaa ccaccaaaat ggatttcaac acagctctaa    180
agccaagggc gtggccggct ctcccaacac agcgactcct ggaggccagg tgcccatggg    240
cctacatccc ctctcagcac tgaacagtga gttgattttt cttttttacaa taaaaaaagc    300 tgagtaatat tgcataggag taccaagaaa ctgcctcatt ggaaacaaaa actatttaca    360
ttaaataaaa agcctggccg caggctgcgt ctgccacatt tacagcacgg tgcgatgcac    420
acggtgacca aaccacggag gcaagcttct ggcactcaca ccacgacccg c             471

<210> SEQ ID NO 139
<211> LENGTH: 481
<212> TYPE: DNA
<213> ORGANISM: Homo sapien
<220> FEATURE:
<221> NAME/KEY: misc_feature
<222> LOCATION: (1)...(481)
<223> OTHER INFORMATION: n = A,T,C or G

<400> SEQUENCE: 139
gtcgcggccg aggtctgttc tttagctcag atttaaacct gctgtctctt ctttatttgc     60
agaatgaatt cccagttcct gagcagttca agaccctatg gaacgggcag aagttggtca    120
ccacagtgac agaaattgct ggataagcga agtgccactg ggttctttgc cctcccttca    180
caccatggga taaatctgta tcaagacggt tcttttctag atttcctcta ccttttttgct   240 cttaaaactg cttctctgct ctgagaagca cagctacctg ccttcactga aatatacctc    300
aggctgaaat ttggggtggg atagcaggtc agttgatctt ctgcaggaag gtgcagcttt    360
tccatatcag ctcaaccacg ccgncagtcc attcttaagg aactgccgac taggactgat    420
gatgcatttt agcttttgag cttttggggg gtattctacc aaccaacagt ccatttggaa    480
a                                                                    481

<210> SEQ ID NO 140
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 140
gtcgcggccg aggtttccca tttaagaaaa atagatcttg agattctgat tcttttccaa     60
acagtcccct gctttcatgt acagcttttt ctttaccttA cccaaaattc tggccttgaa    120
gcagttttcc tctatggctt tgcctttctg attttctcag aggctcgagt ctttaatata    180
accccaaatg aaagaaccaa ggggaggggt gggatggcac ttttttttgt tggtcttgtt    240
ttgttttgtt ttttggttgg ttgggttccg ttatttttta agattagcca ttctctgctg    300
ctatttccct acataatgtc aattttttaac cataattttg acatgattga gatgtacttg    360 aggcttttt gntttaattg agaaaagact ttgcaatttt ttttttagga tgagcctctc     420
c                                                                    421
```

<210> SEQ ID NO 141
<211> LENGTH: 242
<212> TYPE: DNA
<213> ORGANISM: Homo sapien
<220> FEATURE:
<221> NAME/KEY: misc_feature
<222> LOCATION: (1)...(242)
<223> OTHER INFORMATION: n = A,T,C or G

<400> SEQUENCE: 141

| | | | | | |
|---|---|---|---|---|---|
| cgantngccc | gcccgggcan | gtctgtctaa | ntttntcang | gaccacgaac | agaaactcgt | 60 |
| gcttcaccga | anaacaatat | cttaaacatc | gaanaattta | aatattatga | aaaaaaacat | 120 |
| tgcaaaatat | aaaataaata | nnaaaaggaa | aggaaacttt | gaaccttatg | taccgagcaa | 180 |
| atccaggtct | agcaaacagt | gctagtccta | nattacttga | tntacaacaa | cacatgaata | 240 |
| ca | | | | | | 242 |

<210> SEQ ID NO 142
<211> LENGTH: 551
<212> TYPE: DNA
<213> ORGANISM: Homo sapien
<220> FEATURE:
<221> NAME/KEY: misc_feature
<222> LOCATION: (1)...(551)
<223> OTHER INFORMATION: n = A,T,C or G

<400> SEQUENCE: 142

| | | | | | |
|---|---|---|---|---|---|
| agcgtggtcg | cggcncgang | tccacagggc | anatattctt | ttagtgtctg | gaattaaaat | 60 |
| gtttgaggtt | tangtttgcc | attgtctttc | caaaaggcca | ataattcan | atgtaaccac | 120 |
| accaagtgca | aacctgtgct | ttctatttca | cgtactgttg | tccatacagt | tctaaataca | 180 |
| tgtgcagggg | attgtagcta | atgcattaca | cagtcgttca | gtcttctctg | cagacacact | 240 |
| aagtgatcat | accaacgtgt | tatacactca | actagaaaat | aataagcttt | aatctgaggg | 300 |
| caagtacagt | cctgacaaaa | gggcaagttt | gcataataga | tcttcgatca | attctctctc | 360 |
| caaggggccc | gcaactaggc | tattattcat | aaaacacaac | tgaanagggg | attggtttta | 420 |
| ctggtaaatc | atgtgntgct | aaatcatttt | ctgaacagtg | gggtctaaat | cantcattga | 480 |
| tttagtggca | gccacctgcc | cggcggccgn | tcgaagccca | attctgcaga | tatccatcac | 540 |
| actggcggcc | g | | | | | 551 |

<210> SEQ ID NO 143
<211> LENGTH: 515
<212> TYPE: DNA
<213> ORGANISM: Homo sapien
<220> FEATURE:
<221> NAME/KEY: misc_feature
<222> LOCATION: (1)...(515)
<223> OTHER INFORMATION: n = A,T,C or G

<400> SEQUENCE: 143

| | | | | | |
|---|---|---|---|---|---|
| cgagnggccc | gcccgggcag | gtatcttcac | aaactcaaca | aaggcactac | atgagacttc | 60 |
| acattcccct | agtccaatag | ctgacaaatt | tttgcaacgt | tctgcaatgc | gaattaactc | 120 |
| ttcatcaagt | ggccgtaatc | catttgcaca | cactactagt | tcaaccagtc | tagggcatgt | 180 |
| cattcccaca | cggccaagca | catctttgct | tactgatctc | ccaaagtaca | gatgggtggc | 240 |
| aggtatttca | tagcgaaaga | agggtcaaa | ttcttcttca | tataanaaaa | aatacatcac | 300 |
| taagttcact | ttgggtgaat | gtctgatgaa | agcatcccag | ctactcttct | gaatagtatg | 360 |
| gaagtgtgtc | tgtccaggat | tctcactgac | tacatcaatg | cgcaaatgtt | ctaatcgaac | 420 |

```
atgtttttca gaagacaatg caagtaacaa ctcatcactc aataagtggt aagttcaggg      480
ctagttctct taagccgnga cactgatcag cacac                                 515

<210> SEQ ID NO 144
<211> LENGTH: 247
<212> TYPE: DNA
<213> ORGANISM: Homo sapien
<220> FEATURE:
<221> NAME/KEY: misc_feature
<222> LOCATION: (1)...(247)
<223> OTHER INFORMATION: n = A,T,C or G

<400> SEQUENCE: 144
tgcattctct ntggatgcan acctgcccgt tggtagggac tntgctcaca cggaacatgg      607
acggttacac ctgtgccgtg ggtgacgtcc accagcttct ggatcatctc ggcgngggtg     120
ttgtggaagg gcagactatc cacctccatg cncacgatgc ccganacgcc actccggact      180
ntgtgctgca ccaanatgcc cagcattnta tcttcaagca nagcacttat cagggtcctt      240
ggcacac                                                                247

<210> SEQ ID NO 145
<211> LENGTH: 309
<212> TYPE: DNA
<213> ORGANISM: Homo sapien
<220> FEATURE:
<221> NAME/KEY: misc_feature
<222> LOCATION: (1)...(309)
<223> OTHER INFORMATION: n = A,T,C or G

<400> SEQUENCE: 145
cgtgggtcgc ggcccgangt ctgctgtaac aaaacaccat agtctgggca gctcatagac       60
aatggaattt tatttctcac gcttctggag gctggattcc aagatcaagg ttccaggaga      120
ctcagtgtct ggcaaggtct cggtttctgc ctcanagatg gtgccatctg gctgtgtcct      180
cacaagtagg aaggtgcaag aagctcccct caggctctgt ctgtaagaca ctgatcccat      240
tcatganggg gaaacgtaat gacctaatca gcccccagag accccacttc taacaccatc      300
accttgggg                                                              309

<210> SEQ ID NO 146
<211> LENGTH: 486
<212> TYPE: DNA
<213> ORGANISM: Homo sapien
<220> FEATURE:
<221> NAME/KEY: misc_feature
<222> LOCATION: (1)...(486)
<223> OTHER INFORMATION: n = A,T,C or G

<400> SEQUENCE: 146
agcgtgggtc gcggcncgac gtcctgtcca tatttcacag cccgagaact aatacaagat       60
gctgacatca tattttgtcc ctacaactat cttctanatg cacaaataag ggaaagtatg      120
gatttaaatc tgaaagaaca ggttgtcatt ttanatgaag ctcataacat cgaggactgt      180
gctcgggaat cagcaagtta cagtgtaaca gaagttcagc ttcggtttgc tcgggatgaa      240
ctanatagta tggtcaacaa taatataagg aaganagatc atgaacccct acgagctgtg      300
tgctgtagcc tcattaattg gntagaagca aacgctgaat atcttgnana angagantat      360
gaatcagctt gtaaaatatg gagtggaaat gaaatgctct aactttaca caaaatgggt      420 atcaccactg ctacttttcc cattttgcng gtaagatatn ttttctacct gngaaacgta      480
```

```
tttaag                                                              486

<210> SEQ ID NO 147
<211> LENGTH: 430
<212> TYPE: DNA
<213> ORGANISM: Homo sapien
<220> FEATURE:
<221> NAME/KEY: misc_feature
<222> LOCATION: (1)...(430)
<223> OTHER INFORMATION: n = A,T,C or G

<400> SEQUENCE: 147
gccgcccggg cangttcgac attacntnga gttccatgat gtacaattct ttcacgaaaa    60
acaatgaatg caagaatttg aggatctcct tactcctccc ttttacagat ggtctctcaa   120
tcccttcttc ttcctcttca tcttcatctt cttctgaacg cgctgccggg taccacggct   180
ttctttgtct ttatcgtgag atgaaggtga tgcttctgtt tcttctacca taactgaaga   240
aatttcgctg caagtctctt gactggctgt ttctccgact tcgcctttnt gtcaaacgng   300
agtcttttta cctcatgccc ctcagcttca cagcatcttc atctggatgt tnatttctca   360
aagggctcac tgaggaaact tctgattcan atgtcgaana gcactgtgaa gttttctctt   420
cattttgctg                                                         430

<210> SEQ ID NO 148
<211> LENGTH: 483
<212> TYPE: DNA
<213> ORGANISM: Homo sapien
<220> FEATURE:
<221> NAME/KEY: misc_feature
<222> LOCATION: (1)...(483)
<223> OTHER INFORMATION: n = A,T,C or G

<400> SEQUENCE: 148
cccgggcagg tctgtgttgn tttncaaccg gtgtcctccc cagcgtccag aananggaaa    60
tgtggagcgg gtgatgatga cccctcgctg tcctgtcacc tcctgcacag cttcgtatgt   120
gggtctggtc tgggaccacc cgtacaggtt gtgcacgttg tagtgctcca cggggggagct  180 gtccggcagg atctgctgac tctccatgca cagagtcttg ctgctcaggc ccttgtccct   240
agattccaaa tatggcatat agggtggggt tatttagcat tcattgctg cagcccctga    300 cagatccatc cacaaaattt gatggctcat tcatatcaat ccacaatcca tcaaacttca   360
agctcttctc tggntctcga nggtttgcat agaactcttc tatctctttc ttccaccacg   420
canacctcgg ncgcgaccac gctaagccga attctgcana tatccatcac actggcggcc   480
gct                                                                483

<210> SEQ ID NO 149
<211> LENGTH: 439
<212> TYPE: DNA
<213> ORGANISM: Homo sapien
<220> FEATURE:
<221> NAME/KEY: misc_feature
<222> LOCATION: (1)...(439)
<223> OTHER INFORMATION: n = A,T,C or G

<400> SEQUENCE: 149
ctttcacgaa nacaatgaat gcaagaattt gaggatctcc ttactcctcc cttttacaga    60
tggtctctca atcccttctt cttcctcttc atcttcatct tcttctgaac gcgctgccgg   120
gtaccacggc tttctttgtc tttatcgtga gatgaaggtg atgcttctgt ttcttctacc   180
ataactgaag aaatttcgct gcaagtctct tgactggctg tttctccgac ttcgcctttt   240
```

```
tgcaaacgtg agtctttta cctcatgccc ctcagcttcc acagcatctt catctggatg    300
ttcatttctc aaagggctca ctgaggaaac ttctgactca catgtcgaag aagcactgng    360
agtttctctt catttgctgc aaanttgctc tttgctggct gngctctcag accacccatt    420
tggctgcatg ggggctgac                                                 439

<210> SEQ ID NO 150
<211> LENGTH: 578
<212> TYPE: DNA
<213> ORGANISM: Homo sapien
<220> FEATURE:
<221> NAME/KEY: misc_feature
<222> LOCATION: (1)...(578)
<223> OTHER INFORMATION: n = A,T,C or G

<400> SEQUENCE: 150
ggcncgcccg ggcangtcca ctccactttt gagctctgag ggaataccctt caggagggac    60 agggtcaggg agtcctggca gctccgcagc agagattcac attcattcag agacttgttg   120
tccagtgcaa tgccattgat cgcaacgatc ctgtctccca cagcaaggga cccttcttta   180
gcggcagggc ttccaggcag cacagcggca gcatacactc cattctccag actgatgcca   240
ctgtctttct gtccactgan gttgatgtgc agcggcgtga ccaccttccc acccagggac   300
ttcctccgcc gcacgaccat gttgatgggc cccctnccca ttgaggagcg ccttgatggc   360
ctgcttcttg nccttggtga tgaagtccac atcggtgatt ctcacagcca gtcattgacc   420
cttaagcggn catcagcaat gcttcctttg gccactttag ngacaaatat gccacagtcc   480
ccgggaaaca agggtcattc acaccttctg gcatatcaaa cacctcggcc gggancacta   540
agccgaattc tgcagatatc catcacactg gngggccg                           578

<210> SEQ ID NO 151
<211> LENGTH: 503
<212> TYPE: DNA
<213> ORGANISM: Homo sapien
<220> FEATURE:
<221> NAME/KEY: misc_feature
<222> LOCATION: (1)...(503)
<223> OTHER INFORMATION: n = A,T,C or G

<400> SEQUENCE: 151
cgagcggccc gcccgggcag gtctgggaga tcagcgactg ctgccacgtg cccagaaatg    60
gctcgtcctt tcactacagc ggaatgcaat gagggtgggt gagaagatga tgggtcggtt   120
atttcattcc ttttcttttt acaacttcac tttcagagac ttcagcgttc catgtctgct   180
gtgctgtgga acccagagtg ctcttgcctg gatggctgag aatcccttgg acctggaag    240 cacctactcc atgatggccc ggtatagtgc aggctcaata taatcttccc ggtatcttga   300
gttgataact cgttgccgtt tcttttcttg cttaacctct ttctctgtga aaatctcatt   360
gaagcgcatg tctgaagcta ctgacagtct anatttgact ctcttgggaa gctcttcatc   420
cagtgtgtat acatcatctc tcttaaccac aagttggagc catncttaaa cttcacctgg   480
tacatttgga tagggtggga ggc                                            503

<210> SEQ ID NO 152
<211> LENGTH: 553
<212> TYPE: DNA
<213> ORGANISM: Homo sapien
<220> FEATURE:
<221> NAME/KEY: misc_feature
<222> LOCATION: (1)...(553)
```

<223> OTHER INFORMATION: n = A,T,C or G

<400> SEQUENCE: 152

| | | | | |
|---|---|---|---|---|
| agcgtggtcg | cggcccgagg | tccactgagc | tccgccttcc | ccgggctccc | tgaggaagca | 60 |
| gagtcctgac | ttccaggaag | gacaggacac | agaggcaaga | actcagcctg | tgaggctctg | 120 |
| ggtggctcct | gaggccagag | gacgccttcc | gcgatccatg | gctcagcatc | gtccttctgg | 180 |
| cttcccagcc | ccgggccgaa | cgttcgggtt | aataagcaga | gcagttattc | ggctcctggc | 240 |
| aggagctccc | ccgttagttt | ccacgttgtg | agcacattca | tacttaagac | tgnttctctt | 300 |
| tgtgttttaa | gcgtctgtct | ctgtagtaaa | ctgaaatgtt | aacagaaatg | cagacctgcc | 360 |
| cgggcggccg | ctcgaaagcc | gaattctgca | gatatccatc | acactggcgg | ccgctcgagc | 420 |
| atgcatctag | anggcccaat | tcgccctata | gtgagtcgna | ttacaattca | ctgggccgcg | 480 |
| ntttacaacg | tcgtgactgg | gaaaaccctg | cggtacccac | ttaatcgcct | tgcagnacat | 540 |
| ccccctttcg | cca | | | | | 553 |

<210> SEQ ID NO 153
<211> LENGTH: 454
<212> TYPE: DNA
<213> ORGANISM: Homo sapien
<220> FEATURE:
<221> NAME/KEY: misc_feature
<222> LOCATION: (1)...(454)
<223> OTHER INFORMATION: n = A,T,C or G

<400> SEQUENCE: 153

| | | | | | | |
|---|---|---|---|---|---|---|
| tcgagcggct | cgcccgggca | ggtccaccta | gcatggctcc | tctaaacacg | caactcagcg | 60 |
| agggaccccc | cttcacctct | ggcaagagag | ctgggtagat | cagaaacttg | gtgacacctg | 120 |
| gctagcacag | agcaggctca | cttgtcttgg | tcccactacc | cagattcctg | cagacattgc | 180 |
| aaaccaaatg | aaggttgntg | aatgacccct | gtccccagcc | acttgttttg | gtatcatctg | 240 |
| ctctgcagtg | gaatgcctgt | gtgtttgagt | tcactctgca | tctgtatatt | tgagtataga | 300 |
| aaccgantca | agtgatctgt | gcatncagac | acactggggc | acctgancac | agaacaaatc | 360 |
| accttaacga | tctggaatga | aactgnganc | antgcccgcc | tgggtgggtc | tgganaaact | 420 |
| gccgncttct | tgttggacct | tggccgcacc | acct | | | 454 |

<210> SEQ ID NO 154
<211> LENGTH: 596
<212> TYPE: DNA
<213> ORGANISM: Homo sapien
<220> FEATURE:
<221> NAME/KEY: misc_feature
<222> LOCATION: (1)...(596)
<223> OTHER INFORMATION: n = A,T,C or G

<400> SEQUENCE: 154

| | | | | | | |
|---|---|---|---|---|---|---|
| agcgtggtcg | cggcccgang | gcggcctcct | gantganggg | aagggacgtg | ggggcggcca | 60 |
| cggcaggatt | aacctccatt | tcagctaatc | atgggagaga | ttaaagtctc | tcctgattat | 120 |
| aactggttta | naggtacagt | tccccttaaa | aagattattg | tggatgatga | tgacagtaag | 180 |
| atatggtcgc | tctatgacgc | gggccccga | agtatcaggt | gtcctctcat | attcctgccc | 240 |
| cctgtcagtg | gaactgcaga | tgtcttttc | cggcagattt | tggctctgac | tggatggggt | 300 |
| taccgggtta | tcgctttgca | gtatccagtt | tattgggacc | atctcgagtt | cttgtgatgg | 360 |
| attcacaaaa | cttttanacc | atttacaatt | ggataaagtt | catcttttg | gcgcttcttt | 420 |
| gggangcttt | ttggcccana | aatttgctga | atacactcac | aaatctccta | gaagccattc | 480 |

```
cctaatcctc tgcaattcct tcagngacac ctctatcttc aaccaacttg gactggaaac    540
agctttggct gatgcctgca tttatgctca aaaaatagtt cttggaaatt ttcatc       596
```

<210> SEQ ID NO 155
<211> LENGTH: 343
<212> TYPE: DNA
<213> ORGANISM: Homo sapien
<220> FEATURE:
<221> NAME/KEY: misc_feature
<222> LOCATION: (1)...(343)
<223> OTHER INFORMATION: n = A,T,C or G

<400> SEQUENCE: 155

```
ctcganttgg cncgcccggg cangtctgcc tggtttttga ccgngcgagc tatttagnct    60
ctggctctgt ttccggagct caaggnaaaa atcttgaana actcgagcag cttctgtgga   120
tagccttggg tacacatact gccgagcata gccaatgtac tttctcaata gctggtgggg   180
aatgggatct attgtttctc caggaaccac ctttagtctt tctgataatg gcttctcaga   240
aactacttca agtacggaag tatttgaatc ttgactatnc atacgagcta ctgtggcact   300
gctaatgggn tctctgctnt ccagctctta ttgcaatcac atg                     343
```

<210> SEQ ID NO 156
<211> LENGTH: 556
<212> TYPE: DNA
<213> ORGANISM: Homo sapien
<220> FEATURE:
<221> NAME/KEY: misc_feature
<222> LOCATION: (1)...(556)
<223> OTHER INFORMATION: n = A,T,C or G

<400> SEQUENCE: 156

```
tcgagcggcc cgcccgggca ggtctggcac cacncagatc gattaactgg ctcatctgat    60
ctcgtggccc ccaccctgga actgacttag cacaaaagga cacctcaatt ccttatgatt   120
tcatctccga cccaaccaat caacacccctt gactcactgg ccttccccct cccaccaaat   180
tatccttaaa aactctgatc cccgaatgct cagggagatc gatttgagta ctaataagac   240
tccagtctcc tgcacaagca gctctgtgta ctcttcctct attgcaattc ctgtcttgat   300
aaatcggctc tgtgtaggcg gcggaagaag tgaacctgtt gggcggttac cacctctgtc   360
gtgtgtgaca gttgntttga atctctaatt gctcagtaca gatccacatg caggttaagt   420
aagaagcttt tgaagaaaat ggaaagtctt aagtgatggc ttccaagaaa tcaaacctac   480
attaattagg gaacaacgga ctttacgtat cacaaatgaa gagactgacn aagtaaatca   540
acttggcctt ttctta                                                   556
```

<210> SEQ ID NO 157
<211> LENGTH: 333
<212> TYPE: DNA
<213> ORGANISM: Homo sapien
<220> FEATURE:
<221> NAME/KEY: misc_feature
<222> LOCATION: (1)...(333)
<223> OTHER INFORMATION: n = A,T,C or G

<400> SEQUENCE: 157

```
ggtccacaaa aatatatnaa ataagctgga tatataaaan caaacactta acatngncan    60
cattccttca gttattcaaa ctcactgata nctaacnggg agnagttggn attctggaag   120
acttcctaag ctaaaagtat atttacatat ttacaacaca ngtaaatata acngaagaac   180
```

```
tacttcaaat aangnngaaa ttccagaatt ctanagattt atagctatag ntnacaanta    240
tcaccaattg gtttgcaatc aanngnccag cactacttat gannaangtt taactannaa    300
accaaaaggg gagaaaacct ggnagggaaa nat                                333
```

<210> SEQ ID NO 158
<211> LENGTH: 629
<212> TYPE: DNA
<213> ORGANISM: Homo sapien
<220> FEATURE:
<221> NAME/KEY: misc_feature
<222> LOCATION: (1)...(629)
<223> OTHER INFORMATION: n = A,T,C or G

<400> SEQUENCE: 158

```
tcgagcggcc gcccgggcag gtctggtaca tttgtgcgag gtccggcact ctgttctcat    60
ccagtaagtg gtcgagccct ttctgcagaa ttgctgttaa atgttctcct aatagctgtt    120
tctccacaca agcaatcagt ggtttctgtg tgctgtggtc caagtaagtg attactctgt    180
ctccctcttc ttctaagcgt ttacttacat ggttaagata ttctggaacc tctctttcct    240
gcattaacct ttggccttcg gcagcatata agcaattagt ctcttccaaa aatttcagtt    300
caaatgaatc tttatacacc tgcaggtcag acagcatgcc caggnaggct ccgcaacagg    360
ctccggtcca cggcctcgcc gctcctctcg cgctcgatca gcagtaggat tccatcaatg    420
gttttactct gaaccatttt atcactaata atatgggttc taaacagttc taatcccata    480
tcccagatgg agggcagcgt ggagttctgc agcacatagg tgcggtccaa gaacaggaag    540
atgcttctga tcatgaatca tttgnctggc aatggtcctg ccagcacgtg gtaatctttc    600 tttaaaaat aaacccttat ctaaacgtc                                      629
```

<210> SEQ ID NO 159
<211> LENGTH: 629
<212> TYPE: DNA
<213> ORGANISM: Homo sapien
<220> FEATURE:
<221> NAME/KEY: misc_feature
<222> LOCATION: (1)...(629)
<223> OTHER INFORMATION: n = A,T,C or G

<400> SEQUENCE: 159

```
tcgagcggcc gcccgggcag gttctagagg ganaatctgg ctgatttggg aataaaatat    60
aatcgaatat tcaacaccat gaagataaat cttattttgg aaatctactg accttaatac    120
cccaagcttg ccctgaatac tttgattgga attggaatat atcaaaaaag gttagtatt    180 ttgttgtagt taggatacta aaaggatatt agttacccaa gagatccaat ttgtttttct    240
gatgaatagt gttcagtaaa atgaagcagt cttaagagtg actaataatt tcaaagtgat    300
ttttcgtcta ttcttaatat ttttttaatta ttttattttta agagttttat accttgagca    360
gatacaatga tccgctttag tgagaggaca atttctgatt gattgttttc tcttcaggcc    420
atctcacctc ttcattctct tgttacattt gaagcagttg atataatggg tttatacttt    480
aaaagataga catggtgcca tgaagtttgg ggaagttggg tgaattatcc cattctagtt    540
acagangagc tttccttaaa tgcccttttac ttctangttt ggtcaagaag tcattttctg    600
agtaaaagtt atttttcatat atgttgggg                                    629
```

<210> SEQ ID NO 160
<211> LENGTH: 519
<212> TYPE: DNA
<213> ORGANISM: Homo sapien
<220> FEATURE:
<221> NAME/KEY: misc_feature
<222> LOCATION: (1)...(519)
<223> OTHER INFORMATION: n = A,T,C or G

<400> SEQUENCE: 160

| | | | | | |
|---|---|---|---|---|---|
| tcgagcggcg | cgcccgggca | ggtctgctgg | gattaatgcc | aagttnttca | gccataaggt | 60 |
| agcgaaatct | agcagaatcc | agattacatc | cacttccaat | cacgcggtgt | ttgggtaatc | 120 |
| cacttagttt | ccagataaca | tacgtaagaa | tgtccactgg | gttggaaacc | acaattatga | 180 |
| tgcaatcagg | actgtacttg | acgatctgag | gaataatgaa | tttgaagaca | ttaacatttc | 240 |
| tctgcaccag | attgagccga | ctctcccctt | cttgctgacg | gactcctgca | gttaccacta | 300 |
| caatcttana | attgggcggg | tcacagaata | atctttatct | gccacaattt | taggtgctga | 360 |
| agaaataagc | tcccatgctg | cagatccatc | atttctnctt | taagcttatc | ttccaaaaca | 420 |
| tccacaagan | caangttcat | cagccagaga | ctttcccaga | atgctgatag | nacacgccat | 480 |
| accaacttgt | ccaacancca | ctacagcgat | cttattggt | | | 519 |

<210> SEQ ID NO 161
<211> LENGTH: 446
<212> TYPE: DNA
<213> ORGANISM: Homo sapien
<220> FEATURE:
<221> NAME/KEY: misc_feature
<222> LOCATION: (1)...(446)
<223> OTHER INFORMATION: n = A,T,C or G

<400> SEQUENCE: 161

| | | | | | |
|---|---|---|---|---|---|
| cgagnggccc | gcccgggcag | gtccagtaag | cntttnacga | tgatgggaaa | ggttatgcaa | 60 |
| ggtcccagcg | gtacaacgag | ctgtttctac | atcatttgta | ttctgcatgg | tacgtacaat | 120 |
| agcagacacc | atctgaggag | aacgcatgat | agcgtgtctg | gaagcttcct | ttttagaaag | 180 |
| ctgatggacc | ataactgcag | ccttattaac | caccacctgg | tcctcgtcat | ttagcagttt | 240 |
| tgtcagttca | gggattgcac | gtgtggcang | ttctgcatca | tcttgatagt | taatcaagtt | 300 |
| tacaactggc | atgtttcagc | atctgcgatg | ggctcagcaa | acgctggaca | ttantgggat | 360 |
| gagcagcatc | aaactgtgta | natgggatct | gcatgccctc | atctaatgtc | tcagggaaca | 420 |
| tagcagctcg | taccctctga | gctcga | | | | 446 |

<210> SEQ ID NO 162
<211> LENGTH: 354
<212> TYPE: DNA
<213> ORGANISM: Homo sapien
<220> FEATURE:
<221> NAME/KEY: misc_feature
<222> LOCATION: (1)...(354)
<223> OTHER INFORMATION: n = A,T,C or G

<400> SEQUENCE: 162

| | | | | | |
|---|---|---|---|---|---|
| agcgtngtcg | cggcccgang | tcctgggaag | cctttnttgc | tgagcctcac | agcctctgtc | 60 |
| aggcggctgc | ggatccagcg | gtccaccagg | ctctcatggc | ctccgggctg | ggaggngggt | 120 |
| gagggcacaa | aacccttccc | aaggccacga | anggcaaact | tggtggcatt | ccanagcttg | 180 |
| ttgcanaagt | ggcggnaacc | cagtatccgg | ttcacatcca | ggntgatgtc | acgaccctgg | 240 |
| gacatgtang | cacataatcc | aaaccggaga | gcatcggtgc | cacattcacg | aatccccgct | 300 |
| gggaagtcag | ctttctgccc | ttctttggcc | ttctccacct | cgctgggatc | cagg | 354 |

<210> SEQ ID NO 163

```
<211> LENGTH: 258
<212> TYPE: DNA
<213> ORGANISM: Homo sapien
<220> FEATURE:
<221> NAME/KEY: misc_feature
<222> LOCATION: (1)...(258)
<223> OTHER INFORMATION: n = A,T,C or G

<400> SEQUENCE: 163
tttttcncca agtcctcttg ccgngggatc tngactgcaa tttaagacac ttctaattag      60
ttatacccag gccctgcaaa attgctgggt ttatataata tattcttgct gcacgaagat     120
ttattattct gttggatgat tctattttaa ttntatttat tctggccaaa aaagaacctt    180
ctccgctcgt caagagangc caatntgtct tgaaggacaa gagaaagatg ctaacacaca    240
ctttcttctt cttgagga                                                   258

<210> SEQ ID NO 164
<211> LENGTH: 282
<212> TYPE: DNA
<213> ORGANISM: Homo sapien
<220> FEATURE:
<221> NAME/KEY: misc_feature
<222> LOCATION: (1)...(282)
<223> OTHER INFORMATION: n = A,T,C or G

<400> SEQUENCE: 164
ggaacatatt acttttaaat tacttgggtc aatgaaacat ttaataaaaa catttgcttc     60
tctatataat acgtatgtat aaaataagcc ttttcanaaa ctctggttct cataatcctc    120
tataaatcan atgatctgac ttctaagagg aacaaattac agnaagtttc atacattnat    180
gaatactggt agtactagag ganngacgct aaaccactct actaccactt gcggaactct    240
cacagggtaa atgacaaagc caatgactga ctctaaaaac aa                       282

<210> SEQ ID NO 165
<211> LENGTH: 462
<212> TYPE: DNA
<213> ORGANISM: Homo sapien
<220> FEATURE:
<221> NAME/KEY: misc_feature
<222> LOCATION: (1)...(462)
<223> OTHER INFORMATION: n = A,T,C or G

<400> SEQUENCE: 165
gcccgggcan gtcctgtaat cccagctact cangangctg agtcatgana atcgcctgaa     60
tccgggaggt agaggccgca gcgagcaaag attaagccac tgcactccag tctgggtgac    120
agagtgagaa tctgtctgtt gctcctctgg cattggtctg aaatgggttt gtagaacatg    180
ccacagaagg accagcanca gcaacaaatg gatttgtgga angcgtagct ccaaatggag    240
cangcacact tgatgaagca cgctgtgtct gtgcagangc aaccactggc actgttccaa    300
aaacattgct gctagcatta cttgtggaag tatacgcatt actggaggtg gctgcanaac    360
tgaaaacgct gtctagttct gccanagctg catacttgnc tgaanatgca cttgactgac    420
tgggaactga accacanaac caacaggacc tttacctgtg ga                       462

<210> SEQ ID NO 166
<211> LENGTH: 365
<212> TYPE: DNA
<213> ORGANISM: Homo sapien
<220> FEATURE:
<221> NAME/KEY: misc_feature
<222> LOCATION: (1)...(365)
<223> OTHER INFORMATION: n = A,T,C or G
```

<400> SEQUENCE: 166

```
cgtgggtcgc ggcncgangt ctgaaaccaa tccagaacta acatcagca cacaaaaaat    60
accaggatag atggaatcaa aagactctga agccaaaagg aggctaggga gagcaactga   120
acttagcaag ctgaggactt cagtgtccat catccgatcc tgccctgtaa caacaggtct   180
atatgataga gatattccat ctgagctgga ggccattatc cttagcaaac taacacagaa   240
cagaaaacca aatacatgtt ctcatttaga agtaggagct aaatgatgag aactcaagga   300
cacaaagaaa ggaacaacag acactggggc ctacttgagg gtggagggtg ggaggaggga   360
gaaga                                                              365
```

<210> SEQ ID NO 167
<211> LENGTH: 364
<212> TYPE: DNA
<213> ORGANISM: Homo sapien
<220> FEATURE:
<221> NAME/KEY: misc_feature
<222> LOCATION: (1)...(364)
<223> OTHER INFORMATION: n = A,T,C or G

<400> SEQUENCE: 167

```
agcgtggtcg cggcgcgang tccagcccta gcttgcctgt gactccgcct tcactgggtg    60
ctctctctaa aagttgctga ctctttactg tatctcccaa ttcccactcc attggttcca   120
taagggagg ggtgtctcac tcaacatggt gttcctggta ccaagaactg gctgacgaag   180
ctgggtgccg tggctcatgc ctgtaatccc agcacttttg ggaggccaag aagggcggat   240
cacctgaggt ctggagttca agatcagcct gaccaacatg atgaaaccaa gtctccacta   300
aaaatataaa acaattagcc aggcatggtg gtgggtgcct gnaatcccag ctactgggga   360
ngct                                                               364
```

<210> SEQ ID NO 168
<211> LENGTH: 447
<212> TYPE: DNA
<213> ORGANISM: Homo sapien
<220> FEATURE:
<221> NAME/KEY: misc_feature
<222> LOCATION: (1)...(447)
<223> OTHER INFORMATION: n = A,T,C or G

<400> SEQUENCE: 168

```
cccgggcagg tcaaaaccca aaacctttca ttttagccca aaccagctca tgattaggta    60
tacaaggata acagaaccag ttgtcaggac gagcatttga caagtaaaag caattcttgc   120
aaagctgcag ttcatccagc tcatggcatg tgtctttata tagcatcctc gcaatgtcag   180
cttgctcact gtctgctcca tagaaaatca cggtattgtg gagaagcaat tgggcatcag   240
cttttgaactc ttcataactt cggtatttcc cttcattcac tttctcttga atggtgggaa   300
cgtccacaga cctcggccgc gaccacgcta agcccgaatt ctgcagatat ccatcacact   360
ggcggccgtt cgagcatggc atctagaagg cccaattcgc ctatagngag tcgnattacc   420
aattcactgg ccgtcgnttt acaacgc                                      447
```

<210> SEQ ID NO 169
<211> LENGTH: 524
<212> TYPE: DNA
<213> ORGANISM: Homo sapien
<220> FEATURE:
<221> NAME/KEY: misc_feature
<222> LOCATION: (1)...(524)

<223> OTHER INFORMATION: n = A,T,C or G

<400> SEQUENCE: 169

```
cgantngcgc gcccgggcag gtctgagcag cctttctgnn tgctggacta ttgggattgg      60
gttcatccaa cagagactgt atggatgtta gaatggaaga cacatcatag gttggactcc     120
aacggttctg aagtatgtcc agacatatac taccatctgc atagactaag aacaaagaag    180
taggtacatt aaacgtaaca agaccactaa ggttttaaca ttatagacaa aacanaaata    240
gtcaaganta ctttgctttt gaagtttaaa gattcctatg ttgcttccca gttaactgcc    300
taaaaagata agncataacc accactagtg aaataatcan gatgatcaga gaatgtcana   360
tgtgatcagt ataaaactgg angatattna gtgtcatcct ttggaaaagg ctgccctatn    420
atccaggaaa tcanaaacat tnttgaacag ggncccctagc tatccacaga catgtgggaa    480
attcattccc caaatngtag gctggatccc ctatctgaaa taac                      524
```

<210> SEQ ID NO 170
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 170

```
tcgancggcn cgcccgggca ggtgacaaac ctgttattga agatgttggt tctgatgagg      60
aanaanatca aagggatgg tgacaagaan aanaanaaga agattaagga aaagtacatc    120
gatcaagaag agctcaacaa aacaaagccc atctggacca gaaatcccga cgatattact    180
aatgangagt acggagaatt ctataanagc ttgaccaatg actgggaaga tcacttggca    240
gtgaagcatt tttcagttga nggacagttg gaattcagag ccccttctatn tgtcccacga    300
cgtgctcctt tgatctgtt tgananccaga aa                                   332
```

<210> SEQ ID NO 171
<211> LENGTH: 334
<212> TYPE: DNA
<213> ORGANISM: Homo sapien
<220> FEATURE:
<221> NAME/KEY: misc_feature
<222> LOCATION: (1)...(334)
<223> OTHER INFORMATION: n = A,T,C or G

<400> SEQUENCE: 171

```
cgagnggcnc gcccgggcag gtctgttgat agcgacttaa cagaaaagtc tagacaaaca      60
taagcataaa aaattacagt ctttctaccc ttgggaatgg ggagaaaaag gaatctctac    120
cccaagacca gaaataataa gtcctgtttc tggtcctgaa catccagaat tatgcgaggct    180
ttggcctgac accacattan aatttggtct ggaaatcaaa ctttaganac angagatcgt    240
aagccatttt atactatcga cctaaattcc agtctaacgg ttcctttaca aagttgcgga    300
aagccctctt atatgctagc tgtaggaaat atag                                  334
```

<210> SEQ ID NO 172
<211> LENGTH: 439
<212> TYPE: DNA
<213> ORGANISM: Homo sapien
<220> FEATURE:
<221> NAME/KEY: misc_feature
<222> LOCATION: (1)...(439)
<223> OTHER INFORMATION: n = A,T,C or G

<400> SEQUENCE: 172

```
agcgtggtcg cggcccgang tctgcctata aaactagact tctgacgctg ggctccagct      60
tcattctcac aggtcatcat cctcatccgg gagagcagtt gtctgagcaa cctctaagtc     120
gtgctcatac tgtgctgcca aagctgggtc catgacaact tctggtgggg cgagagcagg     180
catggcaaca aattccaagt tagggtctcc aatgagcttc ctagcaagcc agaggaaggg     240
cttttcaaag ttgtagttac ttttggcaga aatgtcgtag tactgaagat tcttctttcg     300
gtggaagaca atggatttcg ccttcacttt ctgccttaat atccactttg gtgccacaca     360
acacaatggg gatgntttca cacacttngn accanatctc tatgccagnt aggccatttt     420
ggaagnactt cganggtac                                                  439
```

<210> SEQ ID NO 173
<211> LENGTH: 599
<212> TYPE: DNA
<213> ORGANISM: Homo sapien
<220> FEATURE:
<221> NAME/KEY: misc_feature
<222> LOCATION: (1)...(599)
<223> OTHER INFORMATION: n = A,T,C or G

<400> SEQUENCE: 173

```
cgatnggccg cccgggcagg tcctgtaaaa naggaaattc agacatcgta cgactcgtaa      60
ttaatgtgg agctgactgc aatattttgt caaagcacca gaatagtgcc ctgcactttg     120
cgaagcagtc taacaatgtg cttgtgtacg acttgctgaa gaaccattta gagacacttt     180
caagagtagc agaagagaca ataaaggatt actttgaagc tcgccttgct ctgctagaac     240
cagtttttcc aatcgcatgt catcgactct gtgagggtcc agatttttca acagatttca     300
attaccaacc cccacagaac ataccagaag gctctggcat cctgctgttt atcttccatg     360
caaacttttt gggtaaagaa gttattgctc ggctctgtgg accgtgtagt gtacaagctg     420
tagttctgaa tgataaattt cagcttcctg tttttctggg tctcgctctg ttgtccaggc     480
tggagtgcag tggcgcggat tacagctcac tggagtcttg acttcccagg cacaagcaat     540
cctcccacct cagcctccta actacctggg actaaaaatg caccgccacc acattccgg     599
```

<210> SEQ ID NO 174
<211> LENGTH: 458
<212> TYPE: DNA
<213> ORGANISM: Homo sapien
<220> FEATURE:
<221> NAME/KEY: misc_feature
<222> LOCATION: (1)...(458)
<223> OTHER INFORMATION: n = A,T,C or G

<400> SEQUENCE: 174

```
tcgatttggc cgcccgggca ggtccatgcn gnttntgccc attcccatgg ngcccgacaa      60
ncccatcccc gaggccgaca tccccatgtt catgttcatg cccaccatgc cctggctcat     120
ccctgcgctg ttccccagag gggccattcc catggtgccc gtcattacac gggcatgtt     180
cataggcatg ggtcccccca ggagagggtt agnttgaggc cggacaggaa gcatgtttga     240
tggagaactg aggttcacag nctccaaaac tttgagtcat cacattcata ggctgctgca     300
tattctgtct gctgaatcca ttgtatncag tgatggcctg ctgggntttt ggaaggctng     360
cataccaggt agtaagntcg tctaggctga tgtttacacc tggggtcaga ccaagtanga     420
gggcaaggtt ttgctgactg attttctgga cccatatc                             458
```

<210> SEQ ID NO 175
<211> LENGTH: 1206
<212> TYPE: DNA
<213> ORGANISM: Homo sapien

<400> SEQUENCE: 175

```
ggcacgagga agttttgtgt actgaaaaag aaactgtcag aagcaaaaga aataaaatca    60
cagttagaga accaaaaagt taaatgggaa caagagctct gcagtgtgag gtttctcaca   120
ctcatgaaaa tgaaaattat ctcttacatg aaaattgcat gttgaaaaag gaaattgcca   180
tgctaaaact ggaaatagcc acactgaaac accaatacca ggaaaaggaa ataaaatact   240
ttgaggacat taagatttta aaagaaaaga atgctgaact tcagatgacc ctaaaactga   300
aagaggaatc attaactaaa agggcatctc aatatagtgg gcagcttaaa gttctgatag   360
ctgagaacac aatgctcact tctaaattga aggaaaaaca agacaaagaa atactagagg   420
cagaaattga atcacaccat cctagactgg cttctgctgt acaagaccat gatcaaattg   480
tgacatcaag aaaaagtcaa gaacctgctt ccacattgc aggagatgct tgtttgcaaa   540
gaaaaatgaa tgttgatgtg agtagtacga tatataacaa tgaggtgctc catcaaccac   600
tttctgaagc tcaaaggaaa tccaaaagcc taaaaattaa tctcaattat gccggagatg   660
ctctaagaga aaatacattg gtttcagaac atgcacaaag agaccaacgt gaaacacagt   720
gtcaaatgaa ggaagctgaa cacatgtatc aaaacgaaca agataatgtg aacaaacaca   780
ctgaacagca ggagtctcta gatcagaaat tatttcaact acaaagcaaa aatatgtggc   840
ttcaacagca attagttcat gcacataaga agctgacaa caaaagcaag ataacaattg   900
atattcattt tcttgagagg aaaatgcaac atcatctcct aaaagagaaa aatgaggaga   960
tatttaatta caataaccat ttaaaaaacc gtatatatca atatgaaaaa gagaaagcag  1020
aaacagaagt tatataatag tataacactg ccaaggagcg gattatctca tcttcatcct  1080
gtaattccag tgtttgtcac gtggttgttg aataaatgaa taaagaatga gaaaaccaga  1140
agctctgata cataatcata atgataatta tttcaatgca caactacggg tggtgctgct  1200
cgtgcc                                                             1206
```

<210> SEQ ID NO 176
<211> LENGTH: 317
<212> TYPE: PRT
<213> ORGANISM: Homo sapien

<400> SEQUENCE: 176

```
Met Gly Thr Arg Ala Leu Gln Cys Glu Val Ser His Thr His Glu Asn
 1               5                  10                  15

Glu Asn Tyr Leu Leu His Glu Asn Cys Met Leu Lys Lys Glu Ile Ala
            20                  25                  30

Met Leu Lys Leu Glu Ile Ala Thr Leu Lys His Gln Tyr Gln Glu Lys
        35                  40                  45

Glu Asn Lys Tyr Phe Glu Asp Ile Lys Ile Leu Lys Glu Lys Asn Ala
    50                  55                  60

Glu Leu Gln Met Thr Leu Lys Leu Lys Glu Glu Ser Leu Thr Lys Arg
65                  70                  75                  80

Ala Ser Gln Tyr Ser Gly Gln Leu Lys Val Leu Ile Ala Glu Asn Thr
                85                  90                  95

Met Leu Thr Ser Lys Leu Lys Lys Gln Asp Lys Glu Ile Leu Glu
            100                 105                 110
```

```
Ala Glu Ile Glu Ser His His Pro Arg Leu Ala Ser Ala Val Gln Asp
        115                 120                 125
His Asp Gln Ile Val Thr Ser Arg Lys Ser Gln Glu Pro Ala Phe His
130                 135                 140
Ile Ala Gly Asp Ala Cys Leu Gln Arg Lys Met Asn Val Asp Val Ser
145                 150                 155                 160
Ser Thr Ile Tyr Asn Asn Glu Val Leu His Gln Pro Leu Ser Glu Ala
                165                 170                 175
Gln Arg Lys Ser Lys Ser Leu Lys Ile Asn Leu Asn Tyr Ala Gly Asp
            180                 185                 190
Ala Leu Arg Glu Asn Thr Leu Val Ser Glu His Ala Gln Arg Asp Gln
        195                 200                 205
Arg Glu Thr Gln Cys Gln Met Lys Glu Ala Glu His Met Tyr Gln Asn
    210                 215                 220
Glu Gln Asp Asn Val Asn Lys His Thr Glu Gln Gln Glu Ser Leu Asp
225                 230                 235                 240
Gln Lys Leu Phe Gln Leu Gln Ser Lys Asn Met Trp Leu Gln Gln Gln
                245                 250                 255
Leu Val His Ala His Lys Lys Ala Asp Asn Lys Ser Lys Ile Thr Ile
            260                 265                 270
Asp Ile His Phe Leu Glu Arg Lys Met Gln His His Leu Leu Lys Glu
        275                 280                 285
Lys Asn Glu Glu Ile Phe Asn Tyr Asn Asn His Leu Lys Asn Arg Ile
    290                 295                 300
Tyr Gln Tyr Glu Lys Leu Lys Ala Glu Thr Glu Val Ile
305                 310                 315

<210> SEQ ID NO 177
<211> LENGTH: 20
<212> TYPE: DNA
<213> ORGANISM: Artificial Sequence
<220> FEATURE:
<223> OTHER INFORMATION: Made in the Lab

<400> SEQUENCE: 177
ccaatcatct ccacaggagc                                                     20

<210> SEQ ID NO 178
<211> LENGTH: 1665
<212> TYPE: DNA
<213> ORGANISM: Homo sapien

<400> SEQUENCE: 178
gcaaactttc aagcagagcc tcccgagaag ccatctgcct tcgagcctgc cattgaaatg        60
caaaagtctg ttccaaataa agccttggaa ttgaagaatg aacaaacatt gagagcagat       120
cagatgttcc cttcagaatc aaaacaaaag aaggttgaag aaaattcttg ggattctgag       180
agtctccgtg agactgtttc acagaaggat gtgtgtgtac ccaaggctac acatcaaaaa       240
gaaatggata aaataagtgg aaaattagaa gattcaacta gcctatcaaa aatcttggat       300
acagttcatt cttgtgaaag agcaagggaa cttcaaaaag atcactgtga caacgtaca        360 ggaaaaatgg aacaaatgaa aaagaagttt tgtgtactga aaagaaact gtcagaagca       420 aagaaataa aatcacagtt agagaaccaa aaagttaaat gggaacaaga gctctgcagt       480
gtgaggtttc tcacactcat gaaatgaaa attatctctt acatgaaaat tgcatgttga       540
aaaaggaaat tgccatgcta aaactggaaa tagccacact gaaacaccaa taccaggaaa       600
```

-continued

```
aggaaaataa atactttgag gacattaaga ttttaaaaga aaagaatgct gaacttcaga    660
tgaccctaaa actgaaagag gaatcattaa ctaaaagggc atctcaatat agtgggcagc    720
ttaaagttct gatagctgag aacacaatgc tcacttctaa attgaaggaa aaacaagaca    780
aagaaatact agaggcagaa attgaatcac accatcctag actggcttct gctgtacaag    840
accatgatca aattgtgaca tcaagaaaaa gtcaagaacc tgctttccac attgcaggag    900
atgcttgttt gcaaagaaaa atgaatgttg atgtgagtag tacgatatat aacaatgagg    960
tgctccatca accactttct gaagctcaaa ggaaatccaa aagcctaaaa attaatctca   1020
attatgccgg agatgctcta agagaaaata cattggtttc agaacatgca caaagagacc   1080
aacgtgaaac acagtgtcaa atgaaggaag ctgaacacat gtatcaaaac gaacaagata   1140
atgtgaacaa acacactgaa cagcaggagt ctctagatca gaaattattt caactacaaa   1200
gcaaaaatat gtggcttcaa cagcaattag ttcatgcaca taagaaagct gacaacaaaa   1260
gcaagataac aattgatatt cattttcttg agaggaaaat gcaacatcat ctcctaaaag   1320
agaaaaatga ggagatattt aattacaata accatttaaa aaaccgtata tatcaatatg   1380
aaaaagagaa agcagaaaca gaaaactcat gagagacaag cagtaagaaa cttcttttgg   1440
agaaacaaca gaccagatct ttactcacaa ctcatgctag gaggccagtc ctagcattac   1500
cttatgttga aaatcttacc aatagtctgt gtcaacagaa tacttatttt agaagaaaaa   1560
ttcatgattt cttcctgaag cctgggcgac agagcgagac tctgtctcaa aaaaaaaaa   1620 aaaaaagaa agaaagaaat gcctgtgctt acttcgcttc ccagg                   1665
```

<210> SEQ ID NO 179
<211> LENGTH: 179
<212> TYPE: PRT
<213> ORGANISM: Homo sapien

<400> SEQUENCE: 179

```
Ala Asn Phe Gln Ala Glu Pro Pro Glu Lys Pro Ser Ala Phe Glu Pro
 1               5                  10                  15

Ala Ile Glu Met Gln Lys Ser Val Pro Asn Lys Ala Leu Glu Leu Lys
            20                  25                  30

Asn Glu Gln Thr Leu Arg Ala Asp Gln Met Phe Pro Ser Glu Ser Lys
        35                  40                  45

Gln Lys Lys Val Glu Glu Asn Ser Trp Asp Ser Glu Ser Leu Arg Glu
    50                  55                  60

Thr Val Ser Gln Lys Asp Val Cys Val Pro Lys Ala Thr His Gln Lys
65                  70                  75                  80

Glu Met Asp Lys Ile Ser Gly Lys Leu Glu Asp Ser Thr Ser Leu Ser
                85                  90                  95

Lys Ile Leu Asp Thr Val His Ser Cys Glu Arg Ala Arg Glu Leu Gln
            100                 105                 110

Lys Asp His Cys Glu Gln Arg Thr Gly Lys Met Glu Gln Met Lys Lys
        115                 120                 125

Lys Phe Cys Val Leu Lys Lys Leu Ser Glu Ala Lys Glu Ile Lys
    130                 135                 140

Ser Gln Leu Glu Asn Gln Lys Val Lys Trp Glu Gln Glu Leu Cys Ser
145                 150                 155                 160

Val Arg Phe Leu Thr Leu Met Lys Met Lys Ile Ile Ser Tyr Met Lys
                165                 170                 175

Ile Ala Cys
```

<210> SEQ ID NO 180
<211> LENGTH: 1681
<212> TYPE: DNA
<213> ORGANISM: Homo sapien

<400> SEQUENCE: 180

```
gatacagtca ttcttgtgaa agagcaaggg aacttcaaaa agatcactgt gaacaacgta      60
caggaaaaat ggaacaaatg aaaagaagt tttgtgtact gaaaaagaaa ctgtcagaag     120
caaaagaaat aaaatcacag ttagagaacc aaaaagttaa atgggaacaa gagctctgca     180
gtgtgagatt gactttaaac caagaagaag agaagagaag aaatgccgat atattaaatg     240
aaaaaattag ggaagaatta ggaagaatcg aagagcagca taggaaagag ttagaagtga     300
aacaacaact tgaacaggct ctcagaatac aagatataga attgaagagt gtagaaagta     360
atttgaatca ggtttctcac actcatgaaa atgaaaatta tctcttacat gaaaattgca     420
tgttgaaaaa ggaaattgcc atgctaaaac tggaaatagc cacactgaaa caccaatacc     480
aggaaaagga aataaaatac tttgaggaca ttaagatttt aaaagaaaag aatgctgaac     540
ttcagatgac cctaaaactg aaagaggaat cattaactaa aagggcatct caatatagtg     600
ggcagcttaa agttctgata gctgagaaca caatgctcac ttctaaattg aaggaaaaac     660
aagacaaaga aatactagag gcagaaattg aatcacacca tcctagactg gcttctgctg     720
tacaagacca tgatcaaatt gtgacatcaa gaaaagtca agaacctgct ttccacattg     780
caggagatgc ttgtttgcaa agaaaatga atgttgatgt gagtagtacg atatataaca     840
atgaggtgct ccatcaacca ctttctgaag ctcaaaggaa atccaaaagc ctaaaaatta     900
atctcaatta tgccggagat gctctaagag aaaatacatt ggtttcagaa catgcacaaa     960
gagaccaacg tgaaacacag tgtcaaatga aggaagctga acacatgtat caaaacgaac    1020
aagataatgt gaacaaacac actgaacagc aggagtctct agatcagaaa ttatttcaac    1080
tacaaagcaa aaatatgtgg cttcaacagc aattagttca tgcacataag aaagctgaca    1140
acaaaagcaa gataacaatt gatattcatt tccttgagag gaaatgcaa catcatctcc    1200
taaaagagaa aaatgaggag atatttaatt acaataacca tttaaaaaac cgtatatatc    1260
aatatgaaaa agagaaagca gaaacagaaa actcatgaga gacaagcagt aagaaacttc    1320
ttttggagaa acaacagacc agatctttac tcacaactca tgctaggagg ccagtcctag    1380
cattaccttta tgttgaaaaa tcttaccaat agtctgtgtc aacagaatac ttatttaga    1440
agaaaaattc atgatttctt cctgaagcct acagacataa aataacagtg tgaagaatta    1500
cttgttcacg aattgcataa aagctgccca ggatttccat ctaccctgga tgatgccgga    1560
gacatcattc aatccaacca gaatctcgct ctgtcactca ggctggagtg cagtgggcgc    1620
aatctcggct cactgcaact ctgcctccca ggttcacgcc attctctggc acagcctccc    1680
g                                                                   1681
```

<210> SEQ ID NO 181
<211> LENGTH: 432
<212> TYPE: PRT
<213> ORGANISM: Homo sapien

<400> SEQUENCE: 181

```
Asp Thr Val His Ser Cys Glu Arg Ala Arg Glu Leu Gln Lys Asp His
 1               5                  10                  15

Cys Glu Gln Arg Thr Gly Lys Met Glu Gln Met Lys Lys Lys Phe Cys
             20                  25                  30
```

```
            Val Leu Lys Lys Lys Leu Ser Glu Ala Lys Glu Ile Lys Ser Gln Leu
                         35                  40                  45

Glu Asn Gln Lys Val Lys Trp Glu Gln Glu Leu Cys Ser Val Arg Leu
                     50                  55                  60

Thr Leu Asn Gln Glu Glu Lys Arg Arg Asn Ala Asp Ile Leu Asn
             65                  70                  75                  80

Glu Lys Ile Arg Glu Glu Leu Gly Arg Ile Glu Glu Gln His Arg Lys
                             85                  90                  95

Glu Leu Glu Val Lys Gln Gln Leu Glu Gln Ala Leu Arg Ile Gln Asp
                        100                 105                 110

Ile Glu Leu Lys Ser Val Glu Ser Asn Leu Asn Gln Val Ser His Thr
                        115                 120                 125

His Glu Asn Glu Asn Tyr Leu Leu His Glu Asn Cys Met Leu Lys Lys
                        130                 135                 140

Glu Ile Ala Met Leu Lys Leu Glu Ile Ala Thr Leu Lys His Gln Tyr
            145                 150                 155                 160

Gln Glu Lys Glu Asn Lys Tyr Phe Glu Asp Ile Lys Ile Leu Lys Glu
                            165                 170                 175

Lys Asn Ala Glu Leu Gln Met Thr Leu Lys Leu Lys Glu Glu Ser Leu
                        180                 185                 190

Thr Lys Arg Ala Ser Gln Tyr Ser Gly Gln Leu Lys Val Leu Ile Ala
                        195                 200                 205

Glu Asn Thr Met Leu Thr Ser Lys Leu Lys Glu Lys Gln Asp Lys Glu
                        210                 215                 220

Ile Leu Glu Ala Glu Ile Glu Ser His His Pro Arg Leu Ala Ser Ala
            225                 230                 235                 240

Val Gln Asp His Asp Gln Ile Val Thr Ser Arg Lys Ser Gln Glu Pro
                            245                 250                 255

Ala Phe His Ile Ala Gly Asp Ala Cys Leu Gln Arg Lys Met Asn Val
                        260                 265                 270

Asp Val Ser Ser Thr Ile Tyr Asn Asn Glu Val Leu His Gln Pro Leu
                        275                 280                 285

Ser Glu Ala Gln Arg Lys Ser Lys Ser Leu Lys Ile Asn Leu Asn Tyr
                        290                 295                 300

Ala Gly Asp Ala Leu Arg Glu Asn Thr Leu Val Ser Glu His Ala Gln
            305                 310                 315                 320

Arg Asp Gln Arg Glu Thr Gln Cys Gln Met Lys Glu Ala Glu His Met
                            325                 330                 335

Tyr Gln Asn Glu Gln Asp Asn Val Asn Lys His Thr Glu Gln Gln Glu
                        340                 345                 350

Ser Leu Asp Gln Lys Leu Phe Gln Leu Gln Ser Lys Asn Met Trp Leu
                        355                 360                 365

Gln Gln Gln Leu Val His Ala His Lys Lys Ala Asp Asn Lys Ser Lys
                        370                 375                 380

Ile Thr Ile Asp Ile His Phe Leu Glu Arg Lys Met Gln His His Leu
            385                 390                 395                 400

Leu Lys Glu Lys Asn Glu Glu Ile Phe Asn Tyr Asn Asn His Leu Lys
                            405                 410                 415

Asn Arg Ile Tyr Gln Tyr Glu Lys Glu Lys Ala Glu Thr Glu Asn Ser
                        420                 425                 430

<210> SEQ ID NO 182
            <211> LENGTH: 511
```

```
<212> TYPE: DNA
<213> ORGANISM: Homo sapiens

<400> SEQUENCE: 182
gaagtttcat gaggtttagc ttttctgggc tggggagtgg agagaaagaa gttgcagggc     60
ttacaggaaa tcccagagcc tgaggttttc tcccagattt gagaactcta gattctgcat    120
cattatcttt gagtctatat tctcttgggc tgtaagaaga tgaggaatgt aataggtctg    180
ccccaagcct ttcatgcctt ctgtaccaag cttgtttcct tgtgcatcct tcccaggctc    240
tggctgcccc ttattggaga atgtgattte caagacaatc aatccacaag tgtctaagac    300
tgaatacaaa gaacttcttc aagagttcat agacgacaat gccactacaa atgccataga    360
tgaattgaag gaatgttttc ttaaccaaac ggatgaaact ctgagcaatg ttgaggtgtt    420
tatgcaatta atatatgaca gcagtctttg tgatttattt taactttctg caagaccttt    480
ggctcacaga actgcagggt atggtgagaa a                                   511

<210> SEQ ID NO 183
<211> LENGTH: 260
<212> TYPE: DNA
<213> ORGANISM: Homo sapiens

<400> SEQUENCE: 183
cacctcgcgg ttcagctcct ctgtcttggt gaagaaccat tcctcggcat ccttgcggtt     60
cttctctgcc atcttctcat actggtcacg catctcgttc agaatgcggc tcaggtccac    120
gccaggtgca gcgtccatct ccacattgac atctccaccc acctggcctc tcagggcatt    180
catctcctcc tcgtggttct tcttcaggta ggccagctcc tccttcaggc tctcaatctg    240
catctccagg tcagctctgg                                                260

<210> SEQ ID NO 184
<211> LENGTH: 461
<212> TYPE: DNA
<213> ORGANISM: Homo sapiens

<400> SEQUENCE: 184
gtctgatggg agaccaaaga atttgcaagt ggatggtttg gtatcactgt aaataaaaag     60
agggcctttt ctagctgtat gactgttact tgaccttctt tgaaaagcat tcccaaaatg    120
ctctatttta gatagattaa cattaaccaa cataattttt tttagatcga gtcagcataa    180
atttctaagt cagcctctag tcgtggttca tctctttcac ctgcatttta tttggtgttt    240
gtctgaagaa aggaaagagg aaagcaaata cgaattgtac tatttgtacc aaatctttgg    300
gattcattgg caaataattt cagtgtggtg tattattaaa tagaaaaaaa aaattttgtt    360
tcctaggttg aaggtctaat tgataccgtt tgacttatga tgaccattta tgcactttca    420
aatgaatttg ctttcaaaat aaatgaagag cagacctcgg c                        461

<210> SEQ ID NO 185
<211> LENGTH: 531
<212> TYPE: DNA
<213> ORGANISM: Homo sapiens

<400> SEQUENCE: 185
tctgatttta tttccttctc aaaaaaagtt atttacagaa ggtatatatc aacaatctga     60
caggcagtga acttgacatg attagctggc atgattttt cttttttttc ccccaaacat    120 tgttttttgtg gccttgaatt ttaagacaaa tattctacac ggcatattgc acaggatgga    180
```

```
tggcaaaaaa aagtttaaaa acaaaaaccc ttaacggaac tgcctaaaaa aggcagacgt      240
cctagtgcct gtcatgttat attaaacata catacacaca atctttttgc ttattataat      300
acagacttaa atgtacaaag atgttttcca ctttttttcaa tttttaaaca caacagctat     360
aaacctgaac acatatgcta tcatcatgcc ataagactaa aacaattata tttagcgaca      420
agtagaaagg attaaatagt caaatacaag aatgaaaaac gcagtacata gtgtcgcgaa      480
ctcaaatcgg catttagata gatccagtgg tttaaacggc acgttttgc t                531
```

<210> SEQ ID NO 186
<211> LENGTH: 441
<212> TYPE: DNA
<213> ORGANISM: Homo sapiens
<400> SEQUENCE: 186

```
cattcctttc ctcgcgttgg ggtttctctg tgtcagcgag cctcggtaca ctgatttccg      60
atcaaaagaa tcatcatctt taccttgact tttcagggaa ttactgaact ttcttctcag      120
aagatagggc acagccattg ccttggcctc acttgaaggg tctgcatttg ggtcctctgg      180
tctcttgcca agtttcccaa ccactcgagg gagaaatatc gggaggtttg acttcctccg      240 gggcttccc gagggcttca ccgtgagccc tgcggccctc agggctgcaa tcctggattc       300
aatgtctgaa acctcgctct ctgcctgctg gacttctgag gccgtcactg ccactctgtc      360
ctccagctct gacagctcct catctgtggt cctgttgtac tggacggggt ccccagggtc      420
ctggggcttt ttttcctgtc t                                                441
```

<210> SEQ ID NO 187
<211> LENGTH: 371
<212> TYPE: DNA
<213> ORGANISM: Homo sapiens
<400> SEQUENCE: 187

```
aaaagtgaat gagtaactat tatattgttg gcaataataa gttgcaaaat catcaggctg      60
caggctgctg atggtgagag tgaactctgt cccagatcca ctgccgctga accttgatgg      120
gaccccagat tctaaactag acgccttatg gatcaggagc tttggggctt ccctggtttt      180
ctgttgatac caggccaacc aactactaac actctgactg gcccggcaag tgatggtgac      240
tctgtctcct acagttgcag acagggtgga aggagactgg gtcatctgga tgtcacattt      300
ggcacctggg agccagagca gcaggagccc caggagctga gcggggaccc tcatgtccat      360
gctgagtcct g                                                           371
```

<210> SEQ ID NO 188
<211> LENGTH: 226
<212> TYPE: DNA
<213> ORGANISM: Homo sapiens
<400> SEQUENCE: 188

```
ggtatataaa ttgagatgcc cccccaggcc agcaaatgtt cctttttgtt caaagtctat      60
ttttattcct tgatattttt ctttttttttt tttttgtgga tggggacttg tgaattttc      120 taaaggtgct atttaacatg ggaggagagc gtgtgcggct ccagcccagc ccgctgctca      180
ctttccaccc tctctccacc tgcctctggc ttctcaggac ctgccc                     226
```

<210> SEQ ID NO 189
<211> LENGTH: 391
<212> TYPE: DNA
<213> ORGANISM: Homo sapiens

```
<220> FEATURE:
<221> NAME/KEY: misc_feature
<222> LOCATION: (1)...(391)
<223> OTHER INFORMATION: n=A,T,C or G

<400> SEQUENCE: 189
tgggtgaagt ttattctgtt ttcacatcta ggttgttggg ganagtgata gacaaagttc      60
tggattctgg gcatcgtcgg cgcatgcttg taatcctact tgggaggttg anacaggaga    120
cctcggccgc naccacgcta agggcgaatt ctgcanatat ccatcacact ggcggccgct    180
cgagcatgca tctanagggc ccaattcncc ctatagtgag ncgtattaca attcactggc    240
cgtcgtttta caacgtcgtg actgggaaaa ccctggcgtt acccaactta atcgccttgc    300
agcacatccc cctttcncca gctggcttaa tancgaagag gcccgcaccg atcgcccttc    360
ccaacanttg cgcagcctga atggcgaatg g                                   391

<210> SEQ ID NO 190
<211> LENGTH: 501
<212> TYPE: DNA
<213> ORGANISM: Homo sapiens

<400> SEQUENCE: 190
catcttggcc tttttgagct gtttccgctt cttctcatcc cggtcactgt caccctcatt      60
actggaggag ctggcagagg cgttgctgtc aaactcctct gccacatctt cctcctcttc    120
acctgggttg aatgactcat cggtttcttc tcctgagtca tcgctgctgt cattggcatt    180
ctcctcccgg atcttgcctt cctccttcat cctctccaag taggcatcat gctggtcctc    240
atcagagtca gcatattcat cgtagcttgg gttcatgccc tctttcaatc ctcggttttt    300
gatgttgagc tttttcgcgt tgacaaaatc aaacagtttc ccgtactcct ccctctcaat    360
gctgctgaag gtatactgag tgccctgctt ggtctcaatt tcaaagtcaa aggaacgagt    420
agtagtggta ccacgagcaa agttgacaaa ggagatctca tcgaagcgga tgtgcacagg    480
tggcttgtgg acgtagatga a                                              501

<210> SEQ ID NO 191
<211> LENGTH: 241
<212> TYPE: DNA
<213> ORGANISM: Homo sapiens
<220> FEATURE:
<221> NAME/KEY: misc_feature
<222> LOCATION: (49)
<223> OTHER INFORMATION: n=A,T,C or G

<400> SEQUENCE: 191
ggaaaaactg tgaaaatat atctgaattt attaagtaca gtataaaana gggttgtggc       60
aacagaaagt aaaaactaac atggattgct ataaatatgc tgaagcctag ttgttcaaat    120
gatacaattc tctcatgcta ctctaaagtt tataaagaaa aaggatttac actttacaca    180
ctgtacacaa aaggaatacc ttctgagagc cagggagtgg ggaaaggga aggagacttg    240 a                                                                    241

<210> SEQ ID NO 192
<211> LENGTH: 271
<212> TYPE: DNA
<213> ORGANISM: Homo sapiens
<220> FEATURE:
<221> NAME/KEY: misc_feature
<222> LOCATION: (1)...(271)
<223> OTHER INFORMATION: n=A,T,C or G
```

<400> SEQUENCE: 192

```
tggtcntgga ttcacanata aantanatcg actaaaactg gcagaaattg tgaagcaggt      60
gatagaagan caaaccacgt cccacgaatc ccaataatga cagcttcaga ctttgctttt     120
ttaacaattt gaaaaattat tctttaatgt ataaagtaat tttatgtaaa ttaataaatc     180
ataatttcat ttccacattg attaaagctg ctgtatagat ttagggngca ggacttaata     240
atagnggaaa tgaaattatg atttattaat c                                   271
```

<210> SEQ ID NO 193
<211> LENGTH: 351
<212> TYPE: DNA
<213> ORGANISM: Homo sapiens

<400> SEQUENCE: 193

```
agtcgaggcg ctgatcccta aaatggcgaa catgtgtttt catcatttca gccaaagtcc      60
taacttcctg tgcctttcct atcacctcga gaagtaatta tcagttggtt tggattttg     120
gaccaccgtt cagtcatttt gggttgccgt gctcccaaaa catttaaat gaaagtattg     180
gcattcaaaa agacagcaga caaatgaaa gaaaatgaga gcagaaagta agcatttcca     240
gcctatctaa tttctttagt tttctatttg cctccagtgc agtccatttc ctaatgtata     300
ccagcctact gtactattta aaatgctcaa tttcagcacc gatggacctg c             351
```

<210> SEQ ID NO 194
<211> LENGTH: 311
<212> TYPE: DNA
<213> ORGANISM: Homo sapiens

<400> SEQUENCE: 194

```
ctgagacaca gaggcccact gcgaggggga cagtggcggt gggactgacc tgctgacagt      60
caccctccct ctgctgggat gaggtccagg agccaactaa acaatggca gaggagacat     120
ctctggtgtt cccaccaccc tagatgaaaa tccacagcac agacctctac cgtgtttctc     180
ttccatccct aaaccacttc cttaaaatgt ttggatttgc aaagccaatt tggggcctgt     240
ggagcctggg gttggatagg gccatggctg gtcccccacc atacctcccc tccacatcac     300
tgacacagac c                                                         311
```

<210> SEQ ID NO 195
<211> LENGTH: 381
<212> TYPE: DNA
<213> ORGANISM: Homo sapiens

<400> SEQUENCE: 195

```
tgtcagagtg gcactggtag aagttccagg aaccctgaac tgtaagggtt cttcatcagt      60
gccaacagga tgcatgaaa tgatgtactc agaagtgtcc tggaatgggg cccatgagat     120
ggttgtctga gagagagctt cttgtcctgt cttttccctt ccaatcaggg gctcgctctt     180
ctgattattc ttcagggcaa tgacataaat tgtatattcg gttcccggtt ccaggccagt     240
aatagtagcc tctgtgacac cagggcgggg ccgagggacc acttctctgg gaggagaccc     300
aggcttctca tacttgatga tgtagccggt aatcctggca cgtggcggct gccatgatac     360
cagcagggaa ttgggtgtgg t                                              381
```

<210> SEQ ID NO 196
<211> LENGTH: 401
<212> TYPE: DNA
<213> ORGANISM: Homo sapiens

<400> SEQUENCE: 196

| cacaaacaag aggagcacca gacctcctct tggcttcgag atggcttcgc cacaccaaga | 60 |
| gcccaaacct ggagacctga ttgagatttt ccgccttggc tatgagcact gggccctgta | 120 |
| tataggagat ggctacgtga tccatctggc tcctccaagt gagtaccccg gggctggctc | 180 |
| ctccagtgtc ttctcagtcc tgagcaacag tgcagaggtg aaacgggagc gcctggaaga | 240 |
| tgtggtggga ggctgttgct atcgggtcaa caacagcttg gaccatgagt accaaccacg | 300 |
| gcccgtggag gtgatcacca gttctgcgaa ggagatggtt ggtcagaaga tgaagtacag | 360 |
| tattgtgagc aggaactgtg agcactttgt cacccagacc t | 401 |

<210> SEQ ID NO 197
<211> LENGTH: 471
<212> TYPE: DNA
<213> ORGANISM: Homo sapiens

<400> SEQUENCE: 197

| ctgtaatgat gtgagcaggg agccttcctc cctgggccac tgcagagag ctttcccacc | 60 |
| aactttgtac cttgattgcc ttacaaagtt atttgtttac aaacagcgac catataaaag | 120 |
| cctcctgccc caaagcttgt gggcacatgg gcacatacag actcacatac agacacacac | 180 |
| atatatgtac agacatgtac tctcacacac acaggcacca gcatacacac gttttctag | 240 |
| gtacagctcc caggaacagc taggtgggaa agtcccatca ctgagggagc ctaaccatgt | 300 |
| ccctgaacaa aaattgggca ctcatctatt cctttctct tgtgtcccta ctcattgaaa | 360 |
| ccaaactctg gaaggaccc aatgtaccag tatttatacc tctagtgaag cagagagaga | 420 |
| ggaagagagc tgcttaaact cacacaacaa tgaactgcag acacagacct g | 471 |

<210> SEQ ID NO 198
<211> LENGTH: 201
<212> TYPE: DNA
<213> ORGANISM: Homo sapiens

<400> SEQUENCE: 198

| ggtccattga ggctctgtcg gccatgccca cagttcgaag ctttgccaac gaggagggcg | 60 |
| aagcccagaa gtttagggaa aagctgcaag aaataaagac actcaaccag aaggaggctg | 120 |
| tggcctatgc agtcaactcc tggaccacta gtatttcagg tatgctgctg aaagtgggaa | 180 |
| tcctctacat tggtgggcag a | 201 |

<210> SEQ ID NO 199
<211> LENGTH: 551
<212> TYPE: DNA
<213> ORGANISM: Homo sapiens

<400> SEQUENCE: 199

| tctggcacag atcttcaccc acacggcggt ccacgtgctg atcatcttcc gggtctcacc | 60 |
| gggcctggaa cacaccatct tccccatgag cccggtgccc agtctggtga cttccatctt | 120 |
| ggcccctggc cttatgtccc agttatgacc cctgacttca actctggctc ttaccctgta | 180 |
| actccagtcc atctctgaca tttttaacac ccggccttgt gaccgtggac atagctcctg | 240 |
| acctcgattc ccatcttgag cccagtgtta gtccatgaga tcatgacctg actcctggtc | 300 |
| tccaaccttg tgatcctaat tctgggacct caatcctagc ctctgaactt gggaccctgg | 360 |
| agctcctgac cttagtcctg accgctaccc ttgattctga cctttgatcc tgtaacttag | 420 |

```
gggtggcccc tgaccttatt actgtcattt agctccttga ccttgccact tcaatcctgg    480
ctttatgacc tcctactctc aattttaact ttaaccaaat gaccaaattt gtgacactaa    540
atgaccacaa t                                                          551
```

```
<210> SEQ ID NO 200
<211> LENGTH: 211
<212> TYPE: DNA
<213> ORGANISM: Homo sapiens
<220> FEATURE:
<221> NAME/KEY: misc_feature
<222> LOCATION: (1)...(211)
<223> OTHER INFORMATION: n=A,T,C or G

<400> SEQUENCE: 200
cagctcancg ggcgacatgc ccctacaagt tggcanaagn ggctgccact gctgggtttg     60
tgtaagagag gctgctgnca ccattacctg cagaaacctt ctcatagggg ctacgatcgg    120
tactgctagg gggcacatag cgcccatggg tgtggtaggt ggggnactcn ntnataggat    180
ggtaggtatc ccgggctgga aanatgnnca g                                   211
```

```
<210> SEQ ID NO 201
<211> LENGTH: 111
<212> TYPE: DNA
<213> ORGANISM: Homo sapiens

<400> SEQUENCE: 201
ccagtgaaag gaaacaaaac tggcagtttg tccatttgaa tatcagacct agtttcttct     60
taatttccac actatttctc ccatattcct taaacttctt ggcatccacc t             111
```

```
<210> SEQ ID NO 202
<211> LENGTH: 331
<212> TYPE: DNA
<213> ORGANISM: Homo sapiens

<400> SEQUENCE: 202
tgaaaataca gaataccagg tggtcccaaa tgtttgaagt tctttgaaca gaaagagaga     60
ggagagagag agagaggaaa attccctaac ccttggttta aagacaatat tcatttattg    120
ctcaaatgat gcttttaagg gaggacagtg gaataaaata aactttttt ttctccctac     180 aatacataga agggttatca aaccactcaa gtttccaaaat cttttccaggg tccaatatca   240 ctttttttct ttcggttcaa tgaaaagcta aatgtaataa tactaattat agataaaatt    300
ttattttact ttttaaaaat ttgtccagac c                                   331
```

```
<210> SEQ ID NO 203
<211> LENGTH: 491
<212> TYPE: DNA
<213> ORGANISM: Homo sapiens

<400> SEQUENCE: 203
agtcacccag tctacttagt acctggttgc tgcctctgac cttttcagct tgatacctg      60 ggctttagtg taaccaataa atctgtagtg accttacctg tattccctgt gctatcctgt   120
gggaaggtag gaatgggcta agtatgatga atgtataggt tagggatctt ttggttttaa   180
atcacagaaa acctaattca aactggctta aaataaaaag gatttattgg ttcatgtaac   240
tagaaagtcc ataggtagtg ctggctccag gtgaagactt gacccagtag ttcagtatgt   300
ctctaaatac cggactgact ttttctcac tgttgcatct tctgtaggac catttaagtc    360
tgggccactt aatggctgcc agcattccta agattacact tttccccatt tatgtccaat   420
cagaaaaaga aggcatcttt gtaccagaaa tctcagcaaa agccctaata ttcacactga   480
```

```
ttaggacctg c                                                      491

<210> SEQ ID NO 204
<211> LENGTH: 361
<212> TYPE: DNA
<213> ORGANISM: Homo sapiens

<400> SEQUENCE: 204
tcccttcctc ccccatgtga taaatgggtc cagggctgat caaagaactc tgactgcaga     60
actgccgctc tcagtggaca gggcatctgt tatcctgaga cctgtggcag acacgtcttg    120
ttttcatttg attttttgtta agagtgcagt attgcagagt ctagaggaat ttttgtttcc   180
ttgattaaca tgattttcct ggttgttaca tccaggcat  ggcagtggcc tcagccttaa    240
acttttgttc ctactcccac cctcagcgaa ctgggcagca cggggagggt ttggctaccc    300
ctgcccatcc ctgagccagg taccaccatt gtaaggaaac actttcagaa attcagacct    360
c                                                                    361

<210> SEQ ID NO 205
<211> LENGTH: 471
<212> TYPE: DNA
<213> ORGANISM: Homo sapiens
<220> FEATURE:
<221> NAME/KEY: misc_feature
<222> LOCATION: (2)
<223> OTHER INFORMATION: n=A,T,C or G
<221> NAME/KEY: misc_feature
<222> LOCATION: (3)
<223> OTHER INFORMATION: n=A,T,C or G

<400> SEQUENCE: 205
cnngtacagt tcttcctgga tggccgacac agatcctggg gaaaggcaat cctggcactg     60
ctctgaaacc agagctcctc ctccctcccc gggcagggtg gagctgagaa gggctgctct    120
agcgttggga ctccacctcc atacacctga tattttgata gggcaggtcc ctgctatggg    180
ccactgttct gggcagtata gtatgcttga cagcatcctt ggcatctatc caccagatcc    240
cagagcaccc gctactagct gtgacaacat cctccaaaca ttgcaaaatt tccctgggga    300
ggcaagattg cctcagatgg gagaatcacg ctctagggaa atctgctggt atgagaaccc    360
caactcccca ctccactgag cctccagatg gcgagcaggc tgcagctcca gcacagacac    420
gaagctccct ccagccactg acggtccatg gctgggggtta cccaggacct c            471

<210> SEQ ID NO 206
<211> LENGTH: 261
<212> TYPE: DNA
<213> ORGANISM: Homo sapiens

<400> SEQUENCE: 206
tagagtattt agagtcctga gataacaagg aatccaggca tcctttagac agtcttctgt     60
tgtcctttct tcccaatcag agatttgtgg atgtgtggaa tgacaccacc accagcaatt    120
gtagccttga tgagagaatc caattcttca tctccacgaa tagcaagttg caagtgacga    180
ggggtaatac gctttacctt taagtctttt gatgcatttc ctgccagttc aagtacctct    240
gcggtgaggt actccaggat g                                             261

<210> SEQ ID NO 207
<211> LENGTH: 361
<212> TYPE: DNA
<213> ORGANISM: Homo sapiens
```

<400> SEQUENCE: 207

```
gctctccggg agcttgaaga agaaactggc tacaaagggg acattgccga atgttctcca      60
gcggtctgta tggacccagg cttgtcaaac tgtactatac acatcgtgac agtcaccatt     120
aacggagatg atgccgaaaa cgcaaggccg aagccaaagc caggggatgg agagtttgtg     180
gaagtcattt ctttacccaa gaatgacctg ctgcagagac ttgatgctct ggtagctgaa     240
gaacatctca cagtggacgc cagggtctat cctacgctc tagcactgaa acatgcaaat      300
gcaaagccat tgaagtgcc cttcttgaaa ttttaagccc aaatatgaca ctggacctgc      360
c                                                                     361
```

<210> SEQ ID NO 208
<211> LENGTH: 381
<212> TYPE: DNA
<213> ORGANISM: Homo sapiens
<220> FEATURE:
<221> NAME/KEY: misc_feature
<222> LOCATION: (1)...(381)
<223> OTHER INFORMATION: n=A,T,C or G

<400> SEQUENCE: 208

```
agaggagatn tttgccatgc ctgaatnctt tcctatncca ccctancact taacatatta     60
cttagtctgc tttgntaaaa gcaagtatta ccttnaactt gnctcttact ctttgccctt    120
tagctaacta ataaagnttg atntaggcat tattatataa ttctgagtca ttcatggtat    180
ctctcatgtt tgatgtattt tncaaactaa gatctatgat agttttttt ccanagttcc     240
attaaatcat ttatttcctt tactttctca cctctgtnga aacatttaga aactggattt    300
gggaacccan ttttggaaaa ccagattcat agtcatgaaa atggaaactt ncatattctg    360
tttttgaaaa gatgtggacc t                                              381
```

<210> SEQ ID NO 209
<211> LENGTH: 231
<212> TYPE: DNA
<213> ORGANISM: Homo sapiens
<220> FEATURE:
<221> NAME/KEY: misc_feature
<222> LOCATION: (83)
<223> OTHER INFORMATION: n=A,T,C or G

<400> SEQUENCE: 209

```
gtggagagca agtgatttat taaagcaaga cgttgaaacc tttacattct gcagtgaaga     60
tcagggtgtc attgaaagac agnggaaacc aggatgaaag ttttacatg tcacacacta     120
catttcttca atattttcac caggacttcc gcaatgaggc ttcgtttctg aagggacatc    180
tgatccgtgc atctcttcac tcctaacttg gctgcaacag cttccacctg c             231
```

<210> SEQ ID NO 210
<211> LENGTH: 371
<212> TYPE: DNA
<213> ORGANISM: Homo sapiens

<400> SEQUENCE: 210

```
tccatcctgg ttttgcagag atcaggttgt tgacagttcc tggttgaccc acagctaccc     60
atgtcagtta tctccactaa catatccaag aatctttgta ggacaatttc tccacctgca    120
aggttttta ggtagaactc ttcttttaag gcaattagcc cattgccaaa aggtttact      180
gtcttaaagc tgtctttctg agatctaatt ccaaggactt ctccacagct aagtgagatg    240
cctcacacca ttaggtgatg ctttggacag aacagagtat tttcatcttg tgtttaaagc    300
```

| aattccttgg cttcggctcc tcaccacttt ctatgccagt ctcccattta tgtccctagt | 360 |
| aatgcctatg c | 371 |

<210> SEQ ID NO 211
<211> LENGTH: 471
<212> TYPE: DNA
<213> ORGANISM: Homo sapiens

<400> SEQUENCE: 211

| tttattttaa agaaaaaaa ttaaaataga gccaacaaat gcaattaaga aaaaaaagt | 60 |
| attgagacac aagggggacct acatgttctg gtctaagaag catgcaagta ttacaaagca | 120 |
| ttccagatac agtatgacag aggaacagtg aacaagcatt ggaacgatgc tctttctttc | 180 |
| agaaacggga agtctaacag ttatgttttc acaatggtag tgattaaacc atctttattt | 240 |
| ttaaggaatt ttataggaag aattttagca ccatcattaa aggaaaaata ataatacctt | 300 |
| tttagccctg cctatctcca gtcttggaat aataacagaa gcatagcacc tttcagtatc | 360 |
| taaaatataa acaagaatag taagtccatc ccagcttcta gagatgaggt agctcatgct | 420 |
| aagaaatgtt gggtcatttt tcctatgaaa gttcaaaggc caaatggtca c | 471 |

<210> SEQ ID NO 212
<211> LENGTH: 401
<212> TYPE: DNA
<213> ORGANISM: Homo sapiens

<400> SEQUENCE: 212

| tggcctgtct ccttcacata gtccatatca ccacaaatca cacaacaaaa gggagaggat | 60 |
| atattttggg ttcaaaaaaa gtaaaaagat aatgtagctg catttctttg gttattttgg | 120 |
| gccccaaata tttcctcatc tttttgttgt tgtcatggat ggtggtgaca tggacttgtt | 180 |
| tatagaggac aggtcagctc tctggctcgg tgatctacat tctgaagttg tctgaaaatg | 240 |
| tcttcatgat taaattcagc ctaaacgttt tgccgggaac actgcagaga caatgctgtg | 300 |
| agtttccaac ctcagcccat ctgcgggcag agaaggtcta gtttgtccat caccattatg | 360 |
| atatcaggac tggttacttg gttaaggagg ggtctacctc g | 401 |

<210> SEQ ID NO 213
<211> LENGTH: 461
<212> TYPE: DNA
<213> ORGANISM: Homo sapiens
<220> FEATURE:
<221> NAME/KEY: misc_feature
<222> LOCATION: (1)...(461)
<223> OTHER INFORMATION: n=A,T,C or G

<400> SEQUENCE: 213

| tgtgaagcat acataaataa atgaagtaag ccatactgat ttaatttatt ggatgttatt | 60 |
| ttccctaaga cctgaaaatg aacatagtat gctagttatt tttcagtgtt agccttttac | 120 |
| tttcctcaca caatttggaa tcatataata taggtacttt gtccctgatt aaataatgtg | 180 |
| acggatagaa tgcatcaagt gtttattatg aaagagtgg aaaagtatat agcttttanc | 240 |
| aaaaggtgtt tgcccattct aagaaatgag cgaatatata gaaatagtgn gggcatttct | 300 |
| tcctgttagg tggagtgtat gtgttgacat ttctccccat ctcttcccac tctgttttnnt | 360 |
| ccccattatt tgaataaagt gactgctgaa nangactttg aatccttatc cacttaatttt | 420 |
| aatgtttaaa gaaaaaccta taatggaaag tgagactcct t | 461 |

<210> SEQ ID NO 214
<211> LENGTH: 181
<212> TYPE: DNA
<213> ORGANISM: Homo sapiens

<400> SEQUENCE: 214

```
cctgagcttc tactcctttc ccttaagatt cctccaaagc accagctcca taaaatcctt    60
cagctcccca gacccacacc aagaacccca catgttaatt ggatcagcca aatctacaag   120
cagataagtc ctaaggagaa tgccgaagcg ttttcttct tcctcaagcc tagcatgaga    180
c                                                                  181
```

<210> SEQ ID NO 215
<211> LENGTH: 581
<212> TYPE: DNA
<213> ORGANISM: Homo sapiens

<400> SEQUENCE: 215

```
ctgctttaag aatggttttc cacctttcc ccctaatctc taccaatcag acacatttta    60
ttatttaaat ctgcacctct ctctatttta tttgccaggg gcacgatgtg acatatctgc   120
agtcccagca cagtgggaca aaagaattt agaccccaaa agtgtcctcg gcatggatct    180
tgaacagaac cagtatctgt catggaactg aacattcatc gatggtctcc atgtattcat   240
ttattcactt gttcattcaa gtatttattg aatacctgcc tcaagctaga gagaaaagag   300
agtgcgcttt ggaaatttat tccagttttc agcctacagc agattatcag ctcggtgact   360
tttctttctg ccaccattta ggtgatggtg tttgattcag agatggctga atttctattc   420
ttagcttatt gtgactgttt cagatctagt ttgggaacag attagaggcc attgtcctct   480
gtcctgatca ggtggcctgg ctgtttcttt ggatccctct gtcccagagc cacccagaac   540
cctgactctt gagaatcaag aaaacaccca gaaaggacct c                       581
```

<210> SEQ ID NO 216
<211> LENGTH: 281
<212> TYPE: DNA
<213> ORGANISM: Homo sapiens
<220> FEATURE:
<221> NAME/KEY: misc_feature
<222> LOCATION: (1)...(281)
<223> OTHER INFORMATION: n=A,T,C or G

<400> SEQUENCE: 216

```
ccgatgtcct gcttctgtgg accagggggct cctctgnngg tggcctcaac cacggctgag    60
atccctagaa gtccaggagc tgtggggaag agaagcactt agggccagcc agccgggcac   120
ccccacttgc gccccgaccc acgctcacgc accagacctg cccnggcggt cgctcnaaag   180
ggcgaattct gcagatatcc atcacactgg cggacgctcg agcatgcatc tagagggccc   240
aattcaccct atantgagtc gtattacaat tcactggccg t                       281
```

<210> SEQ ID NO 217
<211> LENGTH: 356
<212> TYPE: DNA
<213> ORGANISM: Homo sapiens
<220> FEATURE:
<221> NAME/KEY: misc_feature
<222> LOCATION: (1)...(356)
<223> OTHER INFORMATION: n=A,T,C or G

<400> SEQUENCE: 217

```
atagcaggtt tcaacaattg tcttgtagtt tgnagtaaaa agacataaga aagagaaggt    60
```

```
gtggtttgca gcaatccgta gttggtttct caccataccc tgcagttctg tgagccaaag    120
gtcttgcaga aagttaaaat aaatcacaaa gactgctgtc atatattaat tgcataaaca    180
cctcaacatt gctcagagtt tcatccgttt ggttaagaaa acattccttc aattcatcta    240
tggcatttgt agtggcattg tcgtctatga actcttgaag aagttctttg tattcagtct    300
tagacacttg tggattgatt gncttggaaa tcacattctc caataaggga cctcgg        356
```

<210> SEQ ID NO 218
<211> LENGTH: 321
<212> TYPE: DNA
<213> ORGANISM: Homo sapiens

<400> SEQUENCE: 218

```
ttgtccatcg ggagaaaggt gtttgtcagt tgtttcataa accagattga ggaggacaaa     60
ctgctctgcc aatttctgga tttctttatt ttcagcaaac actttctttta aagcttgact   120 gtgtgggcac tcatccaagt gatgaataat catcaagggt tgttgcttg tcttggattt    180 atagagct tcttcatatg tctgagtcca atgagttgg tcaccccaac ctctggagag       240
ggtctggggc agtttgggtc gagagtcctt tgtgtccttt ttggctccag gtttgactgt    300
ggtatctctg gacctgcctg g                                              321
```

<210> SEQ ID NO 219
<211> LENGTH: 271
<212> TYPE: DNA
<213> ORGANISM: Homo sapiens
<220> FEATURE:
<221> NAME/KEY: misc_feature
<222> LOCATION: (41)
<223> OTHER INFORMATION: n=A,T,C or G

<400> SEQUENCE: 219

```
ccggttaggt ccacgcgggg gcagtggagg cacaggctca nggtggccgg gctacctggc     60
accctatggc ttacaaagta gagttggccc agtttccttc cacctgaggg gagcactctg    120
actcctaaca gtcttccttg ccctgccatc atctggggtg gctggctgtc aagaaaggcc    180
gggcatgctt tctaaacaca gccacaggag gcttgtaggg catcttccag gtggggaaac    240
agtcttagat aagtaaggtg acttgtctaa g                                   271
```

<210> SEQ ID NO 220
<211> LENGTH: 351
<212> TYPE: DNA
<213> ORGANISM: Homo sapiens
<220> FEATURE:
<221> NAME/KEY: misc_feature
<222> LOCATION: (1)...(351)
<223> OTHER INFORMATION: n=A,T,C or G

<400> SEQUENCE: 220

```
gtcctacgac gaggaccagc ttttcttctt cnactttcc canaacactc gggtgcctcg      60
cctgcccgaa tttgctgact gggctcagga acagggagat gctcctgcca ttttatttga    120
caaagagttc tgcgagtgga tgatccagca ataggccaa aaacttgatg ggaaaatccc     180
ggtgtccaga gggtttccta tcgctgaagt gttcacgctg aagcccctgg agtttggcaa    240
gcccaacact tggtctgtt tgtcagtaa tctcttccca cccatgctga cagtgaactg      300
gtagcatcat tccgtccctg tggaaggatt tgggcctact tttgtctcag a             351
```

<210> SEQ ID NO 221

<211> LENGTH: 371
<212> TYPE: DNA
<213> ORGANISM: Homo sapiens

<400> SEQUENCE: 221

```
gtctgcagaa gcgtgtctga ggtgtccggt ggaggtggca gccgagctct gggactaatc    60
accgtgctgg ggacggcacc gcgtcaggat gcaggcagat ccctgcagaa gtgtctaaaa   120
ttcacactcc tcttctggag ggacgtcgat ggtattagga tagaagcacc aggggacccc   180
acgaacggtg tcgtcgaaac agcagccctt atttgcacac tggagggcg tgacaccagg    240
aaaaccacaa ttctgtcttt cacgggggc cactgtacac gtctctgtct gggcctcggc    300
cagggtgccg agggccagca tggacaccag gaccagggcg cagatcacct tgttctccat    360
ggtggacctc g                                                         371
```

<210> SEQ ID NO 222
<211> LENGTH: 471
<212> TYPE: DNA
<213> ORGANISM: Homo sapiens

<400> SEQUENCE: 222

```
gtccatgttc catcattaat gttccaacat caccagggac acaaagctgc aaaaatgaga    60
agggaaataa ggttagagaa aggatccggg caatcttaag gactgaggaa gacatgttcc   120
ccaacccttg aactcacaaa ccctgaagct caaggattgc atccttcctc caaatctcac   180
tcaacataat aagtgcagaa caacatgcca agcactgta tgaagcacta gggacaaaga    240
caaggtcaaa atccttgtaa ccaaatttaa tggtattgta atgcagtgtt aacacaggac   300
agtaacagaa cacccaagaa ccaaacagaa gagggtaggg ataagcataa atgaagtaac   360
atgaaataaa cttccaaatg gaaaacttgt ccatacccc agggcaagtc aactacagtc     420
tcccaaagga cataaattcc acttagggca cactagacag aaaacaatat t            471
```

<210> SEQ ID NO 223
<211> LENGTH: 411
<212> TYPE: DNA
<213> ORGANISM: Homo sapiens

<400> SEQUENCE: 223

```
agttgctcta caatgacaca caaatcccgt taaataaatt ataaacaagg gtcaattcaa    60
atttgaagta atgttttagt aaggagagat tagaagacaa caggcatagc aaatgacata   120
agctaccgat taactaatcg gaacatgtaa aacagttaca aaaataaacg aactctcctc   180
ttgtcctaca atgaaagccc tcatgtgcag tagagatgca gtttcatcaa agaacaaaca    240
tccttgcaaa tgggtgtgac gcggttccag atgtggattt ggcaaaacct catttaagta   300
aaaggttagc agagcaaagt gcggtgcttt agctgctgct tgtgccgctg tggcgtcggg   360
gaggctcctg cctgagcttc cttccccagc tttgctgcct gagaggaacc a            411
```

<210> SEQ ID NO 224
<211> LENGTH: 321
<212> TYPE: DNA
<213> ORGANISM: Homo sapiens
<220> FEATURE:
<221> NAME/KEY: misc_feature
<222> LOCATION: (31)
<223> OTHER INFORMATION: n=A,T,C or G

<400> SEQUENCE: 224

```
ggtctgaagt ttgataacaa agaaatatat ntaagacaaa aatagacaag agttaacaat    60
```

```
aaaaacacaa ctatctgttg acataacata tggaaacttt ttgtcagaaa gctacatctt        120
cttaatctga ttgtccaaat cattaaaata tggatgattc agtgccattt tgccagaaat        180
tcgtttggct ggatcataga ttaacatttt cgagagcaaa tccaagccat tttcatccaa        240 gttttttgaca tgggatgcta ggcttcctgg tttccatttg ggaaatgtat tcttatagtc        300
ctgtaaagat tccacttctg g                                                  321

<210> SEQ ID NO 225
<211> LENGTH: 251
<212> TYPE: DNA
<213> ORGANISM: Homo sapiens
<220> FEATURE:
<221> NAME/KEY: misc_feature
<222> LOCATION: (34)
<223> OTHER INFORMATION: n=A,T,C or G

<400> SEQUENCE: 225
atgtctgggg aaagagttca ttggcaaaag tgtnctccca agaatggttt acaccaagca         60
gagaggacat gtcactgaat gtgggaaaggg aaccccccgta tccacagtca ctgtaagcat      120
ccagtaggca ggaagatggc tttgggcagt ggctggatga aagcagattt gagatacccca       180 gctccggaac gaggtcatct tctacaggtt cttccttcac tgagacaatg aattcagggt        240
gatcattctc t                                                             251

<210> SEQ ID NO 226
<211> LENGTH: 331
<212> TYPE: DNA
<213> ORGANISM: Homo sapiens
<220> FEATURE:
<221> NAME/KEY: unsure
<222> LOCATION: (1)...(331)
<223> OTHER INFORMATION: n=A,T,C or G

<400> SEQUENCE: 226
gttaggtccc aggcccccccg ccaagnggtt accnnnntna ccactcctga cccaaaaatc        60
aggcatggca ttaaaacgtt gcaaattcct ttactgttat ccccccccacc accaggacca      120 tgtagggtgc agtctttact ccctaaccccg tttcccgaaa aagtgctac ctcctttcca       180 gacagatgag agagggcagg acttcaggct ggatccacca ctgggctctc cctccccccag      240 cctggagcac gggaggggag gtgacggctg gtgactgatg gatgggtagt gggctgagaa       300
gaggggacta ggaagggcta ttccaggctc a                                      331

<210> SEQ ID NO 227
<211> LENGTH: 391
<212> TYPE: DNA
<213> ORGANISM: Homo sapiens

<400> SEQUENCE: 227
aggtctgccc ttgaagtata ggaaggaatc atagttggag gacttctgca ttatttgttg         60
gctgaagcta gaagtgcaac ccctcctga tttctgcagc aagatgaact gccttatccc       120
cagcccgcag gaatgttcat atctgagcaa tcaatgggca ctgtgttcaa ccacgccatt      180
ttcaagattg gctccttaaa ccacccacaa ggcaccagct ctgggagaag ctgcagggag      240
aagagaacaa agccctcgct gtgatcagga tgggtgtctc atacctttc tctggggtca       300 ttccaggtat gagacagagt tgaacctgcg catgagcgtg gaggccgaca tcaacggcct     360
gcgcagggtg ctggatgagc tgaccctgga c                                       391
```

<210> SEQ ID NO 228
<211> LENGTH: 391
<212> TYPE: DNA
<213> ORGANISM: Homo sapiens
<220> FEATURE:
<221> NAME/KEY: misc_feature
<222> LOCATION: (35)
<223> OTHER INFORMATION: n=A,T,C or G

<400> SEQUENCE: 228

| | | | | | |
|---|---|---|---|---|---|
| gttgtccata | gccacctcct | gggatagaag | ctttntagtt | catagttcga | ttagtgtgtc | 60 |
| cttaggacat | aggtccagcc | ctacagatta | gctgggtgaa | aaggcaagt | gtctcgacag | 120 |
| ggcttagtct | ccaccctcag | gcatggaacc | attcaggtg | aagcctggga | tgtgggcaca | 180 |
| ggagactcag | gctgatataa | aaataacaaa | atcagtaata | aaaaaattat | aaaacctgtt | 240 |
| gcttgtctga | atagatttga | gcaacagtct | tgcttttgtt | aaaatcctgg | agccgttaag | 300 |
| tcctgaatat | tcttctggac | atcattgctg | gctggagaaa | ggagcccag | gcccggctcg | 360 |
| gctgacatct | gtcaggtttg | gaagtctcat | c | | | 391 |

<210> SEQ ID NO 229
<211> LENGTH: 341
<212> TYPE: DNA
<213> ORGANISM: Homo sapiens
<220> FEATURE:
<221> NAME/KEY: misc_feature
<222> LOCATION: (202)
<223> OTHER INFORMATION: n=A,T,C or G

<400> SEQUENCE: 229

| | | | | | |
|---|---|---|---|---|---|
| gtccatggct | tctcacccag | acagtctttc | tgggcaactt | ggggaagccc | ctgttctgct | 60 |
| caagtctcac | cccatggaag | aggtggggga | aggggggcctt | ggttttttcag | gaagacgggt | 120 |
| tggagagcac | gagtcactac | aaagcagtaa | aagtgaatgg | tgtctccagg | ggctgggtcc | 180 |
| agaacaccgc | ggagagcccc | anccataaag | gtgtgttccg | cctctggcct | gcaggaatct | 240 |
| ctttgaatct | ctttgattgg | tggctccaag | agcaatggga | agtcaacagc | caggaggctg | 300 |
| gactgggttc | cctgggaccc | cgaggtccca | gaggctgctg | g | | 341 |

<210> SEQ ID NO 230
<211> LENGTH: 511
<212> TYPE: DNA
<213> ORGANISM: Homo sapiens

<400> SEQUENCE: 230

| | | | | | |
|---|---|---|---|---|---|
| gtccaagcca | aggaaaccat | tcccttacag | gagacctccc | tgtacacaca | ggaccgcctg | 60 |
| gggctaaagg | aaatggacaa | tgcaggacag | ctagtgtttc | tggctacaga | aggggaccat | 120 |
| cttcagttgt | ctgaagaatg | gttttatgcc | cacatcatac | cattccttgg | atgaaacccg | 180 |
| tatagttcac | aatagagctc | aggagcccc | taactcttcc | aaaccacatg | ggagacagtt | 240 |
| tccttcatgc | ccaagcctga | gctcagatcc | agcttgcaac | taatccttct | atcatctaac | 300 |
| atgccctact | tggaaagatc | taagatctga | atcttatcct | ttgccatctt | ctgttaccat | 360 |
| atggtgttga | atgcaagttt | aattaccatg | gagattgttt | tacaaacttt | tgatgtggtc | 420 |
| aagttcagtt | ttagaaaagg | gagtctgttc | cagatcagtg | ccagaactgt | gcccaggccc | 480 |
| aaaggagaca | actaactaaa | gtagtgagat | a | | | 511 |

<210> SEQ ID NO 231
<211> LENGTH: 311

```
<212> TYPE: DNA
<213> ORGANISM: Homo sapiens

<400> SEQUENCE: 231
ggtccaagta agctgtgggc aggcaagccc ttcggtcacc tgttggctac acagacccct      60
cccctcgtgt cagctcaggc agctcgaggc ccccgaccaa cacttgcagg ggtccctgct     120
agttagcgcc ccaccgccgt ggagttcgta ccgcttcctt agaacttcta cagaagccaa     180
gctccctgga gccctgttgg cagctctagc tttgcagtcg tgtaattggc ccaagtcatt     240
gtttttctcg cctcactttc caccaagtgt ctagagtcat gtgagcctcg tgtcatctcc     300
ggggtggacc t                                                          311

<210> SEQ ID NO 232
<211> LENGTH: 351
<212> TYPE: DNA
<213> ORGANISM: Homo sapiens

<400> SEQUENCE: 232
tcgtttagct aataatccct tccttgatga tacactccaa cttcttgttt ttctttattt      60
ctaaaaagcg gttctgtaac tctcaatcca gagatgttaa aaatgtttct aggcacggta     120
ttagtaaatc aagtaaattt catgtcctct taaggacaa acttccagag atttgaatat      180
aaatttttat atgtgttatt gattgtcgtg taacaaatgg cccccacaaa ttagtagctt     240
aaaatagcat ttatgatgtc actgttttct ttgccttttc attaatgttc tgtacagacc     300
tatgtaaaca acttttgtat atgcatatag gatagctttt ttgagggtat a              351

<210> SEQ ID NO 233
<211> LENGTH: 511
<212> TYPE: DNA
<213> ORGANISM: Homo sapiens

<400> SEQUENCE: 233
aggtctggat gtaaggatgg atgctctcta tacatgctgg gttggggatg ctgggactgc      60
acagccaccc ccagtatgcc gctccaggac tctgggacta gggcgccaaa gtgtgcaaat     120
gaaaatacag gatacccagg gaactttgaa tttcagattg tgaaaagaaa acaaatcttg     180
agactccaca atcaccaagc taaggaaaa agtcaagctg ggaactgctt agggcaaagc      240
tgcctcccat tctattcaca gtcatccccc tgaggctcac ctgcatagct gattgcttcc     300
tttcccctat cgcttctgta aaaatgcaga ctcactgagc cagactaaat tgtgtgttca     360
gtggaaggct gatcaagaac tcaaaagaat gcaaccttt gtctcttatc tactacaacc      420
aggaagcccc cacttaaggg ttgtcccacc ttactggact gaaccaaggt acatcttaca     480
cctactgatt gatgtctcat gtccccctaa g                                    511

<210> SEQ ID NO 234
<211> LENGTH: 221
<212> TYPE: DNA
<213> ORGANISM: Homo sapiens

<400> SEQUENCE: 234
caggtccagc gaaggggctt cataggctac accaagcatg tccacataac cgaggaagct      60
ctctccatca gcatagcctc cgatgaccat ggtgttccac aaagggttca tcttcgagcg     120
ccggctgtac atggccctgg tcagccatga atgaatagct ctaggactat agctgtgtcc     180
atctcccaga agctcctcat caatcaccat ctggccgaga c                         221
```

<210> SEQ ID NO 235
<211> LENGTH: 381
<212> TYPE: DNA
<213> ORGANISM: Homo sapiens
<220> FEATURE:
<221> NAME/KEY: misc_feature
<222> LOCATION: (33)
<223> OTHER INFORMATION: n=A,T,C or G

<400> SEQUENCE: 235

| | | | | | |
|---|---|---|---|---|---|
| ggtccaagaa | agggacatct | atgtgaaagt | ganactgaga | cagtgctggt | cacaggtcat | 60 |
| gctgcagaat | aatacattcc | caggcactgt | cacgtggggg | acccaagagg | ccccaggagt | 120 |
| gacctataac | ctctccagaa | agaccactct | gtgtggcatc | acagtccaca | cagtttaagg | 180 |
| aaatatttag | acttaacaat | cagacaccag | ctcttactca | cacttacact | cacagcccac | 240 |
| acacaagtgt | gcaaacatac | acacacatat | atatttcctg | atacattcat | ggaatatcag | 300 |
| agccctgccc | tgaagtcgtt | agtgtctctg | ctccccaaac | cgctgctccc | acattggcta | 360 |
| agctccctca | agagacctca | g | | | | 381 |

<210> SEQ ID NO 236
<211> LENGTH: 441
<212> TYPE: DNA
<213> ORGANISM: Homo sapiens

<400> SEQUENCE: 236

| | | | | | |
|---|---|---|---|---|---|
| aggtcctgtt | gccccttcct | tttgcccaac | ttcgccattt | gggaattgga | atatttaccc | 60 |
| aacacctgta | ctgcattgaa | tattggaagc | aaataacttg | gctttgatct | tataggctca | 120 |
| cagatggagg | aacgtacctt | gaagttcaga | tgagatttcg | gacttttgag | ttgatgctga | 180 |
| aacagcttga | gattttgggg | gactactgag | agatgataat | tgtattgtgc | aatatgagaa | 240 |
| ggacatgaga | tttggtgggc | ataggtgtga | aatgacattg | tttggatgtg | tttaccctcc | 300 |
| aaatctcttg | ttgaatgtga | tcttaaacgt | tggtggtggg | cctagtggaa | ggtgttgaat | 360 |
| catgggggtg | gactcttcat | aatttgctta | gctccatccc | cttggtgatg | agcaagtcct | 420 |
| tgctctgttg | tgtcacatga | g | | | | 441 |

<210> SEQ ID NO 237
<211> LENGTH: 281
<212> TYPE: DNA
<213> ORGANISM: Homo sapiens
<220> FEATURE:
<221> NAME/KEY: misc_feature
<222> LOCATION: (1)...(281)
<223> OTHER INFORMATION: n=A,T,C or G

<400> SEQUENCE: 237

| | | | | | |
|---|---|---|---|---|---|
| tcctaaaaaa | ttagctgacc | ttgttaaaaa | tgttggcgtg | agcagtatat | tattacctat | 60 |
| cttttttttat | tgtgtgtgtg | ngtgtgtgtn | ttaaactaat | tggctgaaat | atctgcctgt | 120 |
| ttccctcttt | acatttttct | tgtttctttc | cttatttatc | tttgtccatc | ttgagatcta | 180 |
| ctgtaaagtg | aatnttttaa | tgaaaacann | nccaagtttnt | actctcactg | ggnttgggac | 240 |
| atcagatgta | attgagaggc | caacaggtaa | gtcttcatgt | c | | 281 |

<210> SEQ ID NO 238
<211> LENGTH: 141
<212> TYPE: DNA
<213> ORGANISM: Homo sapiens
<220> FEATURE:
<221> NAME/KEY: misc_feature

```
<222> LOCATION: (1)...(141)
<223> OTHER INFORMATION: n=A,T,C or G

<400> SEQUENCE: 238
gtctgcctcc tcctactgtt tccctctatn aaaaagcctc cttggcgcag gttccctgag      60
ctgtgggatt ctgcactggt gcttnggatt ccctgatatg ttccttcaaa tccactgaga    120
attaaataaa catcgctaaa g                                               141

<210> SEQ ID NO 239
<211> LENGTH: 501
<212> TYPE: DNA
<213> ORGANISM: Homo sapiens
<220> FEATURE:
<221> NAME/KEY: misc_feature
<222> LOCATION: (1)...(501)
<223> OTHER INFORMATION: n=A,T,C or G

<400> SEQUENCE: 239
aacaatctaa acaaatccct cggttctann atacaatgga ttccccatat tggaaggact      60
ctgangcttt attccccac tatgcntatc ttatcatttt attattatac acacatccat     120
cctaaactat actaaagccc ttttcccatg catggatgga aatggaagat tttttttttaa   180 cttgttctag aagtcttaat atgggctgtt gccatgaagg cttgcagaat tgagtccatt    240
ttctagctgc ctttattcac atagtgatgg ggtactaaaa gtactgggtt gactcagaga    300
gtcgctgtca ttctgtcatt gctgctactc taacactgag caacactctc ccagtggcag    360 atccctgta tcattccaag aggagcattc atccctttgc tctaatgatc aggaatgatg     420
cttattagaa acaaactgc ttgacccagg aacaagtggc ttagcttaag naaacttggc     480
tttgctcana tccctgatcc t                                              501

<210> SEQ ID NO 240
<211> LENGTH: 451
<212> TYPE: DNA
<213> ORGANISM: Homo sapiens

<400> SEQUENCE: 240
tgtcctgaaa ggccattact aatagaaaca cagccttttcc aatcctctgg aacatattct    60
gtctgggttt ttaatgtctg tggaaaaaaa ctaaacaagt ctctgtctca gttaagagaa    120
atctattggt ctgaaggttt ctgaacctct ttctggttct cagcagaagt aactgaagta    180
gatcaggaag gggctgcctc aggaaaattc ctagatccta ggaattcagt gagaccctgg    240
gaaggaccag catgctaatc agtgtcagtg aatccacagt ctttacttcc tgcctcataa    300
agggccaggt ctccccagta ccaagtcctt tcctcatgaa gttgtgttgc ctcaggctgt    360
ttagggacca ttgcctgtct tggtcacatg agtctgtctc cttactttag tccctgggca    420
atccttgctt aatgctttg ttgactcaac g                                    451

<210> SEQ ID NO 241
<211> LENGTH: 411
<212> TYPE: DNA
<213> ORGANISM: Homo sapiens
<220> FEATURE:
<221> NAME/KEY: misc_feature
<222> LOCATION: (1)...(411)
<223> OTHER INFORMATION: n=A,T,C or G

<400> SEQUENCE: 241
aatctccagt gtgatggtat cggggttaga gcttcaatct ccagtgtgat ggtactgcag      60
```

| | |
|---|---|
| cnagagcttc aatctccagt gngatggtat tagggttaga tcttcaatct ccagtgtgat | 120 |
| ggtatcaggg ttagagcttc agcctccagt gtgatggtat cagggttaga gcttcagcct | 180 |
| ccagtgtgat ggtatcgggg ttagatcttc aatccccagt ggtggtggtt agagcttcaa | 240 |
| tctccagtgt gatggtattg gggttagagc ttcaatctcc agtctgatgg tgtttcggga | 300 |
| tggggctttt aagatgtaat tagggtttaa gatcataagg gacctggtct gatggggatt | 360 |
| agtncgcttn tatgaagaga cacangaggg cttgctctat ctctgactct c | 411 |

<210> SEQ ID NO 242
<211> LENGTH: 351
<212> TYPE: DNA
<213> ORGANISM: Homo sapiens

<400> SEQUENCE: 242

| | |
|---|---|
| ttccccttca caacagtaga gacctacaca gtgaactttg gggacttctg agatcagcgt | 60 |
| cctaccaaga ccccagccca actcaagcta cagcagcagc acttcccaag cctgctgacc | 120 |
| acagtcacat cacccatcag cacatggaag gcccctggta tggacactga aggaagggc | 180 |
| tggtcctgcc cctttgaggg ggtgcaaaca tgactgggac ctaagagcca gaggctgtgt | 240 |
| agaggctcct gctccacctg ccagtctcgt aagaaatggg gttgctgcag tgttggagta | 300 |
| ggggcagagg gagggagcca aggtcactcc aataaaacaa gctcatggca c | 351 |

<210> SEQ ID NO 243
<211> LENGTH: 241
<212> TYPE: DNA
<213> ORGANISM: Homo sapiens

<400> SEQUENCE: 243

| | |
|---|---|
| tctgtgctt tatcaggaaa agcacaagaa tatgtttttc tacctaaaac cctcttctac | 60 |
| ttaaaaatg gtttgctgaa ttttctatg tttttaaaat gttttatgc tttttttaa | 120 |
| acacgtaaag gatggaacct aatcctctcc cgagacgcct cctttgtgtt aatgcctatt | 180 |
| cttacaacag agaaacaagt acattaatat aaaaacgagt tgattattgg ggtataaaat | 240 |
| a | 241 |

<210> SEQ ID NO 244
<211> LENGTH: 301
<212> TYPE: DNA
<213> ORGANISM: Homo sapiens

<400> SEQUENCE: 244

| | |
|---|---|
| ggtccagagc aatagcgtct gtggtgaagc gcctgcactc ctcgggagac atgcctggct | 60 |
| tatatgctgc atccacataa ccatagataa aggtgctgcc ggagccacca atggcaaaag | 120 |
| gctgtcgagt cagcattcct cccagggttc catatacctg acctccttca cgttggtccc | 180 |
| agccagctac catgagatgt gcagacaagt cctctcgata tttatagctg atatttctca | 240 |
| ccacatttgc agcagccaaa acaagtggag gttcctccag ttctatccca tggagctcca | 300 |
| g | 301 |

<210> SEQ ID NO 245
<211> LENGTH: 391
<212> TYPE: DNA
<213> ORGANISM: Homo sapiens

<400> SEQUENCE: 245

| | |
|---|---|
| ctgacactgc tgatgtgggc cggggggcgc cgaggcacaa ctggtggccg gaccattgag | 60 |

```
gcacctggag ggtaggcagc ttgtggtgca gacaccacag agagagaaaa gttggatgga      120
gtggtgggaa taatcagggt ggcacactgt gcctagaagc ttccagggcc accaagagaa      180
tgggaaggga aactacaaca ttcacaacag aaataggagt caattcactt agacccagaa      240
ctccagaaag ggggagtgta ggaatctaca atttcaaagc cagctcgtgt ctacctagag      300
ccccaaactg cataagcacc aggattgtac accttagtcc ctcaagatag tttcaagtga      360
gcgtgcaatt cactcttaca gaggagggcc t                                    391

<210> SEQ ID NO 246
<211> LENGTH: 291
<212> TYPE: DNA
<213> ORGANISM: Homo sapiens
<220> FEATURE:
<221> NAME/KEY: misc_feature
<222> LOCATION: (1)...(291)
<223> OTHER INFORMATION: n=A,T,C or G

<400> SEQUENCE: 246
tcctccacag gggaagcagg aagttngacc agcttcaggc tggaacgtgc ccagggcaca       60
gagctggcaa ggtgcaaagn cntctgcaga atattcacca ggttgacaca gacctccaca      120
ttcagacata ttccaagctt ctggggtctt cagggcccca gaatttcctg gtcttgggca      180
tggtncacaa gtcatttgtc cttcctcatt ttggaaggtt ccatttggac ataaaatgca      240
agcgttctcg tgctncatna taataggtcc cagcctgcac tgacacattt g              291

<210> SEQ ID NO 247
<211> LENGTH: 471
<212> TYPE: DNA
<213> ORGANISM: Homo sapiens
<220> FEATURE:
<221> NAME/KEY: misc_feature
<222> LOCATION: (1)...(471)
<223> OTHER INFORMATION: n=A,T,C or G

<400> SEQUENCE: 247
cactgagtga atgagtatat aatttatgaa acagaaaag tgctttggaa aaaaaaaag        60 acaacaggag tacatacagn gaaccaaaaa gagtgtacca ggaggagcan acctgaaca       120 gttanaacta tggaaatcgc tatgctttgt gttgtcacag gagttaaaat aggaataccc     180
tgcatacaat aaatatttat tggataaata actaagcctg ataccctttt caatgcgtta    240
tacanactnt atcatcacac cactaatcta agttctcana agttaaacat tacaagactt     300
cagaacaaca taggcgtntt tggctccatt taacanaana aggaccatag tgatcattta    360
atctctatga gtctgtctta tcttctggaa aaggggccta acaccatttc cttttgcaaa    420
aaggtagctg ccttgcttcc agttctacca tcctntagca acccatcttt n             471

<210> SEQ ID NO 248
<211> LENGTH: 551
<212> TYPE: DNA
<213> ORGANISM: Homo sapiens

<400> SEQUENCE: 248
ccatgggatc aggaatgggg tcaggtcagt tgacctgagc atacccatta aacatgttca       60
aatgtcccca tcccacccac tcacatgaca tggctcccga gccctgagat ctgtatccca     120
agaacctcag ttgagaaata tttatggcag cttcactgtt gctcaagagc ctgggtattg    180
tagcagcctg ggggcaggtt gtccctaatg ttctccaagt tcttcacatc agccagaatc    240
```

```
ccatctatgc ttgtctccag caaatggagg tggcccctct gctgacgtgc cctctcttcc    300
agctctgaca tcatgggccg cagttggctg ttgatctggg tcttggctcg ggaaagcttc    360
tgctccagta agaccagccc ctcttcatct acactgagag gctggtccat cagatgcagg    420
aggccgtcta atgtgttgag tgtgtcttgg attgtaaccc cagcgttctt ggctctggta    480
tcaaccttct gggcttctgt aatcaccatc tgtactgcat ccatattcgt gtcgaactcc    540
agctccttcc t                                                         551
```

<210> SEQ ID NO 249
<211> LENGTH: 181
<212> TYPE: DNA
<213> ORGANISM: Homo sapiens
<220> FEATURE:
<221> NAME/KEY: misc_feature
<222> LOCATION: (1)...(181)
<223> OTHER INFORMATION: n=A,T,C or G

<400> SEQUENCE: 249

```
atntccagag ggaccgtaag actggtacaa gtttacacca taagaggcga cgtggtcagc     60
cacaatgtct tcacctccac aggggctcat cacggnggtc agggcaaggg cccccagcat    120
cagagctttg tttaggatca tcctcttccc aaggcagcct tagcagttgc tgacctgccc    180
g                                                                    181
```

<210> SEQ ID NO 250
<211> LENGTH: 551
<212> TYPE: DNA
<213> ORGANISM: Homo sapiens

<400> SEQUENCE: 250

```
tctgtagcta ggatgagctg gctctcaagc aaaagtttgt cttcctgggt ccatttgtgg     60
ttatcacttg ttattgaatg tacatcacaa attaaagtct gcattgttgg acgtaagaga    120
atgtgccgac tttggtaacc aggagatttc atgttactgg actgcctgta gtcacgtatt    180
tctgctatga cacatccgca atgaaaaata ttaacctgag atttttctag gagatcaacc    240
aaaataggag gtaattcttc tgcatccaaa tattcaagca actctccttc ttcatagggc    300
agtcgaatgg tctcggaatc tgatccgttt ttttcccctga gcatcagaga atatccctca    360
tttcctgggt atagattgac cactaaacat gacaaagtct cttgcataac aagcttctct    420
aacaagttca catttcttct taatttctta acttcaggtt ctttttcaca ttcttcaata    480
tacaagtcat aaagtttttg aaatacagat tttcttccac ttgataggta tttccttta    540 ggaggtctct g                                                         551
```

<210> SEQ ID NO 251
<211> LENGTH: 441
<212> TYPE: DNA
<213> ORGANISM: Homo sapiens

<400> SEQUENCE: 251

```
tgtctgctct cccatcctgg ttactatgag tcgctcttgg cagaaaggac cacagatgga     60
gagcttggca ctcgctccaa ctttgccgaa aagaggacaa ccaccaaagt agtaggtaaa    120
aacacaattt tagcagcagt gaaataaaaa gaggaagtga ggatgggcc aggccgcaac    180 tataattaaa ctgtctgttt aggagaagct gaatccagaa gaaacacaag ctgtaaagtg    240
agagaggaca gggagcaggg cctttggaga gcaggagagg acaggctgtc accaagcgct    300
gctcggactc tgccctgaaa gatttgaatt ggacactgtc cagtcacgtg tgtggcaaac    360
```

```
cgtactccaa gcactttct cacggcagag aaggagctg ccatggctgt accctgaac      420 gtttgtgggg ccagcgatgt g                                              441
```

<210> SEQ ID NO 252
<211> LENGTH: 406
<212> TYPE: DNA
<213> ORGANISM: Homo sapiens

<400> SEQUENCE: 252

```
ttttttttg aacaagtaaa aatttcttta tttgctgaca ataagataac ctacagggaa      60
aacctgatga aatctattaa aaagttacta aaactaataa aagaatttag gaaggttata   120
gaatgtaaga ccaagacaca aaaatcaatt acatttctat ataatagcaa tgaacagata   180
ctgaaatttt aaaaactaaa tcattttaca aaagtatcac aatatgaaac actccgggat   240
aaattggata aagatgtgc aagactgtac aaaagctaca aacatttat gaaggaaatt    300 ggaagataga aacaagatag aaaatgaaaa tattgtcaag agtttcagat agaaaatgaa   360
aaacaagcta agacaagtat tggagaagta tagaagatag aaaaat                 406
```

<210> SEQ ID NO 253
<211> LENGTH: 544
<212> TYPE: DNA
<213> ORGANISM: Homo sapiens
<220> FEATURE:
<221> NAME/KEY: misc_feature
<222> LOCATION: (224)
<223> OTHER INFORMATION: n=A,T,C or G

<400> SEQUENCE: 253

```
gaaggagttc agtagcaaag tcacacctgt ccaattccct gagctttgct cactcagcta    60
atgggatggc aaaggtggtg gtgctttcat cttcaggcag aagcctctgc ccatccccct  120
caagggctgc aggcccagtt ctcatgctgc ccttgggtgg gcatctgtta acagaggaga  180
acgtctgggt ggcggcagca gctttgctct gagtgcctac aaanctaatg cttggtgcta  240
gaaacatcat cattattaaa cttcagaaaa gcagcagcca tgttcagtca ggctcatgct  300
gcctcactgc ttaagtgcct gcaggagccg cctgccaagc tccccttcct acacctggca  360 cactgggtc tgcacaaggc tttgtcaacc aaagacagct tccccctttt gattgcctgt    420
agactttgga gccaagaaac actctgtgtg actctacaca cacttcaggt ggtttgtgct  480
tcaaagtcat tgatgcaact tgaaaggaaa cagtttaatg gtggaaatga actaccattt   540
ataa                                                                 544
```

<210> SEQ ID NO 254
<211> LENGTH: 339
<212> TYPE: DNA
<213> ORGANISM: Homo sapiens

<400> SEQUENCE: 254

```
tggcattcag ggcagtgtct tctgcatctc ctaggaacct cgggagcggc agctccggcg    60
cctggtagcg agaggcgggt tccggagatc ccggcctcac ttcgtcccac tgtggttagg  120
ggtgagtcct gcaaatgtta agtgatttgc tcaaggtgcc catttcgcag gaattggagc  180
ccaggccagt tctctgagcc tatcattagg gctaaaggag tgcgtgatca gaatggtgtc  240
tggacggttc tacttgtcct gcctgctgct ggggtccctg ggctctatgt gcatcctctt   300
cactatctac tggatgcagt actggcgtgg tggctttgc                          339
```

<210> SEQ ID NO 255
<211> LENGTH: 405
<212> TYPE: DNA
<213> ORGANISM: Homo sapiens
<220> FEATURE:
<221> NAME/KEY: misc_feature
<222> LOCATION: (1)...(405)
<223> OTHER INFORMATION: n=A,T,C or G

<400> SEQUENCE: 255
gaggtttttt nttttttttt tttttttttt caattaaana tttgatttat tcaagtatgt    60
gaaaacattn tacaatggaa acttttntta aatgctgcat gtnctgtgct atggaccacn   120
cacatacagc catgctgttt caaaaaactt gaaatgccat tgatagttta aaaactntac   180
ncccgatgga aaatcgagga aaacaattta atgtttcatn tgaatccana ggngcatcaa   240
attaaatgac agctccactt ggcaaataat agctgttact tgatggtatc caaaaaaaaa   300
tggttgggga tggataaatt caaaaatgct tccccaaagg ngggnggttt ttaaaaagtt   360
tcaggncaca acccttgcan aaaacactga tgcccaacac antga                   405

<210> SEQ ID NO 256
<211> LENGTH: 209
<212> TYPE: DNA
<213> ORGANISM: Homo sapiens
<220> FEATURE:
<221> NAME/KEY: misc_feature
<222> LOCATION: (6)
<223> OTHER INFORMATION: n=A,T,C or G

<400> SEQUENCE: 256
gggcangtct ggtcctctcc ccacatgtca cactctcctc agcctctccc ccaaccctgc    60
tctccctcct ccctgccct agcccaggga cagagtctag gaggagcctg gggcagagct   120
ggaggcagga agagagcact ggacagacag ctatggtttg gattggggaa gaggttagga   180
agtaggttct taaagaccct tttttagta                                     209

<210> SEQ ID NO 257
<211> LENGTH: 343
<212> TYPE: DNA
<213> ORGANISM: Homo sapiens
<220> FEATURE:
<221> NAME/KEY: misc_feature
<222> LOCATION: (1)...(343)
<223> OTHER INFORMATION: n=A,T,C or G

<400> SEQUENCE: 257
tctggacacc ataatccctt ttaagtggct ggatggtcac acctctccca ttgacaagct    60
gggttaagtc aataggttga ctaggatcaa cacgacccaa atcaataaga tactgcagtc   120
tattgagact caaaggctta tactggcgtc tgaaactatg tccttcgtta aacccgtatt   180
ttgggattcg gatgtaaaat ggagtctggc ctccctcaaa gcccaagcgg ggccgggttc   240
ctctttgcct ttctccttta tggcctctgc cacattttct acctcttctc cgacctcttg   300
gtcttntctc nggtttcttg gagccgggat tcggctttaa gtn                     343

<210> SEQ ID NO 258
<211> LENGTH: 519
<212> TYPE: DNA
<213> ORGANISM: Homo sapiens

<400> SEQUENCE: 258
gcggcttctg acttctagaa gactaaggct ggtctgtgtt tgcttgtttg cccacctttg    60

```
gctgatacccc agagaacctg ggcacttgct gcctgatgcc caccoctgcc agtcattcct    120 ccattcaccc agcgggaggt gggatgtgag acagcccaca ttggaaaatc cagaaaaccg    180
ggaacaggga tttgcccttc acaattctac tccccagatc ctctcccctg acacaggag    240 acccacaggg caggaccta agatctgggg aaaggaggtc ctgagaacct tgaggtaccc    300
ttagatcctt ttctacccac tttcctatgg aggattccaa gtcaccactt ctctcaccgg    360
cttctaccag ggtccaggac taaggcgttt tctccatagc ctcaacattt tgggaatctt    420
cccttaatca cccttgctcc tcctgggtgc ctggaagatg gactggcaga gacctctttg    480
ttgcgttttg tgctttgatg ccaggaatgc cgcctagtt                            519

<210> SEQ ID NO 259
<211> LENGTH: 371
<212> TYPE: DNA
<213> ORGANISM: Homo sapiens

<400> SEQUENCE: 259
attgtcaact atatacacag tagtgaggaa taaaatgcac acaaaacaat ggatagaata     60
tgaaaatgtc ttctaaatat gaccagtcta gcatagaacc ttcttctctt ccttctcagg    120
tcttccagct ccatgtcatc taacccactt aacaaacgtg gacgtatcgc ttccagaggc    180
cgtcttaaca actccatttc caaaagtcat ctccagaaga catgtatttt ctatgatttc    240
ttttaaacaa atgagaattt acaagatgtg taactttcta actctatttt atcatacgtc    300
ggcaacctct ttccatctag aagggctaga tgtgacaaat gttttctatt aaaaggttgg    360
ggtggagttg a                                                         371

<210> SEQ ID NO 260
<211> LENGTH: 430
<212> TYPE: DNA
<213> ORGANISM: Homo sapiens
<220> FEATURE:
<221> NAME/KEY: misc_feature
<222> LOCATION: (1)...(430)
<223> OTHER INFORMATION: n=A,T,C or G

<400> SEQUENCE: 260
ttggattttt tgacttgcga tttcagtttt tttacttttt tttttttttt ttttganaaa     60
tactatattt attgtcaaag agtggtacat aggtgagtgt tcatcttccc tctcatgccg    120
gtatactctg cttcgctgtt tcagtaaaag ttttccgtag ttctgaacgt cccttgacca    180
caccataana caagcgcaag tcactcanaa ttgccactgg aaaactggct caactatcat    240
ttgaggaaag actganaaag cctatcccaa agtaatggac atgcaccaac atcgcggtac    300
ctacatgttc ccgttttttct gccaatctac ctgtgtttcc aagataaatt accacccagg    360
gagtcacttc ctgctatgtg aacaaaaacc cggtttcttt ctggaggtgc ttgactactc    420 tctcgngagc                                                           430

<210> SEQ ID NO 261
<211> LENGTH: 365
<212> TYPE: DNA
<213> ORGANISM: Homo sapiens
<220> FEATURE:
<221> NAME/KEY: misc_feature
<222> LOCATION: (178)
<223> OTHER INFORMATION: n=A,T,C or G

<400> SEQUENCE: 261
```

-continued

| | |
|---|---|
| tcctgacgat agccatggct gtaccactta actatgattc tattccaact gttcagaatc | 60 |
| atatcacaaa atgacttgta cacagtagtt tacaacgact cccaagagag gaaaaaaaaa | 120 |
| aaaaaagacg cctcaaaatt cactcaactt ttgagacagc aatggcaata ggcagcanag | 180 |
| aagctatgct gcaactgagg gcacatatca ttgaagatgt cacaggagtt taagagacag | 240 |
| gctggaaaaa atctcatact aagcaaacag tagtatctca taccaagcaa aaccaagtag | 300 |
| tatctgctca gcctgccgct aacagatctc acaatcacca actgtgcttt aggactgtca | 360 |
| ccaaa | 365 |

<210> SEQ ID NO 262
<211> LENGTH: 500
<212> TYPE: DNA
<213> ORGANISM: Homo sapiens

<400> SEQUENCE: 262

| | |
|---|---|
| cctagatgtc atttgggacc cttcacaacc attttgaagc cctgtttgag tccctgggat | 60 |
| atgtgagctg tttctatgca taatggatat tcggggttaa caacagtccc ctgcttggct | 120 |
| tctattctga atccttttct ttcaccatgg ggtgcctgaa gggtggctga tgcatatggt | 180 |
| acaatggcac ccagtgtaaa gcagctacaa ttaggagtgg atgtgttctg tagcatccta | 240 |
| tttaaataag cctatttat cctttggccc gtcaactctg ttatctgctg cttgtactgg | 300 |
| tgcctgtact tttctgactc tcattgacca tattccacga ccatggttgt catccattac | 360 |
| ttgatcctac tttacatgtc tagtctgtgt ggttggtggt gaataggctt cttttttacat | 420 |
| ggtgctgcca gcccagctaa ttaatggtgc acgtggactt ttagcaagcg ggctcactgg | 480 |
| aagagactga acctggcatg | 500 |

<210> SEQ ID NO 263
<211> LENGTH: 413
<212> TYPE: DNA
<213> ORGANISM: Homo sapiens

<400> SEQUENCE: 263

| | |
|---|---|
| ctcagagagg ttgaaagatt tgcctacgaa agggacagtg atgaagctaa gctctagatc | 60 |
| caggatgtct gacttcaaat tgaaactccc aaagtaatga gtttggaagg gtggggtgtg | 120 |
| gcctttccag gatggggtc ttttctgctc ccagcggata gtgaaacccc tgtctgcacc | 180 |
| tggttgggcg tgttgctttc ccaaaggttt ttttttttagg tccgtcgctg tcttgtggat | 240 |
| taggcattat tatctttact ttgtctccaa ataacctgga gaatggagag agtagtgacc | 300 |
| agctcagggc cacagtgcga tgaggaccat cttctcacct ctctaaatgc aggaagaaac | 360 |
| gcagagtaac gtggaagtgg tccacaccta ccgccagcac attgtgaatg aca | 413 |

<210> SEQ ID NO 264
<211> LENGTH: 524
<212> TYPE: DNA
<213> ORGANISM: Homo sapiens

<400> SEQUENCE: 264

| | |
|---|---|
| tccaatgggg ccctgagagc tgtgacagga actcacactc tggcactggc agcaaaacac | 60 |
| cattccaccc cactcatcgt ctgtgcacct atgttcaaac tttctccaca gttccccaat | 120 |
| gaagaagact catttcataa gtttgtggct cctgaagaag tcctgccatt cacagaaggg | 180 |
| gacattctgg agaaggtcag cgtgcattgc cctgtgtttg actacgttcc cccagagctc | 240 |
| attaccctct ttatctccaa cattggtggg aatgcacctt cctacatcta ccgcctgatg | 300 |

```
agtgaactct accatcctga tgatcatgtt ttatgaccga ccacacgtgt cctaagcaga      360
ttgcttaggc agatacagaa tgaagaggag acttgagtgt tgctgctgaa gcacatcctt      420
gcaatgtggg agtgcacagg agtccaccta aaaaaaaaaa tccttgatac tgttgcctgc      480 cttttagtc accccgtaac aagggcacac atccaggact gtgt                       524
```

<210> SEQ ID NO 265
<211> LENGTH: 344
<212> TYPE: DNA
<213> ORGANISM: Homo sapiens

<400> SEQUENCE: 265

```
tcctttcttc tacttcagga gatgattcaa agttacttgt ggacatttct ttaagttctg       60
aagacaaatg agacaggatt tggcctgcgg gttcttcaga cttctctacc acctccatta      120
actcttcatc ttggcttgac gtaggcaatg cactattttg ctcttttgtt tctggagatg      180
acccagcacc acttctttct cttggcgggg ttctaagtgt gtctttgaat accagtgaag      240
actcaggcct atcctgtact ggaaagggac taaatttgtc tttctgtcta ggaggtgatg      300
cagtagcatc ctcctgaggg ggtaaggcca ttttctcttt ttga                       344
```

<210> SEQ ID NO 266
<211> LENGTH: 210
<212> TYPE: DNA
<213> ORGANISM: Homo sapiens
<220> FEATURE:
<221> NAME/KEY: misc_feature
<222> LOCATION: (78)
<223> OTHER INFORMATION: n=A,T,C or G

<400> SEQUENCE: 266

```
ccacaatgtc cataacttga gcaggctttg gcatcccacc accccttca gaccaataca        60 cactatgttg gaggaacnac tttaaaatgt aaaatgagaa atgggcactg aacactccat      120
cctcactccc aacagcccac ccacacacct cttcaactgc tatccaaaca tggaggagct      180
cttgtggaag agaggctcaa caccaaataa                                       210
```

<210> SEQ ID NO 267
<211> LENGTH: 238
<212> TYPE: DNA
<213> ORGANISM: Homo sapiens
<220> FEATURE:
<221> NAME/KEY: misc_feature
<222> LOCATION: (1)...(238)
<223> OTHER INFORMATION: n = A,T,C or G

<400> SEQUENCE: 267

```
tcggncctcc caccctctna ctgaaattct ntgaaattct cccctttggg atgaggatgg        60
caaccccagg catgtaccct cccaacctgg gacccgacct aatacccttaa catcctgctg     120 acagtggctg ttctcgctgg gcaggcgtcc caaagcacat cgagccagat tcaggcagag     180
tggaactggc ccctcagcca tcagtggagg tggcctggga ggctctaccc tgaacggg       238
```

<210> SEQ ID NO 268
<211> LENGTH: 461
<212> TYPE: DNA
<213> ORGANISM: Homo sapiens
<220> FEATURE:
<221> NAME/KEY: misc_feature
<222> LOCATION: (459)
<223> OTHER INFORMATION: n=A,T,C or G

<400> SEQUENCE: 268

```
tcctcaagga catgcccctt gatagaaact cagttcctgt ctccagttcc ctcctggacc      60
tgatccccca aatgcagggc ctgggactat atccagttcc ttattttcag aggcccatgc     120
acaagatgca cagcaaataa gtgctgaata agacccagc tactgctagc ttaccctgct      180
ccaaacattc accaagtcct cagcaaagag ggccatccat tcacctcttc taaaaacaca    240
ctgagctccc cagtctatac cccaagatat gcttggctcc caactatccc tcctctctca    300
tctccaagcc agtttcccct ttctaagtat actgatatta ccaaagacac tgacaatctt    360
cttttcctac ctctccccag tgactaggtt tgcagcagga gctctataag tcctagtata    420
cagcagaagc tccataaatg tgtgctgacc taacattang c                         461
```

<210> SEQ ID NO 269
<211> LENGTH: 434
<212> TYPE: DNA
<213> ORGANISM: Homo sapiens

<400> SEQUENCE: 269

```
ctgtgttggt gagcaccgat tcccactcaa tatggcgtgg cttacagtct tcattaggtt     60
cccgctccca accagaatga ggaatgatca cttcatctgt caaggcatgc agtgcatggt    120
ccacaatctc cattttgatt gagtcatggg atgaaagatt ccacagggtt ccggtaataa    180
cttcagtaag gtccatatca cgagcctttc gaagcaatcg cacaagggca ggcacaccat    240
cacagttttt tatggcaatc ttgttatcct ggtcacgtcc aaaagagata ttcttgagag    300
ctccacaggc tccaaggtgc acttcctttt tgggatggtc taacaatccc accagtactg    360
ggatgccctt gagcttccgc acgtcagtct tcaccttgtc attgcggtag cataagtgtt    420
gcaggtatgc aaga                                                      434
```

<210> SEQ ID NO 270
<211> LENGTH: 156
<212> TYPE: DNA
<213> ORGANISM: Homo sapiens

<400> SEQUENCE: 270

```
ctgcaccagc gattaccagt ggcattcaaa tactgtgtga ctaaggatttt tgtatgctcc     60
ccagtagaac cagaatcaga caggtatgag ctagtcaaca gcaagtcttt gttggattcg    120
agtaggctca ggatctgctg aaggtcggag gagtta                               156
```

<210> SEQ ID NO 271
<211> LENGTH: 533
<212> TYPE: DNA
<213> ORGANISM: Homo sapiens
<220> FEATURE:
<221> NAME/KEY: misc_feature
<222> LOCATION: (1)...(533)
<223> OTHER INFORMATION: n=A,T,C or G

<400> SEQUENCE: 271

```
ccactgtcac ggtctgtctg acacttactg ccaaacgcat ggcaaggaaa aactgcttag     60
tgaagaactt agaagctgtg gagaccttgg ggtccacgtn caccatctgc tctgataaaa    120
ctggaactct gactcanaac cggatgacag tgcccacat gtggtttgac aatcaaatcc     180
atgaagctga tacgcagag aatcagagtg gtgtctcttt tgacaagact tcagctacct    240
ggcttgctct gtccagaatt gcaggtcttt gtaacagggc agtgtttcag gctaaccagg    300
aaaacctacc tattcttaag cgggcagttg caggagatgc ctctgagtca gcactcttaa    360
```

```
agtgcataga gctgtgctgt ggntncgtga aggagatgag agaaagatac nccaaaatcg    420
tcgagatacc cttcaactcc accaacaagt accagttgtc tattcataag aaccccaaca    480
catcggagcc ccaacacctg ttggtgatga agggcgcccc agaaaggatc cta           533

<210> SEQ ID NO 272
<211> LENGTH: 630
<212> TYPE: DNA
<213> ORGANISM: Homo sapiens

<400> SEQUENCE: 272
tggtattttt cttttctttt tggatgtttt atactttttt ttcttttttc ttctctattc    60
ttttcttcgc ctttcccgtac ttctgtcttc cagttttcca cttcaaactt ctatcttctc    120
caaattgttt catcctacca ctcccaatta atctttccat tttcgtctgc gtttagtaaa    180
tgcgttaact aggctttaaa tgacgcaatt ctccctgcgt catggatttc aaggtctttt    240
aatcaccttc ggtttaatct cttttttaaaa gatcgccttc aaattatttt aatcacctac    300
aacttttaaa ctaaacttta agctgtttaa gtcaccttca ttttaatcta aaagcattgc    360
ccttctattg gtattaattc ggggctctgt agtcctttct ctcaattttc ttttaaatac    420
attttttact ccatgaagaa gcttcatctc aacctccgtc atgttttaga aaccttttat    480
cttttccttc ctcatgctac tcttctaagt cttcatattt tctcttaaaa tcttaagcta    540
ttaaaattac gttaaaaact taacgctaag caatatctta gtaacctatt gactatattt    600
tttaagtagt tgtattaatc tctatctttc                                     630

<210> SEQ ID NO 273
<211> LENGTH: 400
<212> TYPE: DNA
<213> ORGANISM: Homo sapiens

<400> SEQUENCE: 273
tctggtttgc cctccagttc attctgaatc tagacttgct cagcctaatc aagttcctgt    60
acaaccagaa gcgacacagg ttcctttggt atcatccaca agtgagggt acacagcatc    120 tcaacccttg taccagcctt tcatgctac agagcaacga ccacagaagg aaccaattga    180
tcagattcag gcaacaatct ctttaaatac agaccagact acagcatcat catcccttcc    240
tgctgcgtct cagcctcaag tatttcaggc tgggacaagc aaacctttac atagcagtgg    300
aatcaatgta aatgcagctc cattccaatc catgcaaacg tgttcaata tgaatgcccc    360 agttcctcct gttaatgaac cagaaacttt aaaacagcaa                          400

<210> SEQ ID NO 274
<211> LENGTH: 351
<212> TYPE: DNA
<213> ORGANISM: Homo sapiens
<220> FEATURE:
<221> NAME/KEY: misc_feature
<222> LOCATION: (2)
<223> OTHER INFORMATION: n=A,T,C or G

<400> SEQUENCE: 274
tntgagtatg tcccagagaa ggtgaagaaa gcggaaaaga aattagaaga gaatccatat    60
gaccttgatg cttggagcat tctcattcga gaggcacaga atcaacctat agacaaagca    120
cggaagactt atgaacgcct tgttgcccag ttccccagtt ctggcagatt ctggaaactg    180
tacattgaag cagaggttac tattttattt tatttttct tatatcagta ttgcagcatt    240
```

```
cactgtagtg atagaaaaca agttaggaac atagccaatt aggacaagga ggatttaaat       300
gtgtcttacc tttattttgt aaaataggta taaaggagta attaaaatga a                351
```

<210> SEQ ID NO 275
<211> LENGTH: 381
<212> TYPE: DNA
<213> ORGANISM: Homo sapiens
<220> FEATURE:
<221> NAME/KEY: misc_feature
<222> LOCATION: (1)...(381)
<223> OTHER INFORMATION: n=A,T,C or G

<400> SEQUENCE: 275

```
gcgnggtcgc nnncgaggtc tgagaagccc ataccactat ttgttgagaa atgtgtggaa        60
tttattgaag atacagggtt atgtaccgaa ggactctacc gtgtcagcgg gaataaaact       120
gaccaagaca atattcaaaa gcagtttgat caagatcata atatcaatct agtgtcaatg       180
gaagtaacag taaatgctgt agctggagcc cttaaagctt tctttgcaga tctgccagat       240
cctttaattc catattctct tcatccagaa ctattggaag cagcaaaaat cccggataaa       300
acagaacgtc ttcatgcctt gaaagaaatt gttaagaaat ttcatcctgt aaactatgat       360
gtattcagat acgtgataac a                                                 381
```

<210> SEQ ID NO 276
<211> LENGTH: 390
<212> TYPE: DNA
<213> ORGANISM: Homo sapiens
<220> FEATURE:
<221> NAME/KEY: misc_feature
<222> LOCATION: (5)
<223> OTHER INFORMATION: n=A,T,C or G

<400> SEQUENCE: 276

```
gctcngactc cggcgggacc tgctcggagg aatggcgccg ccggggttcaa gcactgtctt       60 cctgttggcc ctgacaatca tagccagcac ctgggctctg acgcccactc actacctcac      120
caagcatgac gtggagagac taaaagcctc gctggatcgc cctttcacaa atttggaatc      180
tgccttctac tccatcgtgg gactcagcag ccttggtgct caggtgccag atgcaaagaa      240
agcatgtacc tacatcagat ctaaccttga tcccagcaat gtggattccc tcttctacgc      300
tgcccaggcc agccaggccc tctcaggatg tgagatctct atttcaaatg agaccaaaga      360
tctgcttctg cagacctcg gccgcgacca                                         390
```

<210> SEQ ID NO 277
<211> LENGTH: 378
<212> TYPE: DNA
<213> ORGANISM: Homo sapiens

<400> SEQUENCE: 277

```
tgggaacttc tggggtagga cgttgtctgc tatctccagt tccacagacc caaccagtta        60
cgatggtttt ggaccattta tgccgggatt cgacatcatt ccctataatg atctgcccgc       120
actggagcgt gctcttcagg atccaaatgt ggctgcgttc atggtagaac caattcaggg       180
tgaagcaggc gttgttgttc cggatccagg ttacctaatg ggagtgcgag agctctgcac       240
caggcaccag gttctcttta ttgctgatga aatacagaca ggattggcca gaactggtag       300
atggctggct gttgattatg aaaatgtcag acctgatata gtcctccttg gaaaggccct       360
ttctgggggc ttataccc                                                     378
```

<210> SEQ ID NO 278
<211> LENGTH: 366
<212> TYPE: DNA
<213> ORGANISM: Homo sapiens

<400> SEQUENCE: 278

| ggagggcaca | ttccttttca | cctcagagtc | ggtcggggaa | ggccacccag | ataagatttg | 60 |
| tgaccaaacc | agtgatgctg | tccttgatgc | ccaccttcag | caggatcctg | atgccaaagt | 120 |
| agcttgtgaa | actgttgcta | aaactggaat | gatccttctt | gctggggaaa | ttacatccag | 180 |
| agctgctgtt | gactaccaga | aagtggttcg | tgaagctgtt | aaacacattg | gatatgatga | 240 |
| ttcttccaaa | ggttttgact | acaagacttg | taacgtgctg | gtagccttgg | agcaacagtc | 300 |
| accagatatt | gctcaaggtg | ttcatcttga | cagaaatgaa | aagacattg | gtgctggaga | 360 |
| ccaggg | | | | | | 366 |

<210> SEQ ID NO 279
<211> LENGTH: 435
<212> TYPE: DNA
<213> ORGANISM: Homo sapiens

<400> SEQUENCE: 279

| cctaagaact | gagacttgtg | acacaaggcc | aacgacctaa | gattagccca | gggttgtagc | 60 |
| tggaagacct | acaacccaag | gatggaaggc | ccctgtcaca | aagcctacct | agatggatag | 120 |
| aggacccaag | cgaaaaagat | atctcaagac | taacggccgg | aatctggagg | cccatgaccc | 180 |
| agaacccagg | aaggatagaa | gcttgaagac | ctggggaaat | cccaagatga | gaaccctaaa | 240 |
| ccctacctct | tttctattgt | ttacacttct | tactcttaga | tatttccagt | tctcctgttt | 300 |
| atctttaagc | ctgattcttt | tgagatgtac | tttttgatgt | tgccggttac | ctttagattg | 360 |
| acaagtatta | tgcctggcca | gtcttgagcc | agctttaaat | cacagctttt | acctatttgt | 420 |
| taggctatag | tgttt | | | | | 435 |

<210> SEQ ID NO 280
<211> LENGTH: 435
<212> TYPE: DNA
<213> ORGANISM: Homo sapiens

<400> SEQUENCE: 280

| tctggatgag | ctgctaactg | agcacaggat | gacctgggac | ccagcccagc | caccccgaga | 60 |
| cctgactgag | gccttcctgg | caaagaagga | gaaggccaag | gggagccctg | agagcagctt | 120 |
| caatgatgag | aacctgcgca | tagtggtggg | taacctgttc | cttgccggga | tggtgaccac | 180 |
| ctcgaccacg | ctggcctggg | gcctcctgct | catgatccta | cacctggatg | tgcagcgtga | 240 |
| gcccagacct | gtccgggcgg | ccgctcgaaa | ttccagcaca | ctggcggccg | ttactagtgg | 300 |
| atccgagctc | ggtaccaagc | ttggcgtaat | catggtcata | gctgtttcct | gtgtgaaatt | 360 |
| gttatccgct | cacaattcca | cacaacatac | gagccggaag | cataaagtgt | aaagcctggg | 420 |
| gtgcctaatg | agtga | | | | | 435 |

<210> SEQ ID NO 281
<211> LENGTH: 440
<212> TYPE: DNA
<213> ORGANISM: Homo sapiens

<400> SEQUENCE: 281

| catctgatct | ataaatgcgg | tggcatcgac | aaaagaacca | ttgaaaaatt | tgagaaggag | 60 |

| | |
|---|---|
| gctgctgaga tgggaaaggg ctccttcaag tatgcctggg tcttggataa actgaaagct | 120 |
| gagcgtgaac gtggtatcac cattgatatc tccttgtgga aatttgagac cagcaagtac | 180 |
| tatgtgacta tcattgatgc cccaggacac agagacttta tcaaaaacat gattacaggg | 240 |
| acatctcagg ctgactgtgc tgtcctgatt gttgctgctg gtgttggtga atttgaagct | 300 |
| ggtatctcca agaatgggca gacccgagag catgcccttc tggcttacac actgggtgtg | 360 |
| aaacaactaa ttgtcggtgt taacaaaatg gattccactg agccccctac agccagaaga | 420 |
| gatatgagga aattgttaag | 440 |

<210> SEQ ID NO 282
<211> LENGTH: 502
<212> TYPE: DNA
<213> ORGANISM: Homo sapiens

<400> SEQUENCE: 282

| | |
|---|---|
| tctgtggcgc aggagccccc tcccccggca gctctgacgt ctccaccgca gggactggtg | 60 |
| cttctcggag ctcccactcc tcagactccg gtggaagtga cgtggacctg gatcccactg | 120 |
| atggcaagct cttcccagc gatggttttc gtgactgcaa gaagggggat cccaagcacg | 180 |
| ggaagcggaa acgaggccgg ccccgaaagc tgagcaaaga gtactgggac tgtctcgagg | 240 |
| gcaagaagag caagcacgcg cccagaggca cccacctgtg ggagttcatc cgggacatcc | 300 |
| tcatccaccc ggagctcaac gagggcctca tgaagtggga aatcggcat gaaggcgtct | 360 |
| tcaagttcct gcgctccgag gctgtggccc aactatgggg ccaaaagaaa agaacagca | 420 |
| acatgaccta cgagaagctg agccgggcca tgaggtacta ctacaaacgg gagatcctgg | 480 |
| aacgggtgga tggccggcga ct | 502 |

<210> SEQ ID NO 283
<211> LENGTH: 433
<212> TYPE: DNA
<213> ORGANISM: Homo sapiens
<220> FEATURE:
<221> NAME/KEY: misc_feature
<222> LOCATION: (1)...(433)
<223> OTHER INFORMATION: n=A,T,C or G

<400> SEQUENCE: 283

| | |
|---|---|
| ccatattaga ttactggaac atctaagcat cagtgtgtga ccatgcgaac aaaagacttc | 60 |
| ggggagtgtc tattttttaaa aaggtttatg tgtgtcgagg cagttgtaaa agatttactg | 120 |
| cagaatcaan cccactttta ggcttangac caggttctaa ctatctaaaa atattgactg | 180 |
| ataacaaaaa gtgttctaaa tgtggctatt ctgatccata nttgnttttt aaagaaaaaa | 240 |
| antgtntata cagaaagagt ntaaaagttc tgtgaattna atgcaaatta gncnccantc | 300 |
| ttgacttccc aaanacttga ttnataccct tnactcctnt cnnttcctgn ncttcnttaa | 360 |
| nntcaatnat tnggnagtnn anggccntcn gnanaacacc nttncncgnt ccncgcaatc | 420 |
| canccgcctt nan | 433 |

<210> SEQ ID NO 284
<211> LENGTH: 479
<212> TYPE: DNA
<213> ORGANISM: Homo sapiens

<400> SEQUENCE: 284

| | |
|---|---|
| tctggaagga tcagggatct gagcaaagcc aagtttactt aagctaagcc acttgttcct | 60 |
| gggtcaagca gtttgttttc taataagcat cattcctgat cattagagca aagggatgaa | 120 |

```
tgctcctctt ggaatgatac aggggatctg ccactgggag agtgttgctc agtgttagag     180
tagcagcaat gacagaatga cagcgactct ctgagtcaac ccagtacttt tagtaccccg     240
tcactatgtg aataaaggca gctagaaaat ggactcaatt ctgcaagcct tcatggcaac     300
agcccatatt aagacttcta gaacaagtta aaaaaaaatc ttccatttcc atccatgcat     360
gggaaaaggg ctttagtata gtttaggatg gatgtgtgta taataataaa atgataagat     420
atgcatagtg ggggaataaa gcctcagagt ccttccagta tggggaatcc attgtatct     479
```

```
<210> SEQ ID NO 285
<211> LENGTH: 435
<212> TYPE: DNA
<213> ORGANISM: Homo sapiens
<220> FEATURE:
<221> NAME/KEY: misc_feature
<222> LOCATION: (1)...(435)
<223> OTHER INFORMATION: n=A,T,C or G

<400> SEQUENCE: 285
tttttttttt tttttttttt tcaatanaaa tgccataatt tattccattg tataaaaaag      60
tcatccttat gtaacaaaat gtnttcttan aanaanaaat atattatttc aggtcataaa     120
taatcagcaa acatacaact gttggcaact aaaaaaaaac ccaacactgg tattttccat     180
cagngctgaa acaaacctg cttaaanata tatttacagg gatagtncag tnctcaaaaa     240
caaaaattga ggtattttgg ttcttctagg agtagacaat gacatttggg ganggggcaga     300 cccctnnccc aaaaaataaa ataagggnat nttcttcant atngaanann ggggggcgccc     360 cggggaaaan naaaccttgg gnngggggtt tggcccaagc ccttgaaaaa aaantttntt     420
tcccaaaaaa aacng                                                      435
```

```
<210> SEQ ID NO 286
<211> LENGTH: 301
<212> TYPE: DNA
<213> ORGANISM: Homo sapiens

<400> SEQUENCE: 286
cctggtttct ggtggcctct atgaatccca tgtagggtgc agaccgtact ccatccctcc      60
ctgtgagcac cacgtcaacg gctcccggcc cccatgcacg ggggagggag ataccccaa     120 gtgtagcaag atctgtgagc ctggctacag cccgacctac aaacaggaca agcactacgg     180
atacaattcc tacagcgtct ccaatagcga gaaggacatc atggccgaga tctacaaaaa     240
cggccccgtg gagggagctt tctctgtgta ttcggacttc ctgctctaca agtcaggagt     300
g                                                                     301
```

```
<210> SEQ ID NO 287
<211> LENGTH: 432
<212> TYPE: DNA
<213> ORGANISM: Homo sapiens

<400> SEQUENCE: 287
tccagcttgt tgccagcatg agaaccgcca ttgatgacat tgaacgccgg gactggcagg      60
atgacttcag agttgccagc caagtcagcg atgtggcggt acagggggac ccccttctca     120
acggcaccag ctttgcagac ggcaagggac accccagaa tggcgttcgc accaaactta     180
gatttatttt ctgttccatc catctcgatc atcagtttgt caatcttctc ttgttctgtg     240
acgttcagtt tcttgctaac cagggcaggc gcaatagttt tattgatgtg ctcaacagcc     300
```

```
tttgagacac ccttccccat atagcgagtc ttatcattgt cccggagctc tagggcctca    360
tagataccag ttgaagcacc actgggcaca gcagctctga agagaccttt tgaggtgaag    420
agatcaacct ca                                                        432
```

<210> SEQ ID NO 288
<211> LENGTH: 326
<212> TYPE: DNA
<213> ORGANISM: Homo sapiens
<220> FEATURE:
<221> NAME/KEY: misc_feature
<222> LOCATION: (254)
<223> OTHER INFORMATION: n=A,T,C or G

<400> SEQUENCE: 288

```
tctggctcaa gtcaaagtcc tggtcctctt ctccgcctcc ttcttcatca tagtaataaa     60
cgttgtcccg ggtgtcatcc tctggggca gtaagggctc tttgaccacc gctctcctcc    120
gaagaaacag caagagcagc agaatcagaa ttagcaaagc aagaattcct ccaagaatcc    180
ccagaatggc aggaatttgc aatcctgctt cgacaggctg tgccttccta cagacgccgg    240
cggccccttc acantcacac acgctgacct ctaaggtggt cacttggtct ttattctggt    300
tatccatgag cttgagattg attttg                                        326
```

<210> SEQ ID NO 289
<211> LENGTH: 451
<212> TYPE: DNA
<213> ORGANISM: Homo sapiens

<400> SEQUENCE: 289

```
gtcccggtgt ggctgtgccg ttggtcctgt gcggtcactt agccaagatg cctgaggaaa     60
cccagaccca agaccaaccg atggaggagg aggaggttga acgttcgcc tttcaggcag    120 aaattgccca gttgatgtca ttgatcatca atactttcta ctcgaacaaa gagatctttc    180
tgagagagct catttcaaat tcatcagatg cattggacaa atccggtat gaaagcttga    240 cagatcccag taaattagac tctgggaaag agctgcatat taaccttata ccgaacaaac    300
aagatcgaac tctcactatt gtggatactg gaattggaat gaccaaggct gacttgatca    360
ataaccttgg tactatcgcc aagtctggga ccaaagcgtt catggaagct ttgcaggctg    420
gtgcagatat ctctatgatt ggacctcggc c                                  451
```

<210> SEQ ID NO 290
<211> LENGTH: 494
<212> TYPE: DNA
<213> ORGANISM: Homo sapiens
<220> FEATURE:
<221> NAME/KEY: misc_feature
<222> LOCATION: (421)
<223> OTHER INFORMATION: n=A,T,C or G

<400> SEQUENCE: 290

```
tttttttttt tcaaaacagt atattttatt ttacaatagc aaccaactcc ccagtttgtt     60
tcaattgtga catctagatg gcttaagatt actttctggt ggtcacccat gctgaacaat    120 attttttcaat cttccaaaca gcaaagactc aaaagagatt ctgcatttca catcagttca    180
caagttcaag agtcttccat ttatcttagc ttttggaata aattatcttt gaggtagaag    240
gacaatgacg aagccactta attccttgtg tctgcataaa agcagattta ttcatcacaa    300
cttcatttat gtgaataaag cagatgatga taaaatgttc tcttattctt gtttaatcag    360
tagtggtagt gatgccagaa acttgtaaat gcacttcaaa ccaattgtgg ctcaagtgta    420
```

```
ngtggttccc caaggctggt accaatgaga ctggggtttg ggaattagtt ggtcatcatc    480
cctcctgctg ccca                                                      494

<210> SEQ ID NO 291
<211> LENGTH: 535
<212> TYPE: DNA
<213> ORGANISM: Homo sapiens

<400> SEQUENCE: 291
tcgcgtgctt aacatgaaaa caaactttgt gctgtttggt tcattgtatg cattgatgga    60
gtcttgtctc tcatcatggg gtgtctgacc atccaacctg cagtactcat aatttctcca   120
catgcaataa tcttccaaaa tgtccaatac ccttgtcatt tgactgaaga ttagtactcg   180
tgaaccttgt tcttttaact tagggagcag cttgtctaaa accaccattt tgccactgtt   240
ggttactaga tgcatatctg ttgtataagg tggaccaggt tctgctccat caaagagata   300
tggatgatta caacattttc tcaactgcat taggatgttc ataaccctca ttttgtccat   360
cttgcctgct gagttgagta tatctatatc cttcattaat atccgagtat accattccct   420
ttgcattttg ctgaggccca catagatttt tacttccttc tttggaggca aactcttttc   480
aacatcagcc ttaattcgac gaaggaggaa tggacgcaaa accatatgaa gcctc        535

<210> SEQ ID NO 292
<211> LENGTH: 376
<212> TYPE: DNA
<213> ORGANISM: Homo sapiens
<220> FEATURE:
<221> NAME/KEY: misc_feature
<222> LOCATION: (1)...(376)
<223> OTHER INFORMATION: n=A,T,C or G

<400> SEQUENCE: 292
tacnagcccg tgctgatcga gatcctggtg gaggtgatgg atccttcctt cgtgtgcttg    60
aaaattggag cctgccccct cggcccataag cccttgttgg gaactgagaa gtgtatatgg   120
ggcccaagct actggtgcca gaacacagag acagcagccc agtgcaatgc tgtcgagcat   180
tgcaaacgcc atgtgtggaa ctaggaggag gaatattcca tcttggcaga accacagca    240 ttggttttttt tctacttgtg tgtctgggg aatgaacgca cagatctgtt tgactttgtt   300
ataaaaatag ggctccccca cctcccccat ttttgtgtcc tttattgnag cattgctgtc   360
tgcaagggag cccta                                                    376

<210> SEQ ID NO 293
<211> LENGTH: 320
<212> TYPE: DNA
<213> ORGANISM: Homo sapiens

<400> SEQUENCE: 293
tcggctgctt cctggtctgg cggggatggg tttgctttgg aaatcctcta ggaggctcct    60
cctcgcatgg cctgcagtct ggcagcagcc ccgagttgtt cctcgctga tcgatttctt   120 tcctccaggt agagttttct ttgcttatgt tgaattccat tgcctctttt ctcatcacag   180
aagtgatgtt ggaatcgttt cttttgtttg tctgatttat ggttttttta agtataaaca   240 aaagttttttt attagcattc tgaaagaagg aaagtaaaat gtacaagttt aataaaaagg   300
ggccttcccc tttagaatag                                               320

<210> SEQ ID NO 294
```

<211> LENGTH: 359
<212> TYPE: DNA
<213> ORGANISM: Homo sapiens

<400> SEQUENCE: 294

```
ctgtcataaa ctggtctgga gtttctgacg actccttgtt caccaaatgc accatttcct      60
gagacttgct ggcctctccg ttgagtccac ttggctttct gtcctccaca gctccattgc     120
cactgttgat cactagcttt ttcttctgcc cacaccttct tcgactgttg actgcaatgc     180
aaactgcaag aatcaaagcc aaggccaaga gggatgccaa gatgatcagc cattctggaa     240
tttggggtgt ccttatagga ccagaggttg tgtttgctcc accttcttga ctcccatgtg     300
agtgtccatc tgattcagat ccatgagtgg tatgggaccc cccactgggg tggaatgtg      359
```

<210> SEQ ID NO 295
<211> LENGTH: 584
<212> TYPE: DNA
<213> ORGANISM: Homo sapiens
<220> FEATURE:
<221> NAME/KEY: misc_feature
<222> LOCATION: (558)
<223> OTHER INFORMATION: n=A,T,C or G

<400> SEQUENCE: 295

```
cctgagttgg gctgactgcc agagacagac ccctctgggt ctcggtgaac cagccaggca      60
tttacctcag tggttggcac ctggaacctg tccagggccc tcacctgact gaggagccgc     120
cgggcagtga agtaattgtc caggtctatg ctcttggggt ggataccata gcatccaag      180
gtattcctca ggttgtggaa ctgggtctga gtataggcag aactgggccc caggatgatc     240
tcccggagtg ggggaagctg tgaggtcagg taagtatcca cgtccacccg taccccaatc     300
aaactcagca gaatggtgaa ctggagaagt ccttccgtta agtatttctt cagagaaagc     360
attgctgaag gaccagaatg tttatgcttt tggttttta aaatcttcca aaagacaaat      420
caaggccact gctctgccgc tccagccagc aggttaccct cctcagtgtc aaacccgta      480
ccccaccctg gcagaacaca agggatgagc tccctgacgg ccccagagga aagcacaccc     540
tgtggagcca aggccaanga cacactccag accacattca cttt                     584
```

<210> SEQ ID NO 296
<211> LENGTH: 287
<212> TYPE: DNA
<213> ORGANISM: Homo sapiens

<400> SEQUENCE: 296

```
ccttatcatt cattcttagc tcttaattgt tcattttgag ctgaaatgct gcattttaat      60
tttaaccaaa acatgtctcc tatcctggtt tttgtagcct tcctccacat cctttctaaa     120
caagatttta aagacatgta ggtgtttgtt catctgtaac tctaaaagat ccttttttaaa     180
ttcagtccta agaaagagga gtgcttgtcc cctaagagtg tttaatggca aggcagccct     240
gtctgaagga cacttcctgc ctaagggaga gtggtatttg cagacta                   287
```

<210> SEQ ID NO 297
<211> LENGTH: 457
<212> TYPE: DNA
<213> ORGANISM: Homo sapiens

<400> SEQUENCE: 297

```
ccaattgaaa caaacagttc tgagaccgtt cttccaccac tgattaagag tggggtggca      60
ggtattaggg ataatattca tttagccttc tgagctttct gggcagactt ggtgaccttg     120
```

```
ccagctccag cagccttctt gtccactgct tgatgacac ccaccgcaac tgtctgtctc      180
atatcacgaa cagcaaagcg acccaaaggt ggatagtctg agaagctctc aacacacatg      240
ggcttgccag gaaccatatc aacaatggca gcatcaccag acttcaagaa tttagggcca      300
tcttccagct ttttaccaga acggcgatca atcttttcct tcagctcagc aaacttgcat      360
gcaatgtgag ccgtgtggca atccaataca ggggcatagc cggcgcttat ttggcctgga      420
tggttcagga taatcacctg agcagtgaag ccagacc                               457
```

```
<210> SEQ ID NO 298
<211> LENGTH: 469
<212> TYPE: DNA
<213> ORGANISM: Homo sapiens

<400> SEQUENCE: 298
tctttgactt tccttgtcta cctcctctgg agatctcaaa ttctccaggt tccatgctcc       60
cagagatctc aatgattcct gattctcctc ttccaggagt ctgaatgtct cttggttcac      120
ttccacagac tccagtggtt cttgaatttc cttttctaga ggattcattg cccctgatt      180 tatttcttct ggagtccaca gtggtgcttg agtttctgga gatttcagtg tttccaggtt      240
ctcttgtccc gcagacttca gtgattctag gatctctgtt tctaaagatt ttactgcctc      300
tatgctctct tctttgagtg actttaagaa ctcttgattc tcattttcaa gaggtctagc      360
tatctcctgg tcaagagact tcagtggttc tagatccact ttttctgggg gtcttaatgt      420
catctgatcc tgttccccta gagacctccg tcgctgttga gtctctttt                  469
```

```
<210> SEQ ID NO 299
<211> LENGTH: 165
<212> TYPE: DNA
<213> ORGANISM: Homo sapiens
<220> FEATURE:
<221> NAME/KEY: misc_feature
<222> LOCATION: (1)...(165)
<223> OTHER INFORMATION: n=A,T,C or G

<400> SEQUENCE: 299
tctgtggaga ggatgaggtt gagggaggtg gggtatntcg ctgctctgac cttaggtaga       60
gtcctccaca gaagcatcaa antggactgg cacatatgga ctcccttcac aggccacaat     120
gatgtgtctc tccttcgggc tggnccggta tgcacagttg gggta                      165
```

```
<210> SEQ ID NO 300
<211> LENGTH: 506
<212> TYPE: DNA
<213> ORGANISM: Homo sapiens

<400> SEQUENCE: 300
tctgaggaaa gtttgggctt attagtattt gctccagcga acctccaagt tttctccatt       60
gcggacaacg taactaccag ctccttggct cagtggttcg cctccactca gaagttccca     120
gtaggttctg tcattattgt tggcacatag gccctgaata caggtgatat agggccccca     180
tgagcgctcc tccattgtga aaccaaatat agtatcattc attttctggg ctttctccat     240
cacactgagg aagacagaac catttagcac agtgacattg gtgaaatatg tttcattgat     300
tctcacagag taattgacgg agatatatga ttgtgagtca ggaggtgtca cagttatagg     360
ctcatcagcg gagatgttga agttacctga agcagagacg caagaagagt ctttgttaat     420
atccaagaag gtctttccca tcagggcagg taagacctgg gctgcagcgt ttggattgct     480
```

```
gaatgctcct tgagaaattt ccgtga                                          506
```

<210> SEQ ID NO 301
<211> LENGTH: 304
<212> TYPE: DNA
<213> ORGANISM: Homo sapiens
<220> FEATURE:
<221> NAME/KEY: misc_feature
<222> LOCATION: (1)...(304)
<223> OTHER INFORMATION: n=A,T,C or G

<400> SEQUENCE: 301

```
tcctaaggca gagcccccat cacctcaggc ttctcagttc ccttagccgt cttactcaac    60
tgccccttc ctctccctca gaatttgtgt ttgctgcctc tatcttgttt tttgttttt    120
cttctggggg gggtctagaa cagtgcctgg cacatagtag gcgctcaata aatacttgtt   180
tgttgaatgt ctcctctctc tttccactct gggaaaccta ngnttctgcc attctgggtg   240
accctgtatt tntttctggt gcccattcca tttgnccagn taatacttcc tcttaaaaat   300
ctcc                                                                304
```

<210> SEQ ID NO 302
<211> LENGTH: 492
<212> TYPE: DNA
<213> ORGANISM: Homo sapiens

<400> SEQUENCE: 302

```
ttttcagtaa gcaacttttc catgctctta atgtattcct ttttagtagg aatccggaag    60
tattagattg aatggaaaag cacttgccat ctctgtctag gggtcacaaa ttgaaatggc   120
tcctgtatca catacggagg tcttgtgtat ctgtggcaac agggagtttc cttattcact   180
ctttatttgc tgctgtttaa gttgccaacc tcccctccca ataaaaattc acttacacct   240
cctgcctttg tagttctggt attcacttta ctatgtgata gaagtagcat gttgctgcca   300
gaatacaagc attgcttttg gcaaattaaa gtgcatgtca tttcttaata cactagaaag   360
gggaaataaa ttaaagtaca caagtccaag tctaaaactt tagtacttt ccatgcagat    420
ttgtgcacat gtgagagggt gtccagtttg tctagtgatt gttatttaga gagttggacc   480
actattgtgt gt                                                       492
```

<210> SEQ ID NO 303
<211> LENGTH: 470
<212> TYPE: DNA
<213> ORGANISM: Homo sapiens

<400> SEQUENCE: 303

```
tctggggcag caggtactcc ctacggcact agtctacagg gggaaggacg ctctgtgctg    60
gcagcggtgg ctcacatggc ctgtctgcac tgtaaccaca ggctgggatg tagccaggac   120
ttggtctcct tggaagacag gtctgatgtt tggccaatcc agtccttcag accctgcctg   180
aaacttgtat cttacgtgaa cttaaagaat aaaatgcatt tctacccga tctcgccccc    240
aggactggca cgacaggccc acggcagatt agatcttttc ccagtactga tcggtgcgtg   300
gaattccagc caccacttct gattcgattc cacagtgatc ctgtcctctg agtattttaa   360
agaagccatt gtcaccccag tcagtgttcc aggagttggc aaccagccag tagggtgtgc   420
cattctccac tccccagccc aggatgcgga tggcatggac ctcggccgcg              470
```

<210> SEQ ID NO 304
<211> LENGTH: 79

```
<212> TYPE: DNA
<213> ORGANISM: Homo sapiens

<400> SEQUENCE: 304
tgtcccattg ttaactcagc ctcaaatctc aactgtcagg ccctacaaag aaaatggaga      60
gcctcttctg gtggatgcg                                                  79

<210> SEQ ID NO 305
<211> LENGTH: 476
<212> TYPE: DNA
<213> ORGANISM: Homo sapiens

<400> SEQUENCE: 305
tcactgagcc accctacagc cagaagagat atgaggaaat tgttaaggaa gtcagcactt      60
acattaagaa aattggctac aaccccgaca cagtagcatt tgtgccaatt tctggttgga    120
atggtgacaa catgctggag ccaagtgcta acgtaagtgg ctttcaagac cattgttaaa    180
aagctctggg aatggcgatt tcatgcttac acaaattggc atgcttgtgt ttcagatgcc    240
ttggttcaag ggatggaaag tcacccgtaa ggatggcaat gccagtggaa ccacgctgct    300
tgaggctctg gactgcatcc taccaccaac tcgtccaact gacaagccct gcgcctgcc    360 tctccaggat gtctacaaaa ttggtggtaa gttggctgta aacaaagttg aatttgagtt    420
gatagagtac tgtctgcctt cataggtatt tagtatgctg taaatatttt taggta        476

<210> SEQ ID NO 306
<211> LENGTH: 404
<212> TYPE: DNA
<213> ORGANISM: Homo sapiens

<400> SEQUENCE: 306
tctgtctcgg agctcagggc gcagccagca cacacaggag cccacaggac agccacgtct      60
tcacagaaac tacagaagtc aggacccagg cgaggacctc aggaacaagt gccccctgca    120
gacagagaga cgcagtagca acagcttctg aacaactaca taataatgcg gggagaatcc    180
tgaagaccac tgcatcccac aagcactgac aaccacttca ggatttttatt tcctccactc    240 taaccccag atccatttat gagaagtgag tgaggatggc aggggcatgg agggtgaagg    300
gacagcaagg atggtctgag ggcctggaaa caatagaaaa tcttcgtcct ttagcatatc    360
ctggactaga aaacaagagt tggagaagag gggggttgat acta                     404

<210> SEQ ID NO 307
<211> LENGTH: 260
<212> TYPE: DNA
<213> ORGANISM: Homo sapiens
<220> FEATURE:
<221> NAME/KEY: misc_feature
<222> LOCATION: (1)...(260)
<223> OTHER INFORMATION: n=A,T,C or G

<400> SEQUENCE: 307
tcctgcctan acatctgtga gggcctcaag ggctgctgcc tcgactttct ccctagctaa      60
gtccacccgt ccagggacac agccagggca ctgctctgtg ctgacttcca ctgcagccaa    120
gggtcaaaat gaagcatctg cggaggccag gactccttgg catcggacac agtcagggga    180
aaagccaccc tgactctgca ggacagaggg tctagggtca tttggcagga gaacactggt    240
gtgccaaggg aagcnancat                                                260

<210> SEQ ID NO 308
```

<211> LENGTH: 449
<212> TYPE: DNA
<213> ORGANISM: Homo sapiens

<400> SEQUENCE: 308

```
tctgtgctcc cgactcctcc atctcaggta ccaccgactg cactgggcgg ggccctctgg      60
ggggaaaggc tccacggggc agggatacat ctcgaggcca gtcatcctct ggaggcagcc     120
caatcaggtc aaagattttg cccaactggt cggcttcaga gtttccacag aagagaggct     180
ttcgacgaaa catctctgca aagatacagc aacactcca catgtccaca ggtgttgcat      240
atgtggactg cagaagaact tcgggagctc ggtaccagag tgtaacaacc ttgatcgttt     300
cggctggcaa gcctggtggg ggtgccttgt ccagatatgt ccttaggtcc tggtctacat     360
gctcaaacac cagggttacc ttgatctccc ggtcagttcg ggatgtggca cagacgtcca     420
tcagccggac aacattggga tgctcaaaa                                        449
```

<210> SEQ ID NO 309
<211> LENGTH: 411
<212> TYPE: DNA
<213> ORGANISM: Homo sapiens
<220> FEATURE:
<221> NAME/KEY: misc_feature
<222> LOCATION: (384)
<223> OTHER INFORMATION: n=A,T,C or G

<400> SEQUENCE: 309

```
ctgtggaaac ctggggtgcc gggtaaatgg agaactccag cttggatttc ttgccataat      60
caactgagag acgttccatg agcagggagg tgaacccaga accagttccc ccaccaaagc     120
tgtggaaaac caagaagccc tgaagaccgg tgcactggtc agccagcttg cgaattcggt     180
ccaacacaag gtcaatgatc tccttgccaa tggtgtagtg ccctcgggca tagttattgg     240
cagcatcttc cttgcctgtg atgagctgct cagggtggaa gagctggcgg taggtgccag     300
tgcgaacttc atcaatgact gtgggttcca agtctacaaa cacagcccgg ggcacgtgct     360
tgccagcgcc cgtctcactt gaanaagggt gtttgaagga agtcatctcc t              411
```

<210> SEQ ID NO 310
<211> LENGTH: 320
<212> TYPE: DNA
<213> ORGANISM: Homo sapiens
<220> FEATURE:
<221> NAME/KEY: misc_feature
<222> LOCATION: (250)
<223> OTHER INFORMATION: n=A,T,C or G

<400> SEQUENCE: 310

```
tcctcgtcca gcttgactcg attagtcctc ataaggtaag caaggcagat ggtggctgac      60
cgggaaatgc ctgcctggca gtggacaaac acccttcctc cagcattctt gatggagtct     120
atgaagtcaa tggcctcgtt gaaccaggag ctgatgtctg ccttgtggtt gtcctccaca     180
gggatgctct tgtactggta gtgaccctca aaatggttgg acaattggc tgagacgttg      240
atcaaggcan ttatgcccaa ggcatccagc atgtccttgc gggaagcgtg atacgcactg     300
cccaggtaca gaaagggcag                                                  320
```

<210> SEQ ID NO 311
<211> LENGTH: 539
<212> TYPE: DNA
<213> ORGANISM: Homo sapiens

<400> SEQUENCE: 311

```
tctggcccat gaagctgaag ttgggagaga tgatgcttcg cctctgcttc acaaactcaa      60
aggcctcgtc cagcttgact cgattagtcc tcataaggta agcaaggcag atggtggctg     120
accgggaaat gcctgcctgg cagtggacaa acacccttcc tccagcattc ttgatggagt     180
ctatgaagtc aatggcctcg ttgaaccagg agctgatgtc tgccttgtgg ttgtcctcca     240
cagggatgct cttgtactgg tagtgaccct caaaatggtt gggacaattg ctgagacgt      300 tgatcaaggc agttatgccc aaggcatcca gcatgtcctt gcgggaagcg tgatacgcac     360
tgcccaggta cagaaagggc aggatttcca ccgggccacc ctgaaatcca gaaatatcca     420
acattcatca agcttgctca aagccaaggc cagtgcccat acccacaaaa actttctgct     480
ggaaaagtca atttcagata ccgagtgaac tcagttctgt gctggaggga taaataaat     539

<210> SEQ ID NO 312
<211> LENGTH: 475
<212> TYPE: DNA
<213> ORGANISM: Homo sapiens

<400> SEQUENCE: 312
tcaaggatct tcctaaagcc accatgtgag aggattcgga cgagagtctg agctgtatgg      60
cagaccatgt cctgctgttc tagggtcatg actgtgtgta ctctaaagtt gccactctca     120 cagggggtcag tgatacccac tgaacctggc aggaacagtc ctgcagccag aatctgcaag    180
cagcgcctgt atgcaacgtt tagggccaaa ggctgtctgg tggggttgtt catcacagca    240
taatggccta gtaggtcaag gatccagggt gtgagggggct caaagccagg aaaacgaatc   300
ctcaagtcct tcagtagtct gatgagaact ttaactgtgg actgagaagc attttcctcg    360
aaccagcggg catgtcggat ggctgctaag gcactctgca atactttgat atccaaatgg    420
agttctggat ccagttttcg aagattgggt ggcactgttg taatgagaat cttca         475

<210> SEQ ID NO 313
<211> LENGTH: 456
<212> TYPE: DNA
<213> ORGANISM: Homo sapiens

<400> SEQUENCE: 313
tccacttaaa gggtgcctct gccaactggt ggaatcatcg ccacttccag caccacgcca      60
agcctaacat cttccacaag gatcccgatg tgaacatgct gcacgtgttt gttctgggcg     120
aatggcagcc catcgagtac ggcaagaaga agctgaaata cctgccctac aatcaccagc    180
acgaatactt cttcctgatt gggccgccgc tgctcatccc catgtatttc cagtaccaga   240
tcatcatgac catgatcgtc cataagaact gggtggacct ggcctgggcc gtcagctact   300
acatccggtt cttcatcacc tacatcccctt tctacggcat cctgggagcc ctccttttcc   360
tcaacttcat caggttcctg gagagccact ggtttgtgtg ggtcacacag atgaatcaca   420
tcgtcatgga gattgaccag gaggacctcg gcccgc                                456

<210> SEQ ID NO 314
<211> LENGTH: 477
<212> TYPE: DNA
<213> ORGANISM: Homo sapiens

<400> SEQUENCE: 314
tgcgtgggct tctggaagcc tggatctgga atcattcacc agattattct ggaaaactat      60
gcgtaccctg gtgttcttct gattggcact gactcccaca cccccaatgg tggcggcctt     120
```

```
ggggcatct gcattggagt tgggggtgcc gatgctgtgg atgtcatggc tgggatcccc    180
tgggagctga agtgccccaa ggtgattggc gtgaagctga cgggctctct ctccggttgg    240
tcctcaccca aagatgtgat cctgaaggtg gcaggcatcc tcacggtgaa aggtggcaca    300
ggtgcaatcg tggaatacca cgggcctggt gtagactcca tctcctgcac tggcatggcg    360
acaatctgca acatgggtgc agaaattggg gccaccactt ccgtgttccc ttacaaccac    420
aggatgaaga agtatctgag caagaccggc cgggaagaca ttgccaatct agctgat      477
```

<210> SEQ ID NO 315
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 315

```
caggtactgg atgtcaggtc tgcgaaactt cttanatttt gacctcagtc cataaaccac    60
actatcacct cggccatcat atgtgtctac tgtggggaca actggagtga aaacttcggt    120
tgctgcaggt ccgtgggaaa atcagtgacc agttcatcag attcatcaga atggtgagac    180
tcatcagact ggtgagaatc atcagtgtca tctacatcat cagagtcgtt cgagtcaatg    240
g                                                                   241
```

<210> SEQ ID NO 316
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 316

```
nttntgtgat agtgtggttt atggactgag gncaaaatnt aagaagtttc gcagacctga    60
catccaancc tgcccgngcg gncgctcgaa aggncgaatt ctgcagatat ccatcacact    120
ggcggccgct cgagcatgca tctagagggc ccaattcgcc ctatantgag tnatattaca    180
attcactggc cgtcnnttta caacgtcgtg actgggaaaa ccctggcgtt acccaactta    240
a                                                                   241
```

<210> SEQ ID NO 317
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 317

```
aggtaccctg ctcancagcc tgggngcctg ggttgtctcc ttgtccatcc actggtccat    60
tctgctctgc attttttttgt tcctcttttg gaggttccac tttgggtttg ggctttgaaa    120
ttatagggct acaantacct cggccgaaac cacnctaagg gcgaattctg cagatatcca    180
tcacactggc ggncgctcga gcatgcatct agagggccca attcgcccta tagtgagtcg    240
t                                                                   241
```

<210> SEQ ID NO 318
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 318
cgngnacaan ntacattgat ggangqtntg nggntctgan tntttantta cantggagca      60
ttaatatttt cttnaacgtn cctcaccttc ctgaantaaa nactctgggt tgtagcgctc     120
tgtgctnana accacntnaa ctttacatcc ctcttttgga ttaatccact gcgcggccac     180
ctctgccgcg accacgctaa gggcnaattc tgcagatatc catcacactg gcggccgctc     240 n                                                                    241

<210> SEQ ID NO 319
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 319
caggtactga tcggtgcgtg gaantccagc caccanttnt gattcgattc cacagtgatc      60
ctgtcctctg agtattttaa agaagccatt gtcaccccag tcagtgttcc aggagttggc     120
aaccagccag tagggtgtgc cattctccac tccccagccc aggatgcgga tggcatggcc     180
acccatcatc tctccggtga cgtgttggta cctcggccgc gaccacgcta agggcgaatt     240
c                                                                    241

<210> SEQ ID NO 320
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 320
ggcaggtacc aacagagctt agtaatntct aaaaagaaaa aatgatcttt ttccgacttc      60
taaacaagtg actatactag cataaatcat tctagtaaaa cagctaaggt atagacattc     120
taataatttg ggaaaaccta tgattacaag tgaaaactca gaaatgcaaa gatgttggtt     180
ttttgtttct cagtctgctt tagcttttaa ctctnnnaan cncatgcaca cttgnaactc     240
t                                                                    241

<210> SEQ ID NO 321
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 321

-continued

```
angtaccaac agagcttagt aattnntaaa agaaaaaat gatcttttc cgacttctaa      60 acaagtgact atactagcat aaatcattct agtaaaacag ctaaggtata gacattctaa   120
taatttggga aaacctatga ttacaagtga aaactcagaa atgcaaagat gttggttttt   180
tgtttctcag tctgctttag cttttaactc tggaagcgca tgcacacntg aactctgctc   240
a                                                                    241
```

<210> SEQ ID NO 322
<211> LENGTH: 241
<212> TYPE: DNA
<213> ORGANISM: Homo sapiens

<400> SEQUENCE: 322

```
ggtaccaaca gagcttagta atttctaaaa agaaaaaatg atcttttcc gacttctaaa    60 caagtgacta tactagcata aatcattctt ctagtaaaac agctaaggta tagacattct   120
aataatttgg gaaacctat gattacaagt aaaaactcag aaatgcaaag atgttggttt    180
tttgtttctc agtctgcttt agcttttaac tctggaagcg catgcacact gaactctgct   240
c                                                                    241
```

<210> SEQ ID NO 323
<211> LENGTH: 241
<212> TYPE: DNA
<213> ORGANISM: Homo sapiens

<400> SEQUENCE: 323

```
cgaggtactg tcgtatcctc agccttgttc tatttcttta ttttagcttt acagagatta    60
ggtctcaagt tatgagaatc tccatggctt tcagggcta aacttttctg ccattctttt    120
gctcttaccg ggctcagaag gacatgtcag gtgggatacg tgtttctctt tcagagctga   180
agaaagggtc tgagctgcgg aatcagtaga gaaagccttg gtctcagtga ctccttggct   240
t                                                                    241
```

<210> SEQ ID NO 324
<211> LENGTH: 241
<212> TYPE: DNA
<213> ORGANISM: Homo sapiens

<400> SEQUENCE: 324

```
aggtactgtc gtatcctcag ccttgttcta tttctttatt ttagctttac agagattagg    60
tctcaagtta tgagaatctc catggctttc agggctaaa cttttctgcc attcttttgc   120
tcttaccggg ctcagaagga catgtcaggt gggatacgtg tttctctttc agagctgaag   180
aaagggtctg agctgcggaa tcagtagaga aagccttggt ctcagtgact ccttggcttt   240
c                                                                    241
```

<210> SEQ ID NO 325
<211> LENGTH: 241
<212> TYPE: DNA
<213> ORGANISM: Homo sapiens

<400> SEQUENCE: 325

```
ggcaggtaca tttgttttgc ccagccatca ctcttttttg tgaggagcct aaatacattc    60
ttcctggggt ccagagtccc cattcaaggc agtcaagtta agacactaac ttggcccttt   120
cctgatggaa atatttcctc catagcagaa gttgtgttct gacaagactg agagagttac   180
atgttgggaa aaaaaagaa gcattaactt agtagaactg aaccaggagc attaagttct   240
``` g                                                                              241

<210> SEQ ID NO 326
<211> LENGTH: 241
<212> TYPE: DNA
<213> ORGANISM: Homo sapiens

<400> SEQUENCE: 326
gcaggtacat tgttttgcc cagccatcac tcttttttgt gaggagccta aatacattct      60
tcctggggtc cagagtcccc attcaaggca gtcaagttaa dacactaact tggcccttc     120 ctgatggaaa tatttcctcc atagcagaag ttgtgttctg acaagactga gagagttaca    180
tgttgggaaa aaaagaagc attaacttag tagaactgat ccaggagcat taagttctga    240
a                                                                              241

<210> SEQ ID NO 327
<211> LENGTH: 241
<212> TYPE: DNA
<213> ORGANISM: Homo sapiens

<400> SEQUENCE: 327
ggtaccagac caagtgaatg cgacagggaa ttatttcctg tgttgataat tcatgaagta     60
gaacagtata atcaaaatca attgtatcat cattagtttt ccactgcctc acactagtga    120
gctgtgccaa gtagtagtgt gacacctgtg ttgtcatttc ccacatcacg taagagcttc    180
caaggaaagc caaatcccag atgagtctca gagagggatc aatatgtcca tgattatcag    240
g                                                                              241

<210> SEQ ID NO 328
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 328
ggtacnagac caaatgaang ccacagggaa ttatttcctg tgttgataat tcatgaagta     60
gaacantata atcaaaatca attgtatcat cattagtttt ccactgcctc acactagtga    120
gctgtgccaa gtagtagtgt gacacctgtg ttgtcatttc ccacatcacg taagagcttc    180
caaggaaagc caaatcccag atgagtctca gagagggatc aatatgtcca tnatcatcan    240
g                                                                              241

<210> SEQ ID NO 329
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 329
ttcaggtcga gttggctgca gatttgtggt gcnttctgag ccgtctgtcc tgcgccaaaa     60
ngcttcaaag tattattaaa aacatatgga tccccatgaa gccctactac accaaagttt    120
accaggagat ttggatagga atggggctga tgggcttcat cgtttataaa atccgggctg    180

```
ctgataagaa gtaaggcttt gaaagcttca gcgcctgctn ctggtcanna ctaaccatan    240 n                                                                    241
```

<210> SEQ ID NO 330
<211> LENGTH: 241
<212> TYPE: DNA
<213> ORGANISM: Homo sapiens

<400> SEQUENCE: 330

```
ttttgtgcag atttgtggtg cgttctgagc cgtctgtcct gcgccaagat gcttcaaagt    60
attattaaaa acatatggat ccccatgaag ccctactaca ccaaagttta ccaggagatt   120
tggataggaa tggggctgat gggcttcatc gtttataaaa tccgggctgc tgataaaaga   180
agtaaggctt tgaaagcttc agcgcctgct cctggtcatc actaaccaga tttacttgga   240
g                                                                   241
```

<210> SEQ ID NO 331
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 331

```
nttttaggna ctttgggctc cagacttcac tggtcttagg nattgaaacc atcacctggn    60
ntgcattcct catgactgag gttaacttaa aacaaaaatg gtaggaaagc tttcctatnc   120
ttcnggtaag anacaaatnt nctttaaaaa aangtggaag gcatgacnta cgtgagaact   180
gcacaaactg gccactgaca aaaatgaccc ccatttgtgt gacttcattg agacacatta   240
c                                                                   241
```

<210> SEQ ID NO 332
<211> LENGTH: 241
<212> TYPE: DNA
<213> ORGANISM: Homo sapiens

<400> SEQUENCE: 332

```
tgtgaggaga gggaacatgc tgagaaactg atgaagctgc agaaccaacg aggtggccga    60
atcttccttc aggatatcaa gaaaccagac tgtgatgact gggagagcgg gctgaatgca   120
atggagtgtg cattacattt ggaaaaaaat gtgaatcagt cactactgga actgcacaaa   180
ctggccactg acaaaaatga cccccatttg tgtgacttca ttgagacaca ttacctgaat   240
g                                                                   241
```

<210> SEQ ID NO 333
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 333

```
caggtacaag cttttttttt ttttttttt tttttttttt ttgnaaatac tntttattgn    60
aaatattcta tcctaaattc catatagcca attaattntt acanaatntt ttgttaattt   120
ttgngngtat aaatttttaca aaaataaagg gtatgttttgt tgcacacaac ttacaaataa  180
```

-continued

```
taataaactn tttattgnaa atattnttta ttgnaaatat tctttatcct aaattccata    240
t                                                                   241

<210> SEQ ID NO 334
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 334
tacctgctgn agggqntgaa gncntctctg ctgccccagg catctgcanc ccctgctgct     60
ggttctgccc ctgctgcagc agaggagaag aaagatgaga agaaggagga gtctgaagag    120
tcagatgatg acatgggatt tggccttttt gattaaannc ctgctcccct gcaaataaag    180 ccttttttaca caaaaaaaaa aaaaaaaaa aaaaaaaaa aagcttgtac ctgcccnggc    240
g                                                                   241

<210> SEQ ID NO 335
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 335
ctatgtgctg ggatgactat ggagacccaa atgtctcana atgtatgtcc cagaaacctg     60
tggctgcttc aaccattgac agttttgctg ctgctggctt ctgcagacag tcaagctgca    120
gctcccccaa aggctgtgct gaaacttgag cccccgtgga tcaacgtgct ccaggaggac    180
tctgtgactc tgacatgcca gggggctcgc agccctgaga gcgactccat tcagtggttc    240
c                                                                   241

<210> SEQ ID NO 336
<211> LENGTH: 241
<212> TYPE: DNA
<213> ORGANISM: Homo sapiens

<400> SEQUENCE: 336
taccaaccta tgcagccaag caacctcagc agttcccatc aaggccacct ccaccacaac     60
cgaaagtatc atctcaggga aacttaattc ctgcccgtcc tgctcctgca cctcctttat    120
atagttccct cacttgattt ttttaacctt cttttttgcaa atgtcttcag ggaactgagc    180
taatactttt ttttttcttg atgttttctt gaaaagcctt tctgttgcaa ctatgaatga    240
a                                                                   241

<210> SEQ ID NO 337
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 337
```

```
ggtactgtat gtagctgcac tacaacagat tcttaccgtc tccacanagg tcatanattg    60
taaatggtna atactgactt ttttttttatt cccttgactc aagacagcta acttcatttt   120
cagaactgtt ttaaaccttt gtgtgctggt ttataaaata atgtgtgtaa tccttgttgc   180
tttcctgata ccagactgtt tcccgtggtt ggttagaata tattttgntt tgatgcttat   240
a                                                                    241
```

<210> SEQ ID NO 338
<211> LENGTH: 241
<212> TYPE: DNA
<213> ORGANISM: Homo sapiens

<400> SEQUENCE: 338

```
aggtacaggt gtgcgctgag ccgagtttac acggaaagga taaagcccat ttagtttctt    60
ctcaaatgga gttttccact ttcctttgaa gtagacagca ttcaccagga tcatcctggt   120
atccccatct acagaacctt caggtaacaa gtttgggatt ttgcctttgg tttgagtctt   180
gacccaggaa ttaatctttt ttctagcttc ttctgcacat tctaggaagt ctactgcctg   240
g                                                                    241
```

<210> SEQ ID NO 339
<211> LENGTH: 241
<212> TYPE: DNA
<213> ORGANISM: Homo sapiens

<400> SEQUENCE: 339

```
taccgacggc tcctggaggg agagagtgaa gggacacggg aagaatcaaa gtcgagcatg    60
aaagtgtctg caactccaaa gatcaaggcc ataacccagg agaccatcaa cggaagatta   120
gttctttgtc aagtgaatga atccaaaag cacgcatgag accaatgaaa gtttccgcct   180
gttgtaaaat ctattttccc ccaaggaaag tccttgcaca gacaccagtg agtgagttct   240
a                                                                    241
```

<210> SEQ ID NO 340
<211> LENGTH: 241
<212> TYPE: DNA
<213> ORGANISM: Homo sapiens

<400> SEQUENCE: 340

```
gtagccctca cacacacatg cccgtaacag gatttatcac aagacacgcc tgcatgtaga    60
ccagacacag ggcgtatgga agcacgtcc tcaagactgt agtattccag atgagctgca   120
gatgcttacc taccacggcc gtctccacca gaaaaccatc gccaactcct gcgatcagct   180
tgtgacttac aaaccttgtt taaagctgc ttacatggac ttctgtcctt taaaagcttc   240
c                                                                    241
```

<210> SEQ ID NO 341
<211> LENGTH: 241
<212> TYPE: DNA
<213> ORGANISM: Homo sapiens

<400> SEQUENCE: 341

```
gtaccgccta ctttcgtctc atgtctccga acttcttgct gatggccgtt ccaacgttgc    60
tgaaagctgc agttgccttt tgccctgcgt gactcagggt ttcatgtgtt ttcttgtagg   120
cagtggtagt ctgcatgtca tgccagcttt tgctgaagtt ctgtttttaat tcattcatca   180 ggttcatgcc gagttttgtt ttatctcaac tagatgcctt tctttcgctg acaaaacttg   240
```

<210> SEQ ID NO 342
<211> LENGTH: 241
<212> TYPE: DNA
<213> ORGANISM: Homo sapiens

<400> SEQUENCE: 342

```
gtacattggt gctataaata taaatgctac ttatgaagca tgaaattaag cttcttttt     60
cttcaagttt tttctcttgt ctagcaatct gttaggcttc tgaaccaaga ccaaatgttt    120
acgttcctct gctgcatacc aacgttactc caaacaataa aaatctatca tttctgctct    180
gtgctgagga atggaaaatg aaaccccac cccctgaccc ctaggactat acagtggaaa     240
c                                                                    241
```

<210> SEQ ID NO 343
<211> LENGTH: 241
<212> TYPE: DNA
<213> ORGANISM: Homo sapiens

<400> SEQUENCE: 343

```
gtacatgtgg tagcagtaat ttttttgaag caactgcact gacattcatt tgagttttct     60
ctcattatca gattctgttc caaacaagta ttctgtagat ccaatggat taccagtgtg     120
ctacagactt cttattatag aacagcattc tattctacat caaaaatagt ttgtgtaagt    180
tagttttggt taccatctaa aatattttta aatgttcttt acataaaaat ttatgttgtg    240
t                                                                    241
```

<210> SEQ ID NO 344
<211> LENGTH: 241
<212> TYPE: DNA
<213> ORGANISM: Homo sapiens

<400> SEQUENCE: 344

```
ggtacaaaat tgttggaatt tagctaatag aaaaacatag taaatattta caaaaacgtt     60
gataacatta ctcaagtcac acacatataa caatgtagac aggtcttaac aaagtttaca    120
aattgaaatt atggagattt cccaaaatga atctaatagc tcattgctga gcatggttat    180
caatataaca tttaagatct tggatcaaat gttgtccccg agtcttctgc aatccagtcc    240
t                                                                    241
```

<210> SEQ ID NO 345
<211> LENGTH: 241
<212> TYPE: DNA
<213> ORGANISM: Homo sapiens

<400> SEQUENCE: 345

```
ggtacgaagc tgagcgcacg ggggttgccc cagcgtggag cctggacctc aaacttcacg     60
gaaaatgctc tctctctttg acaggcttcc agctgtctcc taatttcctg gatgaactct    120
ccccggcgat ttaactgatc ctgaaaagtg gtgagaggac tgaggaagac aaccaggtca    180
gcgttagatc ggcctctgag ggtggtgccc ttgcctgagg agccacccct taccaccttg    240
g                                                                    241
```

<210> SEQ ID NO 346
<211> LENGTH: 241
<212> TYPE: DNA

<213> ORGANISM: Homo sapiens

<400> SEQUENCE: 346

```
caggtaccac tgagcctgag atggggatga gggcagagag aggggagccc cctcttccac    60
tcagttgttc ctactcagac tgttgcactc taaacctagg gaggttgaag aatgagaccc   120
ttaggtttta acacgaatcc tgacaccacc atctataggg tcccaacttg gttattgtag   180
gcaaccttcc ctctctcctt ggtgaagaac atcccaagcc agaaagaagt taactacagt   240
g                                                                  241
```

<210> SEQ ID NO 347
<211> LENGTH: 241
<212> TYPE: DNA
<213> ORGANISM: Homo sapiens

<400> SEQUENCE: 347

```
aggtacatct aaaggcatga agcactcaat tgggcaatta acattagtgt ttgttctctg    60
atggtatctc tgagaatact ggttgtagga ctggccagta gtgccttcgg gactgggttc   120
accccccagt ctgcggcagt tgtcacagcg ccagcccgc tggcctccaa agcatgtgca    180
ggagcaaatg gcaccgagat attccttctg ccactgttct cctacgtggt atgtcttccc   240
a                                                                  241
```

<210> SEQ ID NO 348
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 348

```
angtacttgg caagattnga tgctcttgng ctcantgaca tcattcataa cttgtnngtg    60
tgancagagg aggagnncat catcntgtcc tcattcgtca gnnncctctc ctctctgaat   120
ctcaaacaag ttgataatgg agaaaaattt gaattctcag gattgaggct ggactggttc   180
cgcctacang catacactag cgtggctaag gcccctctgc accctgcatg anaaccctga   240
c                                                                  241
```

<210> SEQ ID NO 349
<211> LENGTH: 241
<212> TYPE: DNA
<213> ORGANISM: Homo sapiens

<400> SEQUENCE: 349

```
gcaggtacca tttgtctgac ctctgtaaaa aatgtgatcc tacagaagtg gagctggata    60
atcagatagt tactgctacc cagagcaata tctgtgatga agacagtgct acagagacct   120
gctacactta tgcagaaaac aagtgctaca gcagctgtgg tcccactcgta tatggtggtg  180
agaccaaaat ggtggaaaca gccttaaccc cagatgcctg ctatcctgac taatttaagt   240
c                                                                  241
```

<210> SEQ ID NO 350
<211> LENGTH: 241
<212> TYPE: DNA
<213> ORGANISM: Homo sapiens

<400> SEQUENCE: 350

```
aggtactgtg gatatttaaa atatcacagt aacaagatca tgcttgttcc tacagtattg      60
cgggccagac acttaagtga aagcagaagt gtttgggtga ctttcctact taaaattttg     120
gtcatatcat ttcaaaacat ttgcatcttg gttggctgca tatgctttcc tattgatccc     180
aaaccaaatc ttagaatcac ttcatttaaa atactgagcg gtattgaata cttcgaagca     240
g                                                                     241

<210> SEQ ID NO 351
<211> LENGTH: 241
<212> TYPE: DNA
<213> ORGANISM: Homo sapiens

<400> SEQUENCE: 351
tacagaaatc atttggagcc gttttgagac agaagtagag gctctgtcaa gtcaatactg      60
cattgcagct tggtccactg aagaagccac gcctgagata caaaagatgc actacacttg     120 acccgctttta tgttcgcttc ctctcccctt ctctctcatc aactttatta ggttaaaaca    180
ccacatacag gctttctcca aatgactccc tatgtctggg gtttggttag aattttatgc     240
c                                                                     241

<210> SEQ ID NO 352
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 352
gtaccctgtn gagctgcacc aagattannt ggggccatca tgactgcanc cacnacgang      60
acgcaggcgt gnagtgcatc gtctgacccg gaaacccttt cacttctctg ctcccgaggt     120
gtcctcnggc tcatatgtgg gaaggcanan gatctctgan gagttncctg gggacaactg     180
ancagcctct ggagaggggc cattaataaa gctcaacatc attggcaaaa aaaaaaaaaa     240
a                                                                     241

<210> SEQ ID NO 353
<211> LENGTH: 241
<212> TYPE: DNA
<213> ORGANISM: Homo sapiens

<400> SEQUENCE: 353
aggtaccagt gcattaattt gggcaaggaa agtgtcataa tttgatactg tatctgttttt     60 ccttcaaagt atagagcttt tgggaaggaa aagtattgaa ctgggggttg gtctggccta     120
ctgggctgac attaactaca attatgggaa atgcaaaagt tgtttggata tggtagtgtg     180
tggttctctt ttggaatttt tttcaggtga tttaataata atttaaaact actataaaaa     240
c                                                                     241

<210> SEQ ID NO 354
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G
```

<400> SEQUENCE: 354
ngcaggtccg ggcaggtacc aagattcatt ctcatcaaaa actagaaaca gaagggcaaa    60
ttccagtttc cttctgggat tgaatacttt caagtaaggt cttcgacaaa caatcagggg   120
gccaattaat ccactgtaga ggtccttaac ttgatccaca gttgaataat aagcccatgg   180
aatacaagca gaatcctctg ttccagctcc agatctttct gggattttcc atacgtaagt   240
g                                                                   241

<210> SEQ ID NO 355
<211> LENGTH: 241
<212> TYPE: DNA
<213> ORGANISM: Homo sapiens

<400> SEQUENCE: 355
ggtacccacc ctaaatttga actcttatca agaggctgat gaatctgacc atcaaatagg    60
ataggatgga cctttttttg agttcattgt ataaacaaat tttctgattt ggacttaatt   120
cccaaaggat taggtctact cctgctcatt cactctttca agctctgtc cactctaact   180 tttctccagt gtcatagata gggaattgct cactgcgtgc ctagtctttc ttcacttacc   240
t                                                                   241

<210> SEQ ID NO 356
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 356
aggtactgta attgagcatc cggaatntgg agaagtaatt tagctacagg gtgaccaacg    60
caagaacata tgccagttcc tcgtagagat tggactggct aaggacgatc agctgaaggt   120
tcatgggttt taagtgcttg tggctcactg aagcttaagt gaggatttcc ttgcaatgag   180
tagaatttcc cttctctccc ttgtcacagg tttaaaaacc tcacagcttg tataatgtaa   240
c                                                                   241

<210> SEQ ID NO 357
<211> LENGTH: 241
<212> TYPE: DNA
<213> ORGANISM: Homo sapiens

<400> SEQUENCE: 357
ttttgtacca ccgatatgat caaggaaaat tctgcccatt tttatggctg aagttctaaa    60
aacctaattc aaagttcttc catgatccta cactgcctcc aagatggtcc aggctggcat   120
aaggcctgag cggcggtgag atccgcggct gccagcagct tgtcgctctt cagctggtat   180
gaagcccctc ggccacccga gtctccagga cctgcccggg cgccgctcga aagggcgaat   240
t                                                                   241

<210> SEQ ID NO 358
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 358

| aggtacgggg agtgggggtg aagcntgttc tctacatagg caacacagcc gcctaantca | 60 |
| caaagtcagt ggtcggccgc ttcgaccaac atgtggtgag cattccacgg gcgcatgaag | 120 |
| tctgggtgct gtgctcgagt ctctgaatat tttgatagga agcgacaaga aaattcaaac | 180 |
| tgctctttgc tgactactgg aaagtgaaaa gatgctcaag tttaccattc aaagaaacca | 240 |
| t | 241 |

<210> SEQ ID NO 359
<211> LENGTH: 241
<212> TYPE: DNA
<213> ORGANISM: Homo sapiens

<400> SEQUENCE: 359

| gaggtacaca aaaggaatac cttctgagag ccagggagtg aggaaagggg aaggagactt | 60 |
| gacgtcaagg gtgcttttga ggaacatgac gggccagcca gcctgcccca actttgaggc | 120 |
| cctgctgggc tcttgtgact ataaatatac tgtctatttc taatgcaatc cgtctttcct | 180 |
| gaaagatctt gttatctttt actattgaga catgctttca tttttgtggt cctgtttcca | 240 |
| a | 241 |

<210> SEQ ID NO 360
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 360

| ngtactctat actaattctg cctttttata cttaattcta aatttctccc ctctaattta | 60 |
| caacaaattt tgtgattttt ataagaatct atgcctcccc aattctcaga ttcttctctt | 120 |
| ttctccttta tttctttgct taaattcagt ataagctttc ttggtatttt aggcttcatg | 180 |
| cacattctta ttcctaaaca ccagcagttc ttcagagacc taaaatccag tataggaata | 240 |
| a | 241 |

<210> SEQ ID NO 361
<211> LENGTH: 241
<212> TYPE: DNA
<213> ORGANISM: Homo sapiens

<400> SEQUENCE: 361

| aggtactctc cgtgccccga cactgaacat tatccagcca gatctgccca gtgccagctc | 60 |
| ccactttgta cttttcttac tatcctgtct agaatcatgt cttatgattt aacagatat | 120 |
| agaaccactc ctagaaaatg ttctttcact ttctcgtttc cttttaatc tatcatcctg | 180 |
| actactgaac ttaaaatctt tttcttccct tttttgtttc tctttctttt tatcctgttc | 240 |
| a | 241 |

<210> SEQ ID NO 362
<211> LENGTH: 241
<212> TYPE: DNA
<213> ORGANISM: Homo sapiens
<220> FEATURE:
<221> NAME/KEY: misc_feature
<222> LOCATION: (1)...(241)

```
<223> OTHER INFORMATION: n = A,T,C or G

<400> SEQUENCE: 362
aggtactttt atacctngct tangtcagtg acagatttac caatgacaac acaattttaa    60
aattccaaca catatattac tttgtcctat gaagggcaaa aagtcaatat attttaaatt   120
ttaaaaacag aatggatata atgacctttt tacacatcag tgatatttaa aagacttaaa   180
gagacaatac tatggttgag acactggctt cctattccag ccctaattaa agaaaaaata   240
g                                                                  241

<210> SEQ ID NO 363
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 363
ttangtacta aaacaaaat cctaattctg ttttaaagag ctgggagatg ttaatcatat     60
gctcagtttt tccacgttat aatttcctaa atgcaaactt ttcaatcagg gcagttcaaa   120
ttcattacat cacagtaaat aacagtagcc aactttgatt ttatgcttat aggaaaaaaa   180
atcctgtaga tataaaaaca gcaaattttg acaaataaaa ctcaaaccat tcatccctaa   240
a                                                                  241

<210> SEQ ID NO 364
<211> LENGTH: 241
<212> TYPE: DNA
<213> ORGANISM: Homo sapiens

<400> SEQUENCE: 364
ggtacaagca gttagtcctg aaggccctg ataagaatgt catcttctcc ccactgagca    60
tctccaccgc cttggccttc ctgtctctgg gggcccataa taccaccctg acagagattc   120
tcaaaggcct caagttcaac ctcacggaga cttctgaggc agaaattcac cagagcttcc   180
agcacctcct gcgcaccctc aatcagtcca gcgatgagct gcagctgagt atgggaaatg   240
c                                                                  241

<210> SEQ ID NO 365
<211> LENGTH: 241
<212> TYPE: DNA
<213> ORGANISM: Homo sapiens

<400> SEQUENCE: 365
cgaggtactg agattacagg catgagccac cacgcccggc caaaaacatt taaaaaatga    60
ctgtccctgc tcaaatactg cagtaggaaa tgtaatttga catatatcac ttccagaaaa   120
aaactttaaa tctttctata aaatgaattt gatacatcat cagcatgaag tgaagttaaa   180
atctcttaca aagtaaattc aggtatatca acaatgagat ccaaaagtat cggttcaaga   240
t                                                                  241

<210> SEQ ID NO 366
<211> LENGTH: 241
<212> TYPE: DNA
<213> ORGANISM: Homo sapiens

<400> SEQUENCE: 366
```

```
ggcaggtaca catcaaacac ttcattgcct aaatgcaggg acatgcttcc atctgaccac      60
ttgactatcc gagcattgct ttctttaatt tcatttcctt cttcatctcg gcgtatcctc     120
catcttatag tattttctac ctttaatttt aacctggttc taccttcttc atccagcatt     180
tcttcatctt caaattcatc ttcataatac tgggctctac acttgagaaa gttgggcagt     240
t                                                                     241

<210> SEQ ID NO 367
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 367
gcaggtacaa ataattcctg ttgtnacatt tagtggacgc gattatctgt atacctcaaa      60
ttttaattta agaaagtatc acttaaagag catctcattt tctatagatt gaggcttaat    120
tactgaaaag tgactcaacc aaaaagcaca taaccttta aaggagctac acctaccgca     180
gaaagtcaga tgccctgtaa ataactttgg tctttcaaaa tagtggcaat gcttaagata    240
c                                                                     241

<210> SEQ ID NO 368
<211> LENGTH: 241
<212> TYPE: DNA
<213> ORGANISM: Homo sapiens

<400> SEQUENCE: 368
tttgtacatt gttaatagtg accctcggag gaaatggatt tctcttctat taaaaactct     60
atggtatata agcattacat aataatgcta cttaaccacc ttttgtctca agaattatca    120
ccaaagtttt ctggaaataa gtccacataa gaattaaata tttaaaaggt gaaatgttcc    180
ttattttaac tttagcaaga tcttttcttt ttcattaaga aacactttaa taattttaaa    240
g                                                                     241

<210> SEQ ID NO 369
<211> LENGTH: 241
<212> TYPE: DNA
<213> ORGANISM: Homo sapiens

<400> SEQUENCE: 369
gcaggtactt tattcttatt tcttatccta tattctgtgt tacagaaaaa ctactaccat      60
aaacaaaaca ccaaccagcc acagcagttg tgtcaagcat gacaattggt ctagtcttca    120
cattttatta gtaagtctat caagtaagag atgaagggtc tagaaaacta gacacaaagc    180
aaccagggtc caaatcacca aggtagatct gtgcttagct aaagggaaac acccgaagat    240
t                                                                     241

<210> SEQ ID NO 370
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G
```

```
<400> SEQUENCE: 370
ngttcacagt gcccctccgg cctcgccatg aggctcttcc tgtcgctccc ggtcctggtg      60
gtggttctgt cgatcgtctt ggaaggccca gccccagccc aggggacccc agacgtctcc    120
agtgccttgg ataagctgaa ggagtttgga aacacactgg aggacaaggc tcgggaactc    180
atcagccgca tcaaacagag tgaactttct gccaagatgc gggagtggtt ttcagaagac    240
a                                                                    241

<210> SEQ ID NO 371
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 371
ggcaggtcat cttgagcctt gcacatgata ctcagattcc tcacccttgc ttaggagtaa     60
aacaatatac tttacagggt gataataatc tccatagtta tttgaagtgg cttgaaaaag   120
gcaagattga cttttatgac attggataaa atctacaaat cagccctcga gttattcaat   180
gataactgac aaactaaatt atttccctag aaaggaagat gaaaggnagt ggagtgtggt   240
t                                                                    241

<210> SEQ ID NO 372
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 372
aggtacagca aagcgaccct tggtgnnata gatcagacgg aaattctctc ccgtcttgnc     60
aatgctgatg acatccatga atccagcagg gtaggttata tcagttcgga ccttgccatc   120
gattttaatg aaccgctgca tgcaaatctt ctttacttca tctcctgtca gggcatactt   180
aagtctgttc ctcaggaaaa tgatgagggg agacactct ctcaacttgt ggggaccggt    240
g                                                                    241

<210> SEQ ID NO 373
<211> LENGTH: 241
<212> TYPE: DNA
<213> ORGANISM: Homo sapiens

<400> SEQUENCE: 373
tactgaaaca gaaaaaatgt attcccacaa aagctgttac acagcggttt cccgtcccca     60
gaagcagtag aaaatcttag cattccaatg gaaggcatgt atttgtaaaa tattctaaaa   120
tcagctctat agtttccttg tcctctttga taagggatca gacagagggt gtgtccccct   180
tcagcagcta cccttcttga caaactggtc tccaataata cctttcagaa acttacaaga   240
c                                                                    241

<210> SEQ ID NO 374
<211> LENGTH: 241
<212> TYPE: DNA
<213> ORGANISM: Homo sapiens
```

<400> SEQUENCE: 374

```
caggtactaa aacttacaat aaatatcaga gaagccgtta gttttttacag catcgtctgc    60
ttaaaagcta agttgaccag gtgcataatt tcccatcagt ctgtccttgt agtaggcagg   120
gcaattctg ttttcatgat cggaatactc aaatatatcc aaacatcttt ttaaaacttt   180
gatttatagc tcctagaaag ttatgttttt taatagtcac tctactctaa tcaggcctag   240
c                                                                   241
```

<210> SEQ ID NO 375
<211> LENGTH: 241
<212> TYPE: DNA
<213> ORGANISM: Homo sapiens

<400> SEQUENCE: 375

```
aggtacaaag gaccagtatc cctacctgaa gtctgtgtgt gagatggcag agaacggtgt    60
gaagaccatc acctccgtgg ccatgaccag tgctctgccc atcatccaga agctagagcc   120
gcaaattgca gttgccaata cctatgcctg taaggggcta gacaggattg aggagagact   180
gcctattctg aatcagccat caactcagat tgttgccaat gccaaaggcg ctgtgactgg   240
g                                                                   241
```

<210> SEQ ID NO 376
<211> LENGTH: 241
<212> TYPE: DNA
<213> ORGANISM: Homo sapiens

<400> SEQUENCE: 376

```
ggtacatttt actttccttc tttcagaatg ctaataaaaa acttttgttt atacttaaaa    60
aaaccataaa tcagacaaac aaaagaaacg attccaacat cacttctgtg atgagaaaag   120
aggcaatgga attcaacata agcaaagaaa actctacctg gaggaaagaa atcgatcagc   180
gaagaaacaa ctcggggctg ctgccagact gcaggccatg cgaggaggag cctcctagag   240
g                                                                   241
```

<210> SEQ ID NO 377
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 377

```
tcctttctgt ccaggtgatt cacagactag acctttctta tcctcctcct agagttttga    60
cttgggactc tagtgttaag atgatgagcc cgtgcatcag gtccttctgc actttggtgg   120
aagtctccca gggtaggttt cctatttgaa acagtggaat catgtttcca gtgataaagt   180
ttaatgacct catccttttt ttttttttttc tcatctgcca tttgtgtgtc ttanatgggt   240
t                                                                   241
```

<210> SEQ ID NO 378
<211> LENGTH: 241
<212> TYPE: DNA
<213> ORGANISM: Homo sapiens

<400> SEQUENCE: 378

| | |
|---|---|
| aggtcagcga tcaggtcctt tatgggcagc tgctgggcag ccccacaagc ccagggccag | 60 |
| ggcactatct ccgctgcgac tccactcagc ccctcttggc gggcctcacc cccagcccca | 120 |
| agtcctatga gaacctctgg ttccaggcca gccccttggg gaccctggta accccagccc | 180 |
| caagccagga ggacgactgt gtctttgggc cactgctcaa cttccccctc ctgcagggga | 240 |
| t | 241 |

<210> SEQ ID NO 379
<211> LENGTH: 241
<212> TYPE: DNA
<213> ORGANISM: Homo sapiens

<400> SEQUENCE: 379

| | |
|---|---|
| tacggagcaa tcgaagaggc atatccacac ttggggtggc tatagggctg gaaaatgctg | 60 |
| aagatgactg ctttcactga ggtcaaggat tgtaatattg ccagctttgt aaagccatta | 120 |
| aagcagaagt ttcttcagtg atcttctctc taagaaacac catcacctcc atgtgcctta | 180 |
| cagaggcccc ctgcgttctg ctgcattgct tttgcgcaat cccttgatga tgaagatggt | 240 |
| c | 241 |

<210> SEQ ID NO 380
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 380

| | |
|---|---|
| acgtacacgc agaccgacat gggnnnttca ggcntnagat caaactcaaa acctgnaatg | 60 |
| atatccactc tcttttcctt aagctcaggg aaatattcca agtagaagtc canaaagtca | 120 |
| tcggctaana tgcttcngaa tttgaattca tgcacatagg ccttgaaaaa actgtcaaac | 180 |
| tgannctgat cacccaccaa gtgggccntn tatgacacaa agcagaaacc tttctctntan | 240 |
| g | 241 |

<210> SEQ ID NO 381
<211> LENGTH: 241
<212> TYPE: DNA
<213> ORGANISM: Homo sapiens

<400> SEQUENCE: 381

| | |
|---|---|
| aggtacaact taatggatta gcttttgggt ttaactgaat atatgaagaa attgggtctg | 60 |
| tctaaagaga gggtatttca tatggctttt agttcacttg tttgtatttc atcttgattt | 120 |
| ttttctttgg aaaataaagc attctatttg gttcagattt ctcagatttg aaaaggctc | 180 |
| tatctcagat gtagtaaatt atttcctttc agtttgtgaa agcaggattt gactctgaaa | 240 |
| g | 241 |

<210> SEQ ID NO 382
<211> LENGTH: 241
<212> TYPE: DNA
<213> ORGANISM: Homo sapiens

<400> SEQUENCE: 382

| | |
|---|---|
| gtactgctat aatcaatacg tctgatagac aggtttatcc actatattga ccctacctct | 60 |
| aaaaggattg tcataattta tatgctttat gtttacacct atgatacagt tgccttggaa | 120 |

```
cacaaaattt ttcattgtaa ttaaaaaaag aagagttgtg cagacagaag aaatcaaatc      180
taagaaaatc acaggagtag ataaatactc tagaattcat ataccettgg aagatgggtt      240 t                                                                     241
```

<210> SEQ ID NO 383
<211> LENGTH: 241
<212> TYPE: DNA
<213> ORGANISM: Homo sapiens

<400> SEQUENCE: 383

```
ggcaggtaca aagtcttctc tttgcttttt ataattttaa agcaaataac acatttaact      60
gtatttaagt ctgtgcaaat aatccttcag aagaaatatc caagattctg tttgcagagg      120
tcattttgtc tctcaaagat gattaaatga gtttgtcttc agataaagtg ctcctgtcca      180
gcagaactca aaaggccttc aagctgttca gtaagtgtag ttcagataag actccgtcat      240
a                                                                     241
```

<210> SEQ ID NO 384
<211> LENGTH: 241
<212> TYPE: DNA
<213> ORGANISM: Homo sapiens

<400> SEQUENCE: 384

```
ggtacacaaa atacacttgc aagcttgctt acagagacct gttaaacaaa gaacagacag      60
attctataaa atcagttata tcaacatata aaggagtgtg attttcagtt tgttttttta      120
agtaaatatg accaaactga ctaaataaga aggcaaaaca aaaaattatg cttccttgac      180
aaggcctttg gagtaaacaa aatgctttaa ggctcctggt gaatggggtt gcaaggatga      240
a                                                                     241
```

<210> SEQ ID NO 385
<211> LENGTH: 241
<212> TYPE: DNA
<213> ORGANISM: Homo sapiens

<400> SEQUENCE: 385

```
ggcaggtcta caatggctct gtcccttctg tggaatcgtt acaccaagag gtctcagtcc      60
tggtccctga ccccacagtg agctgtttag atgatccttc acatcttcct gatcaactgg      120
aagacactcc aatcctcagt gaagactctc tggagcccte caactctctg caccaggta      180 ggtttggagg ctatgtccct ttaacttatc catgcagagt agccaaactt tacctgaaag      240
a                                                                     241
```

<210> SEQ ID NO 386
<211> LENGTH: 241
<212> TYPE: DNA
<213> ORGANISM: Homo sapiens

<400> SEQUENCE: 386

```
aggtaccttt ttcctctcca aaggaacagt ttctaaagtt ttctgggggg aaaaaaaact      60
tacatcaaat ttaaaccata tgttaaactg catattagtt gtgttacacc aaaaaattgc      120
ctcagctgat ctacacaagt ttcaaagtca ttaatgcttg atataaattt actcaacatt      180
aaattatctt aaattattaa ttaaaaaaaa aactttctaa gggaaaaata aacaaatgta      240
g                                                                     241
```

<210> SEQ ID NO 387
<211> LENGTH: 241
<212> TYPE: DNA
<213> ORGANISM: Homo sapiens

<400> SEQUENCE: 387

```
accccactgg ccgctgtgga gtatctccac tctcccctcg tgagggccgc tcccaccgac      60
cagtcgaact ttcgtaaatg gagttaatgt gtttccactc ccctttccc ctttctggcc     120
ttttggtcca gaatttcctg gccttccggc atatcctggg agtcctcgac ttccaggaaa     180
gccaattgct ccccgatcac ctttaagacc cggaggacct attggacctg gaaatcctcg     240
t                                                                    241
```

<210> SEQ ID NO 388
<211> LENGTH: 241
<212> TYPE: DNA
<213> ORGANISM: Homo sapiens

<400> SEQUENCE: 388

```
tttgtactct tgtccacagc agagacattg agtataccat tggcatcaat gtcaaaagtg      60
acttcaatct gaggaacacc tcggggtgca ggaggtatgc ctgtgagttc aaacttgcca     120
agcaggttgt tatcctttgt catggcacgc tcgccttcat aaacctgaat aagtacacca     180
ggctggttgt cagaataggt agtgaaggtc tgtgtctgct tggtaggaat ggtggtatta     240
c                                                                    241
```

<210> SEQ ID NO 389
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 389

```
tacctntgtt agtgagcacc ttgtcttntg tgcttatntc ttnaagataa atacatggaa      60
ggatgtgaaa atcggaacac caactatgtg tctcactgca tctaagtgaa gcagccacag     120
ctgtgagagt tttcaaagca gaaagatgct gatgtgacct ctggaattca gacatactga     180
gctatgggtc agaagtgttt tacttaaaaa gcaaacaatc cccaggaaat actgaatagg     240
a                                                                    241
```

<210> SEQ ID NO 390
<211> LENGTH: 241
<212> TYPE: DNA
<213> ORGANISM: Homo sapiens

<400> SEQUENCE: 390

```
gcaggtacat ccacatgttc ctccaaatga cgtttggggt cctgcttgcc aacattcttt      60
attgccagct gttcaggtgt catcttatct tcttcttcta cagccttatt gtaattcttg     120
gctaattcca acatctcttt taccactgat tcattgcgtt acaatgttc actgtagtcc      180
tgaagtgtca aaccttccat ccaactcttc ttatgcaaat ttagcaacat cttctgttcc     240
a                                                                    241
```

<210> SEQ ID NO 391
<211> LENGTH: 241

```
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 391
cnggcacaan cttntgtttt tnntnttttt tttttttttn tctttatttn ttttttantnt    60 taaanaaaaa nnntannnaa annngggttt aaatnctntn nncagancat taaaactgaa   120
ggggaaaaaa aaaccaaaaa cgagcttntt anttnacntg ggnttgggnn gntgctgatn   180
tnaagaagca anntttanan cnngcnnnat ganngagngn tcannttgaa atttnnaccc   240
t                                                                    241

<210> SEQ ID NO 392
<211> LENGTH: 241
<212> TYPE: DNA
<213> ORGANISM: Homo sapiens

<400> SEQUENCE: 392
gaggtactaa atggtatcct tagattaaaa ttttgtgctt gataacagct gttttttcta    60
cattagaaat aagatgccac acaaggaact acattccaga tttaaagaaa tgaaaggata   120
ccattagtgt gtataacaga ttattgttca tacttgtaaa gcatcttatg tcattgagaa   180
tataaagaac agtgccttag aagacagtga aaggtaagct ctagcttaat gtctatgatt   240
t                                                                    241

<210> SEQ ID NO 393
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 393
ggcaggtaca taagcataat cagttatgga cagcttcttg tataaattgc tattcancaa    60
tacataaact gcctnaaaga tttatgctta caggtagaca ttcaatttac caataaaaca   120
gcatgttctg aaaatatggg cacattttaa aacatattaa gacagttctg ttaaccataa   180
tagtcccaca gtatgactga gtaataagaa tctacttcaa aagnaaaaaa aaaattaatc   240
a                                                                    241

<210> SEQ ID NO 394
<211> LENGTH: 241
<212> TYPE: DNA
<213> ORGANISM: Homo sapiens

<400> SEQUENCE: 394
aggtacagca gcagtagatg gctgcaacaa ccttcctcct accccagccc agaaaatatt    60
tctgccccac cccaggatcc gggaccaaaa taaagagcaa gcaggccccc ttcactgagg   120
tgctgggtag ggctcagtgc cacattactg tgctttgaga aagaggaagg ggatttgttt   180
ggcactttaa aaatagagga gtaagcagga ctggagaggc cagagaagat accaaaattg   240
g                                                                    241

<210> SEQ ID NO 395
```

```
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 395
nggcnggnnc caanatatga aatntnanta tnatacatga tnaaaagctt tatntatttt      60
agtgagtaat taagtttaca ctgtgaataa ggattaattc ccagatgacc atctacagtt     120
actaccacat agagggtata cacggatgga tcgattacaa gaatataaaa cttattttcc     180
ttcctgtatc cacatttctt tgcaatgtga atttgcaggc cctctcaaga agtggagtct     240
a                                                                    241

<210> SEQ ID NO 396
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 396
gaggtacacc ttgaatgaca atgctnggag ccccctgtg gtcatcgacg cctccactgc       60
cattgatgca ccatccaacc tgcgtttcct ggccaccaca cccaattcct tgctggtatc    120
atggcagccg ccacgtgcca ggattaccgg ctacatcatc aagtatgaga agcctgggtc    180
tcctcccaga gaagtggtcc ctcggccccg ccctggtgtc acagaggcta ctattactgg    240
c                                                                    241

<210> SEQ ID NO 397
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 397
ggcaggtacc agcaggggga tgtgtttctg gggaattgtg gctctggaag cttcacggtt      60
tcccagaatg tggaaaatat atctgtgcan gatagaaatc ctgcccagag gctgtttctg    120
tctcatttga gctctccttc atgtggcaga gctgactgtg gcggtttagg agcctacatt    180
ttagaaaagc ttacctcaaa gttctgcatt gagcctgagc actggaaagg agataaaata    240
a                                                                    241

<210> SEQ ID NO 398
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 398
gangtgacca ngacatcacc tnacacntgg aaagcganga nttgaatggt gcntacaang      60
ccntacccnt tgcccannac ctgaacgcgc cttntgattg ggacagccgt gggaaggaca    120
```

```
gttatgaaac nantcanctg gatgaccana gtgntgaaac cnacanncac angcnntcna        180
cattatataa ncggaaagct aatgatgaga gcaatgatca ttccgatgtn attgatagtc        240
a                                                                       241
```

<210> SEQ ID NO 399
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 399

```
cagagtgaga tgggagtggg agggccaatc tgatacagaa gggggtgaag ggtagggccc        60
ctgagcagcc cacccttac cctgacgaag gcaatcctcc tctggaatgt ctcttccctc         120
ttcagtctgg gttctgcctc agccacgaac tgggaaggag tgaggaacat cccaacggca        180
atgagagtat cccagtgact ccaaacagga angaatcagt gttcanaaag tcagggccct        240
t                                                                       241
```

<210> SEQ ID NO 400
<211> LENGTH: 241
<212> TYPE: DNA
<213> ORGANISM: Homo sapiens

<400> SEQUENCE: 400

```
ggtactcttg ctcttttagc tagagtgtat gtgaaaataa agaaatacat cattgtattc        60
acaaccatgt gtcttcattt ataacttttt gtttaaaaaa tttttagttc aagtttagtt        120
cattgatatt atcctctgaa tgcagttaag gctgggcaga aattctactc atgtgacatc        180
tgccacaggt ctattttgaa gcttttcttc taatgggcaa tgtttgtcct taccaggatt        240
t                                                                       241
```

<210> SEQ ID NO 401
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 401

```
nncaggtact ttgtagagca gagagaggct ttggttcctc ctttcttcaa tcacgtggag        60
atgtgtcatc acctgggatt tcatctgggc cgccttttct gggtcaacag ccaacacatg        120
ctggtaatga cggatggtat gtaagcgatc tttgttctca gcacggacat aacgccgtaa        180
ggcctggaga atgcgatgag gccgtggcgg gtcagactgc aaggcagcca ggtagttctc        240
c                                                                       241
```

<210> SEQ ID NO 402
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 402

```
ggcaggtcca aaaaaaacct aaaaanngtt tcaggaatgt agagaaatat ccaacttaaa      60
tagcgaaaaa gtgcaccata attactgctg cactgcagtc atttctgcaa ttcccatgtt     120
tcttaaataa ctatcttgtc agataacaca caatataaag agcaattatg aaaaacagac    180
atttacatat acttctaaag tcttattggg aatatcctgt ttggccattg ggataaccaa    240
t                                                                    241
```

<210> SEQ ID NO 403
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 403

```
aggtgttaac tacccgctcc gagacgggat tgatgacgag tcctatgang ccattttcaa     60
gccggtcatg tccaaagtaa tggagatgtt ccagcctagt gcggtggtct tacagtgtgg    120
ctcagactcc ctatctgggg atcggttagg ttgcttcaat ctaactatca aaggacacgc    180
caagtgtgtg gaatttgtca agagctttaa cctgcctatg ctgatgctgg gaggcggtgg    240
t                                                                    241
```

<210> SEQ ID NO 404
<211> LENGTH: 241
<212> TYPE: DNA
<213> ORGANISM: Homo sapiens

<400> SEQUENCE: 404

```
caggtactgc aacccataaa atactgtttc ctcatatttc accttcctta atttggagtt     60
ttctgtcttc ttttcacggc attcaaagta ggaataaact ttgcttgtgt tgggtggata    120
ttgtttatag tgagtaacct tgtaggagtc ggtggccagg aggatgttga actcggcttc    180
tgccgcagga ttcatctcgg gccggaggac aaggggcccg cgcgccgcga gctccctgac    240
c                                                                    241
```

<210> SEQ ID NO 405
<211> LENGTH: 266
<212> TYPE: DNA
<213> ORGANISM: Homo sapiens

<400> SEQUENCE: 405

```
ttctgggctg gggagtggag agaaagaagt tgcagggctt acaggaaatc ccagagcctg     60
aggttttctc ccagatttga gaactctaga ttctgcatca ttatctttga gtctatattc    120
tcttgggctg taagaagatg aggaatgtaa taggtctgcc ccaagccttt catgccttct    180
gtaccaagct tgtttccttg tgcatccttc ccaggctctg ctgcccctt attggagaat    240
gtgatttcca agacaatcaa tccaca                                         266
```

<210> SEQ ID NO 406
<211> LENGTH: 231
<212> TYPE: DNA
<213> ORGANISM: Homo sapiens

<400> SEQUENCE: 406

```
ttggtgaaga accattcctc ggcatccttg cggttcttct ctgccatctt ctcatactgg     60
```

```
tcacgcatct cgttcagaat gcggctcagg tccacgccag gtgcagcgtc catctccaca    120
ttgacatctc cacccacctg gcctctcagg gcattcatct cctcctcgtg gttcttcttc    180
aggtaggcca gctcctcctt caggctctca atctgcatct ccaggtcagc t             231

<210> SEQ ID NO 407
<211> LENGTH: 266
<212> TYPE: DNA
<213> ORGANISM: Homo sapiens

<400> SEQUENCE: 407
cagcatcatt gtttataatc agaaactctg gtccttctgt ctggtggcac ttagagtctt     60
ttgtgccata atgcagcagt atggagggag gattttatgg agaaatgggg atagtcttca    120
tgaccacaaa taaataaagg aaaactaagc tgcattgtgg gttttgaaaa ggttattata    180
cttcttaaca attctttttt tcagggactt ttctagctgt atgactgtta cttgaccttc    240
tttgaaaagc attcccaaaa tgctct                                         266

<210> SEQ ID NO 408
<211> LENGTH: 261
<212> TYPE: DNA
<213> ORGANISM: Homo sapiens

<400> SEQUENCE: 408
ctgtgtcagc gagcctcggt acactgattt ccgatcaaaa gaatcatcat ctttaccttg     60
acttttcagg gaattactga actttcttct cagaagatag ggcacagcca ttgccttggc    120
ctcacttgaa gggtctgcat ttgggtcctc tggtctcttg ccaagtttcc cagccactcg    180
agggagtaat atctggaggg caagaagag acttatgtta ttgttgaacc tccagccaca    240
gggaggagca tgggcatggg t                                              261

<210> SEQ ID NO 409
<211> LENGTH: 266
<212> TYPE: DNA
<213> ORGANISM: Homo sapiens

<400> SEQUENCE: 409
gctgacagta atacactgcc acatcttcag cctgcaggct gctgatggtg agagtgaaat     60
ctgtcccaga cccgctgcca ctgaatcggt cagggatccc ggattcccgg gtagatgccc    120
agtaaatgag cagtttagga ggctgtcctg gtttctgctg gtaccaagct aagtagttct    180
tattgttgga gctgtctaaa acactctggc tggtcttgca gttgatggtg gccctctcgc    240
ccagagacac agccagggag tgtgga                                         266

<210> SEQ ID NO 410
<211> LENGTH: 181
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 410
caaaaggtnc ttttgntca aaancnattt ttattccttg atattttct tttttttt         60 tttgnggatg gggacttgtg aattttttcta aggggnnnn ttnannnngg aagaaaaccn    120
ngntccggtt ccagccaaac cngtngctna ctttccacct tntttccacc tccctcnggt    180
```

<210> SEQ ID NO 411
<211> LENGTH: 261
<212> TYPE: DNA
<213> ORGANISM: Homo sapiens

<400> SEQUENCE: 411

```
gcccctgcag tacttggccg atgtggacac ctctgatgag gaaagcatcc gggctcacgt    60
gatggcctcc caccattcca agcggagagg ccgggcgtct tctgagagtc agggtctagg   120
tgctggagtg cgcacggagg ccgatgtaga ggaggaggcc ctgaggagga agctggagga   180
gctggccagc aacgtcagtg accaggagac ctcgtccgag gaggaggaag ccaaggacga   240
aaaggcagag cccaacaggg a                                             261
```

<210> SEQ ID NO 412
<211> LENGTH: 171
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 412

```
nttttntctt tacaattcag tcttcaacaa cttgagagct ttcttcatgt tgncaagcaa    60
cagagctgta tctgcaggnt cgtaagcata nagacngttt gaatatcttc cagngatatc   120
ggctctaact gncagagatg ggtcaacaaa cataatcctg gggacatact g            171
```

<210> SEQ ID NO 413
<211> LENGTH: 266
<212> TYPE: DNA
<213> ORGANISM: Homo sapiens

<400> SEQUENCE: 413

```
ttaggaccaa agatagcatc aactgtattt gaaggaactg tagtttgcgc attttatgac    60
atttttataa agtactgtaa ttctttcatt gagggctat gtgatggaga cagactaact    120
cattttgtta tttgcattaa aattattttg ggtctctgtt caaatgagtt tggagaatgc   180
ttgacttgtt ggtctgtgta aatgtgtata tatatatacc tgaatacagg aacatcggag   240
acctattcac tcccacacac tctgct                                        266
```

<210> SEQ ID NO 414
<211> LENGTH: 266
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 414

```
tttgccataa ttgagtgaaa agtggcagat ggcattaact ctgctccgct tcaagctggc    60
tccatgacca ctcaaggcct ccccanccctg tcgtcaagt tgtcctcaag tccaagcaat   120
ggaatccatg tgtttgcaaa aaaagtgtgc tanttttaag gnctttcgta taagaatnaa   180
tganacaatt ttcctaccaa aggangaaca aaaggataaa tataatacaa aatatatgta   240
tatggttgtt tgacaaatta tataac                                        266
```

<210> SEQ ID NO 415
<211> LENGTH: 266
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 415

```
cctccatcca gtctattaat tgttgccggg aagctanagt aagtagttcg ccagttaata      60
gtttgcgcaa cgttgttgcc attgctacag gcatcgtggt gtnacgctcg tcgattggta     120
tggcttcatt cagctccggt tcccaacgat caaggcgagt tacatgatcc cccatgttgt     180
gcaaaaaagc ggttagctcc ttcggtcctc cgatcgttgt canaagtaag ttggccgcag     240
tgttatcact catggttatg gcagca                                          266
```

<210> SEQ ID NO 416
<211> LENGTH: 878
<212> TYPE: DNA
<213> ORGANISM: Homo sapiens

<400> SEQUENCE: 416

```
cctgacgata gccatggctg taccacttaa ctatgattct attccaactg ttcagaatca      60
tatcacaaaa tgacttgtac acagtagttt acaacgactc ccaagagagg aaaaaaaaaa     120
aaaaagacgc ctcaaaattc actcaacttt tgagacagca atggcaatag gcagcagaga     180
agctatgctg caactgaggg cacatatcat tgaagatgtc acaggagttt aagagacagg     240
ctggaaaaaa tctcatacta agcaaacagt agtatctcat accaagcaaa accaagtagt     300
atctgctcag cctgccgcta acagatctca caatcaccaa ctgtgcttta ggactgtcac     360
caaagtcaga ttcggtgcta accaggtggc atctatgatc aacgtcgccc ctcttattta     420
acaaagggct ctgaaggagg tgttctccaa gcaacaagga gactgcttca gtacaagact     480
ttgcaccttg aattcaattg catcaagtgt ggatagcaaa ataagtatct taccattgaa     540
atatgtgttc agcctaagat tttacccacc agcagaacaa aagtgagggt gagagggatg     600
ggccagtgag gggatggggg agaaaaaaaa atcacaggat taccaccaaa gccttgtttt     660
aaaagggctc ccttcactat tcaggaaggg aagtggaagg agaaattaac caattcctgc     720
cacagcagcc cttttggct gcttccacaa tagatacttt atggagtggc acagccaacc     780
ctatctgtga cctgccctgc ggataaacac agccaagcag gtttaattag atcaaagaca     840
caaagggcta ttccctcctt tcataacaac gcagacct                             878
```

<210> SEQ ID NO 417
<211> LENGTH: 514
<212> TYPE: DNA
<213> ORGANISM: Homo sapiens

<400> SEQUENCE: 417

```
ttctgacttc tagaagacta aggctggtct gtgtttgctt gtttgcccac ctttggctga      60
tacccagaga acctgggcac ttgctgcctg atgcccaccc ctgccagtca ttcctccatt     120
cacccagcgg gaggtgggat gtgagacagc ccacattgga aaatccagaa aaccgggaac     180
agggatttgc ccttcacaat tctactcccc agatcctctc ccctggacac aggagaccca     240
cagggcagga ccctaagatc tggggaaagg aggtcctgag aaccttgagg taccttaga     300
tccttttcta cccactttcc tatggaggat tccaagtcac cacttctctc accggcttct     360
```

-continued

```
accagggtcc aggactaagg cgtttttctcc atagcctcaa cattttggga atcttccctt      420
aatcacccct gctcctcctg ggtgcctgga agatggactg gcagagacct ctttgttgcg      480
ttttgtgctt tgatgccagg aatgccgcct agtt                                  514
```

<210> SEQ ID NO 418
<211> LENGTH: 352
<212> TYPE: DNA
<213> ORGANISM: Homo sapiens

<400> SEQUENCE: 418

```
ctgcaccagc gattaccagt ggcattcaaa tactgtgtga ctaaggattt tgtatgctcc       60
ccagtagaac cagaatcaga caggtatgag ctagtcaaca gcaagtcttt gttggattcg      120
agtaggctca ggatctgctg aaggtcggag gagttagtcc ccgcaatcaa gagcctgtct      180
tcctgaagcc cttggtgata ttttgccact cagccaagaa tgaggatgca tccttcagat      240
tctctatgtc ccgaacctgg aacccatcca cgccagcttg cagccaaaac tccagagcat      300
ccttcacctt ggtggaaaaa aaaaaaaaaa aaaaaaaaaa aaaaaaaaaa aa              352
```

<210> SEQ ID NO 419
<211> LENGTH: 344
<212> TYPE: DNA
<213> ORGANISM: Homo sapiens

<400> SEQUENCE: 419

```
ctggacacca taatcccttt taagtggctg gatggtcaca cctctcccat tgacaagctg       60
ggttaagtca ataggttgac taggatcaac acgacccaaa tcaataagat actgcagtct      120
attgagactc aaaggcttat actggcgtct gaaactatgt ccttcgttaa acccgtattt      180
tgggattcgg atgtaaaatg gagtctggcc tccctcaaag cccaagcggg gccgggttcc      240
tctttgcctt tctcctttat ggcctctgcc acattttcta cctcttctcc gacctcttgg      300
tcttctctcc ggtttcttgg agccgggatt cggctttaag ttgg                      344
```

<210> SEQ ID NO 420
<211> LENGTH: 935
<212> TYPE: DNA
<213> ORGANISM: Homo sapiens

<400> SEQUENCE: 420

```
cgaaagtcaa cgttaagggg ctcaggtgaa ccatgatgat gaccttctgt tgactttgaa       60
atattggctc ttgtgggtga caaaagccag acaagctgtg gctgtggtcc gattttaaga      120
cgaggttctc aaagatccaa aggagggaaa gggtattgga acactgtgt atcatctgag       180 acacacgtgt cctcatgatc ttaaatgcct actttaaagc cacctaatac tgcccttcat      240
tgtggtcaga agagatttct acaaaagcac tcagaattct ggaggcagtt gtgattttgc      300
catgtggcag ttggtttgtg gagttgggca ggtgtgaaag ggtaaaactc cacttctgaa      360
tgctgcttct gccccctggg acccagcaca ttgttagacc atcttcttga ctgaaaattc      420
tctcctgatg ctgagccctg caccaccacc ttccttttcc taactatgaa ttgatggcaa      480
agtccactca aaacaaccag ttaagtgctc acgagagagt agtcaagcac ctccagaaag      540
aaaccgggtt tttgttcaca tagcaggaag tgactccctg ggtggtaatt tatcttggaa      600
acacaggtag attggcagaa aaacgggaac atgtaggtac cgcgatgttg gtgcatgtcc      660
attactttgg gataggcttt tcagtctttt cctcaaatga tagttgagcc agttttccag      720
tggcaattct gagtgacttg cgcttgtctt atggtgtggt caagggacgt tcagaactac      780
```

| | |
|---|---|
| ggaaaactttt tactgaaaca gcgaagcaga gtataccggc atgagaggga agatgaacac | 840 |
| tcacctatgt accactcttt gacaataaat atagtatttc tcaaaaaaaa aaaaaaaaaa | 900 |
| agtaaaaaaa ctgaaatcgc aagtcaaaaa atcca | 935 |

<210> SEQ ID NO 421
<211> LENGTH: 745
<212> TYPE: DNA
<213> ORGANISM: Homo sapiens

<400> SEQUENCE: 421

| | |
|---|---|
| ggcttcgagc ggccgcccgg gcaggtccta gatgtcattt gggacccttc acaaccattt | 60 |
| tgaagccctg tttgagtccc tgggatatgt gagctgtttc tatgcataat ggatattcgg | 120 |
| ggttaacaac agtcccctgc ttggcttcta ttctgaatcc ttttctttca ccatggggtg | 180 |
| cctgaagggt ggctgatgca tatggtacaa tggcacccag tgtaaagcag ctacaattag | 240 |
| gagtggatgt gttctgtagc atcctattta aataagccta ttttatcctt tggcccgtca | 300 |
| actctgttat ctgctgcttg tactggtgcc tgtacttttc tgactctcat tgaccatatt | 360 |
| ccacgaccat ggttgtcatc cattacttga tcctacttta catgtctagt ctgtgtggtt | 420 |
| ggtggtgaat aggcttcttt ttacatggtg ctgccagccc agctaattaa tggtgcacgt | 480 |
| ggacttttag caagcgggct cactggaaga gactgaacct ggcatggaat tcctgaagat | 540 |
| gtttggggtt ttttttcttc ttaatcgaaa gttaacattg tctgaaaagt tttgttagaa | 600 |
| ctactgcgga acctcaaaat cagtagattt ggaagtgatt caaagctaaa cttttttcctt | 660 |
| ggccctcctt gtgttctaat tgcttgcaag tgtaatacta ggatgtccaa gatgccagtt | 720 |
| tttgcttctt tgttagttgt cagac | 745 |

<210> SEQ ID NO 422
<211> LENGTH: 764
<212> TYPE: DNA
<213> ORGANISM: Homo sapiens

<400> SEQUENCE: 422

| | |
|---|---|
| gagttcagta gcaaagtcac acctgtccaa ttccctgagc tttgctcact cagctaatgg | 60 |
| gatggcaaag gtggtggtgc tttcatcttc aggcagaagc ctctgcccat ccccctcaag | 120 |
| ggctgcaggc ccagttctca tgctgcccctt gggtgggcat ctgttaacag aggagaacgt | 180 |
| ctgggtggcg gcagcagctt tgctctgagt gcctacaaag ctaatgcttg gtgctagaaa | 240 |
| catcatcatt attaaacttc agaaaagcag cagccatgtt cagtcaggct catgctgcct | 300 |
| cactgcttaa gtgcctgcag gagccgcctg ccaagctccc cttcctacac ctggcacact | 360 |
| ggggtctgca caaggctttg tcaaccaaag acagcttccc ccttttgatt gcctgtagac | 420 |
| tttggagcca agaaacactc tgtgtgactc tacacacact tcaggtggtt tgtgcttcaa | 480 |
| agtcattgat gcaacttgaa aggaaacagt ttaatggtgg aaatgaacta ccatttataa | 540 |
| cttctgtttt tttattgaga aaatgattca cgaattccaa atcagattgc caggaagaaa | 600 |
| taggacgtga cggtactggg ccctgtgatt ctcccagccc ttgcagtccg ctaggtgaga | 660 |
| ggaaaagctc tttacttccg cccctggcag ggacttctgg gttatgggag aaaccagaga | 720 |
| tgggaatgag gaaaatatga actacagcag aagcccctgg gcag | 764 |

<210> SEQ ID NO 423
<211> LENGTH: 1041
<212> TYPE: DNA

<213> ORGANISM: Homo sapiens

<400> SEQUENCE: 423

| | | | | | |
|---|---|---|---|---|---|
| ctcagagagg | ttgaaagatt | tgcctacgaa | agggacagtg | atgaagctaa | gctctagatc | 60 |
| caggatgtct | gacttcaaat | tgaaactccc | aaagtaatga | gtttggaagg | gtggggtgtg | 120 |
| gcctttccag | gatggggtc | ttttctgctc | ccagcggata | gtgaaacccc | tgtctgcacc | 180 |
| tggttgggcg | tgttgctttc | ccaaaggttt | ttttttagg | tccgtcgctg | tcttgtggat | 240 |
| taggcattat | tatctttact | ttgtctccaa | ataacctgga | gaatgagag | agtagtgacc | 300 |
| agctcagggc | cacagtgcga | tgaggaccat | cttctcacct | ctctaaatgc | aggaagaaac | 360 |
| gcagagtaac | gtggaagtgg | tccacaccta | ccgccagcac | attgtgaatg | acatgaaccc | 420 |
| cggcaacctg | cacctgttca | tcaatgccta | caacaggtat | tgggatgtag | ttcagccaca | 480 |
| tcattgctat | ttatgaggtg | tcttctgtag | atccgaaatg | tgggacagat | gagagggaga | 540 |
| gtataaaatg | agcggaagag | gcaggctctg | agtttgagca | aatagattaa | taggacaggt | 600 |
| gtccccagga | aggacacctg | gcctgtaagc | tggttcctgg | cattcagctc | gccttgcagg | 660 |
| gatctgaaca | aacactccag | accactgggg | gtgcagacg | gagagggacg | cagtcgcaca | 720 |
| ctcagagggt | tgagagtaaa | tatgtgtgcc | cgctgctgac | cttcacgaaa | ggccaaatgt | 780 |
| aagaagagct | aagtgagaga | gcagcaaagc | actcctggga | gccggggata | atccaggcag | 840 |
| gcttctggga | gtttgtcatt | ccaaggataa | ggaggacctg | aacatggcct | ttgcctaagg | 900 |
| cgtggccctc | tcaaccagca | ctaggtgctt | atctggagct | cagctagggg | aggagacagc | 960 |
| tcagggccat | tggtgtcagc | cagagactct | gtaatcttcc | agggagctcg | ctcaacctgc | 1020 |
| tgagctcgct | ctgccacgca | c | | | | 1041 |

<210> SEQ ID NO 424
<211> LENGTH: 1288
<212> TYPE: DNA
<213> ORGANISM: Homo sapiens

<400> SEQUENCE: 424

| | | | | | |
|---|---|---|---|---|---|
| ctaagaactg | agacttgtga | cacaaggcca | acgacctaag | attagcccag | ggttgtagct | 60 |
| ggaagaccta | caaccccaagg | atggaaggcc | cctgtcacaa | agcctaccta | gatggataga | 120 |
| ggacccaagc | gaaaaaggta | tctcaagact | aacggccgga | atctggaggc | ccatgaccca | 180 |
| gaacccagga | aggatagaag | cttgaagacc | tggggaaatc | ccaagatgag | aaccctaaac | 240 |
| cctacctctt | ttctattgtt | tacacttctt | actcttagat | atttccagtt | ctcctgtttt | 300 |
| tctttaagcc | tgattctttt | gagatgtact | ttttgatgtt | gccggttacc | tttagattga | 360 |
| cagtattatg | cctgggccag | tcttgagcca | gctttaaatc | acagctttta | cctatttgtt | 420 |
| aggctatagt | gttttgtaaa | cttctgtttc | tattcacatc | ttctccactt | gagagagaca | 480 |
| ccaaaatcca | gtcagtatct | aatctggctt | tgttaacttt | ccctcaggag | cagacattca | 540 |
| tataggtgat | actgtatttc | agtcctttct | tttgaccca | gaagcccag | actgagaaga | 600 |
| taaaatggtc | aggttgttgg | ggaaaaaaaa | gtgccaggct | ctctagagaa | aaatgtgaag | 660 |
| agatgctcca | ggccaatgag | aagaattaga | caagaaatac | acagatgtgc | cagacttctg | 720 |
| agaagcacct | gccagcaaca | gcttccttct | ttgagcttag | tccatccctc | atgaaaaatg | 780 |
| actgaccact | gctgggcagc | aggagggatg | atgaccaact | aattcccaaa | ccccagtctc | 840 |
| attggtacca | gccttgggga | accacctaca | cttgagccac | aattggtttt | gaagtgcatt | 900 |
| tacaagtttc | tggcatcact | accactactg | attaaacaag | aataagagaa | catttatca | 960 |

```
tcatctgctt tattcacata aatgaagttg tgatgaataa atctgctttt atgcagacac    1020
aaggaattaa gtggcttcgt cattgtcctt ctacctcaaa gataatttat tccaaaagct    1080
aagataaatg gaagactctt gaacttgtga actgatgtga aatgcagaat ctcttttgag    1140
tctttgctgt ttggaagatt gaaaaatatt gttcagcatg ggtgaccacc agaaagtaat    1200
cttaagccat ctagatgtca caattgaaac aaactgggga gttggttgct attgtaaaat    1260
aaaatatact gttttgaaaa aaaaaaac                                       1288

<210> SEQ ID NO 425
<211> LENGTH: 446
<212> TYPE: DNA
<213> ORGANISM: Homo sapiens

<400> SEQUENCE: 425
ccacttaaag ggtgcctctg ccaactggtg gaatcatcgc cacttccagc accacgccaa      60
gcctaacatc ttccacaagg atcccgatgt gaacatgctg cacgtgtttg ttctgggcga    120
atggcagccc atcgagtacg gcaagaagaa gctgaaatac ctgccctaca atcaccagca    180
cgaatacttc ttcctgattg ggccgccgct gctcatcccc atgtatttcc agtaccagat    240
catcatgacc atgatcgtcc ataagaactg ggtggacctg gcctgggccg tcagctacta    300
catccggttc ttcatcacct acatcccttt ctacggcatc ctgggagccc tccttttcct    360
caacttcatc aggttcctgg agagccactg gtttgtgtgg gtcacacaga tgaatcacat    420
cgtcatggag attgaccagg aggacc                                         446

<210> SEQ ID NO 426
<211> LENGTH: 874
<212> TYPE: DNA
<213> ORGANISM: Homo sapiens

<400> SEQUENCE: 426
tttttttttt tttttttttt tttttcaat taaagatttg atttattcaa gtatgtgaaa      60
acattctaca atggaaactt ttattaaatg ctgcatgtac tgtgctatgg accacgcaca    120
tacagccatg ctgttttcaga agacttgaaa tgccattgat agtttaaaaa ctctacaccc    180
gatggagaat cgaggaagac aatttaatgt ttcatctgaa tccagaggtg catcaaatta    240
aatgacagct ccacttggca ataatagct gttacttgat ggtatccaag aagaaatggt    300
tggtgatgga taaattcaga aatgcttccc caaaggtggg tggtttttaa aaagttttca    360
ggtcacaacc cttgcagaaa acactgatgc ccaacacact gattcgcggt ccaggaaaca    420
cgggtcttcc aagttccaag gggctggggt tccccaacga tcaagttcct gtgctgtaat    480
caagagggtc ctttggactg gatagggagc acttgggagc tgtacaccat cagtcataat    540
ggatggcagt gtaaaagatg atccaaatga cctgagatgc tcctgaggag tggtgcacca    600
gacccaggag tgccactgta gggctgcttc tttgctttag tcatcacaca cacacagc     660 tccagagcag caatggcctt tcctgtaaca ggaaaaaagc ctcctgctat tcccaagaac    720
cctcgtaatg gcaaaactcc ccaaatgaca cccaggacca cagcaatgat ctgtcggaac    780
cagtagatca catctaaaaa ttcatcctta tcctcccagg ccgcgtcgct ccgcagcacc    840
ttactccaga cggagacttt gagggccccg ttgg                                874

<210> SEQ ID NO 427
<211> LENGTH: 638
<212> TYPE: DNA
```

<213> ORGANISM: Homo sapiens

<400> SEQUENCE: 427

| | | | | | |
|---|---|---|---|---|---|
| acttgtaatt | agcacttggt | gaaagctgga | aggaagataa | ataacactaa | actatgctat | 60 |
| ttgattttc | ttcttgaaag | agtaaggttt | acctgttaca | ttttcaagtt | aattcatgta | 120 |
| aaaaatgata | gtgattttga | tgtaatttat | ctcttgtttg | aatctgtcat | tcaaaggcca | 180 |
| ataatttaag | ttgctatcag | ctgatattag | tagctttgca | accctgatag | agtaaataaa | 240 |
| ttttatgggc | gggtgccaaa | tactgctgtg | aatctatttg | tatagtatcc | atgaatgaat | 300 |
| ttatggaaat | agatatttgt | gcagctcaat | ttatgcagag | attaaatgac | atcataatac | 360 |
| tggatgaaaa | cttgcataga | attctgatta | aatagtgggt | ctgtttcaca | tgtgcagttt | 420 |
| gaagtattta | ataaccact | cctttcacag | tttatttct | tctcaagcgt | tttcaagatc | 480 |
| tagcatgtgg | attttaaaag | atttgccctc | attaacaaga | ataacattta | aaggagattg | 540 |
| tttcaaaata | tttttgcaaa | ttgagataag | gacagaaaga | ttgagaaaca | ttgtatattt | 600 |
| tgcaaaaaca | agatgtttgt | agctgtttca | gagagagt | | | 638 |

<210> SEQ ID NO 428
<211> LENGTH: 535
<212> TYPE: DNA
<213> ORGANISM: Homo sapiens

<400> SEQUENCE: 428

| | | | | | |
|---|---|---|---|---|---|
| acaagatgat | tcttcctcct | caatttgaca | gatcaaagaa | gtatcccttg | ctaattcaag | 60 |
| tgtatggtgg | tccctgcagt | cagagtgtaa | ggtctgtatt | tgctgttaat | tggatatctt | 120 |
| atcttgcaag | taaggaaggg | atggtcattg | ccttggtgga | tggtcgagga | acagctttcc | 180 |
| aaggtgacaa | actcctctat | gcagtgtatc | gaaagctggg | tgtttatgaa | gttgaagacc | 240 |
| agattacagc | tgtcagaaaa | ttcatagaaa | tgggtttcat | tgatgaaaaa | agaatagcca | 300 |
| tatgggctg | gtcctatgga | ggatacgttt | catcactggc | ccttgcatct | ggaactggtc | 360 |
| ttttcaaatg | tggtatagca | gtggctccag | tctccagctg | gaatattac | gcgtctgtct | 420 |
| acacagagag | attcatgggt | ctcccaacaa | aggatgataa | tcttgagcac | tataagaatt | 480 |
| caactgtgat | ggcaagagca | gaatatttca | gaaatgtaga | ctatcttctc | atcca | 535 |

<210> SEQ ID NO 429
<211> LENGTH: 675
<212> TYPE: DNA
<213> ORGANISM: Homo sapiens

<400> SEQUENCE: 429

| | | | | | |
|---|---|---|---|---|---|
| actattttca | accctgagca | ttaacactgc | ataccaaggg | ggggtgggtc | aagaagctgg | 60 |
| ttagatcgaa | gcacaagcac | aagccactga | tattctctat | gtgatcaggt | ttttacaaaa | 120 |
| aaatacatag | ttttcaataa | ataatgctta | attttacaac | tttgatacag | caatgtcata | 180 |
| caccgtttca | acacactaca | ctctgcatgc | tagatagtct | acgagaagac | gaaacttgc | 240 |
| catgcatttt | ctttccccc | tagtgctatc | aaacacttca | tcctccagcg | cactgcctca | 300 |
| ggtagcttta | ccttctctct | gtttcacagc | aataggccgt | gcgctggcat | gcaaactcta | 360 |
| aaaaggtcc | cccccacaaa | ccactcagac | ttctacacaa | aagggttttt | cagcttttct | 420 |
| gctcccaaac | ctggagtggc | taagaaagta | agtttcatgt | ggccttggaa | atacacact | 480 |
| tgttaacagt | gtcatgctga | aaactgctct | aaaacatcag | gtggttctgt | cctggtggcc | 540 |
| gtcacgaagc | attatgggat | gccataacca | ctaggagtcc | caaaccggaa | aaaataggcc | 600 |

```
tccgttttaa aacagtcaat tcaaaaaagg tgtcacagaa caaatgcaaa agactcttaa      660
acccacaaca tatgt                                                      675
```

<210> SEQ ID NO 430
<211> LENGTH: 434
<212> TYPE: DNA
<213> ORGANISM: Homo sapiens

<400> SEQUENCE: 430

```
acctctgcca gaagtccagc gagaggacct cacagtagag cacaggccac tccgggagtg       60
catcagaaga ttcatcctca tggaggaaga aggcttcaaa cgtgaatggg taggagaagt      120
gagccacctt gtccattgcc agggacttgg tggtgcaggt ctgtgttact cctgagagct      180
gctggaatgc tgggcttgac cagtgagcag ttggcaattc tacaaagaag tggacgtaga      240
gattgtcata ctcatagcct tgggctgaaa cgacctctcc atttacaaag accggaggg      300 cacctgggac agtcatctca aagtcggtgc ctacgaggct gctgagatac tccttgtgcc      360
ggccataaag atccttgaac actcgccgtt cccgctcctc ctcctccggc tgtgcgtggg      420
gggaaacatt gtcg                                                       434
```

<210> SEQ ID NO 431
<211> LENGTH: 581
<212> TYPE: DNA
<213> ORGANISM: Homo sapiens

<400> SEQUENCE: 431

```
acacaagcct ccagcccgac ccagcggcct aatgaaactc tggcaaccta tcctgggcgt       60
ggccacgagt atccagctcc aagcccaagt gaggcgggga gtcaacttcc ccatgattgc      120
caagtgacca agaccagaag cagggacgat taggctagtt ctgcggcaag gtgaactgga      180
gaccctgtct ctgccctcct tccctggcct gtcccacaga catcccgttg tttaacccac      240
tgcctttgca aggacctgct ctgtccactc caaatcaaag gatacttgca tccttcttac      300
acagactccc atctctctgc tcatagtggt cccaggctgc ccgagaaaaa gaaacttggg      360
tcagtagaag gctcattagt gtgaaggagt gagaggccag gccttcctgt gacataatgc      420
ttctatgctt gtttcctaaa cacttggtcc acacacaata cctgggcagg aagagagaac      480
caagcaccac tggatggctc tggagccagg ggacttctat gcacatacaa ccaacatcac      540
cccactctgc tcatctgtgc ctccaccctg aacagcagag t                         581
```

<210> SEQ ID NO 432
<211> LENGTH: 532
<212> TYPE: DNA
<213> ORGANISM: Homo sapiens

<400> SEQUENCE: 432

```
actccaactc aagtttacaa gttacacctt tgccacagcc ttggctaaat cttgaactag       60
tgcagaattc agctgtggta gagtgctgat cttagcatgc ttcgatgtgg catacttgtt      120
cttgacagtc atgtgctttg taagtccttg atttaccatg actacattct tagccaggtg      180
ctgcataact ggaagaagag attcttcagt atatgacagg taatgttgta gagttggtgt      240
ccattcacca ttatccagaa ttttcagtgc taagcaaaaa gctcctgctg caatttgaga      300
aggaggaaag tgcaccatgt catagtccaa catagttagt tccatcaggt atttggccaa      360
agtatgttgc tcgacatcaa cctctccaat cttagatgct ctccgaagga agtgcaaagg      420
```

```
tagaggccga cccagaccaa agtttaaagc tcttagaatc ttcatttcca tctgtctgat    480
ttggtgctta gtataagtgt tgtcagtcac aaaagcaaag tcaccaattt ct           532

<210> SEQ ID NO 433
<211> LENGTH: 531
<212> TYPE: DNA
<213> ORGANISM: Homo sapiens

<400> SEQUENCE: 433
acttggtttt acagctcctt tgaaaactct gtgtttggaa tatctctaaa aacatagaaa    60
acactacagt ggtttagaaa ttactaattt tacttctaag tcattcataa accttgtcta   120
tgaaatgact tcttaaatat ttagttgata gactgctaca ggtaatagggg acttagcaag   180 ctctttttata tgctaaagga gcatctatca gattaagtta gaacatttgc tgtcagccac   240
atattgagat gacactaggt gcaatagcag ggatagattt tgttggtgag tagtctcatg   300
ccttgagatc tgtggtggtc ttcaaaatgg tggccagcca gatcaaggat gtagtatctc   360
atagttccca ggtgatattt ttcttattag aaaaatatta taactcatttt gttgtttgac   420 acttatagat tgaaatttcc taatttattc taaatttaa gtggttcttt ggttccagtg    480
ctttatgttg ttgttgtttt tggatggtgt tacatattat atgttctaga a             531

<210> SEQ ID NO 434
<211> LENGTH: 530
<212> TYPE: DNA
<213> ORGANISM: Homo sapiens

<400> SEQUENCE: 434
acaagagaaa accctaaaa aaaggatggc tttagatgac aagctctacc agagagactt     60
agaagttgca ctagctttat cagtgaagga acttccaaca gtcaccacta atgtgcagaa   120
ctctcaagat aaaagcattg aaaaacatgg cagtagtaaa atagaaacaa tgaataagtc   180
tcctcatatc tctaattgca gtgtagccag tgattattta gatttggata agattactgt   240
ggaagatgat gttggtggtg ttcaagggaa agaaaagca gcatctaaag ctgcagcaca    300
gcagaggaag attcttctgg aaggcagtga tggtgatagt gctaatgaca ctgaaccaga   360
ctttgcacct ggtgaagatt ctgaggatga ttctgatttt tgtgagagtg aggataatga   420
cgaagacttc tctatgagaa aaagtaaagt taaagaaatt aaaaagaaag aagtgaaggt   480
aaaatcccca gtagaaaaga aagagaagaa atctaaatcc aaatgtaatg               530

<210> SEQ ID NO 435
<211> LENGTH: 677
<212> TYPE: DNA
<213> ORGANISM: Homo sapiens

<400> SEQUENCE: 435
accttatgat ctaattaata gatattagaa acagtagaaa gacaagttac acgtcaatgc    60
ccaatgacta gagtcaacat taaagagttg taatttaagt aatccaaaact gacatctaat   120 tccaaaatca tttataaaat gtatttggct ttggaatcca caggacttca aacaagcaaa   180
gtttcactgc agatagtcac aaagatgcag atacactgaa atacttaaga gccttattaa   240 tgattttgt tatttggat cttctgtttt tttcttatta tggtccgaag cctccttaat     300
accaatttat cagacagaag catgtcatct tgttgttcaa gataatccag taaattttca   360
gtccattcaa gtgccgcttt atggctaata cgcttctctg gattcagttc tgttttttcta   420 ctcttactgg aaggcttttg ctcagcagcc ttggtctggt cctcagcact ttcactgtca   480
```

```
gtcagcacct gacagcttga gtcactgctc cgagagtcga accactgatc aatattctca    540
atgtcaacat gttcacattc ttctgtgttc tgtaaaactg ttgctaaatt agctgctaaa    600
atggctcctt catcaatgtt catacctgaa ttctcttcat tgccagggaa aagttttttc    660
catgctttgg ttatggt                                                    677

<210> SEQ ID NO 436
<211> LENGTH: 573
<212> TYPE: DNA
<213> ORGANISM: Homo sapiens

<400> SEQUENCE: 436
acctcttagg gtgggagaaa tggtgaagag ttgttcctac aacttgctaa cctagtggac     60
agggtagtag attagcatca tccggataga tgtgaagagg acggctgttt ggataataat    120
taaggataaa atttggccag ttgacagatt ctgtttccag cagttttac agcaacagtg     180 gagtgcttca gtattgtgtt cctgtaaatt taattttgat ccgcaatcat ttggtataca    240
atgctgtttg aagttttgtc ctattggaaa agtcttgtgt tgcaggggtg cagttaagat    300
ctttgtgatg aggaatggga tgggctaatt ttttgccgtt ttcttggaat tgggggcatg    360
gcaaatacag tagggtagtt tagttctttta cacagaacat gataaactac acctgttgat    420
gtcaccgtct gtcaatgaat attatagaag gtatgaaggt gtaattacca taataacaaa    480
acaccctgtc tttagggctg acctttcgtc ctttgacctc ctcagcctcc attcccatct    540
tcgctcagac tgcaagtatg tttgtattaa tgt                                 573

<210> SEQ ID NO 437
<211> LENGTH: 645
<212> TYPE: DNA
<213> ORGANISM: Homo sapiens
<220> FEATURE:
<221> NAME/KEY: misc_feature
<222> LOCATION: (1)...(645)
<223> OTHER INFORMATION: n = A,T,C or G

<400> SEQUENCE: 437
acaattggta tccatatctt gttgaaattg taatgggaaa acaatatatt tcaatctcta     60
tgtagatagt gggttttttgt tttcataata tattcttta gtttactgta tgagttttgc    120
aggactgcat aatagatcac cacaatcata acatcttagg accacagaca tttatgagat    180
catggcttct gtgggttaga agtatgctca tgtcttaact gggtcctctg ctcagtctta    240
tctggctgca atcaaggtgt cagctgggct gaattttcat ttggaatctt gactgggaaa    300
gagtctgctt ccaaggtcat gaagtttgct ggcaaaatgt atgtttttat gacagtatga    360
ctgaaatccc aagctatctc ctgacttta gctgggtaat ctcaggccct aaatgttgcc    420
tacagttcct agaggctggt cacagttctt agccatgtgg atttcctcaa catggctgct    480
tgcttcatca agtcagcaag aatagcctgt catatcagtg tatatcaggc tcactcagga    540
taatttccct actgatgagc caaacactaa ctgattttag agcttaacta catctgcaaa    600
attcngttca ccagaggcaa gtcatattca gggaaggaga agtgt                    645

<210> SEQ ID NO 438
<211> LENGTH: 485
<212> TYPE: DNA
<213> ORGANISM: Homo sapiens

<400> SEQUENCE: 438
```

```
acagaattga gagacaagat tgcttgtaat ggagatgctt ctagctctca gataatacat      60
atttctgatg aaaatgaagg aaaagaaatg tgtgttctgc gaatgactcg agctagacgt     120
tcccaggtag aacagcagca gctcatcact gttgaaaagg ctttggcaat tctttctcag     180
cctacaccct cacttgttgt ggatcatgag cgattaaaaa atcttttgaa gactgttgtt     240
aaaaaaagtc aaaactacaa catatttcag ttggaaaatt tgtatgcagt aatcagccaa     300
tgtatttatc ggcatcgcaa ggaccatgat aaaacatcac ttattcagaa aatggagcaa     360
gaggtagaaa acttcagttg ttccagatga tgatgtcatg gtatcgagta ttctttatat     420
tcagttccta tttaagtcat ttttgtcatg tccgcctaat tgatgtagta tgaaaccctg     480
catct                                                                 485

<210> SEQ ID NO 439
<211> LENGTH: 533
<212> TYPE: DNA
<213> ORGANISM: Homo sapiens

<400> SEQUENCE: 439
acagcagttt cctcatccct gcagctgtgt ttgaacaggt catttaccat actgtcctcc      60
aggttcaaca gtatggctcc aaatgatgaa atttcattct gattttctgg ctgaagacta     120
ttctgtttgt gtatgtccac cacagttact ttatcccttc atctgtggat gggcagaatg     180
aaacatatat ggaaatgttc tgtgcaataa aaacagcagt ggtaacacag atgtaggctc     240
tgagtgtctc actggagact gaagtccaca gatatgcaac aaagcctttg tctccctgat     300 gttttttgcct cctgctggtc atgtgctttc acacatcaag agaggacatt taacatttga     360
gccacagtgt catttgctgt tgtctgatgg ttggttggca gagaatttga actggagatg     420
aactttatta tccaggacgc tgagagtata acatgcatga cagagctttt agagcactgt     480
gatgtaacat gtcaagcaga aatagggagc atgtttacag ccattctatg aaa            533

<210> SEQ ID NO 440
<211> LENGTH: 341
<212> TYPE: DNA
<213> ORGANISM: Homo sapiens

<400> SEQUENCE: 440
catggggtag gggggtcggg gattcattga attgtggttg gcaggagcaa gccctgctca      60
cactctcaca ctcgcaccca gaattgtcaa agatacagat tgtaaaaatc tacgatccct     120
cagtctcact cacaaaaaat aaaatctcat gtccccaacg aacccagagt cagacgacag     180
ctggagcatt ggcagggaca gtcagaaagg agacaagtga aaacggtcag atggacacag     240
gcggaggaga aaagacagag ggagagagac catcgggaac aatcagaggg gccgagacga     300
tcagaaaagg gtcagcccga gacaggctga gccagagttt c                         341

<210> SEQ ID NO 441
<211> LENGTH: 572
<212> TYPE: DNA
<213> ORGANISM: Homo sapiens
<220> FEATURE:
<221> NAME/KEY: misc_feature
<222> LOCATION: (1)...(572)
<223> OTHER INFORMATION: n = A,T,C or G

<400> SEQUENCE: 441
aagtttgggg ataatttatt atgcagcaag agataataca caggacttct canagcactt      60
aatatgttaa tataaatctc caanaaaaaa gatatacaat gaaacattcc tcttagttat     120
```

```
ctggccaagg anactttntt tttttganaa tattcttcaa aaagctgatc taatgatatg      180
gctctggtcc tacaattcca tgtaacttct aaccttgatt ttatctcatg agcaaatcat      240
ttatccttcc agaacctcaa cttttccctt ttacaaagta gaaataaacc atctgccttt      300
acataaatca ttaatacagc cctggatggg cagattctga gctattttg gctgggggt       360 gggaaatagc ctgtggaggt cctaaaaaga tctacgggc tcgagatggt tctctgcaag      420
gtagcaggtg ggctcaggc ccatttcagt ctttgttccc caggccattt ccacaaaatg      480
gtgagaaata gtgtcttctt ttagcttgct cataactcaa agatgggggg catggacctg      540
ggcctttcta ggctagggca tgaacctcct cc                                   572
```

<210> SEQ ID NO 442
<211> LENGTH: 379
<212> TYPE: DNA
<213> ORGANISM: Homo sapiens
<220> FEATURE:
<221> NAME/KEY: misc_feature
<222> LOCATION: (1)...(379)
<223> OTHER INFORMATION: n = A,T,C or G

<400> SEQUENCE: 442

```
tcccagctgc actgcttaca cgtcttcctt cgtnttcacc taccccgagg ctgactcctt      60
ccccagntgt gcagctgccc accgcaaggg cagcagcagc aatgagcctt cctctgactc      120
gctcagctca cccacgctgc tggccctgtg aggggcagg gaaggggagg cagccggcac       180
ccacaagtgc cactgcccga gctggtgcat tacagagagg agaaacacat cttccctaga      240
gggttcctgt agacctaggg aggacctat ctgtgcgtga acacaccag gctgtgggcc       300 tcaaggactt gaaagcatcc atgtgtggac tcaagtcctt acctcttccg agatgtagc       360 aaaacgcatg gagtgtgta                                                   379
```

<210> SEQ ID NO 443
<211> LENGTH: 511
<212> TYPE: DNA
<213> ORGANISM: Homo sapiens
<220> FEATURE:
<221> NAME/KEY: misc_feature
<222> LOCATION: (1)...(511)
<223> OTHER INFORMATION: n = A,T,C or G

<400> SEQUENCE: 443

```
acatgccccc aaaggctcgc ttcattgcta cgattctcta cttaaatcca cattcacagc      60
tattgcctca gaccctctgg aggaggggcc aggggttagc tggctttgaa tagcatgtag      120
agcacaggca gtgtggccac aaatgtcaca caggtgacca gggtgctata gatggtgttc      180
ctgttgactt gggcttctag tctctgctcc gtgtctgaca gtgccaagat catgctcccc      240
tgctccagca agaagctggg catagcccg tctgctggtt ccaccaggcc tgggtgtgct       300
gcagacttta caagctgaac caccccagcc atttggctac aagtcttttc taggccatca      360
agctgctctc gtaagccttc tagacatgaa tggacttgcc tggaatgact aagctgctct      420
ttcaaggcag ctgaaaggac atcnacatct ctgtctctgg tcggggact acctgcctgt       480 gacccagagt cctgccctgg cccagcagca t                                     511
```

<210> SEQ ID NO 444
<211> LENGTH: 612
<212> TYPE: DNA
<213> ORGANISM: Homo sapiens
<220> FEATURE:

<221> NAME/KEY: misc_feature
<222> LOCATION: (1)...(612)
<223> OTHER INFORMATION: n = A,T,C or G

<400> SEQUENCE: 444

| | | | | | |
|---|---|---|---|---|---|
| acaggaagaa | ttctacagtt | aatctatcac | agtgttccag | caaagcatat | gttgaaaact | 60 |
| acagttttca | atctaacatc | taaattttaa | aaagtagcat | ttcagcaaca | aacaagctca | 120 |
| gagaggctca | tggcaaaagt | gaaataacag | aactattgct | cagatgtctg | caaagtcaag | 180 |
| ctgctgccct | cagctccgcc | cacttgaagg | cttaggcaga | cacgtaaggt | ggcggtggct | 240 |
| ccttggcagc | accattcaca | gtggcatcat | catacggagg | tagcagcacc | gtagtgtcat | 300 |
| tgctggtaac | ataaaccagg | acatcagagg | agttcctacc | attgatgtat | cggtagcagt | 360 |
| tccaaacaca | gctaatcaag | taaccettaa | aagtcaagat | aatgctaata | aacagaagaa | 420 |
| taataaggac | caaacaggta | ggattcactg | acatgacatc | atctctgtag | ggaaaattag | 480 |
| gaggcagttg | ccgtatgtat | tcctgaatgg | agtttggata | aataagcaca | gtgattgcaa | 540 |
| ccaacanctt | cagggcaaag | tcaaagatct | ggtaacagaa | gaatgggatg | atccaggctg | 600 |
| gcgttgcttt | gt | | | | | 612 |

<210> SEQ ID NO 445
<211> LENGTH: 708
<212> TYPE: DNA
<213> ORGANISM: Homo sapiens
<220> FEATURE:
<221> NAME/KEY: misc_feature
<222> LOCATION: (1)...(708)
<223> OTHER INFORMATION: n = A,T,C or G

<400> SEQUENCE: 445

| | | | | | |
|---|---|---|---|---|---|
| accatcctgt | tccaacagag | ccattgccta | ttcctaaatt | gaatctgact | gggtgtgccc | 60 |
| ctcctcggaa | cacaacagta | gaccttaata | gtggaaacat | cgatgtgcct | ccaacatga | 120 |
| caagctgggc | cagctttcat | aatggtgtgg | ctgctggcct | aagatagct | cctgcctccc | 180 |
| agatcgactc | agcttggatt | gtttacaata | agcccaagca | tgctgagttg | gccaatgagt | 240 |
| atgctggctt | tctcatggct | ctgggtttga | atgggcacct | taccaagctg | gcgactctca | 300 |
| atatccatga | ctacttgacc | aagggccatg | aaatgacaag | cattggactg | ctacttggtg | 360 |
| tttctgctgc | aaaactaggc | accatggata | tgtctattac | tcggcttgtt | agcattcgca | 420 |
| ttcctgctct | cttaccccca | acgtccacag | agttggatgt | tcctcacaat | gtccaagtgg | 480 |
| ctgcagtggt | tggcattggc | cttgtatatc | aagggacagc | tcacagacat | actgcagaag | 540 |
| tcctgttggc | tgagatagga | cggcctcctg | gtcctgaaat | ggaatactgc | actgacagag | 600 |
| agtcatactc | cttagctgct | ggcttggccc | tgggcatggt | ctncttgggg | catggcagca | 660 |
| atttgatagg | tatgtntgat | ctcaatgtgc | ctgagcagct | ctatcagt | | 708 |

<210> SEQ ID NO 446
<211> LENGTH: 612
<212> TYPE: DNA
<213> ORGANISM: Homo sapiens

<400> SEQUENCE: 446

| | | | | | |
|---|---|---|---|---|---|
| acaagcaacg | cgcagcctgg | atcatcccat | tcttctgtta | ccagatcttt | gactttgccc | 60 |
| tgaacatgtt | ggttgcaatc | actgtgctta | tttatccaaa | ctccattcag | gaatacatac | 120 |
| ggcaactgcc | tcctaatttt | ccctacagag | atgatgtcat | gtcagtgaat | cctacctgtt | 180 |
| tggtccttat | tattcttctg | tttattagca | ttatcttgac | ttttaagggt | tacttgatta | 240 |

```
gctgtgtttg gaactgctac cgatacatca atggtaggaa ctcctctgat gtcctggttt      300
atgttaccag caatgacact acggtgctgc taccccgta tgatgatgcc actgtgaatg      360
gtgctgccaa ggagccaccg ccaccttacg tgtctgccta agccttcaag tgggcggagc      420
tgagggcagc agcttgactt tgcagacatc tgagcaatag ttctgttatt tcacttttgc      480
catgagcctc tctgagcttg tttgttgctg aaatgctact ttttaaaatt tagatgttag      540
attgaaaact gtagttttca acatatgctt tgctggaaca ctgtgataga ttaactgtag      600
aattcttcct gt                                                         612
```

<210> SEQ ID NO 447
<211> LENGTH: 642
<212> TYPE: DNA
<213> ORGANISM: Homo sapiens

<400> SEQUENCE: 447

```
actgaaagaa ttaaagtcag aagtcttccc aaaacaaaaa gaactgccca cagagaaaat       60
cctttctgat acttttcatt gctaaaataa acaggcggg aaatgtggaa aagaaattca      120
acaaaataat gtagcaccag aagaacaagt cctagatgat tcaagttcaa aaggtaagct      180
ccagcaatgt ggaagaggta aagaccaatg tagacaagct gacgaggaat atcttctttt      240
ttggttttct ggaagtagag ttcaggaaaa gcatgaagcc agtaagccag ctgtgatatg      300
tagaaaaact tcatttgaaa tgtcatcagg ttatggggat aagccctcca taagatagtt      360
gggtctgaga tgtagttttc agagatgaga atgaatgtgc cccaaacaca ggcaaaaagg      420
tagaacgcac taagctgacc agattcatta aacttgctgt gttttgtttt ggagaagtgc      480
attcgcctgt taattttatc caacatatac tcttgaatta cggcatgaat aattatcgcc      540
actagcatgt agaagaaaac agtagccaaa tctttgatgc catagtaata aagggacact      600
gattcagtag cttgttcttc tgttgctggg agggtgacat tg                        642
```

<210> SEQ ID NO 448
<211> LENGTH: 394
<212> TYPE: DNA
<213> ORGANISM: Homo sapiens
<220> FEATURE:
<221> NAME/KEY: misc_feature
<222> LOCATION: (1)...(394)
<223> OTHER INFORMATION: n = A,T,C or G

<400> SEQUENCE: 448

```
accagaagac cttagaaaaa ggaggaaagg aggagaggca gataatttgg atgaattcct       60
caaagngttt gaaaatccag aggttcctag agaggaccag caacagcagc atcagcagcg      120
tgatgttatc gatgagccca ttattgaaga gccagccgc ctccaggagt cagtgatgga      180
ggccagcaga acaaacatag atgagtcagc tatgcctcca ccaccacctc agggagttaa      240
gcgaaaagct ggacaaattg acccagagcc tgtgatgcct cctcagcagg tagagcagat      300
ggaaatacca cctgtagagc ttcccccaga agaacctcca aatatctgtc agctaatacc      360
agagttagaa cttctgccag aaaaagagaa ggag                                 394
```

<210> SEQ ID NO 449
<211> LENGTH: 494
<212> TYPE: DNA
<213> ORGANISM: Homo sapiens
<220> FEATURE:
<221> NAME/KEY: misc_feature
<222> LOCATION: (1)...(494)

<223> OTHER INFORMATION: n = A,T,C or G

<400> SEQUENCE: 449

| acaaaaaaca caaggaatac aacccaatag aaaatagtcc tgggaatgtg gtcagaagca | 60 |
| aaggcntgag tgtctttctc aaccgtgcaa aagccgtgtt cttcccggga aaccaggaaa | 120 |
| aggatccgct actcaaaaac caagaattta aaggagtttc ttaaatttcg accttgtttc | 180 |
| tgaagctcac ttttcagtgc cattgatgtg agatgtgctg gagtggctat taacctttt | 240 |
| ttcctaaaga ttattgttaa atagatattg tggtttgggg aagttgaatt ttttataggt | 300 |
| taaatgtcat tttagagatg gggagaggga ttatactgca ggcagcttca gccatgttgt | 360 |
| gaaactgata aaagcaactt agcaaggctt cttttcatta ttttttatgt ttcacttata | 420 |
| aagtcttagg taactagtag gatagaaaca ctgtgtcccg agagtaagga gagaagctac | 480 |
| tattgattag agcc | 494 |

<210> SEQ ID NO 450
<211> LENGTH: 547
<212> TYPE: DNA
<213> ORGANISM: Homo sapiens

<400> SEQUENCE: 450

| actttgggct ccagacttca ctgtccttag gcattgaaac catcacctgg tttgcattct | 60 |
| tcatgactga ggttaactta aaacaaaaat ggtaggaaag ctttcctatg cttcgggtaa | 120 |
| gagacaaatt tgcttttgta gaattggtgg ctgagaaagg cagacagggc ctgattaaag | 180 |
| aagacatttg tcaccactag ccaccaagtt aagttgtgga acccaaaggt gacggccatg | 240 |
| gaaacgtaga tcatcagctc tgctaagtag ttaggggaag aaacatattc aaaccagtct | 300 |
| ccaaatggga tcctgtggtt acagtgaatg gccactcctg ctttattttt cctgagattg | 360 |
| ccgagaataa catggcactt atactgatgg gcagatgacc agatgaacat catcatccca | 420 |
| agaatatgga accaccgtgc ttgcatcaat agatttttcc ctgttatgta ggcattcctg | 480 |
| ccatccattg gcacttggct cagcacagtt aggccaacaa ggacataata gacaagtcca | 540 |
| aaacagt | 547 |

<210> SEQ ID NO 451
<211> LENGTH: 384
<212> TYPE: DNA
<213> ORGANISM: Homo sapiens
<220> FEATURE:
<221> NAME/KEY: misc_feature
<222> LOCATION: (1)...(384)
<223> OTHER INFORMATION: n = A,T,C or G

<400> SEQUENCE: 451

| actacttnnt ggttaaaang ccactggtag agtcatctga ntgtaaacaa tgtccctgca | 60 |
| ctgctggaaa aatccactgg ctcccaagaa aagaaaatgg tctgaagcct ctgttgtggc | 120 |
| tctcacaact catctttccc taagtcatca agctccacat cactgaggtc aatgtcatcc | 180 |
| tccacgggaa gctcgccatc cctgccgtcc caaggctctc tctcaacgat ggtagggaaa | 240 |
| gccccgcctc ctacaggtgc cgtggagcca cgcccaaaag agagctccct gagaaactcg | 300 |
| ttgatgcctt gctcactgaa ggagcctttt agcagagcaa atttcatctt gcgtgcattg | 360 |
| atggcggcca tggcgggta ccca | 384 |

<210> SEQ ID NO 452
<211> LENGTH: 381

<212> TYPE: DNA
<213> ORGANISM: Homo sapiens
<220> FEATURE:
<221> NAME/KEY: misc_feature
<222> LOCATION: (1)...(381)
<223> OTHER INFORMATION: n = A,T,C or G

<400> SEQUENCE: 452

```
actctaaagt tgccactctc acagggtca gtgataccca ctgaacctgg caggaacagt      60
cctgcagcca gaatctgcaa gcagcgcctg tatgcaacgt ttagggccaa aggctgtctg    120
gtggggttgt tcatcacagc ataatggcct agtaggtcaa ggatccaggg tgtgaggggc    180
tcaaagccag gaaaacgaat cctcaagtcc ttcagtagtc tgatgagaac tttaactgtg    240
gactgagaag cattttcctc gaaccagcgg gcatgtcgga tggctgctaa ngcactctgc    300
aatactttga tatccaaatg gagttctgga tccagttttc naagattggg tggcactgtt    360
gtaatganaa tcttcactgt a                                              381
```

<210> SEQ ID NO 453
<211> LENGTH: 455
<212> TYPE: DNA
<213> ORGANISM: Homo sapiens

<400> SEQUENCE: 453

```
actgtgctaa acagcctata gccaagtttt aaagagttac aggaacaact gctacacatt     60
caaagaacag gcattcactg cagcctcctg atttgacctg atgggaggga caggagaatg    120
agtcactctg ccaccacttt tcctgccttg gatttgtaga ggatttgttt tgctctaatt    180
tgtttttcct atatctgccc tactaaggta cacagtctgg gcactttgaa aatgttaaag    240
tttttaacgt ttgactgaca gaagcagcac ttaaaggctt catgaatcta ttttccaaaa    300
aaagtatgct tcagtaaaa cattttacca ttttatctaa ctatgcactg acatttttgt    360
tcttcctgaa aaggggattt atgctaacac tgtattttta atgtaaaaat atacgtgtag    420
agatatttta acttcctgag tgacttatac ctcaa                               455
```

<210> SEQ ID NO 454
<211> LENGTH: 383
<212> TYPE: DNA
<213> ORGANISM: Homo sapiens
<220> FEATURE:
<221> NAME/KEY: misc_feature
<222> LOCATION: (1)...(383)
<223> OTHER INFORMATION: n = A,T,C or G

<400> SEQUENCE: 454

```
acagagcanc tttacaagtt gtcacatttc tttataaatt tttttaaagc tacagtttaa     60
tacaaaatga attgcggttt tattacatta ataaccttc acctcagggt tttatgaaga    120
ggaaagggtt ttatgcaaaa gaaagtgcta caattcctaa tcattttaga cactttagga    180
ggggtgaag ttgtatgata aagcagatat tttaattatt tgttatcttt ttgtattgca    240
agaaatttct tgctagtgaa tcaagaaaac atccagattg acagtctaaa atggctactg    300
gtattttagt taattcaaaa atgaaacttt tcagtgattc actttactaa cattctattt    360
gagaaggctt attggtaaag ttt                                             383
```

<210> SEQ ID NO 455
<211> LENGTH: 383
<212> TYPE: DNA
<213> ORGANISM: Homo sapiens
<220> FEATURE:

```
<221> NAME/KEY: misc_feature
<222> LOCATION: (1)...(383)
<223> OTHER INFORMATION: n = A,T,C or G

<400> SEQUENCE: 455
actcctttan gacaaggaaa caggtatcag catgatggta gcagaaacct tatcaccaag      60
gtgcaggagc tgacttcttc caaagagttg tggttccggg cagcgtcat tgccgtgccc     120 attgctggag ggctgatttt agtgttgctt attatgttgg ccctgaggat gcttcgaagt    180
gaaaataaga ggctgcagga tcagcggcaa cagatgctct cccgtttgca ctacagcttt    240
cacggacacc attccaaaaa ggggcaggtt gcaaagttag acttggaatg catggtgccg    300
gtcagtgggc acgagaactg ctgtctgacc tgtgataaaa tgagacaagc agacctcagc    360
aacgataaga tcctctcgct tgt                                            383

<210> SEQ ID NO 456
<211> LENGTH: 543
<212> TYPE: DNA
<213> ORGANISM: Homo sapiens
<220> FEATURE:
<221> NAME/KEY: misc_feature
<222> LOCATION: (1)...(543)
<223> OTHER INFORMATION: n = A,T,C or G

<400> SEQUENCE: 456
acaaacattt tacaaaaaag aacattacca atatcagtgg cagtaagggc aagctgaaga     60
atangtagac tgagtttccg ggcaatgtct gtcctcaaag acatccaaac tgcgttcagg    120
cagctgaaac aggcttcttt cccagtgaca agcatatgtg gtcagtaata caaacgatgg    180
taaatgaggc tactacatag gcccagttaa caaactcctc ttctcctcgg gtaggccatg    240
atacaagtgg aactcatcaa ataatttaaa cccaaggcga taacaacact atttcccatc    300
taaactcatt taagccttca caatgtcgca atggattcag ttacttgcaa acgatcccgg    360
gttgtcatac agatacttgt tttttacaca taacgctgtg ccatcccttc cttcactgcc    420
ccagtcaggt ttcctgttgt tggaccgaaa gggggatacat tttagaaatg cttccctcaa   480
gacagaagtg agaaagaaag gagaccctga ggccaggatc tattaaacct ggtgtgtgcg    540
caa                                                                   543

<210> SEQ ID NO 457
<211> LENGTH: 544
<212> TYPE: DNA
<213> ORGANISM: Homo sapiens
<220> FEATURE:
<221> NAME/KEY: misc_feature
<222> LOCATION: (1)...(544)
<223> OTHER INFORMATION: n = A,T,C or G

<400> SEQUENCE: 457
actggtgcca atattgncat ggtgagctcc tctctaatgt cttccagggc accaatatct     60
gcccatgtca cattagggac agtgacaaag ccttcccttt tggcagaggg ttggactgag    120
gatagagcaa caatgaaatc attcagttca atgcacagtc cttgcatctg ctcctctgag    180 agggatctt ggtctcttag caaccccagc agcctttgta attcatcctg tgtttcagaa     240
gtgggctcag ttcccagcct ttcctcctgg actcctttag atggcaaatc ttccatttca    300
ggatttttct tctgctgttc ctgtagcttc attaagactc tattgactgc acacattgct    360
gcctctcggc acagtgccat gagatcagca ccaacaaagc ctggagttag gtgtgctaag    420
tgacagaaat caaaagcttg aggaagcctc agttttctgc acaatgtttg aagtattctt    480
```

```
tccctggatg cttcatctgg gataccatgg catatttctc ggtcgaacct tcccgcacgt    540
ctca                                                                 544
```

<210> SEQ ID NO 458
<211> LENGTH: 382
<212> TYPE: DNA
<213> ORGANISM: Homo sapiens
<220> FEATURE:
<221> NAME/KEY: misc_feature
<222> LOCATION: (1)...(382)
<223> OTHER INFORMATION: n = A,T,C or G

<400> SEQUENCE: 458

```
acctntaggc tcaacggcag aancttcacc acaaaagcga aatgggcaca ccacagggag     60
aaaactggtt gtcctggatg tttgaaaagt tggtcgttgt catggtgtgt tacttcatcc    120
tatctatcat taactccatg gcacaaagtt atgccaaacg aatccagcag cggttgaact    180
cagaggagaa aactaaataa gtagagaaag ttttaaactg cagaaattgg agtggatggg    240
ttctgcctta aattgggagg actccaagcc gggaaggaaa attccctttt ccaacctgta    300
tcaattttta caactttttt cctgaaagca gtttagtcca tactttgcac tgacatactt    360
tttccttctg tgctaaggta ag                                             382
```

<210> SEQ ID NO 459
<211> LENGTH: 168
<212> TYPE: DNA
<213> ORGANISM: Homo sapiens

<400> SEQUENCE: 459

```
ctcgtactct agccaggcac gaaaccatga agtagcctga tccttcttag ccatcctggc     60
cgccttagcg gtagtaactt tgtgttatga atcacatgaa agcatggaat cttatgaact    120
taatcccttc attaacagga gaaatgcaaa taccttcata tcccctca                 168
```

<210> SEQ ID NO 460
<211> LENGTH: 190
<212> TYPE: DNA
<213> ORGANISM: Homo sapiens
<220> FEATURE:
<221> NAME/KEY: misc_feature
<222> LOCATION: (1)...(190)
<223> OTHER INFORMATION: n = A,T,C or G

<400> SEQUENCE: 460

```
acanctgcta ccagggagcc gagagctgac tatcccagcc tcggctaatg tattctacgc     60
catggatgga gcttcacacg atttcctcct gcggcagcgg cgaaggtcct ctactgctac    120
acctggcgtc accagtggcc cgtctgcctc aggaactcct ccgagtgagg gaggaggggg    180
ctcctttccc                                                           190
```

<210> SEQ ID NO 461
<211> LENGTH: 495
<212> TYPE: DNA
<213> ORGANISM: Homo sapiens

<400> SEQUENCE: 461

```
acagacaggc ttctctgcta tcctccaggc agtgtaatag tcaaggaaaa gggcaacagt     60
attggatcat tccttagaca ctaatcagct ggggaaagag ttcattggca aaagtgtcct    120
cccaagaatg gtttacacca agcagagagg acatgtcact gaatggggaa agggaacccc    180
```

-continued

```
cgtatccaca gtcactgtaa gcatccagta ggcaggaaga tggctttggg cagtggctgg      240
atgaaagcag atttgagata cccagctccg gaacgaggtc atcttctaca ggttcttcct      300
tcactgagac aatgaattca gggtgatcat tctctgaggg gctgagaggt gcttcctcga      360
ttttcactac acattagct tggctctctg tctcagaggg tatctctaag actaggggct       420
tggtatatat gtggtcaaaa cgaattagtt cattaatggc ttccagcttg gctgatgacg      480
tccccactga cagag                                                      495
```

<210> SEQ ID NO 462
<211> LENGTH: 493
<212> TYPE: DNA
<213> ORGANISM: Homo sapiens
<220> FEATURE:
<221> NAME/KEY: misc_feature
<222> LOCATION: (1)...(493)
<223> OTHER INFORMATION: n = A,T,C or G

<400> SEQUENCE: 462

```
acactgaaac ataaatccgc aagtcaccac acatacaaca cccggcagga aaaaaacaaa       60
aacagggngt ttacatgatc cctgtaacag ccatggtctc aaactcagat gcttcctcca     120
tctgccaagt gtgttttgga tacagagcac atcgtggctt ctgggtcac actcagctta      180 ggctgtgggt ccacagagca ctcatctggc tgggctatgg tggtggtggc tctactcaag     240
aagcaaagca gttaccagca cattcaaaca gtgtattgaa catcttttaa atatcaaagt     300
gagaaacaag aaggcaacat aataatgtta tcagaaagat gttaggaagt aaggacagct     360
gtgtaaagct tgaggctgaa aagtagcttg ccagcttcat ttctttggtt tcttgggtag     420
tgggcgccgg aacagcaaga tgtgaggttc tggttcatgg atcatataat ggacccatcc     480
ctgactctgc tga                                                       493
```

<210> SEQ ID NO 463
<211> LENGTH: 3681
<212> TYPE: DNA
<213> ORGANISM: Homo sapiens

<400> SEQUENCE: 463

```
tccgagctga ttacagacac caaggaagat gctgtaaaga gtcagcagcc acagccctgg       60
ctagctggcc ctgtgggcat ttattagtaa agttttaatg acaaaagctt tgagtcaaca      120
cacccgtggg taattaacct ggtcatcccc accctggaga gccatcctgc ccatgggtga      180
tcaaagaagg aacatctgca ggaacacctg atgaggctgc acccttggcg gaaagaacac      240
ctgacacagc tgaaagcttg gtggaaaaaa cacctgatga ggctgcaccc ttggtggaaa      300
gaacacctga cacggctgaa agcttggtgg aaaaaacacc tgatgaggct gcatccttgg      360 tgagggaac atctgacaaa attcaatgtt tggagaaagc gacatctgga agttcgaac        420 agtcagcaga agaaacacct agggaaatta cgagtcctgc aaaagaaaca tctgagaaat      480
ttacgtggcc agcaaaagga agacctagga agatcgcatg ggagaaaaaa gaagacacac      540
ctagggaaat tatgagtccc gcaaaagaaa catctgagaa atttacgtgg gcagcaaaag      600
gaagacctag gaagatcgca tgggagaaaa agaaacacc tgtaaagact ggatgcgtgg       660
caagagtaac atctaataaa actaaagttt tggaaaaagg aagatctaag atgattgcat      720
gtcctacaaa agaatcatct acaaaagcaa gtgccaatga tcagaggttc ccatcagaat      780
ccaaacaaga ggaagatgaa gaatattctt gtgattctcg gagtctcttt gagagttctg      840
caaagattca agtgtgtata cctgagtcta tatcaaaa agtaatggag ataaatagag          900
```

```
aagtagaaga gcctcctaag aagccatctg ccttcaagcc tgccattgaa atgcaaaact    960
ctgttccaaa taaagccttt gaattgaaga atgaacaaac attgagagca gatccgatgt   1020
tcccaccaga atccaaacaa aaggactatg aagaaaattc ttgggattct gagagtctct   1080
gtgagactgt ttcacagaag gatgtgtgtt tacccaaggc tacacatcaa aaagaaatag   1140
ataaaataaa tggaaaatta aagagtctc ctaataaaga tggtcttctg aaggctacct    1200
gcggaatgaa agtttctatt ccaactaaag ccttagaatt gaaggacatg caaactttca   1260
aagcagagcc tccggggaag ccatctgcct tcgagcctgc cactgaaatg caaaagtctg   1320
tcccaaataa agccttggaa ttgaaaaatg aacaaacatt gagagcagat gagatactcc   1380
catcagaatc caaacaaaag gactatgaag aaagttcttg ggattctgag agtctctgtg   1440
agactgtttc acagaaggat gtgtgtttac ccaaggctrc rcatcaaaaa gaaatagata   1500
aaataaatgg aaaattagaa gggtctcctg ttaaagatgg tcttctgaag ctaactgcg    1560 gaatgaaagt ttctattcca actaaagcct tagaattgat ggacatgcaa actttcaaag   1620
cagagcctcc cgagaagcca tctgccttcg agcctgccat tgaaatgcaa aagtctgttc   1680
caaataaagc cttggaattg aagaatgaac aaacattgag agcagatgag atactcccat   1740
cagaatccaa acaaaaggac tatgaagaaa gttcttggga ttctgagagt ctctgtgaga   1800
ctgtttcaca gaaggatgtg tgtttaccca aggctrcrca tcaaaaagaa atagataaaa   1860
taaatggaaa attagaagag tctcctgata atgatggttt tctgaaggct ccctgcagaa   1920
tgaaagtttc tattccaact aaagccttag aattgatgga catgcaaact ttcaaagcag   1980
agcctcccga gaagccatct gccttcgagc ctgccattga aatgcaaaag tctgttccaa   2040
ataaagcctt ggaattgaag aatgaacaaa cattgagagc agatcagatg ttcccttcag   2100
aatcaaaaca aaagaasgtt gaagaaaatt cttgggattc tgagagtctc cgtgagactg   2160
tttcacagaa ggatgtgtgt gtacccaagg ctacacatca aaaagaaatg gataaaataa   2220
gtggaaaatt agaagattca actagccatt caaaaatctt ggatacagtt cattcttgtg   2280
aaagagcaag ggaacttcaa aaagatcact gtgaacaacg tacaggaaaa atggaacaaa   2340
tgaaaaagaa gttttgtgta ctgaaaaaga aactgtcaga agcaaaagaa ataaaatcac   2400
agttagagaa ccaaaaagtt aaatgggaac aagagctctg cagtgtgagg tttctcacac   2460
tcatgaaaat gaaaattatc tcttacatga aaattgcatg ttgaaaaagg aaattgccat   2520
gctaaaactg gaaatagcca cactgaaaca ccaataccag gaaaaggaaa ataaatactt   2580
tgaggacatt aagattttaa agaaaaagaa tgctgaactt cagatgaccc taaaactgaa   2640
agaggaatca ttaactaaaa gggcatctca atatagtggg cagcttaaag ttctgatagc   2700
tgagaacaca atgctcactt ctaaattgaa ggaaaaacaa gacaaagaaa tactagaggc   2760
agaaattgaa tcacaccatc ctagactggc ttctgctgta caagaccatg atcaaattgt   2820
gacatcaaga aaaagtcaag aacctgcttt ccacattgca ggagatgctt gtttgcaaag   2880
aaaaatgaat gttgatgtga gtagtacgat atataacaat gaggtgctcc atcaaccact   2940
ttctgaagct caaaggaaat ccaaaagcct aaaaattaat ctcaattatg cmggagatgc   3000
tctaagagaa aatacattgg tttcagaaca tgcacaaaga gaccaacgtg aaacacagtg   3060
tcaaatgaag gaagctgaac acatgtatca aaacgaacaa gataatgtga caaacacac    3120 tgaacagcag gagtctctag atcagaaatt atttcaacta caaagcaaaa atatgtggct   3180
tcaacagcaa ttagttcatg cacataagaa agctgacaac aaaagcaaga taacaattga   3240
```

| | |
|---|---|
| tattcattttt cttgagagga aaatgcaaca tcatctccta aaagagaaaa atgaggagat | 3300 |
| atttaattac aataaccatt taaaaaaccg tatatatcaa tatgaaaaag agaaagcaga | 3360 |
| aacagaaaac tcatgagaga caagcagtaa gaaacttctt ttggagaaac aacagaccag | 3420 |
| atctttactc acaactcatg ctaggaggcc agtcctagca tcaccttatg ttgaaaatct | 3480 |
| taccaatagt ctgtgtcaac agaatactta ttttagaaga aaaattcatg atttcttcct | 3540 |
| gaagcctaca gacataaaat aacagtgtga agaattactt gttcacgaat tgcataaagc | 3600 |
| tgcacaggat tcccatctac cctgatgatg cagcagacat cattcaatcc aaccagaatc | 3660 |
| tcgctctgtc actcaggctg g | 3681 |

<210> SEQ ID NO 464
<211> LENGTH: 1424
<212> TYPE: DNA
<213> ORGANISM: Homo sapiens
<400> SEQUENCE: 464

| | |
|---|---|
| tccgagctga ttacagacac caaggaagat gctgtaaaga gtcagcagcc acagccctgg | 60 |
| ctagctggcc ctgtgggcat ttattagtaa agttttaatg acaaaagctt tgagtcaaca | 120 |
| cacccgtggg taattaacct ggtcatcccc accctggaga gccatcctgc ccatgggtga | 180 |
| tcaaagaagg aacatctgca ggaacacctg atgaggctgc acccttggcg aaagaacac | 240 |
| ctgacacagc tgaaagcttg gtggaaaaaa cacctgatga ggctgcaccc ttggtggaaa | 300 |
| gaacacctga cacggctgaa agcttggtgg aaaaaacacc tgatgaggct gcatccttgg | 360 |
| tggagggaac atctgacaaa attcaatgtt tggagaaagc gacatctgga aagttcgaac | 420 |
| agtcagcaga gaaacacct agggaaatta cgagtcctgc aaaagaaaca tctgagaaat | 480 |
| ttacgtggcc agcaaaagga agacctagga agatcgcatg ggagaaaaaa gaagacacac | 540 |
| ctagggaaat tatgagtccc gcaaaagaaa catctgagaa atttacgtgg gcagcaaaag | 600 |
| gaagacctag gaagatcgca tgggagaaaa aagaaacacc tgtaaagact ggatgcgtgg | 660 |
| caagagtaac atcaataaa actaaagttt tggaaaagg aagatctaag atgattgcat | 720 |
| gtcctacaaa agaatcatct acaaaagcaa gtgccaatga tcagaggttc ccatcagaat | 780 |
| ccaaacaaga ggaagatgaa gaatattctt gtgattctcg gagtctcttt gagagttctg | 840 |
| caaagattca agtgtgtata cctgagtcta tatatcaaaa agtaatggag ataaatagag | 900 |
| aagtagaaga gcctcctaag aagccatctg ccttcaagcc tgccattgaa atgcaaaact | 960 |
| ctgttccaaa taaagccttt gaattgaaga atgaacaaac attgagagca gatccgatgt | 1020 |
| tcccaccaga atccaaacaa aaggactatg aagaaaattc ttgggattct gagagtctct | 1080 |
| gtgagactgt tcacagaag gatgtgtgtt tacccaaggc tacacatcaa aaagaaatag | 1140 |
| ataaaataaa tggaaaatta gaaggtaaga accgtttttt atttaaaaat cagttgaccg | 1200 |
| aatatttctc taaactgatg aggagggata tcctctagta gctgaagaaa attacctcct | 1260 |
| aaatgcaaac catggaaaaa aagagaagtg caatggtcgt aagttgtatg tctcatcagg | 1320 |
| tgttggcaac agactatatt gagagtgctg aaaaggagct gaattattag tttgaattca | 1380 |
| agatattgca agacctgaga gaaaaaaaaa aaaaaaaaa aaaa | 1424 |

<210> SEQ ID NO 465
<211> LENGTH: 674
<212> TYPE: DNA
<213> ORGANISM: Homo sapiens
<400> SEQUENCE: 465

```
attccgagct gattacagac accaaggaag atgctgtaaa gagtcagcag ccacagccct    60
ggctagctgg ccctgtgggc atttattagt aaagttttaa tgacaaaagc tttgagtcaa   120
cacaccgtg  ggtaattaac ctggtcatcc ccaccctgga gagccatcct gcccatgggt   180
gatcaaagaa ggaacatctg caggaacacc tgatgaggct gcacccttgg cggaaagaac   240
acctgacaca gctgaaagct tggtggaaaa acacctgat  gaggctgcac ccttggtgga   300
aagaacacct gacacggctg aaagcttggt ggaaaaaaca cctgatgagg ctgcatcctt   360
ggtggaggga acatctgaca aaattcaatg tttggagaaa gcgacatctg gaaagttcga   420
acagtcagca agagaaacac ctagggaaat tacgagtcct gcaaaagaaa catctgagaa   480
atttacgtgg ccagcaaaag gaagacctag gaagatcgca tgggagaaaa aagatgactc   540
agttaaggca aaaaaaaaaa aaaaaaaaaa aaaaaaaaaa aaaaaaaaaa aaaaaaaaaa   600
aaaaaaaaaa aaaaaaaaaa aaaaaaaaaa aaaaaaaaaa aaaaaaaaaa aaaaaaaaaa   660
aaaaaaaaaa aaaa                                                     674

<210> SEQ ID NO 466
<211> LENGTH: 1729
<212> TYPE: DNA
<213> ORGANISM: Homo sapiens
<220> FEATURE:
<221> NAME/KEY: unsure
<222> LOCATION: (11)
<223> OTHER INFORMATION: n=A,T,C or G
<221> NAME/KEY: unsure
<222> LOCATION: (1128)
<223> OTHER INFORMATION: n=A,T,C or G

<400> SEQUENCE: 466
gaaagttcga ncagtcagca agagaaacac ctagggaaat tacgagtcct gcaaaagaaa    60
catctgagaa atttacgtgg ccagcaaaag gaagacctag gaagatcgca tgggagaaaa   120
aagaagacac acctagggaa attatgagtc cgcaaaaga  aacatctgag aaatttacgt   180
gggcagcaaa aggaagacct aggaagatcg catgggagaa aaaagaaaca cctgtaaaga   240
ctggatgcgt ggcaagagta acatctaata aaactaaagt tttggaaaaa ggaagatcta   300
agatgattgc atgtcctaca aaagaatcat ctacaaaagc aagtgccaat gatcagaggt   360
tcccatcaga atccaaacaa gaggaagatg aagaatattc ttgtgattct cggagtctct   420
ttgagagttc tgcaaagatt caagtgtgta tacctgagtc tatatatcaa aaagtaatgg   480
agataaatag agaagtagaa gagcctccta agaagccatc tgccttcaag cctgccattg   540
aaaatgcaaa ctctgttcca ataaagcctt tgaattgaa  gaatgaacaa acattgagag   600
cagatccgat gttcccacca gaatccaaac aaaaggacta tgaagaaaat tcttgggatt   660
ctgagagtct ctgtgagact gtttcacaga aggatgtgtg tttacccaag gctacacatc   720
aaaaagaaat agataaaata aatggaaaat tagaagagtc tcctaataaa gatggtcttc   780
tgaaggctac ctgcggaatg aaagtttcta ttccaactaa agccttagaa ttgaaggaca   840
tgcaaacttt caaagcagag cctccgggga agccatctgc cttcgagcct gccactgaaa   900
tgcaaaagtc tgtcccaaat aaagccttgg aattgaaaaa tgaacaaaca ttgagagcag   960
atgagatact cccatcagaa tccaaacaaa aggactatga agaaaattct tgggatactg  1020
agagtctctg tgagactgtt tcacagaagg atgtgtgttt acccaaggct gcgcatcaaa  1080
aagaaataga taaatataaat ggaaaattag aagggtctcc tggtaaanat ggtcttctga  1140
aggctaactg cggaatgaaa gtttctattc caactaaagc cttagaattg atggacatgc  1200
```

```
aaactttcaa agcagagcct cccgagaagc catctgcctt cgagcctgcc attgaaatgc    1260
aaaagtctgt tccaaataaa gccttggaat tgaagaatga acaaacattg agagcagatg    1320
agatactccc atcagaatcc aaacaaaagg actatgaaga aagttcttgg gattctgaga    1380
gtctctgtga gactgtttca cagaaggatg tgtgtttacc caaggctgcg catcaaaaag    1440
aaatagataa aataaatgga aaattagaag gtaagaaccg ttttttattt aaaaatcatt    1500
tgaccaaata tttctctaaa ttgatgagga aggatatcct ctagtagctg aagaaaatta    1560
cctcctaaat gcaaaccatg gaaaaaaaga gaagtgcaat ggtcataagc tatgtgtctc    1620
atcaggcatt ggcaacagac tatattgtga gtgctgaaga ggagctgaat tactagttta    1680
aattcaagat attccaagac gtgaggaaaa tgagaaaaaa aaaaaaaa                 1729
```

<210> SEQ ID NO 467
<211> LENGTH: 1337
<212> TYPE: DNA
<213> ORGANISM: Homo sapiens

<400> SEQUENCE: 467

```
aaaaagaaat agataaaata aatggaaaat tagaagggtc tcctgttaaa gatggtcttc      60
tgaaggctaa ctgcggaatg aaagtttcta ttccaactaa agccttagaa ttgatggaca     120
tgcaaacttt caaagcagag cctcccgaga agccatctgc cttcgagcct gccattgaaa     180
tgcaaaagtc tgttccaaat aaagccttgg aattgaagaa tgaacaaaca ttgagagcag     240
atgagatact cccatcagaa tccaaacaaa aggactatga gaaagttct tgggattctg      300 agagtctctg tgagactgtt tcacagaagg atgtgtgttt acccaaggct gcgcatcaaa     360
aagaaataga taaataaat ggaaaattag aagagtctcc tgataatgat ggttttctga      420
aggctccctg cagaatgaaa gtttctattc caactaaagc cttagaattg atggacatgc     480
aaactttcaa agcagagcct cccgagaagc catctgcctt cgagcctgcc attgaaatgc     540
aaaagtctgt tccaaataaa gccttggaat tgaagaatga acaaacattg agagcagatc     600
agatgttccc ttcagaatca aacaaaagaa aggttgaaga aaattcttgg gattctgaga     660
gtctccgtga gactgtttca cagaaggatg tgtgtgtacc caaggctaca catcaaaaag     720
aaatggataa aataagtgga aaattagaag attcaactag cctatcaaaa atcttggata     780
cagttcattc ttgtgaaaga gcaagggaac ttcaaaaaga tcactgtgaa caacgtacag     840
gaaaaatgga acaaatgaaa aagaagtttt gtgtactgaa aaagaaactg tcagaagcaa     900
aagaaataaa atcacagtta gagaaccaaa aagttaaatg ggaacaagag ctctgcagtg     960
tgagattgac tttaaaccaa gaagaagaga agagaagaaa tgccgatata ttaaatgaaa    1020
aaattaggga agaattagga agaatcgaag agcagcatag gaaagagtta gaagtgaaac    1080
aacaacttga acaggctctc agaatacaag atatagaatt gaagagtgta gaaagtaatt    1140
tgaatcaggt ttctcacact catgaaaatg aaaattatct cttacatgaa aattgcatgt    1200
tgaaaaagga aattgccatg ctaaaactgg aaatagccac actgaaacac caataccagg    1260
aaaaggaaaa taaatacttt gaggacatta agattttaaa agaaaagaat gctgaacttc    1320
agatgacccc tcgtgcc                                                   1337
```

<210> SEQ ID NO 468
<211> LENGTH: 2307
<212> TYPE: DNA
<213> ORGANISM: Homo sapiens

```
<400> SEQUENCE: 468
attgagagca gatgagatac tcccatcaga atccaaacaa aaggactatg aagaaagttc      60
ttgggattct gagagtctct gtgagactgt ttcacagaag gatgtgtgtt tacccaaggc     120
tacacatcaa aaagaaatag ataaaataaa tggaaaatta aagggtctc ctgttaaaga      180
tggtcttctg aaggctaact gcggaatgaa agtttctatt ccaactaaag ccttagaatt     240
gatggacatg caaactttca aagcagagcc tcccgagaag ccatctgcct tcgagcctgc     300
cattgaaatg caaaagtctg ttccaaataa agccttggaa ttgaagaatg aacaaacatt     360
gagagcagat gagatactcc catcagaatc caaacaaaag gactatgaag aagttcttg     420
ggattctgag agtctctgtg agactgtttc acagaaggat gtgtgtttac ccaaggctac     480
acatcaaaaa gaaatagata aataaatgg aaaattagaa gagtctcctg ataatgatgg      540
ttttctgaag tctccctgca gaatgaaagt ttctattcca actaaagcct tagaattgat     600
ggacatgcaa actttcaaag cagagcctcc cgagaagcca tctgccttcg agcctgccat     660
tgaaatgcaa aagtctgttc caaataaagc cttggaattg aagaatgaac aaacattgag     720
agcagatcag atgttccctt cagaatcaaa acaaagaac gttgaagaaa attcttggga      780
ttctgagagt ctccgtgaga ctgttcaca gaaggatgtg tgtgtaccca aggctacaca     840
tcaaaaagaa atggataaaa taagtggaaa attagaagat tcaactagcc tatcaaaaat     900
cttggataca gttcattctt gtgaaagagc aagggaactt caaaaagatc actgtgaaca     960
acgtacagga aaaatggaac aaatgaaaaa gaagttttgt gtactgaaaa agaaactgtc    1020
agaagcaaaa gaaataaaat cacagttaga gaaccaaaaa gttaaatggg aacaagagct    1080
ctgcagtgtg aggtttctca cactcatgaa aatgaaaatt atctcttaca tgaaaattgc    1140
atgttgaaaa aggaaattgc catgctaaaa ctggaaatag ccacactgaa acaccaatac    1200
caggaaaagg aaaataaata ctttgaggac attaagattt taaagaaaaa gaatgctgaa    1260
cttcagatga ccctaaaact gaaagaggaa tcattaacta aaggcatc tcaatatagt      1320
gggcagctta aagttctgat agctgagaac acaatgctca cttctaaatt gaaggaaaaa    1380
caagacaaag aaatactaga ggcagaaatt gaatcacacc atcctagact ggcttctgct    1440
gtacaagacc atgatcaaat tgtgacatca agaaaaagtc aagaacctgc tttccacatt    1500
gcaggagatg cttgtttgca agaaaaatg aatgttgatg tgagtagtac gatatataac     1560
aatgaggtgc tccatcaacc actttctgaa gctcaaagga atccaaaag cctaaaaatt     1620
aatctcaatt atgcaggaga tgctctaaga gaaaatacat tggtttcaga acatgcacaa    1680
agagaccaac gtgaaacaca gtgtcaaatg aaggaagctg aacacatgta tcaaaacgaa    1740
caagataatg tgaacaaaca cactgaacag caggagtctc tagatcagaa attatttcaa    1800
ctacaaagca aaaatatgtg gcttcaacag caattagttc atgcacataa gaaagctgac    1860
aacaaaagca agataacaat tgatattcat tttcttgaga ggaaaatgca acatcatctc    1920
ctaaaagaga aaaatgagga gatatttaat tacaataacc attaaaaaaa ccgtatatat    1980
caatatgaaa aagagaaagc agaaacagaa aactcatgag agacaagcag taagaaactt    2040
cttttggaga aacaacagac cagatctttta ctcacaactc atgctaggag gccagtccta    2100
gcatcacctt atgttgaaaa tcttaccaat agtctgtgtc aacagaatac ttatttaga    2160
agaaaaattc atgatttctt cctgaagcct acagacataa aataacagtg tgaagaatta    2220
cttgttcacg aattgcataa agctgcacag gattcccatc taccctgatg atgcagcaga    2280
catcattcaa tccaaccaga atctcgc                                        2307
```

```
<210> SEQ ID NO 469
<211> LENGTH: 650
<212> TYPE: PRT
<213> ORGANISM: Homo sapiens
<220> FEATURE:
<221> NAME/KEY: unsure
<222> LOCATION: (310)
<223> OTHER INFORMATION: Xaa = Any Amino Acid
<221> NAME/KEY: unsure
<222> LOCATION: (429)
<223> OTHER INFORMATION: Xaa = Any Amino Acid
<221> NAME/KEY: unsure
<222> LOCATION: (522)
<223> OTHER INFORMATION: Xaa = Any Amino Acid

<400> SEQUENCE: 469

Met Ser Pro Ala Lys Glu Thr Ser Glu Lys Phe Thr Trp Ala Ala Lys
                  5                  10                  15

Gly Arg Pro Arg Lys Ile Ala Trp Glu Lys Lys Glu Thr Pro Val Lys
             20                  25                  30

Thr Gly Cys Val Ala Arg Val Thr Ser Asn Lys Thr Lys Val Leu Glu
         35                  40                  45

Lys Gly Arg Ser Lys Met Ile Ala Cys Pro Thr Lys Glu Ser Ser Thr
     50                  55                  60

Lys Ala Ser Ala Asn Asp Gln Arg Phe Pro Ser Glu Ser Lys Gln Glu
 65                  70                  75                  80

Glu Asp Glu Glu Tyr Ser Cys Asp Ser Arg Ser Leu Phe Glu Ser Ser
                 85                  90                  95

Ala Lys Ile Gln Val Cys Ile Pro Glu Ser Ile Tyr Gln Lys Val Met
            100                 105                 110

Glu Ile Asn Arg Glu Val Glu Glu Pro Pro Lys Lys Pro Ser Ala Phe
        115                 120                 125

Lys Pro Ala Ile Glu Met Gln Asn Ser Val Pro Asn Lys Ala Phe Glu
    130                 135                 140

Leu Lys Asn Glu Gln Thr Leu Arg Ala Asp Pro Met Phe Pro Pro Glu
145                 150                 155                 160

Ser Lys Gln Lys Asp Tyr Glu Glu Asn Ser Trp Asp Ser Glu Ser Leu
                165                 170                 175

Cys Glu Thr Val Ser Gln Lys Asp Val Cys Leu Pro Lys Ala Thr His
            180                 185                 190

Gln Lys Glu Ile Asp Lys Ile Asn Gly Lys Leu Glu Glu Ser Pro Asn
        195                 200                 205

Lys Asp Gly Leu Leu Lys Ala Thr Cys Gly Met Lys Val Ser Ile Pro
    210                 215                 220

Thr Lys Ala Leu Glu Leu Lys Asp Met Gln Thr Phe Lys Ala Glu Pro
225                 230                 235                 240

Pro Gly Lys Pro Ser Ala Phe Glu Pro Ala Thr Glu Met Gln Lys Ser
                245                 250                 255

Val Pro Asn Lys Ala Leu Glu Leu Lys Asn Glu Gln Thr Leu Arg Ala
            260                 265                 270

Asp Glu Ile Leu Pro Ser Glu Ser Lys Gln Lys Asp Tyr Glu Glu Ser
        275                 280                 285

Ser Trp Asp Ser Glu Ser Leu Cys Glu Thr Val Ser Gln Lys Asp Val
    290                 295                 300

Cys Leu Pro Lys Ala Xaa His Gln Lys Glu Ile Asp Lys Ile Asn Gly
305                 310                 315                 320
```

```
Lys Leu Glu Gly Ser Pro Val Lys Asp Gly Leu Leu Lys Ala Asn Cys
                325                 330                 335
Gly Met Lys Val Ser Ile Pro Thr Lys Ala Leu Glu Leu Met Asp Met
            340                 345                 350
Gln Thr Phe Lys Ala Glu Pro Glu Lys Pro Ser Ala Phe Glu Pro
        355                 360                 365
Ala Ile Glu Met Gln Lys Ser Val Pro Asn Lys Ala Leu Glu Leu Lys
370                 375                 380
Asn Glu Gln Thr Leu Arg Ala Asp Glu Ile Leu Pro Ser Glu Ser Lys
385                 390                 395                 400
Gln Lys Asp Tyr Glu Glu Ser Ser Trp Asp Ser Glu Ser Leu Cys Glu
                405                 410                 415
Thr Val Ser Gln Lys Asp Val Cys Leu Pro Lys Ala Xaa His Gln Lys
                420                 425                 430
Glu Ile Asp Lys Ile Asn Gly Lys Leu Glu Glu Ser Pro Asp Asn Asp
                435                 440                 445
Gly Phe Leu Lys Ala Pro Cys Arg Met Lys Val Ser Ile Pro Thr Lys
            450                 455                 460
Ala Leu Glu Leu Met Asp Met Gln Thr Phe Lys Ala Glu Pro Pro Glu
465                 470                 475                 480
Lys Pro Ser Ala Phe Glu Pro Ala Ile Glu Met Gln Lys Ser Val Pro
                485                 490                 495
Asn Lys Ala Leu Glu Leu Lys Asn Glu Gln Thr Leu Arg Ala Asp Gln
                500                 505                 510
Met Phe Pro Ser Glu Ser Lys Gln Lys Xaa Val Glu Glu Asn Ser Trp
                515                 520                 525
Asp Ser Glu Ser Leu Arg Glu Thr Val Ser Gln Lys Asp Val Cys Val
            530                 535                 540
Pro Lys Ala Thr His Gln Lys Glu Met Asp Lys Ile Ser Gly Lys Leu
545                 550                 555                 560
Glu Asp Ser Thr Ser Leu Ser Lys Ile Leu Asp Thr Val His Ser Cys
                565                 570                 575
Glu Arg Ala Arg Glu Leu Gln Lys Asp His Cys Glu Gln Arg Thr Gly
            580                 585                 590
Lys Met Glu Gln Met Lys Lys Phe Cys Val Leu Lys Lys Lys Leu
            595                 600                 605
Ser Glu Ala Lys Glu Ile Lys Ser Gln Leu Glu Asn Gln Lys Val Lys
            610                 615                 620
Trp Glu Gln Glu Leu Cys Ser Val Arg Phe Leu Thr Leu Met Lys Met
625                 630                 635                 640
Lys Ile Ile Ser Tyr Met Lys Ile Ala Cys
                645                 650

<210> SEQ ID NO 470
<211> LENGTH: 228
<212> TYPE: PRT
<213> ORGANISM: Homo sapiens

<400> SEQUENCE: 470

Met Ser Pro Ala Lys Glu Thr Ser Glu Lys Phe Thr Trp Ala Ala Lys
                5                   10                  15
Gly Arg Pro Arg Lys Ile Ala Trp Glu Lys Lys Glu Thr Pro Val Lys
            20                  25                  30
Thr Gly Cys Val Ala Arg Val Thr Ser Asn Lys Thr Lys Val Leu Glu
        35                  40                  45
```

```
Lys Gly Arg Ser Lys Met Ile Ala Cys Pro Thr Lys Glu Ser Ser Thr
        50                  55                  60

Lys Ala Ser Ala Asn Asp Gln Arg Phe Pro Ser Glu Ser Lys Gln Glu
 65                  70                  75                  80

Glu Asp Glu Glu Tyr Ser Cys Asp Ser Arg Ser Leu Phe Glu Ser Ser
                 85                  90                  95

Ala Lys Ile Gln Val Cys Ile Pro Glu Ser Ile Tyr Gln Lys Val Met
                100                 105                 110

Glu Ile Asn Arg Glu Val Glu Glu Pro Pro Lys Pro Ser Ala Phe
            115                 120                 125

Lys Pro Ala Ile Glu Met Gln Asn Ser Val Pro Asn Lys Ala Phe Glu
130                 135                 140

Leu Lys Asn Glu Gln Thr Leu Arg Ala Asp Pro Met Phe Pro Pro Glu
145                 150                 155                 160

Ser Lys Gln Lys Asp Tyr Glu Glu Asn Ser Trp Asp Ser Glu Ser Leu
                165                 170                 175

Cys Glu Thr Val Ser Gln Lys Asp Val Cys Leu Pro Lys Ala Thr His
                180                 185                 190

Gln Lys Glu Ile Asp Lys Ile Asn Gly Lys Leu Glu Gly Lys Asn Arg
                195                 200                 205

Phe Leu Phe Lys Asn Gln Leu Thr Glu Tyr Phe Ser Lys Leu Met Arg
210                 215                 220

Arg Asp Ile Leu
225

<210> SEQ ID NO 471
<211> LENGTH: 154
<212> TYPE: PRT
<213> ORGANISM: Homo sapiens
<220> FEATURE:
<221> NAME/KEY: unsure
<222> LOCATION: (148)
<223> OTHER INFORMATION: Xaa = Any Amino Acid

<400> SEQUENCE: 471

Met Arg Leu His Pro Trp Arg Lys Glu His Leu Thr Gln Leu Lys Ala
                  5                  10                  15

Trp Trp Lys Lys His Leu Met Arg Leu His Pro Trp Lys Glu His
             20                  25                  30

Leu Thr Arg Leu Lys Ala Trp Trp Lys Lys His Leu Met Arg Leu His
             35                  40                  45

Pro Trp Trp Arg Glu His Leu Thr Lys Phe Asn Val Trp Arg Lys Arg
 50                  55                  60

His Leu Glu Ser Ser Asn Ser Gln Gln Lys His Leu Gly Lys Leu
 65                  70                  75                  80

Arg Val Leu Gln Lys His Leu Arg Asn Leu Arg Gly Gln Gln Lys
                 85                  90                  95

Glu Asp Leu Gly Arg Ser His Arg Lys Met Thr Gln Leu Arg
            100                 105                 110

Gln Lys Lys Lys Lys Lys Lys Lys Lys Lys Lys Lys Lys
            115                 120                 125

Lys Lys Lys Lys Lys Lys Lys Lys Lys Lys Lys Lys
130                 135                 140

Lys Lys Lys Xaa Lys Lys Lys Lys Lys Lys
145                 150
```

-continued

```
<210> SEQ ID NO 472
<211> LENGTH: 466
<212> TYPE: PRT
<213> ORGANISM: Homo sapiens
<220> FEATURE:
<221> NAME/KEY: unsure
<222> LOCATION: (329)
<223> OTHER INFORMATION: Xaa = Any Amino Acid

<400> SEQUENCE: 472

Met Ser Pro Ala Lys Glu Thr Ser Glu Lys Phe Thr Trp Ala Ala Lys
                 5                  10                  15

Gly Arg Pro Arg Lys Ile Ala Trp Glu Lys Glu Thr Pro Val Lys
             20                  25                  30

Thr Gly Cys Val Ala Arg Val Thr Ser Asn Lys Thr Lys Val Leu Glu
             35                  40                  45

Lys Gly Arg Ser Lys Met Ile Ala Cys Pro Thr Lys Glu Ser Ser Thr
     50                  55                  60

Lys Ala Ser Ala Asn Asp Gln Arg Phe Pro Ser Glu Ser Lys Gln Glu
 65                  70                  75                  80

Glu Asp Glu Glu Tyr Ser Cys Asp Ser Arg Ser Leu Phe Glu Ser Ser
                 85                  90                  95

Ala Lys Ile Gln Val Cys Ile Pro Glu Ser Ile Tyr Gln Lys Val Met
            100                 105                 110

Glu Ile Asn Arg Glu Val Glu Pro Pro Lys Pro Ser Ala Phe
        115                 120                 125

Lys Pro Ala Ile Glu Met Gln Asn Ser Val Pro Asn Lys Ala Phe Glu
    130                 135                 140

Leu Lys Asn Glu Gln Thr Leu Arg Ala Asp Pro Met Phe Pro Pro Glu
145                 150                 155                 160

Ser Lys Gln Lys Asp Tyr Glu Glu Asn Ser Trp Asp Ser Glu Ser Leu
                165                 170                 175

Cys Glu Thr Val Ser Gln Lys Asp Val Cys Leu Pro Lys Ala Thr His
            180                 185                 190

Gln Lys Glu Ile Asp Lys Ile Asn Gly Lys Leu Glu Glu Ser Pro Asn
        195                 200                 205

Lys Asp Gly Leu Leu Lys Ala Thr Cys Gly Met Lys Val Ser Ile Pro
    210                 215                 220

Thr Lys Ala Leu Glu Leu Lys Asp Met Gln Thr Phe Lys Ala Glu Pro
225                 230                 235                 240

Pro Gly Lys Pro Ser Ala Phe Glu Pro Ala Thr Glu Met Gln Lys Ser
                245                 250                 255

Val Pro Asn Lys Ala Leu Glu Leu Lys Asn Glu Gln Thr Leu Arg Ala
            260                 265                 270

Asp Glu Ile Leu Pro Ser Glu Ser Lys Gln Lys Asp Tyr Glu Glu Asn
        275                 280                 285

Ser Trp Asp Thr Glu Ser Leu Cys Glu Thr Val Ser Gln Lys Asp Val
    290                 295                 300

Cys Leu Pro Lys Ala Ala His Gln Lys Glu Ile Asp Lys Ile Asn Gly
305                 310                 315                 320

Lys Leu Glu Gly Ser Pro Gly Lys Xaa Gly Leu Leu Lys Ala Asn Cys
                325                 330                 335

Gly Met Lys Val Ser Ile Pro Thr Lys Ala Leu Glu Leu Met Asp Met
            340                 345                 350

Gln Thr Phe Lys Ala Glu Pro Pro Glu Lys Pro Ser Ala Phe Glu Pro
```

-continued

```
            355                 360                 365
Ala Ile Glu Met Gln Lys Ser Val Pro Asn Lys Ala Leu Glu Leu Lys
            370                 375                 380

Asn Glu Gln Thr Leu Arg Ala Asp Glu Ile Leu Pro Ser Glu Ser Lys
385                 390                 395                 400

Gln Lys Asp Tyr Glu Glu Ser Ser Trp Asp Ser Glu Ser Leu Cys Glu
                405                 410                 415

Thr Val Ser Gln Lys Asp Val Cys Leu Pro Lys Ala Ala His Gln Lys
            420                 425                 430

Glu Ile Asp Lys Ile Asn Gly Lys Leu Glu Gly Lys Asn Arg Phe Leu
            435                 440                 445

Phe Lys Asn His Leu Thr Lys Tyr Phe Ser Lys Leu Met Arg Lys Asp
    450                 455                 460

Ile Leu
465

<210> SEQ ID NO 473
<211> LENGTH: 445
<212> TYPE: PRT
<213> ORGANISM: Homo sapiens

<400> SEQUENCE: 473

Lys Glu Ile Asp Lys Ile Asn Gly Lys Leu Glu Gly Ser Pro Val Lys
                5                   10                  15

Asp Gly Leu Leu Lys Ala Asn Cys Gly Met Lys Val Ser Ile Pro Thr
            20                  25                  30

Lys Ala Leu Glu Leu Met Asp Met Gln Thr Phe Lys Ala Glu Pro Pro
        35                  40                  45

Glu Lys Pro Ser Ala Phe Glu Pro Ala Ile Glu Met Gln Lys Ser Val
    50                  55                  60

Pro Asn Lys Ala Leu Glu Leu Lys Asn Glu Gln Thr Leu Arg Ala Asp
65                  70                  75                  80

Glu Ile Leu Pro Ser Glu Ser Gln Lys Asp Tyr Glu Glu Ser Ser
                85                  90                  95

Trp Asp Ser Glu Ser Leu Cys Glu Thr Val Ser Gln Lys Asp Val Cys
            100                 105                 110

Leu Pro Lys Ala Ala His Gln Lys Glu Ile Asp Lys Ile Asn Gly Lys
        115                 120                 125

Leu Glu Glu Ser Pro Asp Asn Asp Gly Phe Leu Lys Ala Pro Cys Arg
    130                 135                 140

Met Lys Val Ser Ile Pro Thr Lys Ala Leu Glu Leu Met Asp Met Gln
145                 150                 155                 160

Thr Phe Lys Ala Glu Pro Pro Glu Lys Pro Ser Ala Phe Glu Pro Ala
                165                 170                 175

Ile Glu Met Gln Lys Ser Val Pro Asn Lys Ala Leu Glu Leu Lys Asn
            180                 185                 190

Glu Gln Thr Leu Arg Ala Asp Gln Met Phe Pro Ser Glu Ser Lys Gln
        195                 200                 205

Lys Lys Val Glu Glu Asn Ser Trp Asp Ser Glu Ser Leu Arg Glu Thr
    210                 215                 220

Val Ser Gln Lys Asp Val Cys Val Pro Lys Ala Thr His Gln Lys Glu
225                 230                 235                 240

Met Asp Lys Ile Ser Gly Lys Leu Glu Asp Ser Thr Ser Leu Ser Lys
                245                 250                 255
```

```
Ile Leu Asp Thr Val His Ser Cys Glu Arg Ala Arg Glu Leu Gln Lys
            260                 265                 270

Asp His Cys Glu Gln Arg Thr Gly Lys Met Glu Gln Met Lys Lys
    275                 280                 285

Phe Cys Val Leu Lys Lys Lys Leu Ser Glu Ala Lys Glu Ile Lys Ser
    290                 295                 300

Gln Leu Glu Asn Gln Lys Val Lys Trp Glu Gln Glu Leu Cys Ser Val
305                 310                 315                 320

Arg Leu Thr Leu Asn Gln Glu Glu Lys Arg Arg Asn Ala Asp Ile
            325                 330                 335

Leu Asn Glu Lys Ile Arg Glu Glu Leu Gly Arg Ile Glu Glu Gln His
            340                 345                 350

Arg Lys Glu Leu Glu Val Lys Gln Gln Leu Glu Gln Ala Leu Arg Ile
            355                 360                 365

Gln Asp Ile Glu Leu Lys Ser Val Glu Ser Asn Leu Asn Gln Val Ser
            370                 375                 380

His Thr His Glu Asn Glu Asn Tyr Leu Leu His Glu Asn Cys Met Leu
385                 390                 395                 400

Lys Lys Glu Ile Ala Met Leu Lys Leu Glu Ile Ala Thr Leu Lys His
                    405                 410                 415

Gln Tyr Gln Glu Lys Glu Asn Lys Tyr Phe Glu Asp Ile Lys Ile Leu
            420                 425                 430

Lys Glu Lys Asn Ala Glu Leu Gln Met Thr Pro Arg Ala
            435                 440                 445

<210> SEQ ID NO 474
<211> LENGTH: 3865
<212> TYPE: DNA
<213> ORGANISM: Homo sapien
<220> FEATURE:
<221> NAME/KEY: misc_feature
<222> LOCATION: (2448)...(2631)
<223> OTHER INFORMATION: 184 bp insert of B726P splice form

<400> SEQUENCE: 474
tccgagctga ttacagacac caaggaagat gctgtaaaga gtcagcagcc acagccctgg      60
ctagctggcc ctgtgggcat ttattagtaa agttttaatg acaaaagctt tgagtcaaca     120
cacccgtggg taattaacct ggtcatcccc accctggaga gccatcctgc ccatgggtga     180
tcaaagaagg aacatctgca ggaacacctg atgaggctgc acccttggcg aaagaacac      240 ctgacacagc tgaaagcttg gtggaaaaaa cacctgatga ggctgcaccc ttggtggaaa     300
gaacacctga cacggctgaa agcttggtgg aaaaaacacc tgatgaggct gcatccttgg     360
tggagggaac atctgacaaa attcaatgtt tggagaaagc gacatctgga agttcgaac      420 agtcagcaga agaaacacct agggaaatta cgagtcctgc aaaagaaaca tctgagaaat     480
ttacgtggcc agcaaaagga agacctagga agatcgcatg ggagaaaaaa gaagacacac     540
ctagggaaat tatgagtccc gcaaaagaaa catctgagaa atttacgtgg cagcaaaag      600 gaagacctag gaagatcgca tgggagaaaa aagaaacacc tgtaaagact ggatgcgtgg     660
caagagtaac atctaataaa actaaagttt tggaaaaagg aagatctaag atgattgcat     720
gtcctacaaa agaatcatct acaaaagcaa gtgccaatga tcagaggttc ccatcagaat     780
ccaaacaaga ggaagatgaa gaatattctt gtgattctcg gagtctcttt gagagttctg     840
caaagattca agtgtgtata cctgagtcta tatcaaaa agtaatggag ataaatagag     900
aagtagaaga gcctcctaag aagccatctg ccttcaagcc tgccattgaa atgcaaaact     960
```

-continued

```
ctgttccaaa taaagccttt gaattgaaga atgaacaaac attgagagca gatccgatgt    1020
tcccaccaga atccaaacaa aaggactatg aagaaaattc ttgggattct gagagtctct    1080 tgagactgt ttcacagaag gatgtgtgtt tacccaaggc tacacatcaa aaagaaatag    1140
ataaaataaa tggaaaatta gaagagtctc ctaataaaga tggtcttctg aaggctacct    1200
gcggaatgaa agtttctatt ccaactaaag ccttagaatt gaaggacatg caaactttca    1260
aagcagagcc tccggggaag ccatctgcct tcgagcctgc cactgaaatg caaaagtctg    1320
tcccaaataa agccttggaa ttgaaaaatg aacaaacatt gagagcagat gagatactcc    1380
catcagaatc caaacaaaag gactatgaag aaagttcttg ggattctgag agtctctgtg    1440
agactgtttc acagaaggat gtgtgtttac ccaaggctrc rcatcaaaaa gaaatagata    1500
aaataaatgg aaaattagaa gggtctcctg ttaaagatgg tcttctgaag gctaactgcg    1560
gaatgaaagt ttctattcca actaaagcct tagaattgat ggacatgcaa actttcaaag    1620
cagagcctcc cgagaagcca tctgccttcg agcctgccat tgaaatgcaa aagtctgttc    1680
caaataaagc cttggaattg aagaatgaac aaacattgag agcagatgag atactcccat    1740
cagaatccaa acaaaaggac tatgaagaaa gttcttggga ttctgagagt ctctgtgaga    1800
ctgtttcaca gaaggatgtg tgtttaccca aggctrcrca tcaaaaagaa atagataaaa    1860
taaatggaaa attagaagag tctcctgata tgatggtttt tctgaaggct ccctgcagaa    1920
tgaaagtttc tattccaact aaagccttag aattgatgga catgcaaact ttcaaagcag    1980
agcctcccga gaagccatct gccttcgagc tgccattga aatgcaaaag tctgttccaa    2040
ataaagccct tggaattgaag aatgaacaaa cattgagagc agatcagatg ttcccttcag    2100
aatcaaaaca aaagaasgtt gaagaaaatt cttgggattc tgagagtctc cgtgagactg    2160
tttcacagaa ggatgtgtgt gtacccaagg ctacacatca aaaagaaatg gataaaataa    2220
gtggaaaatt agaagattca actagcctat caaaaatctt ggatacagtt cattcttgtg    2280
aaagagcaag ggaacttcaa aaagatcact gtgaacaacg tacaggaaaa atggaacaaa    2340
tgaaaaagaa gttttgtgta ctgaaaaaga aactgtcaga agcaaaagaa ataaaatcac    2400
agttagaaga ccaaaaagtt aaatgggaac aagagctctg cagtgtgaga ttgactttaa    2460
accaagaaga agagaagaga agaaatgccg atatattaaa tgaaaaaatt agggaagaat    2520
taggaagaat cgaagagcag cataggaaag agttagaagt gaaacaacaa cttgaacagg    2580
ctctcagaat acaagatata gaattgaaga gtgtagaaag taatttgaat caggtttctc    2640
acactcatga aaatgaaaat tatctcttac atgaaaattg catgttgaaa aaggaaattg    2700
ccatgctaaa actggaaata gccacactga acaccaata ccaggaaaag gaaaataaat    2760
actttgagga cattaagatt ttaaaagaaa agaatgctga acttcagatg accctaaaac    2820
tgaaagagga atcattaact aaaagggcat ctcaatatag tgggcagctt aaagttctga    2880
tagctgagaa cacaatgctc acttctaaat tgaaggaaaa acaagacaaa gaaatactag    2940
aggcagaaat tgaatcacac catcctagac tggcttctgc tgtacaagac catgatcaaa    3000
ttgtgacatc aagaaaaagt caagaacctg cttttccacat tgcaggagat gcttgtttgc    3060
aaagaaaaat gaatgttgat gtgagtagta cgatatataa caatgaggtg ctccatcaac    3120
cactttctga agctcaaagg aaatccaaaa gcctaaaaat taatctcaat tatgcmggag    3180
atgctctaag agaaaataca ttggtttcag aacatgcaca aagagaccaa cgtgaaacac    3240
agtgtcaaat gaaggaagct gaacacatgt atcaaaacga acaagataat gtgaacaaac    3300
```

-continued

```
acactgaaca gcaggagtct ctagatcaga aattatttca actacaaagc aaaaatatgt    3360
ggcttcaaca gcaattagtt catgcacata agaaagctga caacaaaagc aagataacaa    3420
ttgatattca ttttcttgag aggaaaatgc aacatcatct cctaaaagag aaaaatgagg    3480
agatatttaa ttacaataac catttaaaaa accgtatata tcaatatgaa aaagagaaag    3540
cagaaacaga aaactcatga gagacaagca gtaagaaact tcttttggag aaacaacaga    3600
ccagatcttt actcacaact catgctagga ggccagtcct agcatcacct tatgttgaaa    3660
atcttaccaa tagtctgtgt caacagaata cttattttag aagaaaaatt catgatttct    3720
tcctgaagcc tacagacata aaataacagt gtgaagaatt acttgttcac gaattgcata    3780
aagctgcaca ggattcccat ctaccctgat gatgcagcag acatcattca atccaaccag    3840
aatctcgctc tgtcactcag gctgg                                          3865
```

<210> SEQ ID NO 475
<211> LENGTH: 1002
<212> TYPE: PRT
<213> ORGANISM: Homo sapien
<220> FEATURE:
<221> NAME/KEY: VARIANT
<222> LOCATION: (1)...(1002)
<223> OTHER INFORMATION: Xaa = Any Amino Acid

<400> SEQUENCE: 475

```
Met Ser Pro Ala Lys Glu Thr Ser Glu Lys Phe Thr Trp Ala Ala Lys
  1               5                  10                  15

Gly Arg Pro Arg Lys Ile Ala Trp Glu Lys Glu Thr Pro Val Lys
                 20                  25                  30

Thr Gly Cys Val Ala Arg Val Thr Ser Asn Lys Thr Lys Val Leu Glu
             35                  40                  45

Lys Gly Arg Ser Lys Met Ile Ala Cys Pro Thr Lys Glu Ser Ser Thr
         50                  55                  60

Lys Ala Ser Ala Asn Asp Gln Arg Phe Pro Ser Glu Ser Lys Gln Glu
 65                  70                  75                  80

Glu Asp Glu Glu Tyr Ser Cys Asp Ser Arg Ser Leu Phe Glu Ser Ser
                 85                  90                  95

Ala Lys Ile Gln Val Cys Ile Pro Glu Ser Ile Tyr Gln Lys Val Met
            100                 105                 110

Glu Ile Asn Arg Glu Val Glu Pro Pro Lys Lys Pro Ser Ala Phe
        115                 120                 125

Lys Pro Ala Ile Glu Met Gln Asn Ser Val Pro Asn Lys Ala Phe Glu
130                 135                 140

Leu Lys Asn Glu Gln Thr Leu Arg Ala Asp Pro Met Phe Pro Pro Glu
145                 150                 155                 160

Ser Lys Gln Lys Asp Tyr Glu Glu Asn Ser Trp Asp Ser Glu Ser Leu
                165                 170                 175

Cys Glu Thr Val Ser Gln Lys Asp Val Cys Leu Pro Lys Ala Thr His
            180                 185                 190

Gln Lys Glu Ile Asp Lys Ile Asn Gly Lys Leu Glu Glu Ser Pro Asn
        195                 200                 205

Lys Asp Gly Leu Leu Lys Ala Thr Cys Gly Met Lys Val Ser Ile Pro
    210                 215                 220

Thr Lys Ala Leu Glu Leu Lys Asp Met Gln Thr Phe Lys Ala Glu Pro
225                 230                 235                 240

Pro Gly Lys Pro Ser Ala Phe Glu Pro Ala Thr Glu Met Gln Lys Ser
                245                 250                 255
```

-continued

```
Val Pro Asn Lys Ala Leu Glu Leu Lys Asn Glu Gln Thr Leu Arg Ala
            260                 265                 270

Asp Glu Ile Leu Pro Ser Glu Ser Lys Gln Lys Asp Tyr Glu Glu Ser
        275                 280                 285

Ser Trp Asp Ser Glu Ser Leu Cys Glu Thr Val Ser Gln Lys Asp Val
    290                 295                 300

Cys Leu Pro Lys Ala Xaa His Gln Lys Glu Ile Asp Lys Ile Asn Gly
305                 310                 315                 320

Lys Leu Glu Gly Ser Pro Val Lys Asp Gly Leu Leu Lys Ala Asn Cys
                325                 330                 335

Gly Met Lys Val Ser Ile Pro Thr Lys Ala Leu Glu Leu Met Asp Met
            340                 345                 350

Gln Thr Phe Lys Ala Glu Pro Glu Lys Pro Ser Ala Phe Glu Pro
        355                 360                 365

Ala Ile Glu Met Gln Lys Ser Val Pro Asn Lys Ala Leu Glu Leu Lys
        370                 375                 380

Asn Glu Gln Thr Leu Arg Ala Asp Glu Ile Leu Pro Ser Glu Ser Lys
385                 390                 395                 400

Gln Lys Asp Tyr Glu Glu Ser Ser Trp Asp Ser Glu Ser Leu Cys Glu
                405                 410                 415

Thr Val Ser Gln Lys Asp Val Cys Leu Pro Lys Ala Xaa His Gln Lys
            420                 425                 430

Glu Ile Asp Lys Ile Asn Gly Lys Leu Glu Glu Ser Pro Asp Asn Asp
        435                 440                 445

Gly Phe Leu Lys Ala Pro Cys Arg Met Lys Val Ser Ile Pro Thr Lys
450                 455                 460

Ala Leu Glu Leu Met Asp Met Gln Thr Phe Lys Ala Glu Pro Pro Glu
465                 470                 475                 480

Lys Pro Ser Ala Phe Glu Pro Ala Ile Glu Met Gln Lys Ser Val Pro
                485                 490                 495

Asn Lys Ala Leu Glu Leu Lys Asn Glu Gln Thr Leu Arg Ala Asp Gln
            500                 505                 510

Met Phe Pro Ser Glu Ser Lys Gln Lys Xaa Val Glu Glu Asn Ser Trp
        515                 520                 525

Asp Ser Glu Ser Leu Arg Glu Thr Val Ser Gln Lys Asp Val Cys Val
    530                 535                 540

Pro Lys Ala Thr His Gln Lys Glu Met Asp Lys Ile Ser Gly Lys Leu
545                 550                 555                 560

Glu Asp Ser Thr Ser Leu Ser Lys Ile Leu Asp Thr Val His Ser Cys
                565                 570                 575

Glu Arg Ala Arg Glu Leu Gln Lys Asp His Cys Glu Gln Arg Thr Gly
            580                 585                 590

Lys Met Glu Gln Met Lys Lys Phe Cys Val Leu Lys Lys Lys Leu
        595                 600                 605

Ser Glu Ala Lys Glu Ile Lys Ser Gln Leu Glu Asn Gln Lys Val Lys
        610                 615                 620

Trp Glu Gln Glu Leu Cys Ser Val Arg Leu Thr Leu Asn Gln Glu Glu
625                 630                 635                 640

Glu Lys Arg Arg Asn Ala Asp Ile Leu Asn Glu Lys Ile Arg Glu Glu
                645                 650                 655

Leu Gly Arg Ile Glu Glu Gln His Arg Lys Glu Leu Glu Val Lys Gln
            660                 665                 670
```

```
Gln Leu Glu Gln Ala Leu Arg Ile Gln Asp Ile Glu Leu Lys Ser Val
            675                 680                 685

Glu Ser Asn Leu Asn Gln Val Ser His Thr His Glu Asn Glu Asn Tyr
        690                 695                 700

Leu Leu His Glu Asn Cys Met Leu Lys Lys Glu Ile Ala Met Leu Lys
705                 710                 715                 720

Leu Glu Ile Ala Thr Leu Lys His Gln Tyr Gln Glu Lys Glu Asn Lys
                725                 730                 735

Tyr Phe Glu Asp Ile Lys Ile Leu Lys Glu Lys Asn Ala Glu Leu Gln
                740                 745                 750

Met Thr Leu Lys Leu Lys Glu Glu Ser Leu Thr Lys Arg Ala Ser Gln
            755                 760                 765

Tyr Ser Gly Gln Leu Lys Val Leu Ile Ala Glu Asn Thr Met Leu Thr
        770                 775                 780

Ser Lys Leu Lys Glu Lys Gln Asp Lys Glu Ile Leu Glu Ala Glu Ile
785                 790                 795                 800

Glu Ser His His Pro Arg Leu Ala Ser Ala Val Gln Asp His Asp Gln
                805                 810                 815

Ile Val Thr Ser Arg Lys Ser Gln Glu Pro Ala Phe His Ile Ala Gly
            820                 825                 830

Asp Ala Cys Leu Gln Arg Lys Met Asn Val Asp Val Ser Ser Thr Ile
        835                 840                 845

Tyr Asn Asn Glu Val Leu His Gln Pro Leu Ser Glu Ala Gln Arg Lys
    850                 855                 860

Ser Lys Ser Leu Lys Ile Asn Leu Asn Tyr Ala Gly Asp Ala Leu Arg
865                 870                 875                 880

Glu Asn Thr Leu Val Ser Glu His Ala Gln Arg Asp Gln Arg Glu Thr
                885                 890                 895

Gln Cys Gln Met Lys Glu Ala Glu His Met Tyr Gln Asn Glu Gln Asp
            900                 905                 910

Asn Val Asn Lys His Thr Glu Gln Gln Glu Ser Leu Asp Gln Lys Leu
        915                 920                 925

Phe Gln Leu Gln Ser Lys Asn Met Trp Leu Gln Gln Gln Leu Val His
    930                 935                 940

Ala His Lys Lys Ala Asp Asn Lys Ser Lys Ile Thr Ile Asp Ile His
945                 950                 955                 960

Phe Leu Glu Arg Lys Met Gln His His Leu Leu Lys Glu Lys Asn Glu
                965                 970                 975

Glu Ile Phe Asn Tyr Asn Asn His Leu Lys Asn Arg Ile Tyr Gln Tyr
            980                 985                 990

Glu Lys Glu Lys Ala Glu Thr Glu Asn Ser
        995                 1000

<210> SEQ ID NO 476
<211> LENGTH: 356
<212> TYPE: DNA
<213> ORGANISM: Homo sapien

<400> SEQUENCE: 476
aggtctgccg gaaatgttag gcaccccaac tcaagtccca ggccccaggc atctttcctg    60
ccctgccttg cttggcccat ccagtccagg cgcctggagc aagtgctcag ctacttctcc   120
tgcactttga agacccctc ccactcctgg cctcacattt ctctgtgtga tcccccactt    180
ctgggctctg ccaccccaca gtgggaaagg ccaccctaga aagaagtccg ctggcaccca   240
```

```
taggaagggg cctcaggagc aggaagggcc aggaccagaa ccttgcccac ggcaactgcc    300
ttcctgcctc tcccttcct cctctgctct tgatctgtgt ttcaataaat taatgt        356

<210> SEQ ID NO 477
<211> LENGTH: 1876
<212> TYPE: DNA
<213> ORGANISM: Homo sapien

<400> SEQUENCE: 477
atgacctgcg gatcaggatt tggtgggcgc gccttcagct gcatctcggc ctgcgggccg    60
cgccccggcc gctgctgcat caccgccgcc ccctaccgtg gcatctcctg ctaccgcggc   120
ctcaccgggg gcttcggcag ccacagcgtg tgcggaggct tcgggccgg ctcctgcgga    180 cgcagcttcg gctaccgctc cggggggcgtg tgcgggccca gtcccccatg catcaccacc   240
gtgtcggtca acgagagcct cctcacgccc ctcaacctgg agatcgaccc caacgcgcag   300
tgcgtgaagc aggaggagaa ggagcagatc aagtccctca acagcaggtt cgcggccttc   360
atcgacaagg tgcgcttcct ggagcagcag aacaaactgc tggagacaaa gctgcagttc   420
taccagaacc gcgagtgttg ccagagcaac ctggagcccc tgtttgaggg ctacatcgag   480
actctgcggc gggaggccga gtgcgtggag gccgacagcg ggaggctggc ctcagagctt   540
aaccacgtgc aggaggtgct ggagggctac aagaagaagt atgaggagga ggtttctctg   600
agagcaacag ctgagaacga gtttgtggct ctgaagaagg atgtggactg cgcctacctc   660
cgcaagtcag acctggaggc caacgtggag gccctgatcc aggagatcga cttcctgagg   720
cggctgtatg aggaggagat ccgcattctc cagtcgcaca tctcagacac ctccgtggtt   780
gtcaagctgg acaacagccg ggacctgaac atggactgca tcattgccga gattaaggca   840
cagtatgacg acattgtcac ccgcagccgg gccgaggccg agtcctggta ccgcagcaag   900
tgtgaggaga tgaaggccac ggtgatcagg cacggggaga ccctgcgccg caccaaggag   960
gagatcaatg agctgaaccg catgatccaa aggctgacgg ccgaggtgga aatgccaag   1020 tgccagaact ccaagctgga ggccgcggtg gctcagtctg agcagcaggg tgaggcagcc   1080
ctcagtgatg cccgctgcaa gctggccgag ctggaggcg ccctgcagaa ggccaagcag   1140
gacatggcct gcctgatcag ggagtaccag gaggtgatga actccaagct gggcctggac   1200
atcgagatcg ccacctacag gcgcctgctg gagggcgagg agcagaggct atgtgaaggc   1260
attggggctg tgaatgtctg tgtcagcagc tccggggcg gggtcgtgtg cggggacctc   1320
tgcgtgtcag gctcccggcc agtgactggc agtgtctgca gcgctccgtg caacgggaac   1380
gtggcggtga gcaccggcct gtgtgcgccc tgcggccaat tgaacaccac ctgcggaggg   1440
ggttcctgcg gcgtgggctc ctgtggtatc agctccctgg gtgtggggtc ttgcggcagc   1500
agctgccgga atgttaggc accccaactc aagtcccagg ccccaggcat ctttcctgcc    1560
ctgccttgct tggcccatcc agtccaggcg cctggagcaa gtgctcagct acttctcctg   1620
cactttgaaa gaccctccc actcctggcc tcacatttct ctgtgtgatc ccccacttct   1680
gggctctgcc accccacagt gggaaaggcc acctagaaa gaagtccgct ggcacccata   1740
ggaaggggcc tcaggagcag gaagggccag gaccagaacc ttgcccacgg caactgcctt   1800
cctgcctctc cccttcctcc tctgctcttg atctgtgttt caataaatta atgtagccaa   1860
aaaaaaaaaa aaaaaa                                                    1876

<210> SEQ ID NO 478
<211> LENGTH: 505
```

```
<212> TYPE: PRT
<213> ORGANISM: Homo sapien

<400> SEQUENCE: 478
```

| | | | | | | | | | | | | | | |
|---|---|---|---|---|---|---|---|---|---|---|---|---|---|---|
| Met | Thr | Cys | Gly | Ser | Gly | Phe | Gly | Arg | Ala | Phe | Ser | Cys | Ile | Ser |
| 1 | | | | 5 | | | | | 10 | | | | | 15 |
| Ala | Cys | Gly | Pro | Arg | Pro | Gly | Arg | Cys | Cys | Ile | Thr | Ala | Ala | Pro | Tyr |
| | | | 20 | | | | | 25 | | | | | 30 | | |
| Arg | Gly | Ile | Ser | Cys | Tyr | Arg | Gly | Leu | Thr | Gly | Gly | Phe | Gly | Ser | His |
| | | | 35 | | | | | 40 | | | | | 45 | | |
| Ser | Val | Cys | Gly | Gly | Phe | Arg | Ala | Gly | Ser | Cys | Gly | Arg | Ser | Phe | Gly |
| | 50 | | | | | 55 | | | | | 60 | | | | |
| Tyr | Arg | Ser | Gly | Gly | Val | Cys | Gly | Pro | Ser | Pro | Pro | Cys | Ile | Thr | Thr |
| 65 | | | | | 70 | | | | | 75 | | | | | 80 |
| Val | Ser | Val | Asn | Glu | Ser | Leu | Leu | Thr | Pro | Leu | Asn | Leu | Glu | Ile | Asp |
| | | | | 85 | | | | | 90 | | | | | 95 | |
| Pro | Asn | Ala | Gln | Cys | Val | Lys | Gln | Glu | Glu | Lys | Glu | Gln | Ile | Lys | Ser |
| | | | 100 | | | | | 105 | | | | | 110 | | |
| Leu | Asn | Ser | Arg | Phe | Ala | Ala | Phe | Ile | Asp | Lys | Val | Arg | Phe | Leu | Glu |
| | | 115 | | | | | 120 | | | | | 125 | | | |
| Gln | Gln | Asn | Lys | Leu | Leu | Glu | Thr | Lys | Leu | Gln | Phe | Tyr | Gln | Asn | Arg |
| | 130 | | | | | 135 | | | | | 140 | | | | |
| Glu | Cys | Cys | Gln | Ser | Asn | Leu | Glu | Pro | Leu | Phe | Glu | Gly | Tyr | Ile | Glu |
| 145 | | | | | 150 | | | | | 155 | | | | | 160 |
| Thr | Leu | Arg | Arg | Glu | Ala | Glu | Cys | Val | Glu | Ala | Asp | Ser | Gly | Arg | Leu |
| | | | 165 | | | | | 170 | | | | | 175 | | |
| Ala | Ser | Glu | Leu | Asn | His | Val | Gln | Glu | Val | Leu | Glu | Gly | Tyr | Lys | Lys |
| | | | | 180 | | | | | 185 | | | | | 190 | |
| Lys | Tyr | Glu | Glu | Glu | Val | Ser | Leu | Arg | Ala | Thr | Ala | Glu | Asn | Glu | Phe |
| | | | 195 | | | | | 200 | | | | | 205 | | |
| Val | Ala | Leu | Lys | Lys | Asp | Val | Asp | Cys | Ala | Tyr | Leu | Arg | Lys | Ser | Asp |
| | 210 | | | | | 215 | | | | | 220 | | | | |
| Leu | Glu | Ala | Asn | Val | Glu | Ala | Leu | Ile | Gln | Glu | Ile | Asp | Phe | Leu | Arg |
| 225 | | | | | 230 | | | | | 235 | | | | | 240 |
| Arg | Leu | Tyr | Glu | Glu | Glu | Ile | Arg | Ile | Leu | Gln | Ser | His | Ile | Ser | Asp |
| | | | | 245 | | | | | 250 | | | | | 255 | |
| Thr | Ser | Val | Val | Lys | Leu | Asp | Asn | Ser | Arg | Asp | Leu | Asn | Met | Asp |
| | | | 260 | | | | | 265 | | | | | 270 | | |
| Cys | Ile | Ile | Ala | Glu | Ile | Lys | Ala | Gln | Tyr | Asp | Asp | Ile | Val | Thr | Arg |
| | | 275 | | | | | 280 | | | | | 285 | | | |
| Ser | Arg | Ala | Glu | Ala | Glu | Ser | Trp | Tyr | Arg | Ser | Lys | Cys | Glu | Glu | Met |
| | 290 | | | | | 295 | | | | | 300 | | | | |
| Lys | Ala | Thr | Val | Ile | Arg | His | Gly | Glu | Thr | Leu | Arg | Arg | Thr | Lys | Glu |
| 305 | | | | | 310 | | | | | 315 | | | | | 320 |
| Glu | Ile | Asn | Glu | Leu | Asn | Arg | Met | Ile | Gln | Arg | Leu | Thr | Ala | Glu | Val |
| | | | | 325 | | | | | 330 | | | | | 335 | |
| Glu | Asn | Ala | Lys | Cys | Gln | Asn | Ser | Lys | Leu | Glu | Ala | Ala | Val | Ala | Gln |
| | | | 340 | | | | | 345 | | | | | 350 | | |
| Ser | Glu | Gln | Gln | Gly | Glu | Ala | Ala | Leu | Ser | Asp | Ala | Arg | Cys | Lys | Leu |
| | | 355 | | | | | 360 | | | | | 365 | | | |
| Ala | Glu | Leu | Glu | Gly | Ala | Leu | Gln | Lys | Ala | Lys | Gln | Asp | Met | Ala | Cys |
| | 370 | | | | | 375 | | | | | 380 | | | | |
| Leu | Ile | Arg | Glu | Tyr | Gln | Glu | Val | Met | Asn | Ser | Lys | Leu | Gly | Leu | Asp |
| 385 | | | | | 390 | | | | | 395 | | | | | 400 |

```
Ile Glu Ile Ala Thr Tyr Arg Arg Leu Leu Gly Glu Glu Gln Arg
                405                 410                 415

Leu Cys Glu Gly Ile Gly Ala Val Asn Val Cys Val Ser Ser Ser Arg
            420                 425                 430

Gly Gly Val Val Cys Gly Asp Leu Cys Val Ser Gly Ser Arg Pro Val
        435                 440                 445

Thr Gly Ser Val Cys Ser Ala Pro Cys Asn Gly Asn Val Ala Val Ser
    450                 455                 460

Thr Gly Leu Cys Ala Pro Cys Gly Gln Leu Asn Thr Thr Cys Gly Gly
465                 470                 475                 480

Gly Ser Cys Gly Val Gly Ser Cys Gly Ile Ser Ser Leu Gly Val Gly
                485                 490                 495

Ser Cys Gly Ser Ser Cys Arg Lys Cys
                500                 505
```

```
<210> SEQ ID NO 479
<211> LENGTH: 221
<212> TYPE: DNA
<213> ORGANISM: Homo sapiens
<220> FEATURE:
<221> NAME/KEY: misc_feature
<222> LOCATION: (1)...(221)
<223> OTHER INFORMATION: n = A,T,C or G

<400> SEQUENCE: 479
ggtccattcc tttcctcgcg tnggggtttc tctgtgtcag cgagcctcgg tacactgatt      60
tccgatcaaa agaatcatca tctttacctt gacttttcag ggaattactg aactttcttc     120
tcagaagata gggcacagcc attgccttgg cctcacttga agggtctgca tttgggtcct     180
ctggtctctt gccaagtttc ccagccactc gagggagaaa t                         221

<210> SEQ ID NO 480
<211> LENGTH: 36
<212> TYPE: DNA
<213> ORGANISM: Artificial Sequence
<220> FEATURE:
<223> OTHER INFORMATION: PCR primer

<400> SEQUENCE: 480
cggcgaattc accatgggaa caagagctct gcagtg                                36

<210> SEQ ID NO 481
<211> LENGTH: 62
<212> TYPE: DNA
<213> ORGANISM: Artificial Sequence
<220> FEATURE:
<223> OTHER INFORMATION: PCR primer

<400> SEQUENCE: 481
cggcaagctt ttaatggtga tggtgatgat gtataacttc tgtttctgct ttctcttttt      60
ca                                                                    62

<210> SEQ ID NO 482
<211> LENGTH: 972
<212> TYPE: DNA
<213> ORGANISM: Homo sapiens

<400> SEQUENCE: 482
atgggaacaa gagctctgca gtgtgaggtt tctcacactc atgaaaatga aaattatctc      60
ttacatgaaa attgcatgtt gaaaaggaa attgccatgc taaaactgga atagccaca       120
```

```
ctgaaacacc aataccagga aaaggaaaat aaatactttg aggacattaa gattttaaaa    180
gaaaagaatg ctgaacttca gatgacccta aaactgaaag aggaatcatt aactaaaagg    240
gcatctcaat atagtgggca gcttaaagtt ctgatagctg agaacacaat gctcacttct    300
aaattgaagg aaaaacaaga caaagaaata ctagaggcag aaattgaatc acaccatcct    360
agactggctt ctgctgtaca agaccatgat caaattgtga catcaagaaa aagtcaagaa    420
cctgctttcc acattgcagg agatgcttgt ttgcaaagaa aaatgaatgt tgatgtgagt    480
agtacgatat ataacaatga ggtgctccat caaccacttt ctgaagctca aggaaatcc     540 aaaagcctaa aaattaatct caattatgcc ggagatgctc taagagaaaa tacattggtt    600
tcagaacatg cacaaagaga ccaacgtgaa acacagtgtc aaatgaagga agctgaacac    660
atgtatcaaa acgaacaaga taatgtgaac aaacacactg aacagcagga gtctctagat    720
cagaaattat ttcaactaca aagcaaaaat atgtggcttc aacagcaatt agttcatgca    780
cataagaaag ctgacaacaa agcaagata acaattgata ttcattttct tgagaggaaa     840
atgcaacatc atctcctaaa agagaaaaat gaggagatat ttaattacaa taaccattta    900
aaaaaccgta tatatcaata tgaaaaagag aaagcagaaa cagaagttat acatcatcac    960
catcaccatt aa                                                        972

<210> SEQ ID NO 483
<211> LENGTH: 323
<212> TYPE: PRT
<213> ORGANISM: Homo sapiens

<400> SEQUENCE: 483

Met Gly Thr Arg Ala Leu Gln Cys Glu Val Ser His Thr His Glu Asn
                5                  10                  15

Glu Asn Tyr Leu Leu His Glu Asn Cys Met Leu Lys Lys Glu Ile Ala
            20                  25                  30

Met Leu Lys Leu Glu Ile Ala Thr Leu Lys His Gln Tyr Gln Glu Lys
        35                  40                  45

Glu Asn Lys Tyr Phe Glu Asp Ile Lys Ile Leu Lys Glu Lys Asn Ala
    50                  55                  60

Glu Leu Gln Met Thr Leu Lys Leu Lys Glu Glu Ser Leu Thr Lys Arg
65                  70                  75                  80

Ala Ser Gln Tyr Ser Gly Gln Leu Lys Val Leu Ile Ala Glu Asn Thr
                85                  90                  95

Met Leu Thr Ser Lys Leu Lys Glu Lys Gln Asp Lys Glu Ile Leu Glu
            100                 105                 110

Ala Glu Ile Glu Ser His His Pro Arg Leu Ala Ser Ala Val Gln Asp
        115                 120                 125

His Asp Gln Ile Val Thr Ser Arg Lys Ser Gln Glu Pro Ala Phe His
    130                 135                 140

Ile Ala Gly Asp Ala Cys Leu Gln Arg Lys Met Asn Val Asp Val Ser
145                 150                 155                 160

Ser Thr Ile Tyr Asn Asn Glu Val Leu His Gln Pro Leu Ser Glu Ala
                165                 170                 175

Gln Arg Lys Ser Lys Ser Leu Lys Ile Asn Leu Asn Tyr Ala Gly Asp
            180                 185                 190

Ala Leu Arg Glu Asn Thr Leu Val Ser Glu His Ala Gln Arg Asp Gln
        195                 200                 205

Arg Glu Thr Gln Cys Gln Met Lys Glu Ala Glu His Met Tyr Gln Asn
```

```
                210                 215                 220
Glu Gln Asp Asn Val Asn Lys His Thr Glu Gln Gln Glu Ser Leu Asp
225                 230                 235                 240

Gln Lys Leu Phe Gln Leu Gln Ser Lys Asn Met Trp Leu Gln Gln Gln
                245                 250                 255

Leu Val His Ala His Lys Lys Ala Asp Asn Lys Ser Lys Ile Thr Ile
                260                 265                 270

Asp Ile His Phe Leu Glu Arg Lys Met Gln His His Leu Leu Lys Glu
            275                 280                 285

Lys Asn Glu Glu Ile Phe Asn Tyr Asn Asn His Leu Lys Asn Arg Ile
            290                 295                 300

Tyr Gln Tyr Glu Lys Glu Lys Ala Glu Thr Glu Val Ile His His His
305                 310                 315                 320

His His His

<210> SEQ ID NO 484
<211> LENGTH: 1518
<212> TYPE: DNA
<213> ORGANISM: Homo sapiens

<400> SEQUENCE: 484
atgacctgcg gatcaggatt tggtgggcgc gccttccgct gcatctcggc ctgcgggccg      60
cggcccggcc gctgctgcat caccgccgcc ccctaccgtg gcatctcctg ctaccgcggc     120
ctcaccgggg gcttcggcag ccacagcgtg tgcggaggct tcggggccgg ctcctgcgga     180
cgcagcttcg gctaccgctc cggggggcgtg tgcgggccca gtcccccatg catcaccacc     240
gtgtcggtca acgagagcct cctcacgccc tcaacctggg agatcgaccc caacgcgcag     300
tgcgtgaagc aggaggagaa ggagcagatc aagtccctca acagcaggtt cgcggccttc     360
atcgacaagg tgcgcttcct ggagcagcag aacaaactgc tggagacaaa gctgcagttc     420
taccagaacc gcgagtgttg ccagagcaac ctggagcccc tgtttgaggg ctacatcgag     480
actctgcggc gggaggccga gtgcgtggag gccgacagcg ggaggctggc ctcagagctt     540
aaccacgtgc aggaggtgct ggagggctac aagaagaagt atgaggagga ggtttctctg     600
agagcaacag ctgagaacga gtttgtggct ctgaagaagt atgtggactg cgcctacctc     660
cgcaagtcag acctggaggc aacgtggag gccctgatcc aggagatcga cttcctgagg     720
cggctgtatg aggaggagat ccgcattctc cagtcgcaca tctcagacac ctccgtggtt     780
gtcaagctgg acaacagccg ggacctgaac atggactgca tcattgccga gattaaggca     840
cagtatgacg acattgtcac ccgcagccgg gccgaggccg agtcctggta ccgcagcaag     900
tgtgaggaga tgaaggccac ggtgatcagg cacggggaga ccctgcgccg caccaaggag     960
gagatcaatg agctgaaccg catgatccaa aggctgacgg ccgaggtgga gaatgccaag    1020
tgccagaact ccaagctgga ggccgcggtg gcccagtctg agcagcaggg tgaggcagcc    1080
ctcagtgatg cccgctgcaa gctggccgag ctggagggcg ccctgcagaa ggccaagcag    1140
gacatggcct gcctgatcag ggagtaccag gaggtgatga actccaagct gggcctggac    1200
atcgagatcg ccacctacag gcgcctgctg gagggcgagg agcagaggct atgtgaaggc    1260 attgggggctg tgaatgtctg tgtcagcagc tcccggggcg gggtcgtgtg cggggacctc    1320
tgcgtgtcag gctcccggcc agtgactgga gtgtctgca gcgctccgtg caacgggaac    1380
gtggcggtga gcaccggcct gtgtcgcgcc tgcggccaat gaacaccac ctgcggaggg     1440 ggttcctgcg cgcgtgggctc ctgtggtatc agctccctgg gtgtggggtc ttgcggcagc    1500
```
agctgccgga aatgttag 1518

<210> SEQ ID NO 485
<211> LENGTH: 505
<212> TYPE: PRT
<213> ORGANISM: Homo sapiens

<400> SEQUENCE: 485

Met Thr Cys Gly Ser Gly Phe Gly Gly Arg Ala Phe Arg Cys Ile Ser
                5                   10                  15

Ala Cys Gly Pro Arg Pro Gly Arg Cys Cys Ile Thr Ala Ala Pro Tyr
                20                  25                  30

Arg Gly Ile Ser Cys Tyr Arg Gly Leu Thr Gly Phe Gly Ser His
            35                  40                  45

Ser Val Cys Gly Gly Phe Arg Ala Gly Ser Cys Gly Arg Ser Phe Gly
        50                  55                  60

Tyr Arg Ser Gly Gly Val Cys Gly Pro Ser Pro Cys Ile Thr Thr
 65                 70                  75                  80

Val Ser Val Asn Glu Ser Leu Leu Thr Pro Leu Asn Leu Glu Ile Asp
                85                  90                  95

Pro Asn Ala Gln Cys Val Lys Gln Glu Lys Glu Gln Ile Lys Ser
                100                 105                 110

Leu Asn Ser Arg Phe Ala Ala Phe Ile Asp Lys Val Arg Phe Leu Glu
            115                 120                 125

Gln Gln Asn Lys Leu Leu Glu Thr Lys Leu Gln Phe Tyr Gln Asn Arg
    130                 135                 140

Glu Cys Cys Gln Ser Asn Leu Glu Pro Leu Phe Glu Gly Tyr Ile Glu
145                 150                 155                 160

Thr Leu Arg Arg Glu Ala Glu Cys Val Glu Ala Asp Ser Gly Arg Leu
                165                 170                 175

Ala Ser Glu Leu Asn His Val Gln Glu Val Leu Glu Gly Tyr Lys Lys
            180                 185                 190

Lys Tyr Glu Glu Glu Val Ser Leu Arg Ala Thr Ala Glu Asn Glu Phe
        195                 200                 205

Val Ala Leu Lys Lys Asp Val Asp Cys Ala Tyr Leu Arg Lys Ser Asp
    210                 215                 220

Leu Glu Ala Asn Val Glu Ala Leu Ile Gln Glu Ile Asp Phe Leu Arg
225                 230                 235                 240

Arg Leu Tyr Glu Glu Glu Ile Arg Ile Leu Gln Ser His Ile Ser Asp
                245                 250                 255

Thr Ser Val Val Val Lys Leu Asp Asn Ser Arg Asp Leu Asn Met Asp
            260                 265                 270

Cys Ile Ile Ala Glu Ile Lys Ala Gln Tyr Asp Asp Ile Val Thr Arg
        275                 280                 285

Ser Arg Ala Glu Ala Glu Ser Trp Tyr Arg Ser Lys Cys Glu Glu Met
    290                 295                 300

Lys Ala Thr Val Ile Arg His Gly Glu Thr Leu Arg Arg Thr Lys Glu
305                 310                 315                 320

Glu Ile Asn Glu Leu Asn Arg Met Ile Gln Arg Leu Thr Ala Glu Val
                325                 330                 335

Glu Asn Ala Lys Cys Gln Asn Ser Lys Leu Glu Ala Ala Val Ala Gln
            340                 345                 350

Ser Glu Gln Gln Gly Glu Ala Ala Leu Ser Asp Ala Arg Cys Lys Leu
        355                 360                 365

Ala Glu Leu Glu Gly Ala Leu Gln Lys Ala Lys Gln Asp Met Ala Cys
        370                 375                 380

Leu Ile Arg Glu Tyr Gln Glu Val Met Asn Ser Lys Leu Gly Leu Asp
385                 390                 395                 400

Ile Glu Ile Ala Thr Tyr Arg Arg Leu Leu Glu Gly Glu Glu Gln Arg
                405                 410                 415

Leu Cys Glu Gly Ile Gly Ala Val Asn Val Cys Val Ser Ser Ser Arg
                420                 425                 430

Gly Gly Val Val Cys Gly Asp Leu Cys Val Ser Gly Ser Arg Pro Val
                435                 440                 445

Thr Gly Ser Val Cys Ser Ala Pro Cys Asn Gly Asn Val Ala Val Ser
        450                 455                 460

Thr Gly Leu Cys Ala Pro Cys Gly Gln Leu Asn Thr Thr Cys Gly Gly
465                 470                 475                 480

Gly Ser Cys Gly Val Gly Ser Cys Gly Ile Ser Ser Leu Gly Val Gly
                485                 490                 495

Ser Cys Gly Ser Ser Cys Arg Lys Cys
                500                 505

<210> SEQ ID NO 486
<211> LENGTH: 827
<212> TYPE: DNA
<213> ORGANISM: Homo sapiens

<400> SEQUENCE: 486
gcattctcca gtcgcacatc tcagacacct ccgtggttgt caagctggac aacagccggg      60
acctgaacat ggactgcatc attgccgaga ttaaggcaca gtatgacgac attgtcaccc     120
gcagccgggc cgaggccgag tcctggtacc gcagcaagtg tgaggagatg aaggccacgg     180
tgatcaggca cggggagacc ctgcgccgca ccaaggagga gatcaatgag ctgaaccgca     240
tgatccaaag gctgacggcc gaggtggaga atgccaagtg ccagaactcc aagctggagg     300
ccgcggtggc ccagtctgag cagcagggtg aggcagccct cagtgatgcc cgctgcaagc     360
tggccgagct ggagggcgcc ctgcagaagg ccaagcagga catggcctgc ctgatcaggg     420
agtaccagga ggtgatgaac tccaagctgg gcctggacat cgagatcgcc acctacaggc     480
gcctgctgga gggcgaggag cagaggctat gtgaaggcat tggggctgtg aatgtctgtg     540
tcagcagctc ccggggcggg gtcgtgtgcg ggacctctg cgtgtcaggc tcccggccag     600
tgactggcag tgtctgcagc gctccgtgca acgggaacgt ggcggtgagc accggcctgt     660
gtgcgccctg cggccaattg aacaccacct gcggaggggg ttcctgcggc gtgggctcct     720
gtggtatcag ctccctgggt gtggggtctt gcggcagcag ctgccggaaa tgttaggcac     780
cccaactcaa gtcccaggcc ccaggcatct ttcctgccct gccttgc                   827

<210> SEQ ID NO 487
<211> LENGTH: 235
<212> TYPE: PRT
<213> ORGANISM: Homo sapiens

<400> SEQUENCE: 487

Met Asp Cys Ile Ile Ala Glu Ile Lys Ala Gln Tyr Asp Asp Ile Val
                5                   10                  15

Thr Arg Ser Arg Ala Glu Ala Glu Ser Trp Tyr Arg Ser Lys Cys Glu
            20                  25                  30

Glu Met Lys Ala Thr Val Ile Arg His Gly Glu Thr Leu Arg Arg Thr

-continued

```
                35                  40                  45
Lys Glu Glu Ile Asn Glu Leu Asn Arg Met Ile Gln Arg Leu Thr Ala
        50                  55                  60
Glu Val Glu Asn Ala Lys Cys Gln Asn Ser Lys Leu Glu Ala Ala Val
 65                  70                  75                  80
Ala Gln Ser Glu Gln Gln Gly Glu Ala Ala Leu Ser Asp Ala Arg Cys
                85                  90                  95
Lys Leu Ala Glu Leu Glu Gly Ala Leu Gln Lys Ala Lys Gln Asp Met
                100                 105                 110
Ala Cys Leu Ile Arg Glu Tyr Gln Glu Val Met Asn Ser Lys Leu Gly
                115                 120                 125
Leu Asp Ile Glu Ile Ala Thr Tyr Arg Arg Leu Leu Glu Gly Glu Glu
                130                 135                 140
Gln Arg Leu Cys Glu Gly Ile Gly Ala Val Asn Val Cys Val Ser Ser
145                 150                 155                 160
Ser Arg Gly Gly Val Val Cys Gly Asp Leu Cys Val Ser Gly Ser Arg
                165                 170                 175
Pro Val Thr Gly Ser Val Cys Ser Ala Pro Cys Asn Gly Asn Val Ala
                180                 185                 190
Val Ser Thr Gly Leu Cys Ala Pro Cys Gly Gln Leu Asn Thr Thr Cys
                195                 200                 205
Gly Gly Gly Ser Cys Gly Val Gly Ser Cys Gly Ile Ser Ser Leu Gly
        210                 215                 220
Val Gly Ser Cys Gly Ser Ser Cys Arg Lys Cys
25                  230                 235

<210> SEQ ID NO 488
<211> LENGTH: 9
<212> TYPE: PRT
<213> ORGANISM: Homo sapiens

<400> SEQUENCE: 488

Ser Leu Thr Lys Arg Ala Ser Gln Tyr
                5

<210> SEQ ID NO 489
<211> LENGTH: 27
<212> TYPE: DNA
<213> ORGANISM: Homo sapiens

<400> SEQUENCE: 489
tcattaacta aaagggcatc tcaatat                                    27
```

COMPOSITIONS AND METHODS FOR THE THERAPY AND DIAGNOSIS OF BREAST CANCER

CROSS-REFERENCE TO RELATED APPLICATIONS

Figure 1:

This application is a continuation-in-part of U.S. patent application Ser. No. 09/590,751, filed Jun. 8, 2000, which is a continuation-in-part of U.S. patent application Ser. No. 09/551,621, filed Apr. 17, 2000, which is a continuation-in-part of U.S. patent application Ser. No. 09/433,826, filed on Nov. 3, 1999, which is a continuation-in-part of U.S. application Ser. No. 09/389,681, filed on Sep. 2, 1999, which is a continuation-in-part of U.S. application Ser. No. 09/339,338, filed on Jun. 23, 1999, which is a continuation-in-part of U.S. application Ser. No. 09/285,480, filed on Apr. 2, 1999, which is a continuation-in-part of U.S. application Ser. No. 09/222,575, filed Dec. 28, 1998.

TECHNICAL FIELD OF THE INVENTION

The present invention relates generally to therapy and diagnosis of cancer, such as breast cancer. The invention is more specifically related to polypeptides comprising at least a portion of a breast tumor protein, and to polynucleotides encoding such polypeptides. Such polypeptides and polynucleotides may be used in compositions for prevention and treatment of breast cancer, and for the diagnosis and monitoring of such cancers.

BACKGROUND OF THE INVENTION

Breast cancer is a significant health problem for women in the United States and throughout the world. Although advances have been made in detection and treatment of the disease, breast cancer remains the second leading cause of cancer-related deaths in women, affecting more than 180,000 women in the United States each year. For women in North America, the life-time odds of getting breast cancer are one in eight.

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. See, e.g., Porter-Jordan and Lippman, *Breast Cancer* 8:73–100 (1994). However, the use of established markers often leads to a result that is difficult to interpret, and the high mortality observed in breast cancer patients indicates that improvements are needed in the treatment, diagnosis and prevention of the disease.

Accordingly, there is a need in the art for improved methods for the treatment and diagnosis of breast cancer. The present invention fulfills these needs and further provides other related advantages.

SUMMARY OF THE INVENTION

Briefly stated, the present invention provides compositions and methods for the diagnosis and therapy of cancer, such as breast cancer. In one aspect, the present invention provides polypeptides comprising at least a portion of a breast tumor protein, or a variant thereof. Certain portions and other variants are immunogenic, such that the ability of the variant to react with antigen-specific antisera is not substantially diminished. Within certain embodiments, the polypeptide comprises a sequence that is encoded by a polynucleotide sequence selected from the group consisting of: (a) sequences recited in SEQ ID NO:1–175, 178, 180, 182–468, 474, 476, 477 479, 484, 486 and 489; (b) variants of a sequence recited in SEQ ID NO:1–175, 178, 180, 182–468, 474, 476, 477, 479, 484, 486 and 489; and (c) complements of a sequence of (a) or (b). In specific embodiments, the polypeptides of the present invention comprise at least a portion of a tumor protein that includes an amino acid sequence selected from the group consisting of sequences recited in SEQ ID NO:176, 179, 181, 469–473, 475, 485, 487 and 488, and variants thereof.

The present invention further provides polynucleotides that encode a polypeptide as described above, or a portion thereof (such as a portion encoding at least 15 amino acid residues of a breast tumor protein), expression vectors comprising such polynucleotides and host cells transformed or transfected with such expression vectors.

Within other aspects, the present invention provides pharmaceutical compositions comprising a polypeptide or polynucleotide as described above and a physiologically acceptable carrier.

Within a related aspect of the present invention, immunogenic compositions, or vaccines for prophylactic or therapeutic use are provided. Such compositions comprise a polypeptide or polynucleotide as described above and an immunostimulant.

The present invention further provides pharmaceutical compositions that comprise: (a) an antibody or antigen-binding fragment thereof that specifically binds to a breast tumor protein; and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Antigen presenting cells include dendritic cells, macrophages, monocytes, fibroblasts and B cells.

Within related aspects, immunogenic compositions, or vaccines, are provided that comprise: (a) an antigen presenting cell that expresses a polypeptide as described above and (b) an immunostimulant.

The present invention further provides, in other aspects, fusion proteins that comprise at least one polypeptide as described above, as well as polynucleotides encoding such fusion proteins.

Within related aspects, pharmaceutical compositions comprising a fusion protein, or a polynucleotide encoding a fusion protein, in combination with a physiologically acceptable carrier are provided.

Compositions are further provided, within other aspects, that comprise a fusion protein, or a polynucleotide encoding a fusion protein, in combination with an immunostimulant.

Within further aspects, the present invention provides methods for inhibiting the development of a cancer in a patient, comprising administering to a patient a composition as recited above. The patient may be afflicted with breast cancer, in which case the methods provide treatment for the disease, or patient considered at risk for such a disease may be treated prophylactically.

The present invention further provides, within other aspects, methods for removing tumor cells from a biological sample, comprising contacting a biological sample with T cells that specifically react with a breast tumor protein, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a breast tumor protein, comprising contacting T cells with one or more of: (i) a polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Isolated T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating $CD4^+$ and/or $CD8^+$ T cells isolated from a patient with one or more of: (i) a polypeptide comprising at least an immunogenic portion of a breast tumor protein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer in a patient, comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody. The cancer may be breast cancer.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a breast tumor protein; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a breast tumor protein; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS AND SEQUENCE IDENTIFIERS

FIG. 1 shows the results of a Northern blot of the clone SYN18C6 (SEQ ID NO:40).

SEQ ID NO:1 is the determined cDNA sequence of JBT2.

SEQ ID NO:2 is the determined cDNA sequence of JBT6.

SEQ ID NO:3 is the determined cDNA sequence of JBT7.

SEQ ID NO:4 is the determined cDNA sequence of JBT10.

SEQ ID NO:5 is the determined cDNA sequence of JBT13.

SEQ ID NO:6 is the determined cDNA sequence of JBT14.

SEQ ID NO:7 is the determined cDNA sequence of JBT15.

SEQ ID NO:8 is the determined cDNA sequence of JBT16.

SEQ ID NO:9 is the determined cDNA sequence of JBT17.

SEQ ID NO:10 is the determined cDNA sequence of JBT22.

SEQ ID NO:11 is the determined cDNA sequence of JBT25.

SEQ ID NO:12 is the determined cDNA sequence of JBT28.

SEQ ID NO:13 is the determined cDNA sequence of JBT32.

SEQ ID NO:14 is the determined cDNA sequence of JBT33.

SEQ ID NO:15 is the determined cDNA sequence of JBT34.

SEQ ID NO:16 is the determined cDNA sequence of JBT36.

SEQ ID NO:17 is the determined cDNA sequence of JBT37.

SEQ ID NO:18 is the determined cDNA sequence of JBT51.

SEQ ID NO:19 is the determined cDNA sequence of JBTT1.

SEQ ID NO:20 is the determined cDNA sequence of JBTT7.

SEQ ID NO:21 is the determined cDNA sequence of JBTT11.

SEQ ID NO:22 is the determined cDNA sequence of JBTT14.

SEQ ID NO:23 is the determined cDNA sequence of JBTT18.

SEQ ID NO:24 is the determined cDNA sequence of JBTT19.

SEQ ID NO:25 is the determined cDNA sequence of JBTT20.

SEQ ID NO:26 is the determined cDNA sequence of JBTT21.

SEQ ID NO:27 is the determined cDNA sequence of JBTT22.

SEQ ID NO:28 is the determined cDNA sequence of JBTT28.

SEQ ID NO:29 is the determined cDNA sequence of JBTT29.

SEQ ID NO:30 is the determined cDNA sequence of JBTT33.

SEQ ID NO:31 is the determined cDNA sequence of JBTT37.

SEQ ID NO:32 is the determined cDNA sequence of JBTT38.

SEQ ID NO:33 is the determined cDNA sequence of JBTT47.

SEQ ID NO:34 is the determined cDNA sequence of JBTT48.

SEQ ID NO:35 is the determined cDNA sequence of JBTT50.

SEQ ID NO:36 is the determined cDNA sequence of JBTT51.

SEQ ID NO:37 is the determined cDNA sequence of JBTT52.

SEQ ID NO:38 is the determined cDNA sequence of JBTT54.

SEQ ID NO:39 is the determined cDNA sequence of SYN17F4.

SEQ ID NO:40 is the determined cDNA sequence of SYN18C6 (also known as B709P).

SEQ ID NO:41 is the determined cDNA sequence of SYN19A2.

SEQ ID NO:42 is the determined cDNA sequence of SYN19C8.

SEQ ID NO:43 is the determined cDNA sequence of SYN20A12.

SEQ ID NO:44 is the determined cDNA sequence of SYN20G6.

SEQ ID NO:45 is the determined cDNA sequence of SYN20G6-2.

SEQ ID NO:46 is the determined cDNA sequence of SYN21B9.

SEQ ID NO:47 is the determined cDNA sequence of SYN21B9-2.

SEQ ID NO:48 is the determined cDNA sequence of SYN21C10.

SEQ ID NO:49 is the determined cDNA sequence of SYN21G10.

SEQ ID NO:50 is the determined cDNA sequence of SYN21G10-2.

SEQ ID NO:51 is the determined cDNA sequence of SYN21G11.

SEQ ID NO:52 is the determined cDNA sequence of SYN21G11-2.

SEQ ID NO:53 is the determined cDNA sequence of SYN21H8.

SEQ ID NO:54 is the determined cDNA sequence of SYN22A10.

SEQ ID NO:55 is the determined cDNA sequence of SYN22A10-2.

SEQ ID NO:56 is the determined cDNA sequence of SYN22A12.

SEQ ID NO:57 is the determined cDNA sequence of SYN22A2.

SEQ ID NO:58 is the determined cDNA sequence of SYN22B4.

SEQ ID NO:59 is the determined cDNA sequence of SYN22C2.

SEQ ID NO:60 is the determined cDNA sequence of SYN22E10.

SEQ ID NO:61 is the determined cDNA sequence of SYN22F2.

SEQ ID NO:62 is a predicted amino acid sequence for SYN18C6 (also known as B709P).

SEQ ID NO:63 is the determined cDNA sequence of B723P.

SEQ ID NO:64 is the determined cDNA sequence for B724P.

SEQ ID NO:65 is the determined cDNA sequence of B770P.

SEQ ID NO:66 is the determined cDNA sequence of B716P.

SEQ ID NO:67 is the determined cDNA sequence of B725P.

SEQ ID NO:68 is the determined cDNA sequence of B717P.

SEQ ID NO:69 is the determined cDNA sequence of B771P.

SEQ ID NO:70 is the determined cDNA sequence of B722P.

SEQ ID NO:71 is the determined cDNA sequence of B726P.

SEQ ID NO:72 is the determined cDNA sequence of B727P.

SEQ ID NO:73 is the determined cDNA sequence of B728P.

SEQ ID NO:74–87 are the determined cDNA sequences of isolated clones which show homology to known sequences.

SEQ ID NO:88 is the determined cDNA sequence of 13053.

SEQ ID NO:89 is the determined cDNA sequence of 13057.

SEQ ID NO:90 is the determined cDNA sequence of 13059.
SEQ ID NO:91 is the determined cDNA sequence of 13065.
SEQ ID NO:92 is the determined cDNA sequence of 13067.
SEQ ID NO:93 is the determined cDNA sequence of 13068.
SEQ ID NO:94 is the determined cDNA sequence of 13071.
SEQ ID NO:95 is the determined cDNA sequence of 13072.
SEQ ID NO:96 is the determined cDNA sequence of 13073.
SEQ ID NO:97 is the determined cDNA sequence of 13075.
SEQ ID NO:98 is the determined cDNA sequence of 13078.
SEQ ID NO:99 is the determined cDNA sequence of 13079.
SEQ ID NO:100 is the determined cDNA sequence of 13081.
SEQ ID NO:101 is the determined cDNA sequence of 13082.
SEQ ID NO:102 is the determined cDNA sequence of 13092.
SEQ ID NO:103 is the determined cDNA sequence of 13097.
SEQ ID NO:104 is the determined cDNA sequence of 13101.
SEQ ID NO:105 is the determined cDNA sequence of 13102.
SEQ ID NO:106 is the determined cDNA sequence of 13119.
SEQ ID NO:107 is the determined cDNA sequence of 13131.
SEQ ID NO:108 is the determined cDNA sequence of 13133.
SEQ ID NO:109 is the determined cDNA sequence of 13135.
SEQ ID NO:110 is the determined cDNA sequence of 13139.
SEQ ID NO:111 is the determined cDNA sequence of 13140.
SEQ ID NO:112 is the determined cDNA sequence of 13146.
SEQ ID NO:113 is the determined cDNA sequence of 13147.
SEQ ID NO:114 is the determined cDNA sequence of 13148.
SEQ ID NO:115 is the determined cDNA sequence of 13149.
SEQ ID NO:116 is the determined cDNA sequence of 13151.
SEQ ID NO:117 is the determined cDNA sequence of 13051
SEQ ID NO:118 is the determined cDNA sequence of 13052
SEQ ID NO:119 is the determined cDNA sequence of 13055
SEQ ID NO:120 is the determined cDNA sequence of 13058
SEQ ID NO:121 is the determined cDNA sequence of 13062
SEQ ID NO:122 is the determined cDNA sequence of 13064
SEQ ID NO:123 is the determined cDNA sequence of 13080
SEQ ID NO:124 is the determined cDNA sequence of 13093
SEQ ID NO:125 is the determined cDNA sequence of 13094
SEQ ID NO:126 is the determined cDNA sequence of 13095
SEQ ID NO:127 is the determined cDNA sequence of 13096
SEQ ID NO:128 is the determined cDNA sequence of 13099
SEQ ID NO:129 is the determined cDNA sequence of 13100
SEQ ID NO:130 is the determined cDNA sequence of 13103
SEQ ID NO:131 is the determined cDNA sequence of 13106
SEQ ID NO:132 is the determined cDNA sequence of 13107
SEQ ID NO:133 is the determined cDNA sequence of 13108
SEQ ID NO:134 is the determined cDNA sequence of 13121
SEQ ID NO:135 is the determined cDNA sequence of 13126
SEQ ID NO:136 is the determined cDNA sequence of 13129
SEQ ID NO:137 is the determined cDNA sequence of 13130
SEQ ID NO:138 is the determined cDNA sequence of 13134
SEQ ID NO:139 is the determined cDNA sequence of 13141
SEQ ID NO:140 is the determined cDNA sequence of 13142
SEQ ID NO:141 is the determined cDNA sequence of 14376
SEQ ID NO:142 is the determined cDNA sequence of 14377
SEQ ID NO:143 is the determined cDNA sequence of 14383
SEQ ID NO:144 is the determined cDNA sequence of 14384
SEQ ID NO:145 is the determined cDNA sequence of 14387
SEQ ID NO:146 is the determined cDNA sequence of 14392
SEQ ID NO:147 is the determined cDNA sequence of 14394
SEQ ID NO:148 is the determined cDNA sequence of 14398
SEQ ID NO:149 is the determined cDNA sequence of 14401
SEQ ID NO:150 is the determined cDNA sequence of 14402
SEQ ID NO:151 is the determined cDNA sequence of 14405

SEQ ID NO:152 is the determined cDNA sequence of 14409

SEQ ID NO:153 is the determined cDNA sequence of 14412

SEQ ID NO:154 is the determined cDNA sequence of 14414

SEQ ID NO:155 is the determined cDNA sequence of 14415

SEQ ID NO:156 is the determined cDNA sequence of 14416

SEQ ID NO:157 is the determined cDNA sequence of 14419

SEQ ID NO:158 is the determined cDNA sequence of 14426

SEQ ID NO:159 is the determined cDNA sequence of 14427

SEQ ID NO:160 is the determined cDNA sequence of 14375

SEQ ID NO:161 is the determined cDNA sequence of 14378

SEQ ID NO:162 is the determined cDNA sequence of 14379

SEQ ID NO:163 is the determined cDNA sequence of 14380

SEQ ID NO:164 is the determined cDNA sequence of 14381

SEQ ID NO:165 is the determined cDNA sequence of 14382

SEQ ID NO:166 is the determined cDNA sequence of 14388

SEQ ID NO:167 is the determined cDNA sequence of 14399

SEQ ID NO:168 is the determined cDNA sequence of 14406

SEQ ID NO:169 is the determined cDNA sequence of 14407

SEQ ID NO:170 is the determined cDNA sequence of 14408

SEQ ID NO:171 is the determined cDNA sequence of 14417

SEQ ID NO:172 is the determined cDNA sequence of 14418

SEQ ID NO:173 is the determined cDNA sequence of 14423

SEQ ID NO:174 is the determined cDNA sequence of 14424

SEQ ID NO:175 is the determined cDNA sequence of B726P-20

SEQ ID NO:176 is the predicted amino acid sequence of B726P-20

SEQ ID NO:177 is a PCR primer

SEQ ID NO:178 is the determined cDNA sequence of B726P-74

SEQ ID NO:179 is the predicted amino acid sequence of B726P-74

SEQ ID NO:180 is the determined cDNA sequence of B726P-79

SEQ ID NO:181 is the predicted amino acid sequence of B726P-79

SEQ ID NO:182 is the determined cDNA sequence of 19439.1, showing homology to the mammaglobin gene SEQ ID NO:183 is the determined cDNA sequence of 19407.1, showing homology to the human keratin gene SEQ ID NO:184 is the determined cDNA sequence of 19428.1, showing homology to human chromosome 17 clone SEQ ID NO:185 is the determined cDNA sequence of B808P (19408), showing no significant homology to any known gene SEQ ID NO:186 is the determined cDNA sequence of 19460.1, showing no significant homology to any known gene SEQ ID NO:187 is the determined cDNA sequence of 19419.1, showing homology to Ig kappa light chain SEQ ID NO:188 is the determined cDNA sequence of 19411.1, showing homology to human alpha-1 collagen SEQ ID NO:189 is the determined cDNA sequence of 19420.1, showing homology to mus musculus proteinase-3

SEQ ID NO:190 is the determined cDNA sequence of 19432.1, showing homology to human high motility group box SEQ ID NO:191 is the determined cDNA sequence of 19412.1, showing homology to the human plasminogen activator gene SEQ ID NO:192 is the determined cDNA sequence of 19415.1, showing homology to mitogen activated protein kinase SEQ ID NO:193 is the determined cDNA sequence of 19409.1, showing homology to the chondroitin sulfate proteoglycan protein SEQ ID NO:194 is the determined cDNA sequence of 19406.1, showing no significant homology to any known gene SEQ ID NO:195 is the determined cDNA sequence of 19421.1, showing homology to human fibronectin SEQ ID NO:196 is the determined cDNA sequence of 19426.1, showing homology to the retinoic acid receptor responder 3

SEQ ID NO:197 is the determined cDNA sequence of 19425.1, showing homology to MyD88 mRNA SEQ ID NO:198 is the determined cDNA sequence of 19424.1, showing homology to peptide transporter (TAP-1) mRNA SEQ ID NO:199 is the determined cDNA sequence of 19429.1, showing no significant homology to any known gene SEQ ID NO:200 is the determined cDNA sequence of 19435.1, showing homology to human polymorphic epithelial mucin SEQ ID NO:201 is the determined cDNA sequence of B813P (19434.1), showing homology to human GATA-3 transcription factor SEQ ID NO:202 is the determined cDNA sequence of 19461.1, showing homology to the human AP-2 gene SEQ ID NO:203 is the determined cDNA sequence of 19450.1, showing homology to DNA binding regulatory factor SEQ ID NO:204 is the determined cDNA sequence of 19451.1, showing homology to Na/H exchange regulatory co-factor SEQ ID NO:205 is the determined cDNA sequence of 19462.1, showing no significant homology to any known gene SEQ ID NO:206 is the determined cDNA sequence of 19455.1, showing homology to human mRNA for histone HAS.Z SEQ ID NO:207 is the determined cDNA sequence of 19459.1, showing homology to PAC clone 179N16

SEQ ID NO:208 is the determined cDNA sequence of 19464.1, showing no significant homology to any known gene SEQ ID NO:209 is the determined cDNA sequence of 19414.1, showing homology to lipophilin B SEQ ID NO:210 is the determined cDNA sequence of 19413.1, showing homology to chromosome 17 clone hRPK.209_J_20

SEQ ID NO:211 is the determined cDNA sequence of 19416.1, showing no significant homology to any known gene SEQ ID NO:212 is the determined cDNA sequence of 19437.1, showing homology to human clone 24976 mRNA SEQ ID NO:213 is the determined cDNA sequence of 19449.1, showing homology to mouse DNA for PG-M core protein SEQ ID NO:214 is the determined cDNA sequence of 19446.1, showing no significant homology to any known gene SEQ ID NO:215 is the determined cDNA sequence of 19452.1, showing no significant homology to any known gene SEQ ID NO:216 is the determined cDNA sequence of 19483.1, showing no significant homology to any known gene SEQ ID NO:217 is the determined cDNA sequence of 19526.1, showing homology to human lipophilin C SEQ ID NO:218 is the determined cDNA sequence of 19484.1, showing homology to the secreted cement gland protein XAG-2

SEQ ID NO:219 is the determined cDNA sequence of 19470.1, showing no significant homology to any known gene SEQ ID NO:220 is the determined cDNA sequence of 19469.1, showing homology to the human HLA-DM gene SEQ ID NO:221 is the determined cDNA sequence of 19482.1, showing homology to the human pS2 protein gene SEQ ID NO:222 is the determined cDNA sequence of B805P (19468.1), showing no significant homology to any known gene SEQ ID NO:223 is the determined cDNA sequence of 19467.1, showing homology to human thrombospondin mRNA SEQ ID NO:224 is the determined cDNA sequence of 19498.1, showing homology to the CDC2 gene involved in cell cycle control SEQ ID NO:225 is the determined cDNA sequence of 19506.1, showing homology to human cDNA for TREB protein SEQ ID NO:226 is the determined EDNA sequence of B806P (19505.1), showing no significant homology to any known gene SEQ ID NO:227 is the determined EDNA sequence of 19486.1, showing homology to type I epidermal keratin SEQ ID NO:228 is the determined cDNA sequence of 19510.1, showing homology to glucose transporter for glycoprotein SEQ ID NO:229 is the determined cDNA sequence of 19512.1, showing homology to the human lysyl hydroxylase gene SEQ ID NO:230 is the determined cDNA sequence of 19511.1, showing homology to human palimotoyl-protein thioesterase SEQ ID NO:231 is the determined cDNA sequence of 19508.1, showing homology to human alpha enolase SEQ ID NO:232 is the determined cDNA sequence of B807P (19509.1), showing no significant homology to any known gene SEQ ID NO:233 is the determined cDNA sequence of B809P (19520.1), showing homology to clone 102D24 on chromosome 11q13.31

SEQ ID NO:234 is the determined cDNA sequence of 19507.1, showing homology toprosome beta-subunit SEQ ID NO:235 is the determined cDNA sequence of 19525.1, showing homology to human pro-urokinase precursor SEQ ID NO:236 is the determined cDNA sequence of 19513.1, showing no significant homology to any known gene SEQ ID NO:237 is the determined cDNA sequence of 19517.1, showing homology to human PAC 128M19 clone SEQ ID NO:238 is the determined cDNA sequence of 19564.1, showing homology to human cytochrome P450-IIB SEQ ID NO:239 is the determined cDNA sequence of 19553.1, showing homology to human GABA-A receptor pi subunit SEQ ID NO:240 is the determined cDNA sequence of B811P (19575.1), showing no significant homology to any known gene SEQ ID NO:241 is the determined cDNA sequence of B810P (19560.1), showing no significant homology to any known gene SEQ ID NO:242 is the determined cDNA sequence of 19588.1, showing homology to aortic carboxypetidase-like protein SEQ ID NO:243 is the determined cDNA sequence of 19551.1, showing homology to human BCL-1 gene SEQ ID NO:244 is the determined cDNA sequence of 19567.1, showing homology to human proteasome-related mRNA SEQ ID NO:245 is the determined cDNA sequence of B803P (19583.1), showing no significant homology to any known gene SEQ ID NO:246 is the determined cDNA sequence of B812P (19587.1), showing no significant homology to any known gene SEQ ID NO:247 is the determined cDNA sequence of B802P (19392.2), showing homology to human chromosome 17

SEQ ID NO:248 is the determined cDNA sequence of 19393.2, showing homology to human nicein B2 chain SEQ ID NO:249 is the determined cDNA sequence of 19398.2, human MHC class II DQ alpha mRNA SEQ ID NO:250 is the determined cDNA sequence of B804P (19399.2), showing homology to human Xp22 BAC GSHB-184P14

SEQ ID NO:251 is the determined cDNA sequence of 19401.2, showing homology to human ikB kinase-b gene SEQ ID NO:252 is the determined cDNA sequence of 20266, showing no significant homology to any known gene SEQ ID NO:253 is the determined cDNA sequence of B826P (20270), showing no significant homology to any known gene SEQ ID NO:254 is the determined cDNA sequence of 20274, showing no significant homology to any known gene SEQ ID NO:255 is the determined cDNA sequence of 20276, showing no significant homology to any known gene SEQ ID NO:256 is the determined cDNA sequence of 20277, showing no significant homology to any known gene SEQ ID NO:257 is the determined cDNA sequence of B823P (20280), showing no significant homology to any known gene SEQ ID NO:258 is the determined cDNA sequence of B821P (20281), showing no significant homology to any known gene SEQ ID NO:259 is the determined cDNA sequence of B824P (20294), showing no significant homology to any known gene SEQ ID NO:260 is the determined cDNA sequence of 20303, showing no significant homology to any known gene SEQ ID NO:261 is the determined cDNA sequence of B820P (20310), showing no significant homology to any known gene SEQ ID NO:262 is the determined cDNA sequence of B825P (20336), showing no significant homology to any known gene SEQ ID NO:263 is the determined cDNA sequence of B827P (20341), showing no significant homology to any known gene SEQ ID NO:264 is the determined cDNA sequence of 20941, showing no significant homology to any known gene SEQ ID NO:265 is the determined cDNA sequence of 20954, showing no significant homology to any known gene SEQ ID NO:266 is the determined cDNA sequence of 20961, showing no significant homology to any known gene SEQ ID NO:267 is the determined cDNA sequence of 20965, showing no significant homology to any known gene SEQ ID NO:268 is the determined cDNA sequence of 20975, showing no significant homology to any known gene SEQ ID NO:269 is the determined cDNA sequence of 20261, showing homology to Human p120 catenin SEQ ID NO:270 is the determined cDNA sequence of B822P (20262), showing homology to Human membrane glycoprotein 4F2

SEQ ID NO:271 is the determined cDNA sequence of 20265, showing homology to Human Na, K-ATPase Alpha 1

SEQ ID NO:272 is the determined cDNA sequence of 20267, showing homology to Human heart HS 90, partial cds SEQ ID NO:273 is the determined cDNA sequence of 20268, showing homology to Human mRNA GPI-anchored protein p137

SEQ ID NO:274 is the determined cDNA sequence of 20271, showing homology to Human cleavage stimulation factor 77 kDa subunit SEQ ID NO:275 is the determined cDNA sequence of 20272, showing homology to Human p190-B SEQ ID NO:276 is the determined cDNA sequence of 20273, showing homology to Human ribophorin SEQ ID NO:277 is the determined cDNA sequence of 20278, showing homology to Human omithine amino transferase SEQ ID NO:278 is the determined cDNA sequence of 20279, showing homology to Human S-adenosylmethionine synthetase SEQ ID NO:279 is the determined cDNA sequence of 20293, showing homology to Human x inactivation transcript SEQ ID NO:280 is the determined cDNA sequence of 20300, showing homology to Human cytochrome p450

SEQ ID NO:281 is the determined cDNA sequence of 20305, showing homology to Human elongation factor-1 alpha SEQ ID NO:282 is the determined cDNA sequence of 20306, showing homology to Human epithelial ets protein SEQ ID NO:283 is the determined cDNA sequence of 20307, showing homology to Human signal transducer mRNA SEQ ID NO:284 is the determined cDNA sequence of 20313, showing homology to Human GABA-A receptor pi subunit mRNA SEQ ID NO:285 is the determined cDNA sequence of 20317, showing homology to Human tyrosine phosphatase SEQ ID NO:286 is the determined cDNA sequence of 20318, showing homology to Human cathepsine B proteinase SEQ ID NO:287 is the determined cDNA sequence of 20320, showing homology to Human 2-phosphopyruvate-hydratase-alpha-enolase SEQ ID NO:288 is the determined cDNA sequence of 20321, showing homology to Human E-cadherin SEQ ID NO:289 is the determined cDNA sequence of 20322, showing homology to Human hsp86

SEQ ID NO:290 is the determined cDNA sequence of B828P (20326), showing homology to Human x inactivation transcript SEQ ID NO:291 is the determined cDNA sequence of 20333, showing homology to Human chromatin regulator, SMARCA5

SEQ ID NO:292 is the determined cDNA sequence of 20335, showing homology to Human sphingolipid activator protein 1

SEQ ID NO:293 is the determined cDNA sequence of 20337, showing homology to Human hepatocyte growth factor activator inhibitor type 2

SEQ ID NO:294 is the determined cDNA sequence of 20338, showing homology to Human cell adhesion molecule CD44

SEQ ID NO:295 is the determined cDNA sequence of 20340, showing homology to Human nuclear factor (erythroid-derived)-like 1

SEQ ID NO:296 is the determined cDNA sequence of 20938, showing homology to Human vinculin mRNA SEQ ID NO:297 is the determined cDNA sequence of 20939, showing homology to Human elongation factor EF-1-alpha SEQ ID NO:298 is the determined cDNA sequence of 20940, showing homology to Human nestin gene SEQ ID NO:299 is the determined cDNA sequence of 20942, showing homology to Human pancreatic ribonuclease SEQ ID NO:300 is the determined cDNA sequence of 20943, showing homology to Human transcobalamin I SEQ ID NO:301 is the determined cDNA sequence of 20944, showing homology to Human beta-tubulin SEQ ID NO:302 is the determined cDNA sequence of 20946, showing homology to Human HS1 protein SEQ ID NO:303 is the determined cDNA sequence of 20947, showing homology to Human cathepsin B SEQ ID NO:304 is the determined cDNA sequence of 20948, showing homology to Human testis enhanced gene transcript SEQ ID NO:305 is the determined cDNA sequence of 20949, showing homology to Human elongation factor EF-1-alpha SEQ ID NO:306 is the determined cDNA sequence of 20950, showing homology to Human ADP-ribosylation factor 3

SEQ ID NO:307 is the determined cDNA sequence of 20951, showing homology to Human IFP53 or WRS for tryptophanyl-tRNA synthetase SEQ ID NO:308 is the determined cDNA sequence of 20952, showing homology to Human cyclin-dependent protein kinase SEQ ID NO:309 is the determined cDNA sequence of 20957, showing homology to Human alpha-tubulin isoform 1

SEQ ID NO:310 is the determined cDNA sequence of 20959, showing homology to Human tyrosine phosphatase-61bp deletion SEQ ID NO:311 is the determined cDNA sequence of 20966, showing homology to Human tyrosine phosphatase SEQ ID NO:312 is the determined cDNA sequence of B830P (20976), showing homology to Human nuclear factor NF 45

SEQ ID NO:313 is the determined cDNA sequence of B829P (20977), showing homology to Human delta-6 fatty acid desaturase SEQ ID NO:314 is the determined cDNA sequence of 20978, showing homology to Human nuclear aconitase SEQ ID NO:315 is the determined cDNA sequence of clone 23176.

SEQ ID NO:316 is the determined cDNA sequence of clone 23140.

SEQ ID NO:317 is the determined cDNA sequence of clone 23166.

SEQ ID NO:318 is the determined EDNA sequence of clone 23167.

SEQ ID NO:319 is the determined cDNA sequence of clone 23177.

SEQ ID NO:320 is the determined cDNA sequence of clone 23217.

SEQ ID NO:321 is the determined cDNA sequence of clone 23169.

SEQ ID NO:322 is the determined cDNA sequence of clone 23160.

SEQ ID NO:323 is the determined cDNA sequence of clone 23182.

SEQ ID NO:324 is the determined cDNA sequence of clone 23232.

SEQ ID NO:325 is the determined cDNA sequence of clone 23203.

SEQ ID NO:326 is the determined cDNA sequence of clone 23198.

SEQ ID NO:327 is the determined cDNA sequence of clone 23224.

SEQ ID NO:328 is the determined cDNA sequence of clone 23142.

SEQ ID NO:329 is the determined cDNA sequence of clone 23138.

SEQ ID NO:330 is the determined cDNA sequence of clone 23147.

SEQ ID NO:331 is the determined cDNA sequence of clone 23148.

SEQ ID NO:332 is the determined cDNA sequence of clone 23149.

SEQ ID NO:333 is the determined cDNA sequence of clone 23172.

SEQ ID NO:334 is the determined cDNA sequence of clone 23158.

SEQ ID NO:335 is the determined cDNA sequence of clone 23156.

SEQ ID NO:336 is the determined cDNA sequence of clone 23221.

SEQ ID NO:337 is the determined cDNA sequence of clone 23223.

SEQ ID NO:338 is the determined cDNA sequence of clone 23155.

SEQ ID NO:339 is the determined cDNA sequence of clone 23225.

SEQ ID NO:340 is the determined cDNA sequence of clone 23226.

SEQ ID NO:341 is the determined cDNA sequence of clone 23228.

SEQ ID NO:342 is the determined cDNA sequence of clone 23229.

SEQ ID NO:343 is the determined cDNA sequence of clone 23231.

SEQ ID NO:344 is the determined cDNA sequence of clone 23154.

SEQ ID NO:345 is the determined cDNA sequence of clone 23157.

SEQ ID NO:346 is the determined cDNA sequence of clone 23153.

SEQ ID NO:347 is the determined cDNA sequence of clone 23159.

SEQ ID NO:348 is the determined cDNA sequence of clone 23152.

SEQ ID NO:349 is the determined cDNA sequence of clone 23161.

SEQ ID NO:350 is the determined cDNA sequence of clone 23162.

SEQ ID NO:351 is the determined cDNA sequence of clone 23163.

SEQ ID NO:352 is the determined cDNA sequence of clone 23164.

SEQ ID NO:353 is the determined cDNA sequence of clone 23165.

SEQ ID NO:354 is the determined cDNA sequence of clone 23151.

SEQ ID NO:355 is the determined cDNA sequence of clone 23150.

SEQ ID NO:356 is the determined cDNA sequence of clone 23168.

SEQ ID NO:357 is the determined cDNA sequence of clone 23146.

SEQ ID NO:358 is the determined cDNA sequence of clone 23170.

SEQ ID NO:359 is the determined cDNA sequence of clone 23171.

SEQ ID NO:360 is the determined cDNA sequence of clone 23145.

SEQ ID NO:361 is the determined cDNA sequence of clone 23174.

SEQ ID NO:362 is the determined cDNA sequence of clone 23175.

SEQ ID NO:363 is the determined cDNA sequence of clone 23144.
SEQ ID NO:364 is the determined cDNA sequence of clone 23178.
SEQ ID NO:365 is the determined cDNA sequence of clone 23179.
SEQ ID NO:366 is the determined cDNA sequence of clone 23180.
SEQ ID NO:367 is the determined cDNA sequence of clone 23181.
SEQ ID NO:368 is the determined cDNA sequence of clone 23143
SEQ ID NO:369 is the determined cDNA sequence of clone 23183.
SEQ ID NO:370 is the determined cDNA sequence of clone 23184.
SEQ ID NO:371 is the determined cDNA sequence of clone 23185.
SEQ ID NO:372 is the determined cDNA sequence of clone 23186.
SEQ ID NO:373 is the determined cDNA sequence of clone 23187.
SEQ ID NO:374 is the determined cDNA sequence of clone 23190.
SEQ ID NO:375 is the determined cDNA sequence of clone 23189.
SEQ ID NO:376 is the determined cDNA sequence of clone 23202.
SEQ ID NO:378 is the determined cDNA sequence of clone 23191.
SEQ ID NO:379 is the determined cDNA sequence of clone 23188.
SEQ ID NO:380 is the determined cDNA sequence of clone 23194.
SEQ ID NO:381 is the determined cDNA sequence of clone 23196.
SEQ ID NO:382 is the determined cDNA sequence of clone 23195.
SEQ ID NO:383 is the determined cDNA sequence of clone 23193.
SEQ ID NO:384 is the determined cDNA sequence of clone 23199.
SEQ ID NO:385 is the determined cDNA sequence of clone 23200.
SEQ ID NO:386 is the determined cDNA sequence of clone 23192.
SEQ ID NO:387 is the determined cDNA sequence of clone 23201.
SEQ ID NO:388 is the determined cDNA sequence of clone 23141.
SEQ ID NO:389 is the determined cDNA sequence of clone 23139.
SEQ ID NO:390 is the determined cDNA sequence of clone 23204.
SEQ ID NO:391 is the determined cDNA sequence of clone 23205.
SEQ ID NO:392 is the determined cDNA sequence of clone 23206.
SEQ ID NO:393 is the determined cDNA sequence of clone 23207.
SEQ ID NO:394 is the determined cDNA sequence of clone 23208.
SEQ ID NO:395 is the determined cDNA sequence of clone 23209.
SEQ ID NO:396 is the determined cDNA sequence of clone 23210.
SEQ ID NO:397 is the determined cDNA sequence of clone 23211.
SEQ ID NO:398 is the determined cDNA sequence of clone 23212.
SEQ ID NO:399 is the determined cDNA sequence of clone 23214.
SEQ ID NO:400 is the determined cDNA sequence of clone 23215.
SEQ ID NO:401 is the determined cDNA sequence of clone 23216.
SEQ ID NO:402 is the determined cDNA sequence of clone 23137.
SEQ ID NO:403 is the determined cDNA sequence of clone 23218.
SEQ ID NO:404 is the determined cDNA sequence of clone 23220.
SEQ ID NO:405 is the determined cDNA sequence of clone 19462.
SEQ ID NO:406 is the determined cDNA sequence of clone 19430.
SEQ ID NO:407 is the determined cDNA sequence of clone 19407.
SEQ ID NO:408 is the determined cDNA sequence of clone 19448.
SEQ ID NO:409 is the determined cDNA sequence of clone 19447.
SEQ ID NO:410 is the determined cDNA sequence of clone 19426.
SEQ ID NO:411 is the determined cDNA sequence of clone 19441.
SEQ ID NO:412 is the determined cDNA sequence of clone 19454.
SEQ ID NO:413 is the determined cDNA sequence of clone 19463.
SEQ ID NO:414 is the determined cDNA sequence of clone 19419.
SEQ ID NO:415 is the determined cDNA sequence of clone 19434.
SEQ ID NO:416 is the determined extended cDNA sequence of B820P.
SEQ ID NO:417 is the determined extended cDNA sequence of B821P.
SEQ ID NO:418 is the determined extended cDNA sequence of B822P.
SEQ ID NO:419 is the determined extended cDNA sequence of B823P.
SEQ ID NO:420 is the determined extended cDNA sequence of B824P.
SEQ ID NO:421 is the determined extended cDNA sequence of B825P.
SEQ ID NO:422 is the determined extended cDNA sequence of B826P.
SEQ ID NO:423 is the determined extended cDNA sequence of B827P.
SEQ ID NO:424 is the determined extended cDNA sequence of B828P.
SEQ ID NO:425 is the determined extended cDNA sequence of B829P.

SEQ ID NO:426 is the determined extended cDNA sequence of B830P.

SEQ ID NO:427 is the determined cDNA sequence of clone 266B4.

SEQ ID NO:428 is the determined cDNA sequence of clone 22892.

SEQ ID NO:429 is the determined cDNA sequence of clone 266G3.

SEQ ID NO:430 is the determined cDNA sequence of clone 22890.

SEQ ID NO:431 is the determined cDNA sequence of clone 264B4.

SEQ ID NO:432 is the determined cDNA sequence of clone 22883.

SEQ ID NO:433 is the determined cDNA sequence of clone 22882.

SEQ ID NO:434 is the determined cDNA sequence of clone 22880.

SEQ ID NO:435 is the determined cDNA sequence of clone 263G1.

SEQ ID NO:436 is the determined cDNA sequence of clone 263G6.

SEQ ID NO:437 is the determined cDNA sequence of clone 262B2.

SEQ ID NO:438 is the determined cDNA sequence of clone 262B6.

SEQ ID NO:439 is the determined cDNA sequence of clone 22869.

SEQ ID NO:440 is the determined cDNA sequence of clone 21374.

SEQ ID NO:441 is the determined cDNA sequence of clone 21362.

SEQ ID NO:442 is the determined cDNA sequence of clone 21349.

SEQ ID NO:443 is the determined cDNA sequence of clone 21309.

SEQ ID NO:444 is the determined cDNA sequence of clone 21097.

SEQ ID NO:445 is the determined cDNA sequence of clone 21096.

SEQ ID NO:446 is the determined cDNA sequence of clone 21094.

SEQ ID NO:447 is the determined cDNA sequence of clone 21093.

SEQ ID NO:448 is the determined cDNA sequence of clone 21091.

SEQ ID NO:449 is the determined cDNA sequence of clone 21089.

SEQ ID NO:450 is the determined cDNA sequence of clone 21087.

SEQ ID NO:451 is the determined cDNA sequence of clone 21085.

SEQ ID NO:452 is the determined cDNA sequence of clone 21084.

SEQ ID NO:453 is a first partial cDNA sequence of clone 2BT1-40.

SEQ ID NO:454 is a second partial cDNA sequence of clone 2BT1-40.

SEQ ID NO:455 is the determined cDNA sequence of clone 21063.

SEQ ID NO:456 is the determined cDNA sequence of clone 21062.

SEQ ID NO:457 is the determined cDNA sequence of clone 21060.

SEQ ID NO:458 is the determined cDNA sequence of clone 21053.

SEQ ID NO:459 is the determined cDNA sequence of clone 21050.

SEQ ID NO:460 is the determined cDNA sequence of clone 21036.

SEQ ID NO:461 is the determined cDNA sequence of clone 21037.

SEQ ID NO:462 is the determined cDNA sequence of clone 21048.

SEQ ID NO:463 is a consensus DNA sequence of B726P (referred to as B726P-spliced_seq_B726P).

SEQ ID NO:464 is the determined cDNA sequence of a second splice form of B726P (referred to as 27490.seq_B726P).

SEQ ID NO:465 is the determined cDNA sequence of a third splice form of B726P (referred to as 27068.seq_B726P).

SEQ ID NO:466 is the determined cDNA sequence of a second splice form of B726P (referred to as 23113.seq_B726P).

SEQ ID NO:467 is the determined cDNA sequence of a second splice form of B726P (referred to as 23103.seq_B726P).

SEQ ID NO:468 is the determined cDNA sequence of a second splice form of B726P (referred to as 19310.seq_B726P).

SEQ ID NO:469 is the predicted amino acid sequence encoded by the upstream ORF of SEQ ID NO:463.

SEQ ID NO:470 is the predicted amino acid sequence encoded by SEQ ID NO:464.

SEQ ID NO:471 is the predicted amino acid sequence encoded by SEQ ID NO:465.

SEQ ID NO:472 is the predicted amino acid sequence encoded by SEQ ID NO:466.

SEQ ID NO:473 is the predicted amino acid sequence encoded by SEQ ID NO:467.

SEQ ID NO:474 is the determined cDNA sequence for an alternative splice form of B726P.

SEQ ID NO:475 is the amino acid sequence encoded by SEQ ID NO:474.

SEQ ID NO:476 is the isolated cDNA sequence of B720P.

SEQ ID NO:477 is the cDNA sequence of a known keratin gene.

SEQ ID NO:478 is the amino acid sequence encoded by SEQ ID NO:477.

SEQ ID NO:479 is the determined cDNA sequence for clone 19465.

SEQ ID NO:480 and 481 are PCR primers.

SEQ ID NO:482 is the cDNA sequence for the expressed downstream ORF of B726P.

SEQ ID NO:483 is the amino acid sequence for the expressed recombinant downstream ORF of B726P.

SEQ ID NO:484 is the determined full-length cDNA sequence for B720P.

SEQ ID NO:485 is the amino acid sequence encoded by SEQ ID NO:484.

SEQ ID NO:486 is the determined cDNA sequence of a truncated form of B720P, referred to as B720P-tr.

SEQ ID NO:487 is the amino acid sequence of B720P-tr.

SEQ ID NO:488 is the amino acid sequence of a naturally processed epitope of B726P recognized by B726P-specific CTL.

SEQ ID NO:489 is a DNA sequence encoding the B726P epitope set forth in SEQ ID NO:488.

DETAILED DESCRIPTION OF THE INVENTION

As noted above, the present invention is generally directed to compositions and methods for using the compositions, for example in the therapy and diagnosis of cancer, such as breast cancer. Certain illustrative compositions described herein include breast tumor polypeptides, polynucleotides encoding such polypeptides, binding agents such as antibodies, antigen presenting cells (APCs) and/or immune system cells (e.g., T cells). A "breast tumor protein," as the term is used herein, refers generally to a protein that is expressed in breast tumor cells at a level that is at least two fold, and preferably at least five fold, greater than the level of expression in a normal tissue, as determined using a representative assay provided herein. Certain breast tumor proteins are tumor proteins that react detectably (within an immunoassay, such as an ELISA or Western blot) with antisera of a patient afflicted with breast cancer.

Therefore, in accordance with the above, and as described further below, the present invention provides illustrative polynucleotide compositions having sequences set forth in SEQ ID NO:1–175, 178, 180, 182–468, 474, 476, 477, 479, 484, 486 and 489, illustrative polypeptide compositions having amino acid sequences set forth in SEQ ID NO:176, 179, 181, 469–473, 475, 485, 487 and 488, antibody compositions capable of binding such polypeptides, and numerous additional embodiments employing such compositions, for example in the detection, diagnosis and/or therapy of human breast cancer.

Polynucleotide Compositions

As used herein, the terms "DNA segment" and "polynucleotide" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the DNA segments of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

"Isolated," as used herein, means that a polynucleotide is substantially away from other coding sequences, and that the DNA segment does not contain large portions of unrelated coding DNA, such as large chromosomal fragments or other functional genes or polypeptide coding regions. Of course, this refers to the DNA segment as originally isolated, and does not exclude genes or coding regions later added to the segment by the hand of man.

As will be recognized by the skilled artisan, polynucleotides may be single-stranded (coding or antisense) or double-stranded, and may be DNA (genomic, cDNA or synthetic) or RNA molecules. RNA molecules include HNRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a breast tumor protein or a portion thereof) or may comprise a variant, or a biological or antigenic functional equivalent of such a sequence. Polynucleotide variants may contain one or more substitutions, additions, deletions and/or insertions, as further described below, preferably such that the immunogenicity of the encoded polypeptide is not diminished, relative to a native tumor protein. The effect on the immunogenicity of the encoded polypeptide may generally be assessed as described herein. The term "variants" also encompasses homologous genes of xenogenic origin.

When comparing polynucleotide or polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726–730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389–3402 and Altschul et al. (1990) *J. Mol Biol.* 215:403–410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl Acad. Sci. USA* 89:10915) alignments, (B) of 50, expectation (E) of 10, M=5, N=-4 and a comparison of both strands.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Therefore, the present invention encompasses polynucleotide and polypeptide sequences having substantial identity to the sequences disclosed herein, for example those comprising at least 50% sequence identity, preferably at least 55%, 60%, 65%, 70%, 75%, 80%, 85%, 90%, 95%, 96%, 97%, 98%, or 99% or higher, sequence identity compared to a polynucleotide or polypeptide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

In additional embodiments, the present invention provides isolated polynucleotides and polypeptides comprising various lengths of contiguous stretches of sequence identical to or complementary to one or more of the sequences disclosed herein. For example, polynucleotides are provided by this invention that comprise at least about 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200–500; 500–1,000, and the like.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative DNA segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

In other embodiments, the present invention is directed to polynucleotides that are capable of hybridizing under moderately stringent conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5×and 0.2×SSC containing 0.1% SDS.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Probes and Primers

In other embodiments of the present invention, the polynucleotide sequences provided herein can be advantageously used as probes or primers for nucleic acid hybridization. As such, it is contemplated that nucleic acid segments that comprise a sequence region of at least about 15 nucleotide long contiguous sequence that has the same sequence as, or is complementary to, a 15 nucleotide long contiguous sequence disclosed herein will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to a sequence of interest will enable them to be of use in detecting the presence of complementary sequences in a given sample. However, other uses are also envisioned, such as the use of the sequence information for the preparation of mutant species primers, or primers for use in preparing other genetic constructions.

Polynucleotide molecules having sequence regions consisting of contiguous nucleotide stretches of 10–14, 15–20, 30, 50, or even of 100–200 nucleotides or so (including intermediate lengths as well), identical or complementary to a polynucleotide sequence disclosed herein, are particularly contemplated as hybridization probes for use in, e.g., Southern and Northern blotting. This would allow a gene product, or fragment thereof, to be analyzed, both in diverse cell types and also in various bacterial cells. The total size of fragment, as well as the size of the complementary stretch (es), will ultimately depend on the intended use or application of the particular nucleic acid segment. Smaller fragments will generally find use in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15–25 nucleotides in length allows the formation of a duplex molecule that is both stable and selective. Molecules having contiguous complementary sequences over stretches greater than 15 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 25 contiguous nucleotides, or even longer where desired.

Hybridization probes may be selected from any portion of any of the sequences disclosed herein. All that is required is to review the sequence set forth in SEQ ID NO:1–175, 178, 180, 182–468, 474, 476, 477 479, 484, 486 and 489, or to any continuous portion of the sequence, from about 15–25 nucleotides in length up to and including the full length sequence, that one wishes to utilize as a probe or primer. The choice of probe and primer sequences may be governed by various factors. For example, one may wish to employ primers from towards the termini of the total sequence.

Small polynucleotide segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

The nucleotide sequences of the invention may be used for their ability to selectively form duplex molecules with complementary stretches of the entire gene or gene fragments of interest. Depending on the application envisioned, one will typically desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by a salt concentration of from about 0.02 M to about 0.15 M salt at temperatures of from about 50° C. to about 70° C. Such selective conditions tolerate little, if any, mismatch between the probe and the template or target strand, and would be particularly suitable for isolating related sequences.

Of course, for some applications, for example, where one desires to prepare mutants employing a mutant primer strand hybridized to an underlying template, less stringent (reduced stringency) hybridization conditions will typically be needed in order to allow formation of the heteroduplex. In these circumstances, one may desire to employ salt conditions such as those of from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

Polynucleotide Identification and Characterization

Polynucleotides may be identified, prepared and/or manipulated using any of a variety of well established techniques. For example, a polynucleotide may be identified, as described in more detail below, by screening a microarray of cDNAs for tumor-associated expression (i.e., expression that is at least two fold greater in a tumor than in normal tissue, as determined using a representative assay provided herein). Such screens may be performed, for example, using a Synteni microarray (Palo Alto, Calif.) according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997). Alternatively, polynucleotides may be amplified from cDNA prepared from cells expressing the proteins described herein, such as breast tumor cells. Such polynucleotides may be amplified via polymerase chain reaction (PCR). For this approach, sequence-specific primers may be designed based on the sequences provided herein, and may be purchased or synthesized.

An amplified portion of a polynucleotide of the present invention may be used to isolate a full length gene from a suitable library (e.g., a breast tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}$p) using well known techniques. A bacterial or bacteriophage library is then generally screened by hybridizing filters containing denatured bacterial colonies (or lawns containing phage plaques) with the labeled probe (see Sambrook et al., *Molecular Cloning: A Laboratory Manual,* Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111–19, 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

Polynucleotide Expression in Host Cells

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al. (1980) *Nucl. Acids Res. Symp. Ser.* 215–223, Horn, T. et al. (1980) *Nucl. Acids Res. Symp. Ser.* 225–232). Alternatively, the protein itself may be produced using chemical methods to synthesize the amino acid sequence of a polypeptide, or a portion thereof. For example, peptide synthesis can be performed using various solid-phase techniques (Roberge, J. Y. et al. (1995) *Science* 269:202–204) and automated synthesis may be achieved, for example, using the ABI 431 A Peptide Synthesizer (Perkin E1 mer, Palo Alto, Calif.).

A newly synthesized peptide may be substantially purified by preparative high performance liquid chromatography (e.g., Creighton, T. (1983) Proteins, Structures and Molecular Principles, W H Freeman and Co., New York, N.Y.) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems may be utilized to contain and express polynucleotide sequences.

These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non—translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of .beta.-galactosidase so that a hybrid protein is produced; pIN vectors (Van Heeke, G. and S. M. Schuster (1989) *J. Biol. Chem.* 264:5503–5509); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase, and PGH may be used. For reviews, see Ausubel et al. (supra) and Grant et al. (1987) *Methods Enzymol.* 153:516–544.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, N. (1987) *EMBO J.* 6:307–311. Alternatively, plant promoters such as the small subunit of RUBISCO or heat shock promoters may be used (Coruzzi, G. et al. (1984) *EMBO J.* 3:1671–1680; Broglie, R. et al. (1984) *Science* 224:838–843; and Winter, J. et al. (1991) *Results Probl. Cell Differ.* 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191–196).

An insect system may also be used to express a polypeptide of interest. For example, in one such system, Autographa californica nuclear polyhedrosis virus (AcNPV) is used as a vector to express foreign genes in Spodoptera frugiperda cells or in Trichoplusia larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, S. frugiperda cells or Trichoplusia larvae in which the polypeptide of interest may be expressed (Engelhard, E. K. et al. (1994) *Proc. Natl. Acad. Sci.* 91:3224–3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) *Cell* 11:223–32) and adenine phosphoribosyltransferase (Lowy, I. et al. (1990) *Cell* 22:817–23) genes which can be employed in $tk^-$ or $aprt^-$ cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci.* 77:3567–70); npt, which confers resistance to the aminoglycosides, neomycin and G-418 (Colbere-Garapin, F. et al (1981) *J. Mol. Biol.* 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) *Proc. Natl. Acad. Sci.* 85:8047–51). Recently, the use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121–131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells which contain and express a desired polynucleotide sequence may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; *J. Exp. Med.* 158:1211–1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, *Prot. Exp. Purif.* 3:263 –281) while the enterokinase cleavage site provides a means for purifying the desired polypeptide from the fusion protein. A discussion of vectors which contain fusion proteins is provided in Kroll, D. J. et al. (1993; *DNA Cell Biol.* 12:441–453).

In addition to recombinant production methods, polypeptides of the invention, and fragments thereof, may be produced by direct peptide synthesis using solid-phase techniques (Merrifield J. (1963) *J. Am. Chem. Soc.* 85:2149–2154). Protein synthesis may be performed using manual techniques or by automation. Automated synthesis may be achieved, for example, using Applied Biosystems 431A Peptide Synthesizer (Perkin E1 mer). Alternatively, various fragments may be chemically synthesized separately and combined using chemical methods to produce the full length molecule.

Site-Specific Mutagenesis

Site-specific mutagenesis is a technique useful in the preparation of individual peptides, or biologically functional equivalent polypeptides, through specific mutagenesis of the underlying polynucleotides that encode them. The technique, well-known to those of skill in the art, further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to alter one or more properties of the encoded polypeptide, such as the antigenicity of a polypeptide vaccine. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as *E. Coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

Polynucleotide Amplification Techniques

A number of template dependent processes are available to amplify the target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art.

Another method for amplification is the ligase chain reaction (referred to as LCR), disclosed in Eur. Pat. Appl. Publ. No. 320,308 (specifically incorporated herein by reference in its entirety). In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference in its entirety, describes an alternative method of amplification similar to LCR for binding probe pairs to a target sequence.

Qbeta Replicase, described in PCT Intl. Pat. Appl. Publ. No. PCT/US87/00880, incorporated herein by reference in its entirety, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[α-thio] triphosphates in one strand of a restriction site (Walker et al., 1992, incorporated herein by reference in its entirety), may also be useful in the amplification of nucleic acids in the present invention.

Strand Displacement Amplification (SDA) is another method of carrying out isothermal amplification of nucleic acids which involves multiple rounds of strand displacement and synthesis, i.e. nick translation. A similar method, called Repair Chain Reaction (RCR) is another method of amplification which may be useful in the present invention and is involves annealing several probes throughout a region targeted for amplification, followed by a repair reaction in which only two of the four bases are present. The other two bases can be added as biotinylated derivatives for easy detection. A similar approach is used in SDA.

Sequences can also be detected using a cyclic probe reaction (CPR). In CPR, a probe having a 3' and 5' sequences of non-target DNA and an internal or "middle" sequence of the target protein specific RNA is hybridized to DNA which is present in a sample. Upon hybridization, the reaction is treated with RNaseH, and the products of the probe are identified as distinctive products by generating a signal that is released after digestion. The original template is annealed to another cycling probe and the reaction is repeated. Thus, CPR involves amplifying a signal generated by hybridization of a probe to a target gene specific expressed nucleic acid.

Still other amplification methods described in Great Britain Pat. Appl. No. 2 202 328, and in PCT Intl. Pat. Appl. Publ. No. PCT/US89/01025, each of which is incorporated herein by reference in its entirety, may be used in accordance with the present invention. In the former application, "modified" primers are used in a PCR-like, template and enzyme dependent synthesis. The primers may be modified by labeling with a capture moiety (e.g., biotin) and/or a detector moiety (e.g., enzyme). In the latter application, an excess of labeled probes is added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS) (Kwoh et al., 1989; PCT Intl. Pat. Appl. Publ. No. WO 88/10315, incorporated herein by reference in its entirety), including nucleic acid sequence based amplification (NASBA) and 3SR. In NASBA, the nucleic acids can be prepared for amplification by standard phenol/chloroform extraction, heat denaturation of a sample, treatment with lysis buffer and minispin columns for isolation of DNA and RNA or guanidinium chloride extraction of RNA. These amplification techniques involve annealing a primer that has sequences specific to the target sequence. Following polymerization, DNA/RNA hybrids are digested with RNase H while double stranded DNA molecules are heat-denatured again. In either case the single stranded DNA is made fully double stranded by addition of second target-specific primer, followed by polymerization. The double stranded DNA molecules are then multiply transcribed by a polymerase such as T7 or SP6. In an isothermal cyclic reaction, the RNAs are reverse transcribed into DNA, and transcribed once again with a polymerase such as T7 or SP6. The resulting products, whether truncated or complete, indicate target-specific sequences.

Eur. Pat. Appl. Publ. No. 329,822, incorporated herein by reference in its entirety, disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of E. coli DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

PCT Intl. Pat. Appl. Publ. No. WO 89/06700, incorporated herein by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "RACE" (Frohman, 1990), and "one-sided PCR" (Ohara, 1989) which are well-known to those of skill in the art.

Methods based on ligation of two (or more) oligonucleotides in the presence of nucleic acid having the sequence of the resulting "di-oligonucleotide", thereby amplifying the di-oligonucleotide (Wu and Dean, 1996, incorporated herein by reference in its entirety), may also be used in the amplification of DNA sequences of the present invention.

Biobogical Functional Equivalents

Modification and changes may be made in the structure of the polynucleotides and polypeptides of the present invention and still obtain a functional molecule that encodes a polypeptide with desirable characteristics. As mentioned above, it is often desirable to introduce one or more mutations into a specific polynucleotide sequence. In certain circumstances, the resulting encoded polypeptide sequence is altered by this mutation, or in other cases, the sequence of the polypeptide is unchanged by one or more mutations in the encoding polynucleotide.

When it is desirable to alter the amino acid sequence of a polypeptide to create an equivalent, or even an improved, second-generation molecule, the amino acid changes may be achieved by changing one or more of the codons of the encoding DNA sequence, according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

In vivo Polynucleotide Delivery Techniques

In additional embodiments, genetic constructs comprising one or more of the polynucleotides of the invention are introduced into cells in vivo. This may be achieved using any of a variety or well known approaches, several of which are outlined below for the purpose of illustration.

1. Adenovirus

One of the preferred methods for in vivo delivery of one or more nucleic acid sequences involves the use of an adenovirus expression vector. "Adenovirus expression vector" is meant to include those constructs containing adenovirus sequences sufficient to (a) support packaging of the construct and (b) to express a polynucleotide that has been cloned therein in a sense or antisense orientation. Of course, in the context of an antisense construct, expression does not require that the gene product be synthesized.

The expression vector comprises a genetically engineered form of an adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the currently preferred helper cell line is 293.

Recently, Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain a conditional replication-defective adenovirus vector for use in the present invention, since Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

2. Retroviruses

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding one or more oligonucleotide or polynucleotide sequences of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

3. Adeno-Associated Viruses

AAV (Ridgeway, 1988; Hermonat and Muzycska, 1984) is a parovirus, discovered as a contamination of adenoviral stocks. It is a ubiquitous virus (antibodies are present in 85% of the US human population) that has not been linked to any disease. It is also classified as a dependovirus, because its replications is dependent on the presence of a helper virus, such as adenovirus. Five serotypes have been isolated, of which AAV-2 is the best characterized. AAV has a single-stranded linear DNA that is encapsidated into capsid proteins VP1, VP2 and VP3 to form an icosahedral virion of 20 to 24 nm in diameter (Muzyczka and McLaughlin, 1988).

The AAV DNA is approximately 4.7 kilobases long. It contains two open reading frames and is flanked by two ITRs. There are two major genes in the AAV genome: rep and cap. The rep gene codes for proteins responsible for viral replications, whereas cap codes for capsid protein VP1-3. Each ITR forms a T-shaped hairpin structure. These terminal repeats are the only essential cis components of the AAV for chromosomal integration. Therefore, the AAV can be used as a vector with all viral coding sequences removed and replaced by the cassette of genes for delivery. Three viral promoters have been identified and named p5, p19, and p40, according to their map position. Transcription from p5 and p19 results in production of rep proteins, and transcription from p40 produces the capsid proteins (Hermonat and Muzyczka, 1984).

There are several factors that prompted researchers to study the possibility of using rAAV as an expression vector One is that the requirements for delivering a gene to integrate into the host chromosome are surprisingly few. It is necessary to have the 145-bp ITRs, which are only 6% of the AAV genome. This leaves room in the vector to assemble a 4.5-kb DNA insertion. While this carrying capacity may prevent the AAV from delivering large genes, it is amply suited for delivering the antisense constructs of the present invention.

AAV is also a good choice of delivery vehicles due to its safety. There is a relatively complicated rescue mechanism: not only wild type adenovirus but also AAV genes are required to mobilize rAAV. Likewise, AAV is not pathogenic and not associated with any disease. The removal of viral coding sequences minimizes immune reactions to viral gene expression, and therefore, rAAV does not evoke an inflammatory response.

4. Other Viral Vectors as Expression Constructs

Other viral vectors may be employed as expression constructs in the present invention for the delivery of oligonucleotide or polynucleotide sequences to a host cell. Vectors derived from viruses such as vaccinia virus (Ridgeway, 1988; Coupar et al., 1988), lentiviruses, polio viruses and herpes viruses may be employed. They offer several attractive features for various mammalian cells (Friedmann, 1989; Ridgeway, 1988; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. (1991) introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

5. Non-Viral Vectors

In order to effect expression of the oligonucleotide or polynucleotide sequences of the present invention, the expression construct must be delivered into a cell. This delivery may be accomplished in vitro, as in laboratory procedures for transforming cells lines, or in vivo or ex vivo, as in the treatment of certain disease states. As described above, one preferred mechanism for delivery is via viral infection where the expression construct is encapsulated in an infectious viral particle.

Once the expression construct has been delivered into the cell the nucleic acid encoding the desired oligonucleotide or polynucleotide sequences may be positioned and expressed at different sites. In certain embodiments, the nucleic acid encoding the construct may be stably integrated into the genome of the cell. This integration may be in the specific location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In certain embodiments of the invention, the expression construct comprising one or more oligonucleotide or polynucleotide sequences may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomaviras DNA in the form of calcium phosphate precipitates into liver and spleen of adult and newborn mice demonstrating active viral replication and acute infection. Benvenisty and Reshef (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e. ex vivo treatment. Again, DNA encoding a particular gene may be delivered via this method and still be incorporated by the present invention.

Antisense Oligonucleotedes

The end result of the flow of genetic information is the synthesis of protein. DNA is transcribed by polymerases into messenger RNA and translated on the ribosome to yield a folded, functional protein. Thus there are several steps along the route where protein synthesis can be inhibited. The native DNA segment coding for a polypeptide described herein, as all such mammalian DNA strands, has two strands: a sense strand and an antisense strand held together by hydrogen bonding. The messenger RNA coding for polypeptide has the same nucleotide sequence as the sense DNA strand except that the DNA thymidine is replaced by uridine. Thus, synthetic antisense nucleotide sequences will bind to a mRNA and inhibit expression of the protein encoded by that mRNA.

The targeting of antisense oligonucleotides to mRNA is thus one mechanism to shut down protein synthesis, and, consequently, represents a powerful and targeted therapeutic approach. For example, the synthesis of polygalactauronase and the muscarine type 2 acetylcholine receptor are inhibited by antisense oligonucleotides directed to their respective mRNA sequences (U.S. Pat. Nos. 5,739,119 and 5,759,829, each specifically incorporated herein by reference in its entirety). Further, examples of antisense inhibition have been demonstrated with the nuclear protein cyclin, the multiple drug resistance gene (MDG1), ICAM-1, E-selectin, STK-1, striatal $GABA_A$ receptor and human EGF (Jaskulski et al., 1988; Vasanthakumar and Amlued, 1989; Peris et al., 1998; U.S. Pat. Nos. 5,801,154; 5,789,573; 5,718,709 and 5,610,288, each specifically incorporated herein by reference in its entirety). Antisense constructs have also been described that inhibit and can be used to treat a variety of abnormal cellular proliferations, e.g. cancer (U.S. Pat. Nos. 5,747,470; 5,591,317 and 5,783,683, each specifically incorporated herein by reference in its entirety).

Therefore, in exemplary embodiments, the invention provides oligonucleotide sequences that comprise all, or a portion of, any sequence that is capable of specifically binding to polynucleotide sequence described herein, or a complement thereof. In one embodiment, the antisense oligonucleotides comprise DNA or derivatives thereof. In another embodiment, the oligonucleotides comprise RNA or derivatives thereof. In a third embodiment, the oligonucleotides are modified DNAs comprising a phosphorothioated modified backbone. In a fourth embodiment, the oligonucleotide sequences comprise peptide nucleic acids or derivatives thereof. In each case, preferred compositions comprise a sequence region that is complementary, and more preferably substantially-complementary, and even more preferably, completely complementary to one or more portions of polynucleotides disclosed herein.

Selection of antisense compositions specific for a given gene sequence is based upon analysis of the chosen target sequence (i.e. in these illustrative examples the rat and human sequences) and determination of secondary structure, $T_m$, binding energy, relative stability, and antisense compositions were selected based upon their relative inability to form dimers, hairpins, or other secondary structures that would reduce or prohibit specific binding to the target mRNA in a host cell.

Highly preferred target regions of the mRNA, are those which are at or near the AUG translation initiation codon, and those sequences which were substantially complementary to 5' regions of the mRNA. These secondary structure analyses and target site selection considerations were performed using v.4 of the OLIGO primer analysis software (Rychlik, 1997) and the BLASTN 2.0.5 algorithm software (Altschul et al., 1997).

The use of an antisense delivery method employing a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., 1997). It has been demonstrated that several molecules of the MPG peptide coat the antisense oligonucleotides and can be delivered into cultured mammalian cells in less than 1 hour with relatively high efficiency (90%). Further, the interaction with MPG strongly increases both the stability of the oligonucleotide to nuclease and the ability to cross the plasma membrane (Morris et al., 1997).

Ribozymes

Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 (specifically incorporated herein by reference) reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., 1992). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or Neurospora VS RNA motif. Examples of hammerhead motifs are described by Rossi et al (1992). Examples of hairpin motifs are described by Hampel et al. (Eur. Pat. Appl. Publ. No. EP 0360257), Hampel and Tritz (1989), Hampel et al. (1990) and U.S. Pat. No. 5,631,359 (specifically incorporated herein by reference). An example of the hepatitis δ virus motif is described by Perrotta and Been (1992); an example of the RNaseP motif is described by Guerrier-Takada et al. (1983); Neurospora VS RNA ribozyme motif is described by Collins (Saville and Collins, 1990; Saville and Collins, 1991; Collins and Olive, 1993); and an example of the Group I intron is described in (U.S. Pat. No. 4,987,071, specifically incorporated herein by reference). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

In certain embodiments, it may be important to produce enzymatic cleaving agents which exhibit a high degree of specificity for the RNA of a desired target, such as one of the sequences disclosed herein. The enzymatic nucleic acid molecule is preferably targeted to a highly conserved sequence region of a target mRNA. Such enzymatic nucleic acid molecules can be delivered exogenously to specific cells as required. Alternatively, the ribozymes can be expressed from DNA or RNA vectors that are delivered to specific cells.

Small enzymatic nucleic acid motifs (e.g., of the hammerhead or the hairpin structure) may also be used for exogenous delivery. The simple structure of these molecules increases the ability of the enzymatic nucleic acid to invade targeted regions of the mRNA structure. Alternatively, catalytic RNA molecules can be expressed within cells from eukaryotic promoters (e.g., Scanlon et al., 1991; Kashani-Sabet et al., 1992; Dropulic et al., 1992; Weerasinghe et al., 1991; Ojwang et al., 1992; Chen et al., 1992; Sarver et al., 1990). Those skilled in the art realize that any ribozyme can be expressed in eukaryotic cells from the appropriate DNA vector. The activity of such ribozymes can be augmented by their release from the primary transcript by a second ribozyme (Int. Pat. Appl. Publ. No. WO 93/23569, and Int. Pat. Appl. Publ. No. WO 94/02595, both hereby incorporated by reference; Ohkawa et al., 1992; Taira et al., 1991; and Ventura et al., 1993).

Ribozymes may be added directly, or can be complexed with cationic lipids, lipid complexes, packaged within liposomes, or otherwise delivered to target cells. The RNA or RNA complexes can be locally administered to relevant tissues ex vivo, or in vivo through injection, aerosol inhalation, infusion pump or stent, with or without their incorporation in biopolymers.

Ribozymes may be designed as described in Int. Pat. Appl. Publ. No. WO 93/23569 and Int. Pat. Appl. Publ. No. WO 94/02595, each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Hammerhead or hairpin ribozymes may be individually analyzed by computer folding (Jaeger et al., 1989) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 or so bases on each arm are able to bind to, or otherwise interact with, the target RNA.

Ribozymes of the hammerhead or hairpin motif may be designed to anneal to various sites in the mRNA message, and can be chemically synthesized. The method of synthesis used follows the procedure for normal RNA synthesis as described in Usman etal. (1987) and in Scaringe etal. (1990) and makes use of common nucleic acid protecting and coupling groups, such as dimethoxytrityl at the 5'-end, and phosphoramidites at the 3'-end. Average stepwise coupling yields are typically >98%. Hairpin ribozymes may be synthesized in two parts and annealed to reconstruct an active ribozyme (Chowrira and Burke, 1992). Ribozymes may be modified extensively to enhance stability by modification with nuclease resistant groups, for example, 2'-amino, 2'-C-allyl, 2'-flouro, 2'-o-methyl, 2'-H (for a review see e.g., Usman and Cedergren, 1992). Ribozymes may be purified by gel electrophoresis using general methods or by high pressure liquid chromatography and resuspended in water.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Perrault et al., 1990; Pieken etal., 1991; Usman and Cedergren, 1992; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. Pat. Appl. Publ. No. WO 94/02595 and Int. Pat. Appl. Publ. No. WO 93/23569, each specifically incorporated herein by reference.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells (El roy-Stein and Moss, 1990; Gao and Huang, 1993; Lieber et al., 1993; Zhou et al., 1990). Ribozymes expressed from such promoters can function in mammalian cells (e.g. Kashani-Saber et al., 1992; Ojwang et al., 1992; Chen et al., 1992; Yu et al., 1993; L'Huillier et al., 1992; Lisziewicz et al., 1993). Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

Ribozymes may be used as diagnostic tools to examine genetic drift and mutations within diseased cells. They can also be used to assess levels of the target RNA molecule. The close relationship between ribozyme activity and the structure of the target RNA allows the detection of mutations in any region of the molecule which alters the base-pairing and three-dimensional structure of the target RNA. By using multiple ribozymes, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These studies will lead to better treatment of the disease progression by affording the possibility of combinational therapies (e.g., multiple ribozymes targeted to different genes, ribozymes coupled with known small molecule inhibitors, or intermittent treatment with combinations of ribozymes and/ or other chemical or biological molecules). Other in vitro uses of ribozymes are well known in the art, and include detection of the presence of mRNA associated with an IL-5 related condition. Such RNA is detected by determining the presence of a cleavage product after treatment with a ribozyme using standard methodology.

Peptide Nucleic Acids

In certain embodiments, the inventors contemplate the use of peptide nucleic acids (PNAs) in the practice of the methods of the invention. PNA is a DNA mimic in which the nucleobases are attached to a pseudopeptide backbone (Good and Nielsen, 1997). PNA is able to be utilized in a number methods that traditionally have used RNA or DNA. Often PNA sequences perform better in techniques than the corresponding RNA or DNA sequences and have utilities that are not inherent to RNA or DNA. A review of PNA including methods of making, characteristics of, and methods of using, is provided by Corey (1997) and is incorporated herein by reference. As such, in certain embodiments, one may prepare PNA sequences that are complementary to one or more portions of the ACE mRNA sequence, and such PNA compositions may be used to regulate, alter, decrease, or reduce the translation of ACE-specific mRNA, and thereby alter the level of ACE activity in a host cell to which such PNA compositions have been administered.

PNAs have 2-aminoethyl-glycine linkages replacing the normal phosphodiester backbone of DNA (Nielsen et al., 1991; Hanvey et al., 1992; Hyrup and Nielsen, 1996; Neilsen, 1996). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc (Dueholm et al., 1994) or Fmoc (Thomson et al., 1995) protocols for solid-phase peptide synthesis, although other methods, including a modified Merrifield method, have been used (Christensen et al., 1995).

PNA monomers or ready-made oligomers are commercially available from PerSeptive Biosystems (Framingham, Mass.). PNA syntheses by either Boc or Fmoc protocols are straightforward using manual or automated protocols (Norton et al., 1995). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography (Norton et al., 1995) providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (Norton et al., 1995; Haaima et al., 1996; Stetsenko et al., 1996; Petersen et al., 1995; Ulmann et al., 1996; Koch et al., 1995; Orum et al., 1995; Footer et al., 1996; Griffith et al., 1995; Kremsky et al., 1996; Pardridge et al., 1995; Boffa et al., 1995; Landsdorp et al., 1996; Gambacorti-Passerini et al., 1996; Armitage et al., 1997; Seeger et al., 1997; Ruskowski et al., 1997). U.S. Pat. No. 5,700,922 discusses PNA-DNA-PNA chimeric molecules and their uses in diagnostics, modulating protein in organisms, and treatment of conditions susceptible to therapeutics.

In contrast to DNA and RNA, which contain negatively charged linkages, the PNA backbone is neutral. In spite of this dramatic alteration, PNAs recognize complementary DNA and RNA by Watson-Crick pairing (Egholm et al., 1993), validating the initial modeling by Nielsen et al. (1991). PNAs lack 3' to 5' polarity and can bind in either parallel or antiparallel fashion, with the antiparallel mode being preferred (Egholm et al., 1993).

Hybridization of DNA oligonucleotides to DNA and RNA is destabilized by electrostatic repulsion between the negatively charged phosphate backbones of the complementary strands. By contrast, the absence of charge repulsion in PNA-DNA or PNA-RNA duplexes increases the melting temperature ($T_m$) and reduces the dependence of $T_m$ on the concentration of mono- or divalent cations (Nielsen et al., 1991). The enhanced rate and affinity of hybridization are significant because they are responsible for the surprising ability of PNAs to perform strand invasion of complementary sequences within relaxed double-stranded DNA. In addition, the efficient hybridization at inverted repeats suggests that PNAs can recognize secondary structure effectively within double-stranded DNA. Enhanced recognition also occurs with PNAs immobilized on surfaces, and Wang et al. have shown that support-bound PNAs can be used to detect hybridization events (Wang et al., 1996).

One might expect that tight binding of PNAs to complementary sequences would also increase binding to similar (but not identical) sequences, reducing the sequence specificity of PNA recognition. As with DNA hybridization, however, selective recognition can be achieved by balancing oligomer length and incubation temperature. Moreover, selective hybridization of PNAs is encouraged by PNA-DNA hybridization being less tolerant of base mismatches than DNA—DNA hybridization. For example, a single mismatch within a 16 bp PNA-DNA duplex can reduce the $T_m$ by up to 15° C. (Egholm et al., 1993). This high level of discrimination has allowed the development of several PNA-based strategies for the analysis of point mutations (Wang et al., 1996; Carlsson et al., 1996; Thiede et al., 1996; Webb and Hurskainen, 1996; Perry-O'Keefe et al., 1996).

High-affinity binding provides clear advantages for molecular recognition and the development of new applications for PNAs. For example, 11–13 nucleotide PNAs inhibit the activity of telomerase, a ribonucleo-protein that extends telomere ends using an essential RNA template, while the analogous DNA oligomers do not (Norton et al., 1996).

Neutral PNAs are more hydrophobic than analogous DNA oligomers, and this can lead to difficulty solubilizing them at neutral pH, especially if the PNAs have a high purine content or if they have the potential to form secondary structures. Their solubility can be enhanced by attaching one or more positive charges to the PNA termini (Nielsen et al., 1991).

Findings by Allfrey and colleagues suggest that strand invasion will occur spontaneously at sequences within chromosomal DNA (Boffa et al., 1995; Boffa et al., 1996). These studies targeted PNAs to triplet repeats of the nucleotides CAG and used this recognition to purify transcriptionally active DNA (Boffa et al., 1995) and to inhibit transcription (Boffa et al., 1996). This result suggests that if PNAs can be delivered within cells then they will have the potential to be general sequence-specific regulators of gene expression. Studies and reviews concerning the use of PNAs as antisense and anti-gene agents include Nielsen et al. (1993b), Hanvey et al. (1992), and Good and Nielsen (1997). Koppelhus et al. (1997) have used PNAs to inhibit HIV-1 inverse transcription, showing that PNAs may be used for antiviral therapies.

Methods of characterizing the antisense binding properties of PNAs are discussed in Rose (1993) and Jensen et al. (1997). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs include use in DNA strand invasion (Nielsen et al., 1991), antisense inhibition (Hanvey et al., 1992), mutational analysis (Orum et al., 1993), enhancers of transcription (Mollegaard et al., 1994), nucleic acid purification (Orum et al., 1995), isolation of transcriptionally active genes (Boffa et al., 1995), blocking of transcription factor binding (Vickers et al., 1995), genome cleavage (Veselkov et al., 1996), biosensors (Wang et al., 1996), in situ hybridization (Thisted et al., 1996), and in a alternative to Southern blotting (Perry-O'Keefe, 1996).

Polypeptide Compositions

The present invention, in other aspects, provides polypeptide compositions. Generally, a polypeptide of the invention will be an isolated polypeptide (or an epitope, variant, or active fragment thereof) derived from a mammalian species. Preferably, the polypeptide is encoded by a polynucleotide sequence disclosed herein or a sequence which hybridizes under moderately stringent conditions to a polynucleotide sequence disclosed herein. Alternatively, the polypeptide may be defined as a polypeptide which comprises a contiguous amino acid sequence from an amino acid sequence disclosed herein, or which polypeptide comprises an entire amino acid sequence disclosed herein.

In the present invention, a polypeptide composition is also understood to comprise one or more polypeptides that are immunologically reactive with antibodies generated against a polypeptide of the invention, particularly a polypeptide having the amino acid sequence disclosed in SEQ ID NO:176, 179, 181, 469–473, 475, 485, 487 and 488, or to active fragments, or to variants or biological functional equivalents thereof.

Likewise, a polypeptide composition of the present invention is understood to comprise one or more polypeptides that are capable of eliciting antibodies that are immunologically reactive with one or more polypeptides encoded by one or more contiguous nucleic acid sequences contained in SEQ ID NO:1–175, 178, 180, 182–468, 474, 476, 477 479, 484, 486 and 489, or to active fragments, or to variants thereof, or to one or more nucleic acid sequences which hybridize to one or more of these sequences under conditions of moderate to high stringency. Particularly illustrative polypeptides include the amino acid sequence disclosed in SEQ ID NO:176, 179, 181, 469–473, 475, 485, 487 and 488.

As used herein, an active fragment of a polypeptide includes a whole or a portion of a polypeptide which is modified by conventional techniques, e.g., mutagenesis, or by addition, deletion, or substitution, but which active fragment exhibits substantially the same structure function, antigenicity, etc., as a polypeptide as described herein.

In certain illustrative embodiments, the polypeptides of the invention will comprise at least an immunogenic portion of a breast tumor protein or a variant thereof, as described herein. As noted above, a "breast tumor protein" is a protein that is expressed by breast tumor cells. Proteins that are breast tumor proteins also react detectably within an immunoassay (such as an ELISA) with antisera from a patient with breast cancer. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of a protein that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of a breast tumor protein or a variant thereof. Certain preferred immunogenic portions include peptides in which an N-terminal leader sequence and/or transmembrane domain have been deleted. Other preferred immunogenic portions may contain a small N- and/or C-terminal deletion (e.g., 1–30 amino acids, preferably 5–15 amino acids), relative to the mature protein.

Immunogenic portions may generally be identified using well known techniques, such as those summarized in Paul, *Fundamental Immunology*, 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a native breast tumor protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual*. Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a composition may comprise a variant of a native breast tumor protein. A polypeptide "variant," as used herein, is a polypeptide that differs from a native breast tumor protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1–30 amino acids, preferably 5–15 amino acids) has been removed from the N- and/or C-terminal of the mature protein.

Polypeptide variants encompassed by the present invention include those exhibiting at least about 70%, 75%, 80%, 85%, 90%, 91%, 92%, 93%, 94%, 95%, 96% 97%, 98%, or 99% or more identity (determined as described above) to the polypeptides disclosed herein.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, and higher eukaryotic cells, such as mammalian cells and plant cells. Preferably, the host cells employed are *E. coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having less than about 100 amino acids, and generally less than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin E1 mer/Applied BioSystems Division (Foster City, Calif.), and may be operated according to the manufacturer's instructions.

Within certain specific embodiments, a polypeptide may be a fusion protein that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided. Such proteins comprise a polypeptide as described herein together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.*, 336:86–91, 1997).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Binding Agents

The present invention further provides agents, such as antibodies and antigen-binding fragments thereof, that specifically bind to a breast tumor protein. As used herein, an antibody, or antigen-binding fragment thereof, is said to "specifically bind" to a breast tumor protein if it reacts at a detectable level (within, for example, an ELISA) with a breast tumor protein, and does not react detectably with unrelated proteins under similar conditions. As used herein, "binding" refers to a noncovalent association between two separate molecules such that a complex is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant may be determined using methods well known in the art.

Binding agents may be further capable of differentiating between patients with and without a cancer, such as breast cancer, using the representative assays provided herein. In other words, antibodies or other binding agents that bind to a breast tumor protein will generate a signal indicating the presence of a cancer in at least about 20% of patients with the disease, and will generate a negative signal indicating the absence of the disease in at least about 90% of individuals without the cancer. To determine whether a binding agent satisfies this requirement, biological samples (e.g., blood, sera, sputum, urine and/or tumor biopsies) from patients with and without a cancer (as determined using standard clinical tests) may be assayed as described herein for the presence of polypeptides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

T Cells

Immunotherapeutic compositions may also, or alternatively, comprise T cells specific for a breast tumor protein. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. (Irvine, Calif.; see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a breast tumor polypeptide, polynucleotide encoding a breast tumor polypeptide and/or an antigen presenting cell (APC) that expresses such a polypeptide. Such stimulation is performed under conditions and for a time sufficient to permit the generation of T cells that are specific for the polypeptide. Preferably, a breast tumor polypeptide or polynucleotide is present within a delivery vehicle, such as a microsphere, to facilitate the generation of specific T cells.

T cells are considered to be specific for a breast tumor polypeptide if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., Cancer Res. 54:1065 –1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a breast tumor polypeptide (100 ng/ml –100 μg/ml, preferably 200 ng/ml 25 μg/ml) for 3–7 days should result in at least a two fold increase in proliferation of the T cells. Contact as described above for 2–3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a breast tumor polypeptide, polynucleotide or polypeptide-expressing APC may be CD4$^+$ and/or CD8$^+$. Breast tumor protein-specific T cells may be expanded using standard techniques. Within preferred embodiments, the T cells are derived from a patient, a related donor or an unrelated donor, and are administered to the patient following stimulation and expansion.

For therapeutic purposes, CD4$^+$ or CD8$^+$ T cells that proliferate in response to a breast tumor polypeptide, polynucleotide or APC can be expanded in number either in vitro or in vivo. Proliferation of such T cells in vitro may be accomplished in a variety of ways. For example, the T cells can be re-exposed to a breast tumor polypeptide, or a short peptide corresponding to an immunogenic portion of such a polypeptide, with or without the addition of T cell growth factors, such as interleukin-2, and/or stimulator cells that synthesize a breast tumor polypeptide. Alternatively, one or more T cells that proliferate in the presence of a breast tumor protein can be expanded in number by cloning. Methods for cloning cells are well known in the art, and include limiting dilution.

Pharmaceutical Compositions

In additional embodiments, the present invention concerns formulation of one or more of the polynucleotide, polypeptide, T-cell and/or antibody compositions disclosed herein in pharmaceutically-acceptable solutions for administration to a cell or an animal, either alone, or in combination with one or more other modalities of therapy.

It will also be understood that, if desired, the nucleic acid segment, RNA, DNA or PNA compositions that express a polypeptide as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

1. Oral Delivery

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

2. Injectable Delivery

In certain circumstances it will be desirable to deliver the pharmaceutical compositions disclosed herein parenterally, intravenously, intramuscularly, or even intraperitoneally as described in U.S. Pat. Nos. 5,543,158; 5,641,515 and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

3. Nasal Delivery

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

4. Liposome-, Nanocapsule-, and Microparticle-Mediated Delivery

In certain embodiments, the inventors contemplate the use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, or a nanoparticle or the like.

Such formulations may be preferred for the introduction of pharmaceutically-acceptable formulations of the nucleic acids or constructs disclosed herein. The formation and use of liposomes is generally known to those of skill in the art (see for example, Couvreur et al., 1977; Couvreur, 1988; Lasic, 1998; which describes the use of liposomes and nanocapsules in the targeted antibiotic therapy for intracellular bacterial infections and diseases). Recently, liposomes were developed with improved serum stability and circulation half-times (Gabizon and Papahadjopoulos, 1988; Allen and Choun, 1987; U.S. Pat. No. 5,741,516, specifically incorporated herein by reference in its entirety). Further, various methods of liposome and liposome like preparations as potential drug carriers have been reviewed (Takakura, 1998; Chandran et al., 1997; Margalit, 1995; U.S. Pat. Nos. 5,567,434; 5,552,157; 5,565,213; 5,738,868 and 5,795,587, each specifically incorporated herein by reference in its entirety).

Liposomes have been used successfully with a number of cell types that are normally resistant to transfection by other procedures including T cell suspensions, primary hepatocyte cultures and PC 12 cells (Renneisen et al., 1990; Muller et al., 1990). In addition, liposomes are free of the DNA length constraints that are typical of viral-based delivery systems. Liposomes have been used effectively to introduce genes, drugs (Heath and Martin, 1986; Heath et al., 1986; Balazsovits et al., 1989; Fresta and Puglisi, 1996), radiotherapeutic agents (Pikul et al., 1987), enzymes (Imaizumi et al., 1990a; Imaizumi et al., 1990b), viruses (Faller and Baltimore, 1984), transcription factors and allosteric effectors (Nicolau and Gersonde, 1979) into a variety of cultured cell lines and animals. In addition, several successful clinical trails examining the effectiveness of liposome-mediated drug delivery have been completed (Lopez-Berestein et al., 1985a; 1985b; Coune, 1988; Sculier et al., 1988). Furthermore, several studies suggest that the use of liposomes is not associated with autoimmune responses, toxicity or gonadal localization after systemic delivery (Mori and Fukatsu, 1992).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 $\mu$m. Sonication of MLVs results in the formation of small unilamellar vesicles (SUVs) with diameters in the range of 200 to 500 Å, containing an aqueous solution in the core.

Liposomes bear resemblance to cellular membranes and are contemplated for use in connection with the present invention as carriers for the peptide compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

In addition to the teachings of Couvreur et al. (1977; 1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins, such as cytochrome c, bind, deform and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity, and surface charge. They may persist in tissues for h or days, depending on their composition, and half lives in the blood range from min to several h. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow, and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell—cell recognition, interaction and adhesion) may also be used as recognition sites as they have potential in directing liposomes to particular cell types. Mostly, it is contemplated that intravenous injection of liposomal preparations would be used, but other routes of administration are also conceivable.

Alternatively, the invention provides for pharmaceutically-acceptable nanocapsule formulations of the compositions of the present invention. Nanocapsules can generally entrap compounds in a stable and reproducible way (Henry-Michelland et al., 1987; Quintanar-Guerrero et al., 1998; Douglas et al., 1987). To avoid side effects due to intracellular polymeric overloading, such ultrafine particles (sized around 0.1 μm) should be designed using polymers able to be degraded in vivo. Biodegradable polyalkylcyanoacrylate nanoparticles that meet these requirements are contemplated for use in the present invention. Such particles may be are easily made, as described (Couvreur et al., 1980; 1988; zur Muhlen et al., 1998; Zambaux et al. 1998; Pinto-Alphandry et al., 1995 and U.S. Pat. No. 5,145, 684, specifically incorporated herein by reference in its entirety).

Immunogenic Compositions

In certain preferred embodiments of the present invention, immunogenic compositions, or vaccines, are provided. The immunogenic compositions will generally comprise one or more pharmaceutical compositions, such as those discussed above, in combination with an immunostimulant. An immunostimulant may be any substance that enhances or potentiates an immune response (antibody and/or cell-mediated) to an exogenous antigen. Examples of immunostimulants include adjuvants, biodegradable microspheres (e.g., polylactic galactide) and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and immunogenic compositions within the scope of the present invention may also contain other compounds, which may be biologically active or inactive. For example, one or more immunogenic portions of other tumor antigens may be present, either incorporated into a fusion polypeptide or as a separate compound, within the composition.

Illustrative immunogenic compositions may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143–198, 1998, and references cited therein. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *Proc. Natl. Acad. Sci. USA* 86:317–321, 1989; Flexner et al., *Ann. N.Y Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *Proc. Natl. Acad. Sci. USA* 91:215–219, 1994; Kass-Eisler et al., *Proc. Natl. Acad. Sci. USA* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells. It will be apparent that an immunogenic composition may comprise both a polynucleotide and a polypeptide component. Such immunogenic compositions may provide for an enhanced immune response.

It will be apparent that an immunogenic composition may contain pharmaceutically acceptable salts of the polynucleotides and polypeptides provided herein. Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

While any suitable carrier known to those of ordinary skill in the art may be employed in the compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268; 5,075, 109; 5,928,647; 5,811,128; 5,820,883; 5,853,763; 5,814,344 and 5,942,252. One may also employ a carrier comprising the particulate-protein complexes described in U.S. Pat. No. 5,928,647, which are capable of inducing a class I-restricted cytotoxic T lymphocyte responses in a host.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. Compounds may also be encapsulated within liposomes using well known technology.

Any of a variety of immunostimulants may be employed in the immunogenic compositions of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2,-7, or -12, may also be used as adjuvants.

Within the immunogenic compositions provided herein, the adjuvant composition is preferably designed to induce an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of an immunogenic composition as provided herein, a patient will support an immune response that includes Th1- and Th2-type responses. Within a preferred embodiment, in which a response is predominantly Th1type, the level of Th1-type cytokines will increase to a greater extent than the level of Th2-type cytokines. The levels of these cytokines may be readily assessed using standard assays. For a review of the families of cytokines, see Mosmann and Coffinan, *Ann. Rev. Immunol.* 7:145–173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Corixa Corporation (Seattle, Wash.; see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996. Another preferred adjuvant is a saponin, preferably QS21 (Aquila Biopharmaceuticals Inc., Framingham, Mass.), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprise an oil-in-water emulsion and tocopherol. A particularly potent adjuvant formulation involving QS21, 3D-MPL and tocopherol in an oil-in-water emulsion is described in WO 95/17210.

Other preferred adjuvants include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties.

Any immunogenic composition provided herein may be prepared using well known methods that result in a combination of antigen, immune response enhancer and a suitable carrier or excipient. The compositions described herein may be administered as part of a sustained release formulation (i.e., a formulation such as a capsule, sponge or gel (composed of polysaccharides, for example) that effects a slow release of compound following administration). Such formulations may generally be prepared using well known technology (see, e.g., Coombes et al., *Vaccine* 14:1429–1438, 1996) and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane.

Carriers for use within such formulations are biocompatible, and may also be biodegradable; preferably the formulation provides a relatively constant level of active component release. Such carriers include microparticles of poly(lactide-co-glycolide), polyacrylate, latex, starch, cellulose, dextran and the like. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

Any of a variety of delivery vehicles may be employed within pharmaceutical compositions and immunogenic compositions to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245–251, 1998) and have been shown to be effective as a physiological adjuvant for eliciting prophylactic or therapeutic antitumor immunity (see Timmernan and Levy, *Ann. Rev. Med.* 50:507–529, 1999). In general, dendritic cells may be identified based on their typical shape (stellate in situ, with marked cytoplasmic processes (dendrites) visible in vitro), their ability to take up, process and present antigens with high efficiency and their ability to activate naive T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within an immunogenic composition (see Zitvogel et al., *Nature Med.* 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding a breast tumor protein (or portion or other variant thereof) such that the breast tumor polypeptide, or an immunogenic portion thereof, is expressed on the cell surface. Such transfection may take place ex vivo, and a composition comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the breast tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Immunogenic compositions and pharmaceutical compositions may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, a immunogenic composition or pharmaceutical composition may be stored in a freeze-dried condition requiring only the addition of a sterile liquid carrier immediately prior to use.

Cancer Therapy

In further aspects of the present invention, the compositions described herein may be used for immunotherapy of cancer, such as breast cancer. Within such methods, pharmaceutical compositions and immunogenic compositions are typically administered to a patient. As used herein, a "patient" refers to any warm-blooded animal, preferably a human. A patient may or may not be afflicted with cancer. Accordingly, the above pharmaceutical compositions and immunogenic compositions may be used to prevent the development of a cancer or to treat a patient afflicted with a cancer. A cancer may be diagnosed using criteria generally accepted in the art, including the presence of a malignant tumor. Pharmaceutical compositions and immunogenic compositions may be administered either prior to or following surgical removal of primary tumors and/or treatment such as administration of radiotherapy or conventional chemotherapeutic drugs. Administration may be by any suitable method, including administration by intravenous, intraperitoneal, intramuscular, subcutaneous, intranasal, intradermal, anal, vaginal, topical and oral routes.

Within certain embodiments, immunotherapy may be active immunotherapy, in which treatment relies on the in vivo stimulation of the endogenous host immune system to react against tumors with the administration of immune response-modifying agents (such as polypeptides and polynucleotides as provided herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as CD8$^+$ cytotoxic T lymphocytes and CD4$^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions described herein, as well as dosage, will vary from individual to individual, and may be readily established using standard techniques. In general, the pharmaceutical compositions and immunogenic compositions may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such immunogenic compositions should also be capable of causing an immune response that leads to an improved clinical outcome (e.g., more frequent remissions, complete or partial or longer disease-free survival) in treated patients as compared to non-treated patients. In general, for pharmaceutical compositions and immunogenic compositions comprising one or more polypeptides, the amount of each polypeptide present in a dose ranges from about 25 µg to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a breast tumor protein generally correlate with an improved clinical outcome. Such immune responses may generally be evaluated using standard proliferation, cytotoxicity or cytokine assays, which may be performed using samples obtained from a patient before and after treatment.

Cancer Detection and Diagnosis

In general, a cancer may be detected in a patient based on the presence of one or more breast tumor proteins and/or polynucleotides encoding such proteins in a biological sample (for example, blood, sera, sputum urine and/or tumor biopsies) obtained from the patient. In other words, such proteins may be used as markers to indicate the presence or absence of a cancer such as breast cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding a tumor protein, which is also indicative of the presence or absence of a cancer. In general, a breast tumor sequence should be present at a level that is at least three fold higher in tumor tissue than in normal tissue There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length breast tumor proteins and portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with breast cancer. Preferably, the contact time is sufficient to achieve a level of binding that is at least about 95% of that achieved at eqlibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as breast cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use breast tumor polypeptides to detect antibodies that bind to such polypeptides in a biological sample. The detection of such breast tumor protein specific antibodies may correlate with the presence of a cancer.

A cancer may also, or alternatively, be detected based on the presence of T cells that specifically react with a breast tumor protein in a biological sample. Within certain methods, a biological sample comprising $CD4^+$ and/or $CD8^+$ T cells isolated from a patient is incubated with a breast tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with polypeptide (e.g., 5–25 µg/ml). It may be desirable to incubate another aliquot of a T cell sample in the absence of breast tumor polypeptide to serve as a control. For CD4+ T cells, activation is preferably detected by evaluating proliferation of the T cells. For CD8+ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a breast tumor protein in a biological sample. For example, at least two oligonucleotide primers may be employed in a polymerase chain reaction (PCR) based assay to amplify a portion of a breast tumor cDNA derived from a biological sample, wherein at least one of the oligonucleotide primers is specific for (i.e., hybridizes to) a polynucleotide encoding the breast tumor protein. The amplified cDNA is then separated and detected using techniques well known in the art, such as gel electrophoresis. Similarly, oligonucleotide probes that specifically hybridize to a polynucleotide encoding a breast tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a breast tumor protein that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence recited in SEQ ID NO:1–175, 178, 180, 182–468, 474, 476, 477 479, 484, 486 and 489. Techniques for both PCR based assays and hybridization assays are well known in the art (see, for example, Mullis et al., *Cold Spring Harbor Symp. Quant. Biol.,* 51:263, 1987; Erlich ed., *PCR Technology,* Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the compositions described herein may be used as markers for the progression of cancer. In this embodiment, assays as described above for the diagnosis of a cancer may be performed over time, and the change in the level of reactive polypeptide(s) or polynucleotide(s) evaluated. For example, the assays may be performed every 24–72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple breast tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a breast tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a breast tumor protein in a biological sample. Such kits generally comprise at least one oligonucleotide probe or primer, as described above, that hybridizes to a polynucleotide encoding a breast tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a breast tumor protein.

The following Examples are offered by way of illustration and not by way of limitation.

EXAMPLE 1

Isolation and Characterization of Breast Tumor Polypeptides

This Example describes the isolation of breast tumor polypeptides from a breast tumor cDNA library.

A cDNA subtraction library containing cDNA from breast tumor subtracted with normal breast cDNA was constructed as follows. Total RNA was extracted from primary tissues using Trizol reagent (Gibco BRL Life Technologies, Gaithersburg, Md.) as described by the manufacturer. The polyA+ RNA was purified using an oligo(dT) cellulose column according to standard protocols. First strand cDNA was synthesized using the primer supplied in a Clontech PCR-Select cDNA Subtraction Kit (Clontech, Palo Alto, Calif.). The driver DNA consisted of cDNAs from two normal breast tissues with the tester cDNA being from three primary breast tumors. Double-stranded cDNA was synthesized for both tester and driver, and digested with a combination of endonucleases (MluI, MscI, PvuII, SalI and StuI) which recognize six base pairs DNA. This modification increased the average cDNA size dramatically compared with cDNAs generated according to the protocol of Clontech (Palo Alto, Calif.). The digested tester cDNAs were ligated to two different adaptors and the subtraction was performed according to Clontech's protocol. The subtracted cDNAs were subjected to two rounds of PCR amplification, following the manufacturer's protocol. The resulting PCR products were subcloned into the TA cloning vector, pCRII (Invitrogen, San Diego, Calif.) and transformed into E1 ectroMax *E. coli* DHIOB cells (Gibco BRL Life, Technologies) by electroporation. DNA was isolated from independent clones and sequenced using a Perkin E1 mer/ Applied Biosystems Division (Foster City, Calif.) Automated Sequencer Model 373A.

Sixty-three distinct cDNA clones were found in the subtracted breast tumor-specific cDNA library. The determined one strand (5' or 3') cDNA sequences for the clones are provided in SEQ ID NO:1–61, 72 and 73, respectively. Comparison of these cDNA sequences with known sequences in the gene bank using the EMBL and GenBank databases (Release 97) revealed no significant homologies to the sequences provided in SEQ ID NO:14, 21, 22, 27, 29, 30, 32, 38, 44, 45, 53, 72 and 73. The sequences of SEQ ID NO:1, 3, 16, 17, 34, 48, 57, 60 and 61 were found to represent known human genes. The sequences of SEQ ID NO:2, 4, 23, 39 and 50 were found to show some similarity to previously identified non-human genes. The remaining clones (SEQ ID NO:5–13, 15, 18–20, 24–26, 28, 31, 33, 35–37, 40–43, 46, 47, 49, 51, 52, 54–56, 58 and 59) were found to show at least some degree of homology to previously identified expressed sequence tags (ESTs).

To determine mRNA expression levels of the isolated cDNA clones, cDNA clones from the breast subtraction described above were randomly picked and colony PCR amplified. Their mRNA expression levels in breast tumor, normal breast and various other normal tissues were determined using microarray technology (Synteni, Palo Alto, Calif.). Briefly, the PCR amplification products were arrayed onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. Data was analyzed using Synteni provided GEMTOOLS Software. Of the seventeen cDNA clones examined, those of SEQ ID NO:40, 46, 59 and 73 were found to be over-expressed in breast tumor and expressed at low levels in all normal tissues tested (breast, PBMC, colon, fetal tissue, salivary gland, bone marrow, lung, pancreas, large intestine, spinal cord, adrenal gland, kidney, pancreas, liver, stomach, skeletal muscle, heart, small intestine, skin, brain and human mammary epithelial cells). The clones of SEQ ID NO:41 and 48 were found to be over-expressed in breast tumor and expressed at low levels in all other tissues tested, with the exception of bone marrow. The clone of SEQ ID NO:42 was found to be over-expressed in breast tumor and expressed at low levels in all other tissues tested except bone marrow and spinal cord. The clone of SEQ ID NO:43 was found to be over-expressed in breast tumor and expressed at low levels in all other tissues tested with the exception of spinal cord, heart and small intestine. The clone of SEQ ID NO:51 was found to be over-expressed in breast tumor and expressed at low levels in all other tissues tested with the exception of large intestine. The clone of SEQ ID NO:54 was found to be over-expressed in breast tumor and expressed at low levels in all other tissues tested with the exception of PBMC, stomach and small intestine. The clone of SEQ ID NO:56 was found to be over-expressed in breast tumor and expressed at low levels in all other tissues tested with the exception of large and small intestine, human mammary epithelia cells and SCID mouse-passaged breast tumor. The clone of SEQ ID NO:60 was found to be over-expressed in breast tumor and expressed at low levels in all other tissues tested with the exception of spinal cord and heart. The clone of SEQ ID NO:61 was found to be over-expressed in breast tumor and expressed at low levels in all other tissues tested with the exception of small intestine. The clone of SEQ ID NO:72 was found to be over-expressed in breast tumor and expressed at low levels in all other tissues tested with the exception of colon and salivary gland.

The results of a Northern blot analysis of the clone SYN18C6 (SEQ ID NO:40) are shown in FIG. 1. A predicted protein sequence encoded by SYN18C6 is provided in SEQ ID NO:62.

Additional cDNA clones that are over-expressed in breast tumor tissue were isolated from breast cDNA subtraction libraries as follows. Breast subtraction libraries were prepared, as described above, by PCR-based subtraction employing pools of breast tumor cDNA as the tester and pools of either normal breast cDNA or cDNA from other normal tissues as the driver. cDNA clones from breast subtraction were randomly picked and colony PCR amplified and their mRNA expression levels in breast tumor, normal breast and various other normal tissues were determined using the microarray technology described above. Twenty-four distinct cDNA clones were found to be over-expressed in breast tumor and expressed at low levels in all normal tissues tested (breast, brain, liver, pancreas, lung, salivary gland, stomach, colon, kidney, bone marrow, skeletal muscle, PBMC, heart, small intestine, adrenal gland, spinal cord, large intestine and skin). The determined cDNA sequences for these clones are provided in SEQ ID NO:63–87. Comparison of the sequences of SEQ ID NO:74–87 with those in the gene bank as described above, revealed homology to previously identified human genes. No significant homologies were found to the sequences of SEQ ID NO:63–73.

Three DNA isoforms for the clone B726P (partial sequence provided in SEQ ID NO:71) were isolated as follows. A radioactive probe was synthesized from B726P by excising B726P DNA from a pT7Blue vector (Novagen) by a BamHI/XbaI restriction digest and using the resulting DNA as the template in a single-stranded PCR in the presence of [α-32P]dCTP. The sequence of the primer employed for this PCR is provided in SEQ ID NO:177. The resulting radioactive probe was used to probe a directional cDNA library and a random-primed cDNA library made using RNA isolated from breast tumors. Eighty-five clones were identified, excised, purified and sequenced. Of these 85 clones, three were found to each contain a significant open reading frame. The determined cDNA sequence of the isoform B726P-20 is provided in SEQ ID NO:175, with the corresponding predicted amino acid sequence being provided in SEQ ID NO:176. The determined cDNA sequence of the isoform B726P-74 is provided in SEQ ID NO:178, with the corresponding predicted amino acid sequence being provided in SEQ ID NO:179. The determined cDNA sequence of the isoform B726P-79 is provided in SEQ ID NO:180, with the corresponding predicted amino acid sequence being provided in SEQ ID NO:181.

Efforts to obtain a full-Length clone of B726P using standard techniques led to the isolation of five additional clones that represent additional 5' sequence of B726P. These clones appear to be alternative splice forms of the same gene. The determined cDNA sequences of these clones are provided in SEQ ID NO:464–468, with the predicted amino acid sequences encoded by SEQ ID NO:464–467 being provided in SEQ ID NO:470–473, respectively. Using standard computer techniques, a 3,681 bp consensus DNA sequence (SEQ ID NO:463) was created that contains two large open reading frames. The downstream ORF encodes the amino acid sequence of SEQ ID NO:176. The predicted amino acid sequence encoded by the upstream ORF is provided in SEQ ID NO:469. Subsequent studies led to the isolation of an additional splice form of B726P that has 184 bp insert relative to the other forms. This 184 bp insert causes a frameshift that brings the down stream and upstream ORFs together into a single ORF that is 1002 aa in length. The determined cDNA sequence of this alternative splice form is disclosed in SEQ ID NO:474, with the corresponding amino acid sequence being provided in SEQ ID NO:475.

Further isolation of individual clones that are over-expressed in breast tumor tissue was conducted using cDNA subtraction library techniques described above. In particular, a cDNA subtraction library containing cDNA from breast tumors subtracted with five other normal human tissue cDNAs (brain, liver, PBMC, pancreas and normal breast) was utilized in this screening. From the original subtraction, one hundred seventy seven clones were selected to be further characterized by DNA sequencing and microarray analysis. Microarray analysis demonstrated that the sequences in SEQ ID NO:182–251 and 479 were 2 or more fold over-expressed in human breast tumor tissues over normal human tissues. No significant homologies were found for nineteen of these clones, including, SEQ ID NO:185, 186, 194, 199, 205, 208, 211, 214–216, 219, 222, 226, 232, 236, 240, 241, 245, 246 and 479, with the exception of some previously identified expressed sequence tags (ESTs). The remaining clones share some homology to previously identified genes, specifically SEQ ID NO:181–184, 187–193, 195–198, 200–204, 206, 207, 209, 210, 212, 213, 217, 218, 220, 221, 223–225, 227–231, 233–235, 237–239, 242–244 and 247–251.

One of the cDNA clones isolated by PCR subtraction as described above (SEQ ID NO:476; referred to as B720P) which was shown by microarray to be over-expressed in breast tumor tissues, was found to be identical to a known keratin gene. The full-length cDNA sequence of the known keratin gene is provided in SEQ ID NO:477, with the corresponding amino acid sequence being provided in SEQ ID NO:478. Primers were generated based on the sequence of SEQ ID NO:477 and used to clone full-length cDNA from mRNA which was obtained from total RNA showing high expression of B720P in real-time PCR analysis. Products were then cloned and sequenced. The determined full-length cDNA sequence for B720P is provided in SEQ ID NO:484, with the corresponding amino acid sequence being provided in SEQ ID NO:485.

In further studies, a truncated form of B720P (referred to as B720P-tr) was identified in breast carcinomas. This antigen was cloned from mRNA derived from total breast tumor RNA that showed high expression of B720P-tr in real-time PCR analysis. mRNA was used to generate a pool of cDNA which was then used as a template to amplify the cDNA corresponding to B720P-tr by PCR. The determined cDNA sequence for B720P-tr is provided in SEQ ID NO:486. B720P-tr has an ORF of 708 base pairs which encodes a 236 amino acid protein (SEQ ID NO:487). The size of the transcript was confirmed by northern analysis.

Of the seventy clones showing over-expression in breast tumor tissues, fifteen demonstrated particularly good expression levels in breast tumor over normal human tissues. The following eleven clones did not show any significant homology to any known genes. Clone 19463.1 (SEQ ID NO:185) was over-expressed in the majority of breast tumors and also in the SCID breast tumors tested (refer to Example 2); additionally, over-expression was found in a majority of normal breast tissues. Clone 19483.1 (SEQ ID NO:216) was over-expressed in a few breast tumors, with no over-expression in any normal tissues tested. Clone 19470.1 (SEQ ID NO:219) was found to be slightly over-expressed in some breast tumors. Clone 19468.1 (SEQ ID NO:222) was found to be slightly over-expressed in the majority of breast tumors tested. Clone 19505.1 (SEQ ID NO:226) was found to be slightly over-expressed in 50% of breast tumors, as well as in SCID tumor tissues, with some degree of over-expression in found in normal breast. Clone 1509.1 (SEQ ID NO:232) was found to be over-expressed in very few breast tumors, but with a certain degree of over-expression in metastatic breast tumor tissues, as well as no significant over-expression found in normal tissues. Clone 19513.1 (SEQ ID NO:236) was shown to be slightly over-expressed in few breast tumors, with no significant over-expression levels found in normal tissues. Clone 19575.1 (SEQ ID NO:240) showed low level over-expression in some breast tumors and also in normal breast. Clone 19560.1 (SEQ ID NO:241) was over-expressed in 50% of breast tumors tested, as well as in some normal breast tissues. Clone 19583.1 (SEQ ID NO:245) was slightly over-expressed in some breast tumors, with very low levels of over-expression found in normal tissues. Clone 19587.1 (SEQ ID NO:246) showed low level over-expression in some breast tumors and no significant over-expression in normal tissues.

Clone 19520.1 (SEQ ID NO:233), showing homology to clone 102D24 on chromosome 11q13.31, was found to be over-expressed in breast tumors and in SCID tumors. Clone 19517.1 (SEQ ID NO:237), showing homology to human PAC 128M19 clone, was found to be slightly over-expressed in the majority of breast tumors tested. Clone 19392.2 (SEQ ID NO:247), showing homology to human chromosome 17, was shown to be over-expressed in 50% of breast tumors tested. Clone 19399.2 (SEQ ID NO:250), showing homology to human Xp22 BAC GSHB-184P14, was shown to be slightly over-expressed in a limited number of breast tumors tested.

In subsequent studies, 64 individual clones were isolated from a subtracted cDNA library containing cDNA from a pool of breast tumors subtracted with cDNA from five normal tissues (brain, liver, PBMC, pancreas and normal breast). The subtracted cDNA library was prepared as described above with the following modification. A combination of five six-base cutters (MluI, MscI, PvuII, SalI and StuI) was used to digest the cDNA instead of RsaI. This resulted in an increase in the average insert size from 300 bp to 600 bp. The 64 isolated clones were colony PCR amplified and their mRNA expression levels in breast tumor tissue, normal breast and various other normal tissues were examined by microarray technology as described above. The determined cDNA sequences of 11 clones which were found to be over-expressed in breast tumor tissue are provided in SEQ ID NO:405–415. Comparison of these sequences to those in the public database, as outlined above, revealed homologies between the sequences of SEQ ID NO:408, 411, 413 and 414 and previously isolated ESTs. The sequences of SEQ ID NO:405 –407, 409, 410, 412 and 415 were found to show some homology to previously identified sequences.

In further studies, a subtracted cDNA library was prepared from cDNA from metastatic breast tumors subtracted with a pool of cDNA from five normal tissues (breast, brain, lung, pancreas and PBMC) using the PCR-subtraction protocol of Clontech, described above. The determined cDNA sequences of 90 clones isolated from this library are provided in SEQ ID NO:316–404. Comparison of these sequences with those in the public database, as described above, revealed no significant homologies to the sequence of SEQ ID NO:366. The sequences of SEQ ID NO:321–325, 343, 354, 368, 369, 377, 382, 385, 389, 395, 397 and 400 were found to show some homology to previously isolated ESTs. The remaining sequences were found to show homology to previously identified gene sequences.

In yet further studies, a subtracted cDNA library (referred to as 2BT) was prepared from cDNA from breast tumors subtracted with a pool of cDNA from six normal tissues (liver, brain, stomach, small intestine, kidney and heart) using the PCR-subtraction protocol of Clontech, described above. cDNA clones isolated from this subtraction were subjected to DNA microarray analysis as described above and the resulting data subjected to four modified Gemtools analyses. The first analysis compared 28 breast tumors with 28 non-breast normal tissues. A mean over-expression of at least 2.1 fold was used as a selection cut-off. The second analysis compared 6 metastatic breast tumors with 29 non-breast normal tissues. A mean over-expression of at least 2.5 fold was used as a cut-off. The third and fourth analyses compared 2 early SCID mouse-passaged with 2 late SCID mouse-passaged tumors. A mean over-expression in the early or late passaged tumors of 2.0 fold or greater was used as a cut-off. In addition, a visual analysis was performed on the microarray data for the 2BT clones. The determined cDNA sequences of 13 clones identified in the visual analysis are provided in SEQ ID NO:427–439. The determined cDNA sequences of 22 clones identified using the modified Gemtools analysis are provided in SEQ ID NO:440–462, wherein SEQ ID NO:453 and 454 represent two partial, non-overlapping, sequences of the same clone.

Comparison of the clone sequences of SEQ ID NO:436 and 437 (referred to as 263G6 and 262B2) with those in the public databases, as described above, revealed no significant homologies to previously identified sequences. The sequences of SEQ ID NO:427, 429, 431, 435, 438, 441, 443, 444, 445, 446, 450, 453 and 454 (referred to as 266B4, 266G3, 264B4, 263G1, 262B6, 2BT2-34, 2BT1-77, 2BT1-62, 2BT1-60,61, 2 BT1-59 2BT1-52 and 2BT1-40, respectively) showed some homology to previously isolated expressed sequences tags (ESTs). The sequences of SEQ ID NO:428, 430, 432, 433, 434, 439, 440, 442, 447, 448, 449, 451, 452 and 455–462 (referred to as clones 22892, 22890, 22883, 22882, 22880, 22869, 21374, 21349, 21093, 21091, 21089, 21085, 21084, 21063, 21062, 21060, 21053, 21050, 21036, 21037 and 21048, respectively), showed some homology to gene sequences previously identified in humans.

EXAMPLE 2

Isolation and Characterization of Breast Tumor Polypeptides Obtained By PCR-based Subtraction Using Scid-passaged Tumor RNA Human breast tumor antigens were obtained by PCR-based subtraction using SCID mouse passaged breast tumor RNA as follows. Human breast tumor was implanted in SCID mice and harvested on the first or sixth serial passage, as described in patent application Ser. No. 08/556,659 filed 11/13/95, U.S. Pat. No. 5,986,170. Genes found to be differentially expressed between early and late passage SCID tumor may be stage specific and therefore useful in therapeutic and diagnostic applications. Total RNA was prepared from snap frozen SCID passaged human breast tumor from both the first and sixth passage.

PCR-based subtraction was performed essentially as described above. In the first subtraction (referred to as T9), RNA from first passage tumor was subtracted from sixth passage tumor RNA to identify more aggressive, later passage-specific antigens. Of the 64 clones isolated and sequenced from this subtraction, no significant homologies were found to 30 of these clones, here in after referred to as: 13053, 13057, 13059, 13065, 13067, 13068, 13071–13073, 13075, 13078, 13079, 13081, 13082, 13092, 13097, 13101, 13102, 13131, 13133, 13119, 13135, 13139, 13140, 13146–13149, and 13151, with the exception of some previously identified expressed sequence tags (ESTs). The determined cDNA sequences for these clones are provided in SEQ ID NO:88–116, respectively. The isolated cDNA sequences of SEQ ID NO:117–140 showed homology to known genes.

In a second PCR-based subtraction, RNA from sixth passage tumor was subtracted from first passage tumor RNA to identify antigens down-regulated over multiple passages. Of the 36 clones isolated and sequenced, no significant homologies were found to nineteen of these clones, hereinafter referred to as: 14376, 14377, 14383, 14384, 14387, 14392, 14394, 14398, 14401, 14402, 14405, 14409, 14412, 14414–14416, 14419, 14426, and 14427, with the exception of some previously identified expressed sequence tags (ESTs). The determined cDNA sequences for these clones are provided in SEQ ID NO:141–159, respectively. The isolated cDNA sequences of SEQ ID NO:160–174 were found to show homology to previously known genes.

Further analysis of human breast tumor antigens through PCR-based subtraction using first and sixth passage SCID tumor RNA was performed. Sixty three clones were found to be differentially expressed by a two or more fold margin, as determined by microarray analysis, i.e., higher expression in early passage tumor over late passage tumor, or vice versa. Seventeen of these clones showed no significant homology to any known genes, although some degree of homology with previously identified expressed sequence tags (ESTs) was found, hereinafter referred to as 20266, 20270, 20274, 20276, 20277, 20280, 20281, 20294, 20303, 20310, 20336, 20341, 20941, 20954, 20961, 20965 and 20975 (SEQ ID NO:252–268, respectively). The remaining clones were found to share some degree of homology to known genes, which are identified in the Brief Description of the Drawings and Sequence Identifiers section above, hereinafter referred to as 20261, 20262, 20265, 20267, 20268, 20271, 20272, 20273, 20278, 20279, 20293, 20300, 20305, 20306, 20307, 20313, 20317, 20318, 20320, 20321, 20322, 20326, 20333, 20335, 20337, 20338, 20340, 20938, 20939, 20940, 20942, 20943, 20944, 20946, 20947, 20948, 20949, 20950, 20951, 20952, 20957, 20959, 20966, 20976, 20977 and 20978. The determined cDNA sequences for these clones are provided in SEQ ID NO:269–314, respectively.

The clones 20310, 20281, 20262, 20280, 20303, 20336, 20270, 20341, 20326 and 20977 (also referred to as B820P, B821P, B822P, B823P, B824P, B825P, B826P, B827P, B828P and B829P, respectively) were selected for further analysis based on the results obtained with microarray analysis. Specifically, microarray data analysis indicated at least two- to three-fold over expression of these clones in breast tumor RNA compared to normal tissues tested. Subsequent studies led to the determination of the complete insert sequence for the clones B820P, B821P, B822P, B823P, B824P, B825P, B826P, B827P, B828P and B829P. These extended cDNA sequences are provided in SEQ ID NO:416–426, respectively.

EXAMPLE 3

Synthesis of Polypeptides

Polypeptides may be synthesized on an Perkin E1 mer/Applied Biosystems Division 430A peptide synthesizer using FMOC chemistry with HPTU (0-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

EXAMPLE 4

Elicitation of Breast Antigen-specific CTL Responses in Human Blood

This Example illustrates the ability of the breast-specific antigen B726P to elicit a cytotoxic T lymphocyte (CTL) response in peripheral blood lymphocytes from normal humans.

Autologous dendritic cells (DC) were differentiated from monocyte cultures derived from PBMC of a normal donor by growth for five days in RPMI medium containing 10% human serum, 30 ng/ml GM-CSF and 30 ng/ml IL-4. Following five days of culture, DC were infected overnight with adenovirus expressing recombinant B726P (downstream ORF; SEQ ID NO:181) at an M.O.I. of 2.5 and matured for 8 hours by the addition of 2 micrograms/ml CD40 ligand. CD8 positive cells were enriched for by the depletion of CD4 and CD14-positive cells. Priming cultures were initiated in individual wells of several 96-well plates with the cytokines IL-6 and IL-12. These cultures were restimulated in the presence of IL-2 using autologous fibroblasts treated with IFN-gamma and transduced with B726P and CD80. Following three stimulation cycles, the presence of B726P-specific CTL activity was assessed in IFN-gamma E1 ispot assays (Lalvani et al., *J. Exp. Med.* 186:859–865, 1997) using IFN-gamma treated autologous fibroblasts transduced to express either B726P or an irrelevant, control, antigen as antigen presenting cells (APC). Of approximately 96 lines, one line (referred to as 6-2B) was identified that appeared to specifically recognize B726P-transduced APC but not control antigen-transduced APC. This microculture was cloned using standard protocols. B726P-specific CTL were identified by E1 ispot analysis and expanded for further analysis. These CTL clones were demonstrated to recognize B726P-expressing fibroblasts, but not the control antigen MART-1, using chromium-51 release assays. Furthermore, using a panel of allogeneic fibroblasts transduced with B726P in antibody blocking assays, the HLA restriction element for these B726P-specific CTL was identified as HLA-B*1501.

In order to define more accurately the location of the epitope recognized by the B726P-specific CTL clones, a deletion construct comprising only the N-terminal half of B726P (B726Pdelta3') was constructed (a.a. 1–129) into the pBIB retroviral expression plasmid. This plasmid as well as other plasmids containing B726P were transfected into COS-7 cells either alone or in combination with a plasmid expressing HLA-B*1501. Approximately 48 hours after transfection, a B726P-specific CTL clone (1-9B) was added at approximately 1 Oe4 cells per well. The wells were harvested the next day and the amount of IFN-gamma released was measured by ELISA. The CTL responded above background (EGFP) to COS-7 cells that had been transfected with both B726P and HLA-B* 1501. There was no response above background to COS-7 cells that had been transfected with B726P or HLA-B*1501 only. Importantly, a higher response was seen with COS-7 cells that had been transfected with HLA-B*1501 and B726Pdelta3'. This result indicated that the epitope was likely to be located in the N-terminal region (a.a. 1–129) of B726P. This region was examined and amino acid sequences that corresponded to the HLA-B*1501 peptide binding motif (J. Immunol.1999, 162:7277–84) were identified and synthesized. These peptides were pulsed at 10 ug/ml onto autologous B-LCL overnight. The next day the cells were washed and the ability of the cells to stimulate the B726P-specific CTL clone 1-9B was assayed in a IFN-gamma ELISPOT assay. Of the eleven peptides tested, only one peptide, having the amino acid sequence SLTKRASQY (a.a. 76–84; SEQ ID NO: 488) was able to be recognized by the CTL. This result identifies this peptide as being a naturally-processed epitope recognized by this B726P-specific CTL clone.

EXAMPLE 5

Preparation and Characterization of Antibodies Against Breast Tumor Polypeptides Polyclonal antibodies against the breast tumor antigen B726P were prepared as follows.

The downstream ORF of B726P (SEQ ID NO:176) expressed in an *E. coli* recombinant expression system was grown overnight in LB broth with the appropriate antibiotics at 37° C. in a shaking incubator. The next morning, 10 ml of the overnight culture was added to 500 ml to 2×YT plus appropriate antibiotics in a 2L-baffled Erlenmeyer flask. When the Optical Density (at 560 nm) of the culture reached 0.4–0.6, the cells were induced with IPTG (1 mM). Four hours after induction with IPTG, the cells were harvested by centrifugation. The cells were then washed with phosphate buffered saline and centriftiged again. The supernatant was discarded and the cells were either frozen for future use or immediately processed. Twenty ml of lysis buffer was added to the cell pellets and vortexed. To break open the *E. coli* cells, this mixture was then run through the French Press at a pressure of 16,000 psi. The cells were then centrifuged again and the supernatant and pellet were checked by SDS-PAGE for the partitioning of the recombinant protein. For proteins that localized to the cell pellet, the pellet was resuspended in 10 mM Tris pH 8.0, 1% CHAPS and the inclusion body pellet was washed and centrifuged again. This procedure was repeated twice more. The washed inclusion body pellet was solubilized with either 8 M urea or 6 M guanidine HCl containing 10 mM Tris pH 8.0 plus 10 mM imidazole. The solubilized protein was added to 5 ml of nickel-chelate resin (Qiagen) and incubated for 45 min to 1 hour at room temperature with continuous agitation. After incubation, the resin and protein mixture were poured through a disposable column and the flow through was collected. The column was then washed with 10–20 column volumes of the solubilization buffer. The antigen was then eluted from the column using 8M urea, 10 mM Tris pH 8.0 and 300 mM imidazole and collected in 3 ml fractions. A SDS-PAGE gel was run to determine which fractions to pool for further purification.

As a final purification step, a strong anion exchange resin, such as HiPrepQ (Biorad), was equilibrated with the appropriate buffer and the pooled fractions from above were loaded onto the column. Antigen was eluted off the column with a increasing salt gradient. Fractions were collected as the column was run and another SDS-PAGE gel was run to determine which fractions from the column to pool. The pooled fractions were dialyzed against 10 mM Tris pH 8.0. The protein was then vialed after filtration through a 0.22 micron filter and the antigens were frozen until needed for immunization.

Four hundred micrograms of B726P antigen was combined with 100 micrograms of muramyldipeptide (MDP). Every four weeks rabbits were boosted with 100 micrograms mixed with an equal volume of Incomplete Freund's Adjuvant (IFA). Seven days following each boost, the animal was bled. Sera was generated by incubating the blood at 4° C. for 12–24 hours followed by centrifugation.

Ninety-six well plates were coated with B726P antigen by incubating with 50 microliters (typically 1 microgram) of recombinant protein at 4° C. for 20 hours. 250 Microliters of BSA blocking buffer was added to the wells and incubated at room temperature for 2 hours. Plates were washed 6 times with PBS/0.01% Tween. Rabbit sera was diluted in PBS. Fifty microliters of diluted sera was added to each well and incubated at room temperature for 30 min. Plates were washed as described above before 50 microliters of goat anti-rabbit horse radish peroxidase (HRP) at a 1:10000 dilution was added and incubated at room temperature for 30 min. Plates were again washed as described above and 100 microliters of TMB microwell peroxidase substrate was added to each well. Following a 15 min incubation in the dark at room temperature, the colorimetric reaction was stopped with 100 microliters of 1N $H_2SO_4$ and read immediately at 450 nm. The polyclonal antibodies showed immunoreactivity to B726P.

EXAMPLE 6

Protein Expression of Breast Tumor Antigens

The downstream ORF of B726P (SEQ ID NO:176), together with a C-terminal 6×His Tag, was expressed in insect cells using the baculovirus expression system as follows.

The cDNA for the full-length downstream ORF of B726P was PCR amplified using the primers of SEQ ID NO:480 and 481. The PCR product with the expected size was recovered from agarose gel, restriction digested with EcoRI and Hind II, and ligated into the transfer plasmid pFastBacI, which was digested with the same restriction enzymes. The sequence of the insert was confirmed by DNA sequencing. The recombinant transfer plasmid pFBB726P was used to make recombinant bacmid DNA and virus using the Bac-To-Bac Baculovirus expression system (BRL Life Technologies, Gaithersburg, Md.). High Five cells were infected with the recombinant virus BVB726P to produce protein. The cDNA and amino acid sequences of the expressed B726P recombinant protein are provided in SEQ ID NO:482 and 483, respectively.

From the foregoing, it will be appreciated that, although specific embodiments of the invention have been described herein for the purposes of illustration, various modifications may be made without deviating from the spirit and scope of the invention.

What is claimed is:

1. An isolated polypeptide comprising SEQ ID NO:475.

2. A fusion protein comprising at least one polypeptide according to claim 1.

3. A fusion protein according to claim 2, wherein the fusion protein comprises an expression enhancer that increases expression of the fusion protein in a host cell transfected with a polynucleotide encoding the fusion protein.

4. A fusion protein according to claim 2, wherein the fusion protein comprises a T helper epitope that is not present within the polypeptide of claim 1.

5. A fusion protein according to claim 2, wherein the fusion protein comprises an affinity tag.

6. The isolated polypeptide according to claim 1, wherein the polypeptide comprises an amino acid encoded by SEQ ID NO:474.

* * * * *